United States Patent
Barbion et al.

(10) Patent No.: US 10,722,520 B2
(45) Date of Patent: Jul. 28, 2020

(54) HETEROCYCLIC COMPOUNDS AND THEIR USE IN PREVENTING OR TREATING BACTERIAL INFECTIONS

(71) Applicant: MUTABILIS, Romainville (FR)

(72) Inventors: Julien Barbion, Sannois (FR); Audrey Caravano, Enghien les Bains (FR); Sophie Chasset, Nandy (FR); Francis Chevreuil, Chantilly (FR); Fabien Faivre, Drancy (FR); Rémi Lebel, Drancy (FR); Nicolas Lecointe, Paris (FR); Benoît Ledoussal, Pommerit Jaudy (FR); Frédéric Le-Strat, Combs la Ville (FR); Christophe Simon, Chevilly Larue (FR); Chrystelle Oliveira, Saint Prix (FR); Géraldine Le Fralliec, Bondy (FR); Julie Brias, Paris (FR); Laurence Farescour, Chelles (FR); Sophie Vomscheid, Malakoff (FR); Sébastien Richard, Romainville, FL (US)

(73) Assignee: MUTABILIS, Romainville (FR)

( * ) Notice: Subject to any disclaimer, the term of this patent is extended or adjusted under 35 U.S.C. 154(b) by 0 days.

(21) Appl. No.: 16/338,355

(22) PCT Filed: Sep. 29, 2017

(86) PCT No.: PCT/EP2017/074873
§ 371 (c)(1),
(2) Date: Mar. 29, 2019

(87) PCT Pub. No.: WO2018/060481
PCT Pub. Date: Apr. 5, 2018

(65) Prior Publication Data
US 2019/0224210 A1    Jul. 25, 2019

(30) Foreign Application Priority Data

Sep. 30, 2016  (EP) .................................. 16306261

(51) Int. Cl.

| | |
|---|---|
| *A61K 31/551* | (2006.01) |
| *A61K 31/546* | (2006.01) |
| *A61K 31/439* | (2006.01) |
| *A61K 45/06* | (2006.01) |
| *C07D 471/08* | (2006.01) |
| *C07D 403/04* | (2006.01) |
| *C07D 403/14* | (2006.01) |
| *C07D 413/14* | (2006.01) |
| *C07D 417/14* | (2006.01) |
| *A61P 31/04* | (2006.01) |

(52) U.S. Cl.
CPC .......... *A61K 31/551* (2013.01); *A61K 31/439* (2013.01); *A61K 31/546* (2013.01); *A61K 45/06* (2013.01); *A61P 31/04* (2018.01); *C07D 403/04* (2013.01); *C07D 403/14* (2013.01); *C07D 413/14* (2013.01); *C07D 417/14* (2013.01); *C07D 471/08* (2013.01)

(58) Field of Classification Search
CPC .............. A61K 2300/00; A61K 31/439; A61K 31/546; A61K 31/551; A61K 45/06; A61P 31/04; C07D 403/04; C07D 403/14; C07D 413/14; C07D 417/14; C07D 471/08
See application file for complete search history.

(56) References Cited

U.S. PATENT DOCUMENTS

2010/0093784 A1    4/2010  Ledoussal et al.

FOREIGN PATENT DOCUMENTS

| EP | 3091018 A1 | 11/2016 | |
|---|---|---|---|
| WO | 13150296 A1 | 10/2013 | |
| WO | WO 2013/150296 | * 10/2013 | ........... C07D 471/08 |
| WO | 14141132 A1 | 9/2014 | |
| WO | 16081452 A1 | 5/2016 | |
| WO | 16177862 A1 | 11/2016 | |

* cited by examiner

*Primary Examiner* — Erich A Leeser
(74) *Attorney, Agent, or Firm* — Thompson Coburn LLP; Steven M. Ritchey

(57) ABSTRACT

A compound of formula (I)

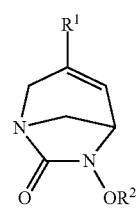

or a racemate, an enantiomer, a diastereoisomer, a geometric isomer or a pharmaceutically acceptable salt thereof, and its use as antibacterial agent.

19 Claims, No Drawings

HETEROCYCLIC COMPOUNDS AND THEIR USE IN PREVENTING OR TREATING BACTERIAL INFECTIONS

CROSS-REFERENCE TO RELATED APPLICATIONS

This application is a U.S. National Phase application of PCT/EP2017/074873, filed on Sep. 29, 2017, claiming the benefit of European Application No. 16306261.5, filed on Sep. 30, 2016, both of which are incorporated herein by reference in their entireties.

The present invention relates to heterocyclic compounds, their process of preparation, pharmaceutical compositions comprising these compounds and use thereof, optionally in combination with other antibacterial agents and/or beta-lactam compounds, for the prevention or treatment of bacterial infections. The present invention also relates to the use of these compounds as β-lactamase inhibitors and/or as antibacterial agents.

It has been described that there is a continuous evolution of antibacterial resistance which could lead to bacterial strains against which known antibacterial compounds are inefficient.

There is thus a need to provide effective compounds and composition that can overcome bacterial antibiotic resistance.

The objective of the present invention is to provide heterocyclic compounds that can be used as antibacterial agents and/or beta-lactamase inhibitors.

An objective of the present invention is also to provide heterocyclic compounds that can be used for the prevention or for the treatment of bacterial infections.

Another objective of the present invention is to provide heterocyclic compounds that can overcome bacterial antibiotic resistance.

An objective of the invention is also to provide pharmaceutical compositions comprising such heterocyclic compounds, optionally in combination with one or more other antibacterial agent, for the prevention or for the treatment of bacterial infections and which can overcome bacterial antibiotic resistance.

Other objectives will appear throughout the description of the invention.

The present invention thus provides a compound of formula (I)

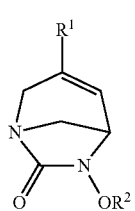

(I)

wherein
  $R^1$ represents a 5-membered heterocycle, optionally substituted by one or more $T^1$, saturated, partially unsaturated or aromatic comprising at least one nitrogen atom, the heterocycle being linked to the structure by the nitrogen atom, at least one of the nitrogen atoms can be quaternized;
  $R^2$ represents —$SO_3H$, —$CFHCOOH$ or —$CF_2COOH$;
  $T^1$, identical or different, independently represents a fluorine atom; =O; —C(O)$Q^1$; —(CH$_2$)$_m$—S(O)$_2$—NQ$^1$Q$^2$; —(CH$_2$)$_m$—C(=NOQ$^1$)Q$^3$; —(X)—(CH$_2$)$_p$—S(O)$_2$NQ$^1$Q$^2$; —C(O)—(CH$_2$)$_n$—S(O)$_2$NQ$^1$Q$^2$; —(CH$_2$)$_m$—O—(CH$_2$)$_p$—O—(CH$_2$)$_p$-NQ$^1$Q$^2$; —(CH$_2$)$_m$OQ$^1$; —(CH$_2$)$_m$—CN; —(CH$_2$)$_m$—OC(O)Q$^1$; —(CH$_2$)$_m$—C(O)OQ$^1$; —(CH$_2$)$_m$—OC(O)OQ$^1$; —(CH$_2$)$_m$—OC(O)NQ$^1$Q$^2$; —(CH$_2$)$_m$—C(O)NQ$^1$Q$^2$; —(CH$_2$)$_m$—C(O)ONQ$^1$Q$^2$; —(CH$_2$)$_m$—C(O)NQ$^1$OQ$^2$; —(CH$_2$)$_m$—C(O)NQ$^1$-NQ$^1$Q$^2$; —(CH$_2$)$_m$-NQ$^1$C(O)Q$^2$; —(CH$_2$)$_m$-NQ$^1$S(O)$_2$NQ$^1$Q$^2$; —(CH$_2$)$_m$-NQ$^1$S(O)$_2$ Q$^2$; —(CH$_2$)$_m$-NQ$^1$C(O)OQ$^2$; —(CH$_2$)$_m$-NQ$^1$C(O)NQ$^1$Q$^2$; —(CH$_2$)$_m$-NQ$^1$Q$^2$; —(CH$_2$)$_m$—NH—C(NHQ$^3$)=NQ$^4$; —(CH$_2$)$_m$—NH—CH=NQ$^3$; —(CH$_2$)$_m$—C(NHQ$^3$)=NQ$^4$; —(X)—(CH$_2$)$_p$OQ$^1$; —(X)—(CH$_2$)$_n$—CN; —(X)—(CH$_2$)$_p$—OC(O)Q$^1$; —(X)—(CH$_2$)$_n$—C(O)OQ$^1$; —(X)—(CH$_2$)$_p$—OC(O)OQ$^1$; —(X)—(CH$_2$)$_p$—OC(O)NQ Q$^2$; —(X)—(CH$_2$)$_n$—C(O)NQ$^1$Q$^2$; —(X)—(CH$_2$)$_n$—C(O)ONQ$^1$Q$^2$; —(X)—(CH$_2$)$_n$—C(O)NQ$^1$OQ$^2$; —(X)—(CH$_2$)$_n$—C(O)NQ$^1$-NQ$^1$Q$^2$; —(X)—(CH$_2$)$_p$-NQ$^1$C(O)Q$^2$; —(X)—(CH$_2$)$_p$—NQ$^1$S(O)$_2$NQ$^1$Q$^2$; —(X)—(CH$_2$)$_p$-NQ$^1$S(O)$_2$Q$^2$; —(X)—(CH$_2$)$_p$-NQ$^1$C(O)OQ$^2$; —(X)—(CH$_2$)$_p$—NQ$^1$C(O)NQ$^1$Q$^2$; —(X)—(CH$_2$)$_p$-NQ$^1$Q$^2$; —(X)—(CH$_2$)$_p$—NH—C(NHQ$^3$)=NQ$^4$; —(X)—(CH$_2$)$_p$—NH—CH=NQ$^3$; —(X)—(CH$_2$)$_n$—C(NHQ$^3$)=NQ$^4$; —C(O)—(CH$_2$)$_n$OQ$^1$; —C(O)—(CH$_2$)$_n$—CN; —C(O)—(CH$_2$)$_n$—OC(O)Q$^1$; —C(O)—(CH$_2$)$_n$—C(O)OQ$^1$; —C(O)—(CH$_2$)$_n$—OC(O)OQ$^1$; —C(O)—(CH$_2$)$_n$—OC(O)NQ$^1$Q$^2$; —C(O)—(CH$_2$)$_n$—C(O)NQ$^1$Q$^2$; —C(O)—(CH$_2$)$_n$—C(O)ONQ$^1$Q$^2$; —C(O)—(CH$_2$)$_n$—C(O)NQ$^1$OQ$^2$; —C(O)—(CH$_2$)$_n$—C(O)NQ$^1$-NQ$^1$Q$^2$; —C(O)—(CH$_2$)$_n$-NQ$^1$C(O)Q$^2$; —C(O)—(CH$_2$)$_n$-NQ$^1$S(O)$_2$NQ$^1$Q$^2$; —C(O)—(CH$_2$)$_n$-NQ$^1$S(O)$_2$Q$^2$; —C(O)—(CH$_2$)$_n$-NQ C(O)OQ$^2$; —C(O)—(CH$_2$)$_n$-NQ$^1$C(O)NQ$^1$Q$^2$; —C(O)—(CH$_2$)$_n$-NQ$^1$Q$^2$; —C(O)—(CH$_2$)$_n$—NH—C(NHQ$^3$)=NQ$^4$; —C(O)—(CH$_2$)$_n$—NH—CH=NQ$^3$; —C(O)—(CH$_2$)$_n$—C(NHQ$^3$)=NQ$^4$ or
  $T^1$, identical or different, independently represents an unsubstituted or substituted by one or more $T^2$, —(CH$_2$)$_m$-(4-, 5- or 6-membered saturated, partially or totally unsaturated or aromatic heterocycle); —(X)—(CH$_2$)$_m$-(4-, 5- or 6-membered saturated, partially or totally unsaturated or aromatic heterocycle); (C$_1$-C$_3$)-alkyl; (C$_1$-C$_3$)-fluoroalkyl; —(X)—(C$_1$-C$_5$)-alkyl; —(X)—(C$_1$-C$_5$)-fluoroalkyl; —(CH$_2$)$_m$—(C$_3$-C$_6$)-cycloalkyl; —(X)—(CH$_2$)$_m$—(C$_3$-C$_6$)-cycloalkyl; —(CH$_2$)$_m$—(C$_3$-C$_6$)-cyclofluoroalkyl; —(X)—(CH$_2$)$_m$—(C$_3$-C$_6$)-cyclofluoroalkyl; —C(O)—(CH$_2$)$_m$-(4-, 5- or 6-membered saturated, partially or totally unsaturated or aromatic heterocycle); —C(O)—(C$_1$-C$_3$)-alkyl; —C(O)—(C$_1$-C$_3$)-fluoroalkyl; —C(O)O—(C$_1$-C$_3$)-fluoroalkyl; —C(O)—(CH$_2$)$_m$—(C$_3$-C$_6$)-cycloalkyl; —C(O)—(CH$_2$)$_m$—(C$_3$-C$_6$)-cycloalkyl; —C(O)—(CH$_2$)$_m$—(C$_3$-C$_6$)-cyclofluoroalkyl; —C(O)—(CH$_2$)$_m$—(C$_3$-C$_6$)-cyclofluoroalkyl;
  $T^2$, identical or different, independently represents —OH; —NH$_2$; —CONH$_2$;
  $Q^1$ and $Q^2$, identical or different, independently represent a hydrogen atom; —(CH$_2$)$_r$—NHQ$^3$; —(CH$_2$)$_r$—NH—C(NHQ$^3$)=NQ$^4$; —(CH$_2$)$_r$—NH—CH=NQ$^3$; (CH$_2$)$_n$—C(NHQ$^3$)=NQ$^4$; —(CH$_2$)$_r$-OQ$^3$; —(CH$_2$)$_n$—CONHQ$^3$; or
  an unsubstituted or substituted by one or more $T^2$, (C$_1$-C$_3$)-alkyl; (C$_1$-C$_3$)-fluoroalkyl; saturated, partially or totally unsaturated or aromatic-(CH$_2$)$_m$-(4-, 5- or 6-membered heterocycle comprising at least one nitrogen atom); or Q¹, Q² and the nitrogen atom to which they are bonded, form together an unsubstituted or substituted by one or more T², saturated or partially unsaturated 4-, 5- or 6-membered heterocycle comprising 1, 2 or 3 heteroatoms;

Q³ and Q⁴, identical or different, independently represent a hydrogen atom or $(C_1-C_3)$-alkyl;

m, identical or different, independently represents 0, 1, 2 or 3;

n, identical or different, independently represents 1, 2 or 3;

p, identical or different, independently represents 2 or 3;

r is 1, 2 or 3 when the $(CH_2)_r$ is directly linked to a carbon atom or 2 or 3 otherwise, preferably r is 2 or 3;

X, identical or different, independently represents O; S; S(O); $S(O)_2$ or $N(Q^3)$;

wherein any carbon atom present within a group selected from alkyl, cycloalkyl, fluoroalkyl, cyclofluoroalkyl and heterocycle can be oxidized to form a C=O group;

any sulphur atom present within a heterocycle can be oxidized to form a S=O group or a $S(O)_2$ group;

any nitrogen atom present within a heterocycle or present within group wherein it is trisubstituted thus forming a tertiary amino group, can be further quaternized by a methyl group;

and a racemate, an enantiomer, a diastereoisomer, a geometric isomer or a pharmaceutically acceptable salt thereof, with the exception of the following compounds:

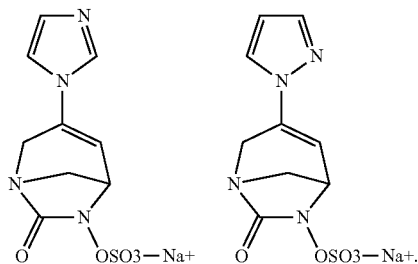

In one embodiment, the invention relates to compounds of formula (I) as defined above, with the exception of the following compounds:

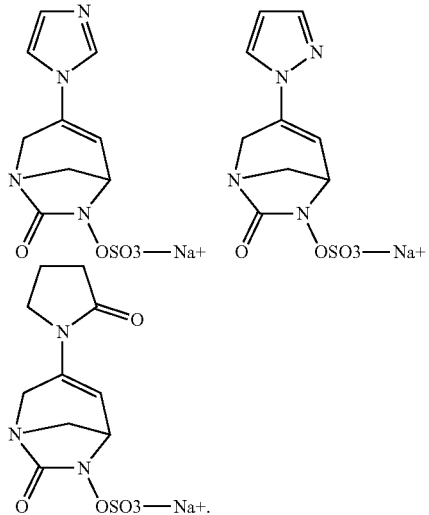

Preferably, the present invention relates to compounds of formula (I) with the exception of the following compounds:

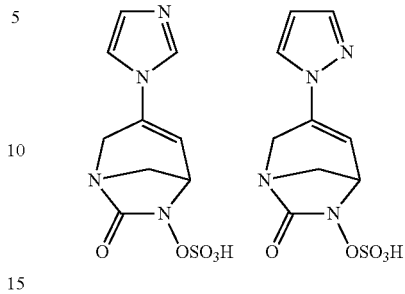

and a racemate, an enantiomer, a diastereoisomer, a geometric isomer or a pharmaceutically acceptable salt thereof.

In one embodiment, the present invention relates to compounds of formula (I) with the exception of the following compounds:

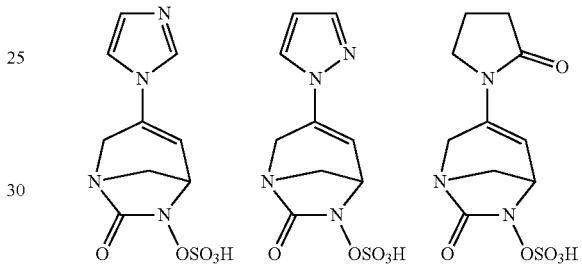

and a racemate, an enantiomer, a diastereoisomer, a geometric isomer or a pharmaceutically acceptable salt thereof.

The present invention also relates to compounds of formula (I*)

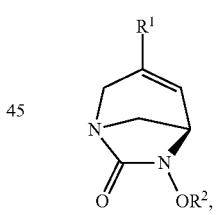

(I*)

wherein $R^1$ and $R^2$ are as defined for compounds of formula (I).

Preferably, in the compounds of formula (I) or (I*), $R^1$ represents an heterocycle, optionally substituted by one or more $T^1$, unsaturated, partially saturated or aromatic comprising at least one nitrogen atom and optionally one, two or three, preferably one or two, other heteroatoms chosen among N, O or S, the heterocycle being linked to the structure by the nitrogen atom, at least one of the nitrogen atoms can be quaternized.

Preferably, in the compounds of formula (I) or (I*), $T^1$ represents =O, a fluorine atom, —$(CH_2)_m$-$NQ^1Q^2$; —CN; —$(CH_2)_m$—C(O)$NQ^1Q^2$; —$(CH_2)_m$-$OQ^1$; —$(CH_2)_m$—$COOQ^1$; —$(CH_2)_m$—C(O)$NQ^1NQ^1Q^2$; —$(CH_2)_m$-$NQ^1NQ^1Q^2$; —$(CH_2)_m$—O—$(CH_2)_p$—O—$(CH_2)_p$-$NQ^1Q^2$; —$(CH_2)_m$-$NQ^1S(O)_2Q^2$; an unsubstituted or substituted by one or more $T^2$, —$(CH_2)_m$-(4-, 5- or 6-membered saturated, partially or totally unsaturated or aromatic heterocycle), —(X)—(CH$_2$)$_m$-(4-, 5- or 6-membered saturated, partially or totally unsaturated or aromatic heterocycle); (C$_1$-C$_3$)-fluoroalkyl; —(CH$_2$)$_m$—C(NOQ$^1$)Q$^3$; —(CH$_2$)$_m$—C(O)NQ$^1$OQ$^2$, wherein Q$^1$, Q$^2$, Q$^3$, m and n are as defined above.

Preferably, in the compounds of formula (I) or (I*), T$^1$ represents =O, a fluorine atom, —(CH$_2$)$_m$—NH$_2$, —CN, —(CH$_2$)$_m$—C(O)NH$_2$, —(CH$_2$)$_m$—COOH, —O—(CH$_2$)$_2$NH$_2$, —C(O)NHNHC(O)Het, —NHCONH$_2$, —(CH$_2$)$_2$—O—(CH$_2$)$_2$—O(CH$_2$)$_2$NH$_2$, —NH—S(O$_2$)—NH$_2$, -Het, C(O)CH$_3$, C(=NOH)CH$_3$, —CF$_3$, —CONHO(CH$_2$)$_2$NH$_2$, —OHet, —CH$_2$—Het, wherein Het is an heterocycle, saturated, partially unsaturated or aromatic, comprising 4, 5 or 6 members and at least one heteroatom chosen among N, O or S, wherein m is as defined above.

Preferably, in the compounds of formula (I) or (I*), T$^1$ represents a fluorine atom; =O; —C(O)Q$^1$; —(CH$_2$)$_m$—S(O)$_2$—NQ$^1$Q$^2$; —(CH$_2$)$_m$—C(=NOQ$^1$)Q$^3$; —(CH$_2$)$_m$OQ$^1$; —(CH$_2$)$_m$—CN; —(CH$_2$)$_m$—C(O)OQ$^1$; —(CH$_2$)$_m$—C(O)NQ$^1$Q$^2$; —(CH$_2$)$_m$—C(O)NQ$^1$OQ$^2$; —(CH$_2$)$_m$-NQ$^1$C(O)Q$^2$; —(CH$_2$)$_m$-NQ$^1$Q$^2$; or T$^1$, identical or different, independently represents an unsubstituted or substituted by one or more T$^2$, —(CH$_2$)$_m$-(4-, 5- or 6-membered saturated, partially or totally unsaturated or aromatic heterocycle); (C$_1$-C$_3$)-alkyl; (C$_1$-C$_3$)-fluoroalkyl.

Preferably, R$^1$ is non-substituted or when R$^1$ is not an aromatic heterocycle T$^1$ can be =O.

In one embodiment, when R$^1$ is not an aromatic heterocycle, it has the following formula:

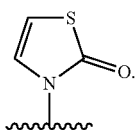

In one embodiment, R$^1$ represents a 5-membered aromatic heterocycle, optionally substituted by one or more T$^1$, comprising at least one nitrogen atom, the heterocycle being linked to the structure by the nitrogen atom, or a 2-oxo-thiazol-3-yl, wherein at least one of the nitrogen atoms can be quaternized.

Preferably, in the compounds of formula (I) or (I*), R$^1$ is chosen among:

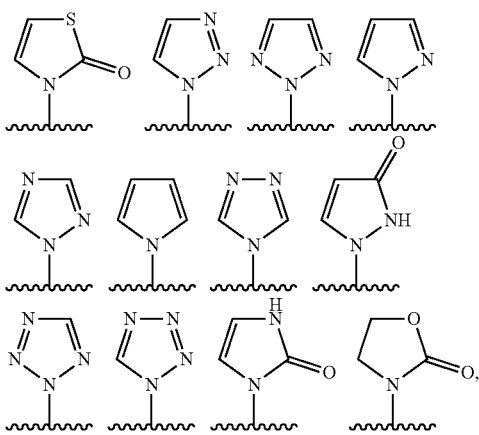

the cycle being optionally substituted by one or more T$^1$ as defined above, preferably no T.

In one embodiment, in the compounds of formula (I) or (I*), R$^1$ is chosen among:

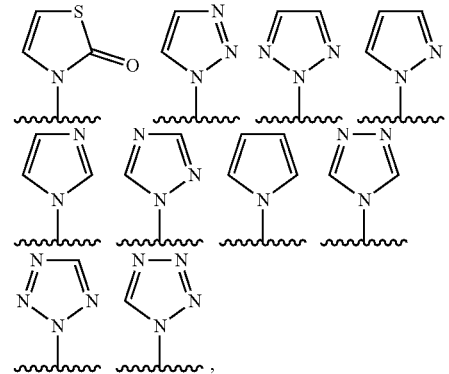

the cycle being optionally substituted by one or more T$^1$ as defined above, preferably no T$^1$.

Preferably, in the compounds of formula (I) or (I*), R$^1$ is chosen among:

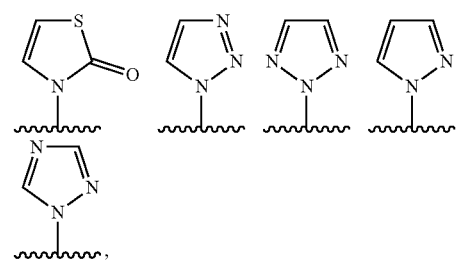

the cycle being optionally substituted by one or more T$^1$ as defined above, preferably there is no substituent.

In one embodiment, in the compounds of formula (I) or (I*), R$^1$ is chosen among:

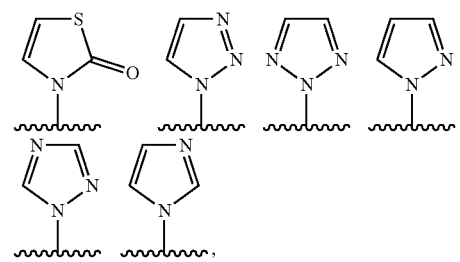

the cycle being optionally substituted by one or more T$^1$ as defined above, preferably there is no substituent T$^1$.

Preferably, in the compounds of formula (I) or (I*), R$^2$ represents —SO$_3$H or —CF$_2$COOH.

In one embodiment, R$^2$ is —SO$_3$H or one of its pharmaceutically acceptable salts.

All the preferences of R$^1$ and R$^2$ can be combined to give embodiments according to the invention.

In one embodiment, Q$^1$ and Q$^2$, identical or different, independently represent a hydrogen atom; —(CH$_2$)$_r$—NHQ$^3$; —(CH$_2$)$_r$-OQ$^3$; —(CH$_2$)$_n$—CONHQ$^3$; or an unsubstituted or substituted by one or more T$^2$, (C$_1$-C$_3$)-alkyl; —(CH$_2$)$_m$-(4-, 5- or 6-membered heterocycle comprising at least one nitrogen atom, saturated, partially or totally unsaturated or aromatic); or $Q^1$, $Q^2$ and the nitrogen atom to which they are bonded, form together an unsubstituted or substituted by one or more $T^2$, saturated or partially unsaturated 4-, 5- or 6-membered heterocycle comprising 1, 2 or 3 heteroatoms.

Preferably, the compounds of formula (I) or (I*) are chosen among:

sodium [7-oxo-3-(2-oxo-thiazol-3-yl)-1,6-diaza-bicyclo[3.2.1]oct-3-en-6-yl]sulfate sodium [7-oxo-3-(triazol-1-yl)-1,6-diazabicyclo[3.2.1]oct-3-en-6-yl]sulfate sodium [7-oxo-3-(triazol-2-yl)-1,6-diazabicyclo[3.2.1]oct-3-en-6-yl]sulfate lithium difluoro-(7-oxo-3-pyrazol-1-yl-1,6-diaza-bicyclo[3.2.1]oct-3-en-6-yloxy)-acetate sodium [7-oxo-3-(1,2,4-triazol-1-yl)-1,6-diazabicyclo[3.2.1]oct-3-en-6-yl]sulfate sodium [(5R)-7-oxo-3-(triazol-1-yl)-1,6-diazabicyclo[3.2.1]oct-3-en-6-yl]sulfate In one embodiment, the compounds of formula (I) or (I*) are chosen among:

sodium [3-(4-carbamoylpyrazol-1-yl)-7-oxo-1,6-diazabicyclo[3.2.1]oct-3-en-6-yl]sulfate (7)

sodium [3-(4-cyanopyrazol-1-yl)-7-oxo-1,6-diazabicyclo[3.2.1]oct-3-en-6-yl]sulfate (8)

sodium [7-oxo-3-(4-methoxypyrazol-1-yl)-1,6-diazabicyclo[3.2.1]oct-3-en-6-yl]sulfate (9)

[3-[3-(2-aminoethyl)pyrazol-1-yl]-7-oxo-1,6-diazabicyclo[3.2.1]oct-3-en-6-yl]hydrogen sulfate (10)

sodium [3-[3-(2-hydroxyethylcarbamoyl)pyrazol-1-yl]-7-oxo-1,6-diazabicyclo[3.2.1]oct-3-en-6-yl]sulfate (11)

triethylammonium [3-[3-(hydroxymethyl)pyrazol-1-yl]-7-oxo-1,6-diazabicyclo[3.2.1]oct-3-en-6-yl]sulfate (12)

sodium [3-[3-[(2-aminothiazole-5-carbonyl)amino]pyrazol-1-yl]-7-oxo-1,6-diazabicyclo[3.2.1]oct-3-en-6-yl]sulfate (13)

sodium (7-oxo-3-(4-fluoropyrazol-1-yl)-1,6-diazabicyclo[3.2.1]oct-3-en-6-yl) sulfate (14)

sodium and 2,2,2-trifluoroacetate [3-(4-methyleneammoniumpyrazol-1-yl)-7-oxo-1,6-diazabicyclo[3.2.1]oct-3-en-6-yl]sulfate (15)

sodium [7-oxo-3-(4-sulfamoylpyrazol-1-yl)-1,6-diazabicyclo[3.2.1]oct-3-en-6-yl]sulfate (16)

sodium [3-(3-carbonitrilepyrazol-1-yl)-7-oxo-1,6-diazabicyclo[3.2.1]oct-3-en-6-yl]sulfate (17)

sodium [7-oxo-3-(3-fluoropyrazol-1-yl)-1,6-diazabicyclo[3.2.1]oct-3-en-6-yl]sulfate (18)

sodium [3-(3-carbamoylpyrazol-1-yl)-7-oxo-1,6-diazabicyclo[3.2.1]oct-3-en-6-yl]sulfate (19)

sodium [7-oxo-3-[4-(N-morpholine)-pyrazol-1-yl)]-1,6-diaza-bicyclo[3.2.1]oct-3-en-6-yl]sulfate (20)

sodium [3-(4-acetamidepyrazol-1-yl)-7-oxo-1,6-diazabicyclo[3.2.1]oct-3-en-6-yl]sulfate (21)

sodium [7-oxo-3-[4-(trifluoromethyl)pyrazol-1-yl]-1,6-diazabicyclo[3.2.1]oct-3-en-6-yl]sulfate (22)

sodium (7-oxo-3-(3-carboxamide-5-methyl-pyrazol-1-yl)-1,6-diazabicyclo[3.2.1]oct-3-en-6-yl) sulfate (23)

sodium and 2,2,2-trifluoroacetate [7-oxo-3-[4-carboxamide,N-(2-ammoniummethoxy)-pyrazol-1-yl)-1,6-diazabicyclo[3.2.1]oct-3-en-6-yl]sulfate (24)

sodium [7-oxo-3-[3-(thiazol-2-ylcarbamoyl)pyrazol-1-yl]-1,6-diazabicyclo[3.2.1]oct-3-en-6-yl]sulfate (25)

sodium (7-oxo-3-(3-carboxamide-4-fluoro-pyrazol-1-yl)-1,6-diazabicyclo[3.2.1]oct-3-en-6-yl) sulfate (26)

sodium (7-oxo-3-(3-(methoxycarbamoyl)-pyrazol-1-yl)-1,6-diazabicyclo[3.2.1]oct-3-en-6-yl) sulfate (27-1)

sodium (7-oxo-3-(5-(methoxycarbamoyl)-pyrazol-1-yl)-1,6-diazabicyclo[3.2.1]oct-3-en-6-yl) sulfate (27-2)

sodium (7-oxo-3-(3-acetylpyrazol-1-yl)-1,6-diazabicyclo[3.2.1]oct-3-en-6-yl) sulfate (28)

(7-oxo-3-(3-[(Z,E)-N-(2-aminoethoxy)-C-methyl-carbonimidoyl]-pyrazol-1-yl)-1,6-diazabicyclo[3.2.1]oct-3-en-6-yl) hydrogen sulfate (29)

sodium (7-oxo-3-(3-carboxamide-5-fluoro-pyrazol-1-yl)-1,6-diazabicyclo[3.2.1]oct-3-en-6-yl) sulfate (30)

sodium (7-oxo-3-[3-(morpholine-4-carbonyl)pyrazol-1-yl]-1,6-diazabicyclo[3.2.1]oct-3-en-6-yl) (31)

(7-oxo-3-[3-(4-piperidylcarbamoyl)pyrazol-1-yl]-1,6-diazabicyclo[3.2.1]oct-3-en-6-yl) hydrogen sulfate (32)

triethylammonium {[3-(N-acetamido)pyrazol-1-yl]-7-oxo-1,6-diazabicyclo[3.2.1]oct-3-en-6-yl}sulfate (33)

sodium {7-oxo-3-[3-(thiazole-2-carbonylamino)pyrazol-1-yl]-1,6-diazabicyclo[3.2.1]oct-3-en-6-yl}sulfate (34)

sodium [7-oxo-3-[3-(methylene-2-ammoniumthiazole)pyrazol-1-yl]-1,6-diazabicyclo[3.2.1]oct-3-en-6-yl]sulfate (35-1)

2,2,2-trifluoroacetate [7-oxo-3-[3-(methylene-2-ammoniumthiazole)pyrazol-1-yl]-1,6-diazabicyclo[3.2.1]oct-3-en-6-yl]sulfate (35-2)

sodium [7-oxo-3-[3-(oxazol-2-ylcarbamoyl)pyrazol-1-yl]-1,6-diazabicyclo[3.2.1]oct-3-en-6-yl]sulfate (37)

3[3-[4-(2-aminoethylcarbamoyl)pyrazol-1-yl]-7-oxo-1,6-diazabicyclo[3.2.1]oct-3-en-6-yl]hydrogen sulfate (38)

sodium [3-[4-[(Z,E)-N-hydroxy-C-methyl-carbonimidoyl]pyrazol-1-yl]-7-oxo-1,6-diazabicyclo[3.2.1]oct-3-en-6-yl]sulfate (39)

sodium [3-(4-acetylpyrazol-1-yl)-7-oxo-1,6-diazabicyclo[3.2.1]oct-3-en-6-yl]sulfate (40)

[3-[4-(2-aminoethyl)pyrazol-1-yl]-7-oxo-1,6-diazabicyclo[3.2.1]oct-3-en-6-yl]hydrogen sulfate (41)

2,2,2-trifluoroacetate [7-oxo-3-(4-piperazin-4-ium-1-ylpyrazol-1-yl)-1,6-diazabicyclo[3.2.1]oct-3-en-6-yl]hydrogen sulfate (42)

sodium [7-oxo-3-(3,4,5-trideuteriopyrazol-1-yl)-1,6-diazabicyclo[3.2.1]oct-3-en-6-yl]sulfate (43)

sodium [7-oxo-3-(tetrazol-2-yl)-1,6-diazabicyclo[3.2.1]oct-3-en-6-yl]sulfate (44)

sodium [3-[3-(2-amino-2-oxo-ethyl)pyrazol-1-yl]-7-oxo-1,6-diazabicyclo[3.2.1]oct-3-en-6-yl]sulfate (45)

[3-[3-(2-aminoethoxycarbamoyl)pyrazol-1-yl]-7-oxo-1,6-diazabicyclo[3.2.1]oct-3-en-6-yl]hydrogen sulfate (46)

sodium [3-[3-(2-hydroxyethylcarbamoyl)pyrazol-1-yl]-7-oxo-1,6-diazabicyclo[3.2.1]oct-3-en-6-yl]sulfate (47)

sodium [3-[3-[2-(2-ammoniumethylamino)-2-oxo-ethyl]pyrazol-1-yl]-7-oxo-1,6-diazabicyclo[3.2.1]oct-3-en-6-yl]sulfate (48-1)

2,2,2-trifluoroacetate [3-[3-[2-(2-ammoniumethylamino)-2-oxo-ethyl]pyrazol-1-yl]-7-oxo-1,6-diazabicyclo[3.2.1]oct-3-en-6-yl]sulfate (48-2)

sodium [3-[3-(ammoniummethyl)pyrazol-1-yl]-7-oxo-1,6-diazabicyclo[3.2.1]oct-3-en-6-yl]sulfate (49-1)

2,2,2-trifluoroacetate [3-[3-(ammoniummethyl)pyrazol-1-yl]-7-oxo-1,6-diazabicyclo[3.2.1]oct-3-en-6-yl]sulfate (49-2)

sodium [3-[3-[(2-hydroxyacetyl)amino]pyrazol-1-yl]-7-oxo-1,6-diazabicyclo[3.2.1]oct-3-en-6-yl]sulfate (50)

sodium [3-[3-(3-hydroxypropanoylamino)pyrazol-1-yl]-7-oxo-1,6-diazabicyclo[3.2.1]oct-3-en-6-yl]sulfate (51)

sodium [3-[3-[(2-amino-2-oxo-ethoxy)carbamoyl]pyrazol-1-yl]-7-oxo-1,6-diazabicyclo[3.2.1]oct-3-en-6-yl]sulfate (52)

sodium [7-oxo-3-(4-thiazol-2-yltriazol-1-yl)-1,6-diazabicyclo[3.2.1]oct-3-en-6-yl]sulfate (55)

sodium [3-(4-carbamoyltriazol-1-yl)-7-oxo-1,6-diazabicyclo[3.2.1]oct-3-en-6-yl]sulfate (56)
sodium [3-[4-(ammoniummethyl)triazol-1-yl]-7-oxo-1,6-diazabicyclo[3.2.1]oct-3-en-6-yl]sulfate (57-1) 2,2,2-trifluoroacetate [3-[4-(ammoniummethyl)triazol-1-yl]-7-oxo-1,6-diazabicyclo[3.2.1]oct-3-en-6-yl]sulfate (57-2)
sodium [3-[4-(dimethylamino)methyltriazol-1-yl]-7-oxo-1,6-diazabicyclo[3.2.1]oct-3-en-6-yl]sulfate (59)
[3-[4-(methylaminomethyl)triazol-1-yl]-7-oxo-1,6-diazabicyclo[3.2.1]oct-3-en-6-yl]hydrogen sulfate (60)
disodium [[3-[4-(carboxymethyl)triazol-1-yl]-7-oxo-1,6-diazabicyclo[3.2.1]oct-3-en-6-yl]sulfate (61)
[3-[4-(2-aminoethoxycarbamoyl)triazol-1-yl]-7-oxo-1,6-diazabicyclo[3.2.1]oct-3-en-6-yl]hydrogen sulfate (63)
sodium [3-[4-(hydroxymethyl)triazol-1-yl]-7-oxo-1,6-diazabicyclo[3.2.1]oct-3-en-6-yl]sulfate (64) disodium [3-[4-(propanoate)triazol-1-yl]-7-oxo-1,6-diazabicyclo[3.2.1]oct-3-en-6-yl]sulfate (65)
[3-(4-(2-(methylamino)acetamide)triazol-1-yl)-7-oxo-1,6-diazabicyclo[3.2.1]oct-3-en-6-yl]hydrogen sulfate (66)
[3-(4-(2-(methylamino)ethanol)triazol-1-yl)-7-oxo-1,6-diazabicyclo[3.2.1]oct-3-en-6-yl]hydrogen sulfate (67)
sodium [3-[5-(2-hydroxyethyl)pyrazol-1-yl]-7-oxo-1,6-diazabicyclo[3.2.1]oct-3-en-6-yl]sulfate (68)
sodium [3-[3-[2-[tert-butyl(dimethyl)silyl]oxyethyl]pyrazol-1-yl]-7-oxo-1,6-diazabicyclo[3.2.1]oct-3-en-6-yl]sulfate (69)
sodium [3-[2-(hydroxymethyl)imidazol-1-yl]-7-oxo-1,6-diazabicyclo[3.2.1]oct-3-en-6-yl]sulfate (70)
sodium [3-[4-(hydroxymethyl)pyrazol-1-yl]-7-oxo-1,6-diazabicyclo[3.2.1]oct-3-en-6-yl]sulfate (71)
[3-[3-(2-morpholinoethylcarbamoyl)pyrazol-1-yl]-7-oxo-1,6-diazabicyclo[3.2.1]oct-3-en-6-yl]hydrogen sulfate (72)
trimethylammonium [3-[2-(3-amino-3-oxo-propyl)imidazol-1-yl]-7-oxo-1,6-diazabicyclo[3.2.1]oct-3-en-6-yl]sulfate (73)
sodium [3-[4-(2-hydroxyethylsulfamoyl)pyrazol-1-yl]-7-oxo-1,6-diazabicyclo[3.2.1]oct-3-en-6-yl]sulfate (74)
sodium [3-[3-[(1S)-1,2-dihydroxyethyl]pyrazol-1-yl]-7-oxo-1,6-diazabicyclo[3.2.1]oct-3-en-6-yl]sulfate (76)
[3-[3-[thiazole-5-carbonyl]amino]pyrazol-1-yl]-7-oxo-1,6-diazabicyclo[3.2.1]oct-3-en-6-yl]hydrogen sulfate (77)
sodium [3-(2-oxazolyl)pyrazol-1-yl]-7-oxo-1,6-diazabicyclo[3.2.1]oct-3-en-6-yl sulfate (78)
[7-oxo-3-[3-(1,2,4-thiadiazol-5-ylcarbamoyl)pyrazol-1-yl]-1,6-diazabicyclo[3.2.1]oct-3-en-6-yl]hydrogen sulfate (79)
sodium [7-oxo-3-[3-(2-pyridylcarbamoyl)pyrazol-1-yl]-1,6-diazabicyclo[3.2.1]oct-3-en-6-yl]sulfate (80)
[7-oxo-3-[3-[[(3S)-pyrrolidin-3-yl]carbamoyl]pyrazol-1-yl]-1,6-diazabicyclo[3.2.1]oct-3-en-6-yl]hydrogen sulfate (82)
[7-oxo-3-[3-[[(3R)-pyrrolidin-3-yl]carbamoyl]pyrazol-1-yl]-1,6-diazabicyclo[3.2.1]oct-3-en-6-yl]hydrogen sulfate (83)
sodium [7-oxo-3-[3-(1,3,4-thiadiazol-2-ylcarbamoyl)pyrazol-1-yl]-1,6-diazabicyclo[3.2.1]oct-3-en-6-yl]sulfate (84)
sodium [7-oxo-3-[3-(pyrazol-3-ylcarbamoyl)pyrazol-1-yl]-1,6-diazabicyclo[3.2.1]oct-3-en-6-yl]sulfate (85).

The term "alkyl", as used herein, refers to an aliphatic-hydrocarbon group which may be straight or branched, having 1 to 3 carbon atoms in the chain unless specified otherwise.

Preferred alkyl groups have 1 or 2 carbon atoms in the chain. Specific examples of alkyl groups include, but are not limited to, methyl, ethyl, n-propyl, isopropyl. Preferably, the alkyl group is methyl or ethyl.

The term "fluoroalkyl", as used herein, refers to an alkyl group substituted with at least one fluorine atom. The term "alkyl" is as defined above. Specific examples of fluoroalkyl groups include but are not limited to trifluoromethyl, difluoromethyl, fluoromethyl.

The term "cycloalkyl" refers to a saturated monocyclic or bicyclic non-aromatic hydrocarbon ring of 3 to 6 carbon atoms, preferably 3 to 4 carbon atoms, which can comprise one or more unsaturation. Specific examples of monocyclic cycloalkyl groups include cyclopropyl, cyclobutyl, cyclopentyl, cyclohexyl. Preferably, the cycloalkyl group is cyclopropyl or cyclobutyl.

The term "cyclofluoroalkyl" refers to a cycloalkyl group substituted with at least one fluorine atom. The term "cycloalkyl" is as defined above. Specific examples of cyclofluoroalkyl groups include cyclofluoropropyl, cyclodifluoropropyl, cyclofluorobutyl, cyclodifluorobutyl.

The term "heterocycle", as used herein and without contrary definition specifically mentioned, either alone or in combination with another radical, refers to a monocyclic saturated, partially or totally unsaturated or aromatic hydrocarbon radical, preferably to a 4- to 10-membered hydrocarbon radical, comprising at least one heteroatom, such as N, O, S, S(O) or S(O)2. Preferably, the heterocycle is a monocyclic saturated, partially or totally unsaturated or aromatic hydrocarbon radical, preferably a 4- to 6-membered hydrocarbon radical, comprising at least one nitrogen atom and at least one further heteroatom, such as N, O, S, S(O) or S(O)2. The carbon atoms of the heterocycle can also be oxidized to form a C(O) group. Suitable heterocycles are also disclosed in the Handbook of Chemistry and Physics, 76th Edition, CRC Press, Inc., 1995-1996, pages 2-25 to 2-26. Exemplary heterocycle groups include but are not limited to azetidinyl, oxetanyl, oxazolyl, oxazolidinyl, oxadiazolyl, pyrrolyl, pyrrolidinyl, pyridyl, tetrahydropyridinyl, piperidinyl, morpholinyl, pyrazolyl, pyrimidinyl, pyrazinyl, tetrazolyl, imidazolyl, thienyl, thiazolyl, furanyl, thiadiazolyl, isothiazolyl, triazolyl, tetrazolyl, pyrazolyl, isoxazolyl, 2-pyrrolidinonyl, imidazol-2,4-dione, 1,2,4-oxadiazol-5-one, 1,5-dihydropyrrolyl-2-one, pyrazinone, pyridazinone, pyridone, pyrimidone, dioxanyl, pyrrolidinyl, imidazolidinyl, pyranyl, tetrahydrofuranyl, dioxolanyl, tetrahydropyranyl. Preferably, the heterocycle comprises 1 to 4 heteroatom chosen among N, O or S, preferably 1, 2 or 3 heteroatoms.

Moreover some compounds according to this invention may contain a basic amino group and thus may form an inner zwitterionic salt (or zwitterion) with the acidic group —OSO$_3$H, —OCFHCO$_2$H or —OCF$_2$CO$_2$H and such inner zwitterionic salts are also included in this invention.

The expression "optionally substituted" means "non-substituted or substituted by chemical groups that are further defined" or "unsubstituted or substituted chemical groups that are further defined".

The term "racemate" is employed herein to refer to an equal amount of two specific enantiomers.

The term "enantiomer" is employed herein to refer to one of the two specific stereoisomers which is a non-superimposable mirror image with one other but is related to one other by reflection.

The compounds according to the invention may include one or more asymmetric carbon atoms and may thus exist in the form of optical isomers as well as in the form of racemic or non-racemic mixtures thereof. The compounds according to the invention can be utilized as a single isomer or as a mixture of stereochemical isomeric forms. Diastereoisomers, i.e., non-superimposable stereochemical isomers can be separated by conventional means such as chromatography, distillation, crystallization or sublimation. The optical isomers (enantiomers) can be obtained by using optically active starting materials, by resolution of the racemic mixtures according to conventional processes, for example by formation of diastereoisomeric salts by treatment with an optically active acid or base or by using chiral chromatography column.

As used herein, the expression "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids or aminohydroxyl-O-sulfonic acid; and the like. The pharmaceutically acceptable salts of the present invention can be synthesized from the parent compound which comprises a basic or an acidic moiety, by conventional chemical methods. Furthermore, the expression "pharmaceutically acceptable salt" refers to relatively non-toxic, inorganic and organic acid or base addition salts of the compounds of the present invention. These salts can be prepared in situ during the final isolation and purification of the compounds. In particular, the acid addition salts can be prepared by separately reacting the purified compound in its purified form with an organic or inorganic acid and by isolating the salt thus formed. Among the examples of acid addition salts are the hydrobromide, hydrochloride, hydroiodide, sulfamate, sulfate, bisulfate, phosphate, nitrate, acetate, propionate, succinate, oxalate, valerate, oleate, palmitate, stearate, laurate, borate, benzoate, lactate, tosylate, citrate, maleate, fumarate, tartrate, naphthylate, mesylate, glucoheptanate, glucoronate, glutamate, lactobionate, malonate, salicylate, methylenebis-b-hydroxynaphthoate, gentisic acid, isethionate, di-p-toluoyltartrate, ethanesulfonate, benzenesulfonate, cyclohexyl sulfamate, quinateslaurylsulfonate salts, and the like. Examples of base addition salts include ammonium salts such as tromethamine, meglumine, epolamine, etc, metal salts such as sodium, lithium, potassium, calcium, zinc or magnesium salts with organic bases such as dicyclohexylamine salts, N-methyl-D-glucamine. Lists of suitable salts may be found in Remington's Pharmaceutical Sciences, 17th ed., Mack Publishing Company, Easton, Pa., 1985, p. 1418, P. H. Stahl, C. G. Wermuth, Handbook of Pharmaceutical salts—Properties, Selection and Use, Wiley-VCH, 2002 and S. M. Berge et al. "Pharmaceutical Salts" J. Pharm. Sci, 66: p. 1-19 (1977).

Compounds according to the invention also include isotopically-labelled compounds wherein one or more atoms is replaced by an atom having the same atomic number, but an atomic mass or mass number different from the atomic mass or mass number usually found in nature. Examples of isotopes suitable for inclusion in the compounds described above and are not limited to $^2H$, $^3H$, $^{11}C$, $^{13}C$, $^{14}C$, $^{18}F$, $^{19}F$, $^{13}N$, $^{15}N$, $^{33}S$, $^{34}S$, $^{35}S$, $^{36}S$, $^{17}O$ or $^{18}O$. Isotopically-labelled compounds are useful in drug and/or substrate tissue distribution studies. Substitution with heavier isotopes such as deuterium ($^2H$) affords greater metabolic stability (for example increased in vivo half-life or reduced dosage requirements). Isotopically-labelled compounds are prepared by any suitable method or by processes using an appropriate isotopically-labelled reagent in replacement of the non-labelled reagent otherwise employed.

The invention provides compounds having antibacterial properties and/or compounds acting as β-lactamase inhibitors.

The invention also provides a process for the preparation of a compound according to the invention.

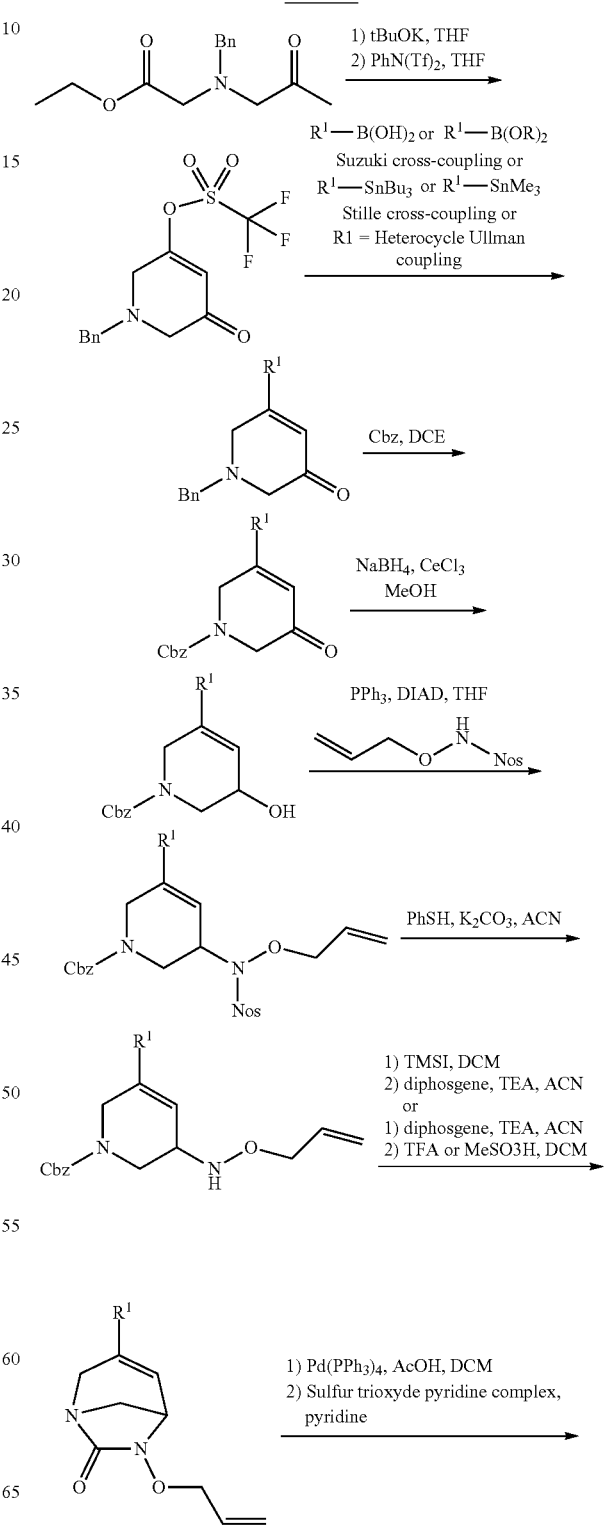

Scheme 1

13
-continued
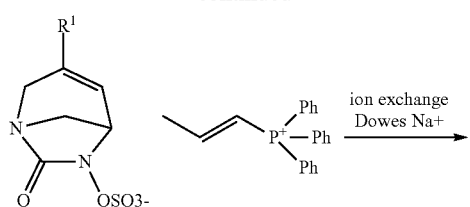
14
-continued
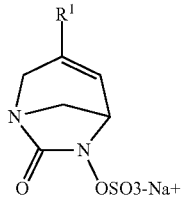
Scheme 3
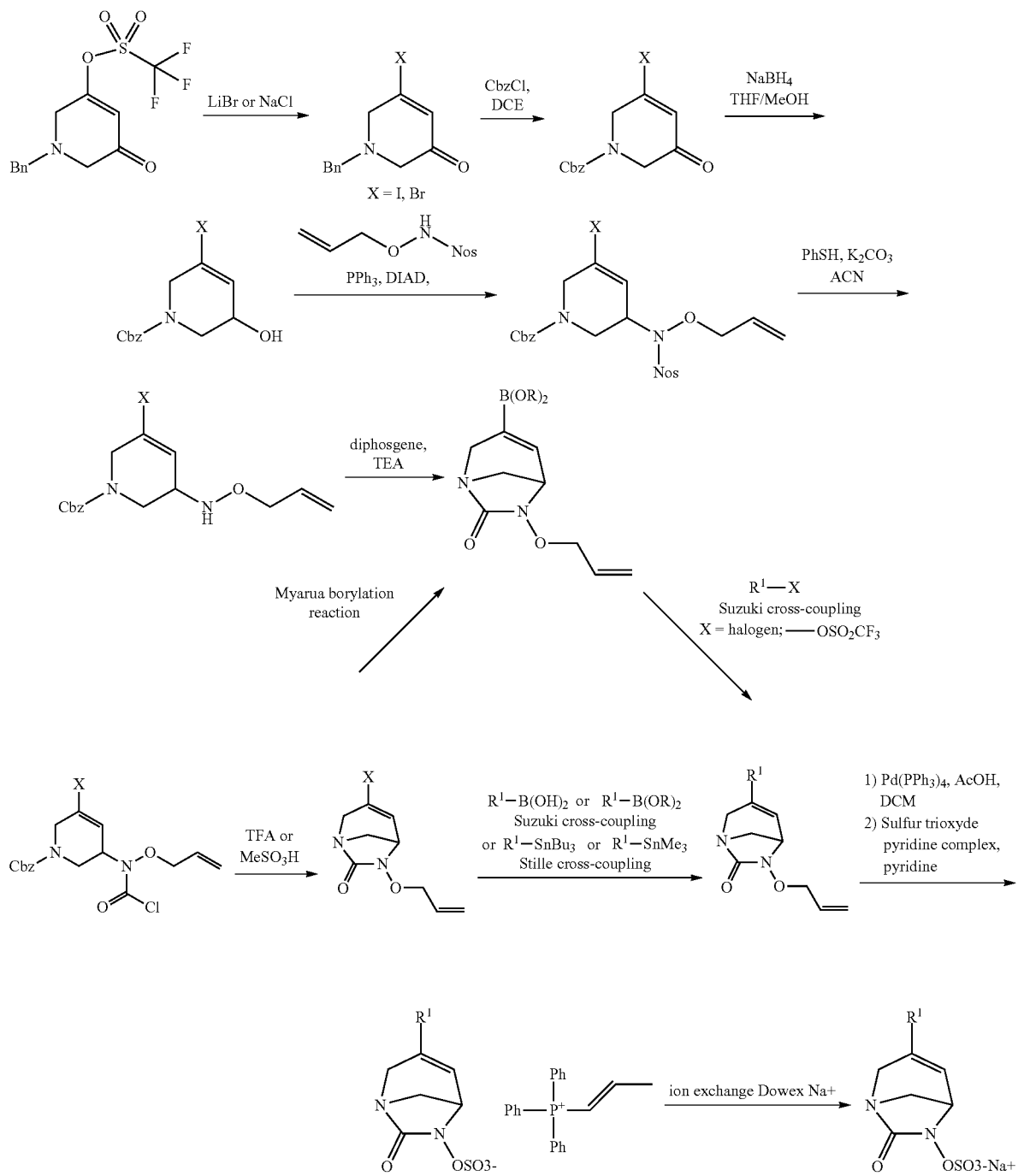

Scheme 4

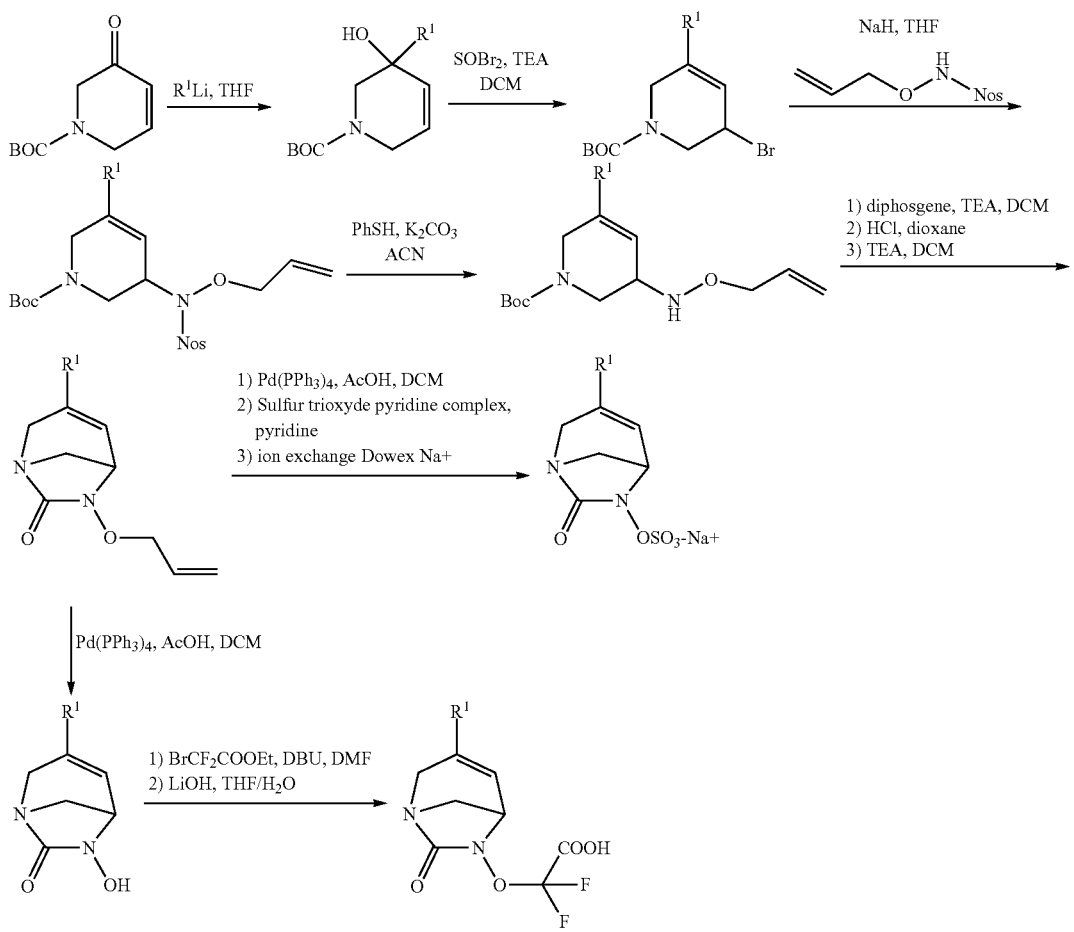

The invention also provides particular processes represented in the schemes of the experimental part that is provided herein for the preparation of compounds according to the invention wherein $R^1$, $R^2$ represent various substituents. These processes can also be adapted for preparing further compounds according to the invention. Further processes for the preparation of compounds according to the invention can be derived from these processes.

The invention relates also to compounds of formula

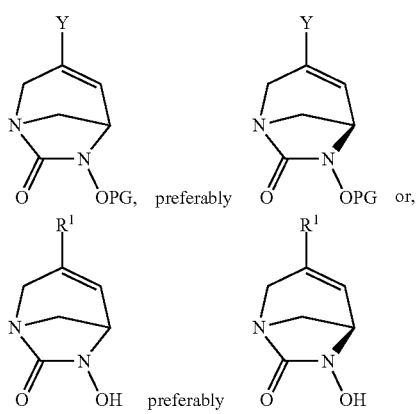

wherein
$R^1$ is as defined for compounds of formula (I) or (I*),
Y is halogen, —B(OR)$_2$ or SnR$_3$ wherein R is alkyl or the OR are linked together with the B to form a cycle comprising for example 5 members; and
PG, is a protective group, for example chosen among allyl, benzyl, tertbutyldimethylsilyl (TBDMS), tert-butoxycarbonyl (Boc).

These compounds are especially intermediates compounds for the preparation of compounds of formula (I), (I*) according to the invention.

The invention also provides the use of the compounds according to the invention in the control of bacteria. The compound according to the invention is then usually used in combination with at least one pharmaceutically acceptable excipient.

The expression "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also provides a composition, preferably a pharmaceutical composition, comprising at least one compound according to the invention in mixture with a pharmaceutically acceptable excipient. The composition according to the invention may thus comprise at least one compound selected from compounds of formulae (I), (I*) in mixture with a pharmaceutically acceptable excipient.

The composition according to the invention can further comprise at least one or more antibacterial agent(s), preferably at least one of these antibacterial agents is a beta-lactam.

The term "beta-lactam" or "β-lactam" refers to antibacterial compounds comprising a β-lactam unit, i.e. a β-lactam chemical group or moiety.

The term "pharmaceutically acceptable carrier" or "pharmaceutically acceptable excipient" is employed for any excipient, solvent, dispersion medium, absorption retardant, diluent or adjuvant etc., such as preserving or antioxidant agents, fillers, binders, disintegrating agents, wetting agents, emulsifying agents, suspending agents, solvents, dispersion media, coatings, antibacterial agents, isotonic and absorption delaying agents and the like, that does not produce a secondary reaction, for example an allergic reaction, in humans or animals. Typical, non-limiting examples of excipients include mannitol, lactose, magnesium stearate, sodium saccharide, talcum, cellulose, sodium crosscarmellose, glucose, gelatine, starch, lactose, dicalcium phosphate, sucrose, kaolin, magnesium carbonate, wetting agents, emulsifying agents, solubilizing agents, sterile water, saline, pH buffers, non-ionic surfactants, lubricants, stabilizing agents, binding agents and edible oils such as peanut oil, sesame oils and the like. In addition, various excipients commonly used in the art may be included. Pharmaceutically acceptable carriers or excipients are well known to a person skilled in the art, and include those described in Remington's Pharmaceutical Sciences (Mack Publishing Company, Easton, USA, 1985), Merck Index (Merck & Company, Rahway, N.J.), Gilman et al (Eds. The pharmacological basis of therapeutics, 8th Ed., Pergamon press, 1990). Except insofar as any conventional media or adjuvant is incompatible with the active ingredient according to the invention, its use in the therapeutic compositions is contemplated.

The expression "antibacterial agent" as used herein, refers to any substance, compound or their combination capable of inhibiting, reducing or preventing growth of bacteria, inhibiting or reducing ability of bacteria to produce infection in a subject, or inhibiting or reducing ability of bacteria to multiply or remain infective in the environment, or decreasing infectivity or virulence of bacteria.

The antibacterial agent can be selected among the following families: aminoglycosides, beta-lactams, glycylcyclines, tetracyclines, quinolones, fluoroquinolones, glycopeptides, lipopeptides, macrolides, ketolides, lincosamides, streptogramins, oxazolidinones and polymyxins alone or in mixture. Preferably, the further antibacterial agent is selected among the beta-lactam families, and more preferably among penicillin, cephalosporins, penems, carbapenems and monobactam, alone or in mixture.

Among the penicillin the antibacterial agent is preferably selected in the group consisting of amoxicillin, ampicillin, azlocillin, mezocillin, apalcillin, hetacillin, bacampicillin, carbenicillin, sulbenicillin, temocillin, ticarcillin, piperacillin, mecillinam, pivmecillinam, methicillin, ciclacillin, talampacillin, aspoxicillin, oxacillin, cloxacillin, dicloxacillin, flucloxacillin, nafcillin, and pivampicillin, alone or in mixture.

Among the cephalosporin, the antibacterial agent is preferably selected in the group consisting of cefatriazine, cefazolin, cefoxitin, cephalexin, cephradine, ceftizoxime, cephacetrile, cefbuperazone, cefprozil, ceftobiprole, ceftobiprole medocaril, ceftaroline, ceftaroline fosaminyl, cefalonium, cefminox, ceforanide, cefotetan, ceftibuten, cefcapene pivoxil, cefditoren pivoxil, cefdaloxime cefroxadine, ceftolozane and S-649266, cephalothin, cephaloridine, cefaclor, cefadroxil, cefamandole, cefazolin, cephalexin, cephradine, ceftizoxime, cephacetrile, cefotiam, cefotaxime, cefsulodin, cefoperazone, cefmenoxime, cefmetazole, cephaloglycin, cefonicid, cefodizime, cefpirome, ceftazidime, ceftriaxone, cefpiramide, cefbuperazone, cefozopran, cefepime, cefoselis, cefluprenam, cefuzonam, cefpimizole, cefclidine, cefixime, ceftibuten, cefdinir, cefpodoxime axetil, cefpodoxime proxetil, cefteram pivoxil, cefetamet pivoxil, cefcapene pivoxil, cefditoren pivoxil, cefuroxime, cefuroxime axetil, loracarbef, and latamoxef, alone or in mixture. Among the carbapenem, the antibacterial agent is preferably selected in the group consisting of imipenem, doripenem, meropenem, biapenem, ertapenem and panipenem, alone or in mixture.

Among the monobactam, the antibacterial agent is preferably selected in the group consisting of aztreonam, tigemonam, carumonam, BAL30072 and nocardicin A, alone or in mixture.

The present invention also relates to a composition comprising at least a compound of formulae (I), (I*), according to the invention and ceftazidime.

The present invention also provides a kit comprising:
a pharmaceutical composition according to the invention, and
at least one other composition comprising one or more antibacterial agents, preferably at least one of these antibacterial agents is a beta-lactam.

The two compositions can each be prepared separately with one specific pharmaceutically acceptable carrier, and can then be mixed, especially extemporaneously.

The present invention also relates to a kit comprising:
a pharmaceutical composition comprising at least a compound of formulae (I) or (I*), according to the invention; and
a pharmaceutical composition comprising ceftazidime.

The present invention also refers to a compound selected within the compounds of formulae (I) or (I*), according to the invention for its use as a medicine.

The present invention also refers to a compound selected within the compounds of formulae (I) or (I*), according to the invention for its use for the preparation of a medicine.

The present invention also refers to a compound selected within the compounds of formulae (I) or (I*) according to the invention for its use as an antibacterial agent.

The present invention also refers to the use of a compound selected within the compounds of formulae (I) or (I*) according to the invention or to the use of a pharmaceutical composition according to the invention for the preparation of an antibacterial agent comprising medicine.

The present invention also refers to the use of a compound selected within the compounds of formulae (I) or (I*) according to the invention or to the use of a pharmaceutical composition according to the invention for the preparation of a beta-lactamase inhibitor comprising medicine.

The present invention also refers to the use of a compound selected within the compounds of formulae (I) or (I*) according to the invention or to the use of a pharmaceutical composition according to the invention for the preparation of a medicine comprising an antibacterial agent and a beta-lactamase inhibitor.

The present invention also refers to the use of a compound selected within the compounds of formulae (I) or (I*) according to the invention or to the use of a pharmaceutical composition according to the invention or to the use of a kit according to the invention for the treatment or for the prevention of at least one bacterial infection.

The present invention also refers to the use of a compound selected within the compounds of formulae (I) or (I*) according to the invention or to the use of a pharmaceutical composition according to the invention or to the use of a kit according to the invention for the preparation of a medicine useful in the treatment or in the prevention of at least one bacterial infection.

The terms "prevention", "prevent" and "preventing" as used herein are intended to mean the administration of a compound or composition according to the invention in order to prevent infection by bacteria or to prevent occurrence of related infection and/or diseases. The terms "prevention", "prevent" and "preventing" also encompass the administration of a compound or composition according to the present invention in order preventing at least one bacterial infection, by administration to a patient susceptible to be infected, or otherwise at a risk of being infected by this bacteria.

The terms "treatment", "treat" and "treating" as used herein are intended to mean in particular the administration of a treatment comprising a compound or composition according to the invention to a patient suffering from an infection. The terms "treatment", "treat" and "treating" as used herein, also refer to administering a compound or composition according to the invention, optionally in combination with one or more further antibacterial agent, in order:
  to reduce or to eliminate either bacterial infection or one or more symptoms associated with a bacterial infection, or
  to retard the progression of a bacterial infection or of one or more symptoms associated with a bacterial infection, or
  to reduce the severity of a bacterial infection or of one or more symptoms associated with a bacterial infection, or
  to suppress the clinical manifestation of a bacterial infection, or
  to suppress the manifestation of adverse symptoms caused by a bacterial infection.

The expression "infection" or "bacterial infection" as used herein, include the presence of bacteria, in or on a subject, which, if its growth were inhibited, would result in a benefit to the subject. As such, the term "infection" or "bacterial infection" in addition to referring to the presence of bacteria also refer to normal flora, which is not desirable. The term "infection" includes infection caused by bacteria. Examples of such bacterial infections are urinary tract infection (UTI), kidney infections (pyelonephritis), gynecological and obstetrical infections, respiratory tract infection (RTI), acute exacerbation of chronic bronchitis (AECB), Community-acquired pneumonia (CAP), hospital-acquired pneumonia (HAP), ventilator associated pneumonia (VAP), intra-abdominal pneumonia (IAI), acute otitis media, acute sinusitis, sepsis, catheter-related sepsis, chancroid, chlamydia, skin infections, bacteremia.

The term "growth" as used herein, refers to the growth of one or more microorganisms and includes reproduction or population expansion of a microorganism, such as bacteria. The term also includes maintenance of on-going metabolic processes of a microorganism, including processes that keep the microorganism alive.

According to the invention, bacteria are chosen amongst gram-positive bacteria or gram-negative bacteria, preferably gram-negative bacteria. According to the invention, bacteria can be also chosen among bacteria producing "beta-lactamase" or "β-lactamase". These bacteria are well known by the person skilled in the art. The term "beta-lactamase" or "β-lactamase" as used herein, refers to any enzyme or protein or any other substance that is able to break down a beta-lactam ring. The term "beta-lactamase" or "β-lactamase" includes enzymes that are produced by bacteria and that have the ability to hydrolyze, either partially or completely, the beta-lactam ring present in a compound such as an antibacterial agent.

Among the gram-positive bacteria, the bacteria according to the invention is preferably chosen among *Staphylococcus, Streptococcus, Staphylococcus* species (including *Staphylococcus aureus, Staphylococcus epidermidis*), *Streptococcus* species (including *Streptococcus pneumonia, Streptococcus agalactiae*), *Enterococcus* species (including *Enterococcus faecalis* and *Enterococcus faecium*).

Among the gram-negative bacteria, the bacteria according to the invention is preferably chosen among *Acinetobacter* species (including *Acinetobacter baumannii*), *Citrobacter* species, *Escherichia* species (including *Escherichia coli*), *Haemophilus* influenza, *Morganella morganii, Klebsiella* species (including *Klebsiella pneumonia*), *Enterobacter* species (including *Enterobacter cloacae*), *Neisseria gonorrhoeae, Burkholderia* species (including *Burkholderia cepacia*), (*Proteus* species (including *Proteus mirabilis*), *Serratia* species (including *Serratia marcescens*), *Pseudomonas aeruginosa*.

The invention thus preferably refers to a compound selected within the compounds of formulae (I) or (I*) according to the invention or to a pharmaceutical composition according to the invention or to a kit according to the invention for its use for the treatment or for the prevention of a bacterial infection, preferably caused by bacteria producing one or more beta-lactamases. Preferably, the bacteria are chosen amongst gram-positive bacteria or gram-negative bacteria, more preferably gram-negative bacteria.

The present invention also refers to the use of a compound selected within the compounds of formulae (I) or (I*) according to the invention or to a pharmaceutical composition according to the invention for the preparation of a medicine for the treatment or for the prevention of a bacterial infection, preferably caused by bacteria producing one or more beta-lactamases. Preferably, the bacteria are chosen amongst gram-positive bacteria or gram-negative bacteria, more preferably gram-negative bacteria.

The present invention also refers to a kit according to the invention, for its simultaneous, separated or sequential administration to a patient in need thereof in the treatment or in the prevention of bacterial infections, preferably caused by bacteria producing one or more beta-lactamases. Preferably, the bacteria are chosen amongst gram-positive bacteria or gram-negative bacteria, more preferably gram-negative bacteria.

The present invention also refers to a compound selected within the compounds of formulae (I) or (I*) according to the invention for its use in combination with one or more further antibacterial agents, preferably at least one of the further antibacterial agents being a beta lactam compound, for the treatment or for the prevention of bacterial infections, preferably caused by bacteria producing one or more beta-lactamases. Preferably, the bacteria are chosen amongst gram-positive bacteria or gram-negative bacteria, more preferably gram-negative bacteria, and wherein a compound selected within the compounds of formulae (I) or (I*) according to the invention and the further antibacterial agent are administered simultaneously, separately or sequentially.

The present invention also refers to the use of a compound selected within the compounds of formulae (I) or (I*) according to the invention or of a pharmaceutical composition according to the invention or of a kit according to the invention for the prevention or for the treatment of bacterial infections, preferably of a bacterial infection, preferably caused by bacteria producing one or more beta-lactamases. Preferably, the bacteria are chosen amongst gram-positive bacteria or gram-negative bacteria, more preferably gram-negative bacteria.

The present invention also relates to a method for the treatment or prevention of bacterial infections, preferably caused by bacteria producing one or more beta-lactamases comprising the administration of a therapeutically effective amount of a compound selected within the compounds of formulae (I) or (I*) according to the invention, or of a pharmaceutical composition according to the invention or of a kit according to the invention to a patient in need thereof. Preferably, the bacteria are chosen amongst gram-positive bacteria or gram-negative bacteria, more preferably gram-negative bacteria.

The term "patient" means a person or an animal at risk of being infected by bacteria or, a person or an animal being infected by bacteria, preferably by gram-positive and by gram-negative bacteria, more preferably by gram-negative bacteria. As used herein, the term "patient" refers to a warm-blooded person or animal such as a mammal, preferably a human or a human child, who is afflicted with, or has the potential to be afflicted with one or more infections and conditions described herein. The identification of those subjects who are in need of treatment of herein-described diseases and conditions is well within the ability and knowledge of one skilled in the art. A veterinarian or a physician skilled in the art can readily identify, by the use of clinical tests, physical examination, medical or family history or biological and diagnostic tests, those subjects who are in need of such a treatment.

The expression "therapeutically effective amount" or "pharmaceutically effective amount" as used herein, refer to an amount of a compound according to the invention, which when administered to a patient in need thereof, is sufficient to effect treatment for disease-states, conditions, or disorders for which the compound has utility. Such an amount would be sufficient to elicit the biological or medical response of a tissue system, or patient that is sought by a researcher or a clinician. The amount of a compound according to the invention which constitutes a "therapeutically effective amount" will vary, notably depending on the compound itself and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a "therapeutically effective amount" can be determined by one of ordinary skilled in the art having regard to its own knowledge, and this disclosure. Preferably, the compound according to the invention is administered in an amount comprised between 0.1 to 30 g per day.

The compound according to the invention may be provided in an aqueous physiological buffer solution for parenteral administration. The compound of the present invention is also capable of being administered in unit dose forms, wherein the expression "unit dose" means a single dose which is capable of being administered to a patient, and which can be readily handled and packaged, remaining as a physically and chemically stable unit dose comprising either the active compound itself, or as a pharmaceutically acceptable composition, as described herein. The compound provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasally, particularly in the form of powders, nasal drops, or aerosols; or dermally, for example, topically in ointments, creams, lotions, gels or sprays, or via trans-dermal patches.

The pharmaceutical composition may be conveniently administered in unit dosage form and may be prepared by any method well-known in the pharmaceutical art, for example, as described in Remington: The Science and Practice of Pharmacy, 20th ed.; Gennaro, A. R., Ed.; Lippincott Williams & Wilkins: Philadelphia, Pa., 2000.

Preferred formulations include pharmaceutical compositions wherein a compound according to the present invention is formulated for oral or parenteral administration.

For oral administration, tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings and flavorings. In addition, the active compounds may be incorporated into fast dissolved, modified-release or sustained-release preparations and formulations, and wherein such sustained-release formulations are preferably bi-modal. Preferred tablets contain lactose, cornstarch, magnesium silicate, crosscarmellose sodium, povidone, magnesium stearate or talc in any combination.

Liquid preparations for parenteral administration include sterile aqueous or non-aqueous solutions, suspensions and emulsions. The liquid compositions may also include binders, buffers, preservatives, chelating agents, sweetening, flavoring and coloring agents, and the like. Non-aqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers may be useful excipients to control the release of the active compound. Intravenous vehicles can include fluid and nutrient replenishers, electrolyte replenishers, such as those based on Ringer's dextrose, and the like. Other potentially useful parenteral delivery systems for the active compound include ethylene-vinyl acetate copolymer particles, osmotic pumps, implantable infusion systems and liposomes.

Alternative modes of administration include formulations for inhalation, which include such means as dry powder, aerosol, or drops. They may be aqueous solutions comprising, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations.

Formulations suitable for transdermal administration can be presented as discrete patches and can be lipophilic emulsions or buffered, aqueous solutions, dissolved and/or dispersed in a polymer or an adhesive.

EXAMPLES

The following examples are provided for the purpose of illustrating the present invention and by no means should be interpreted to limit the scope of the present invention.

The first part represents the preparation of the compounds (intermediates and final compounds) whereas the second part describes the evaluation of antibacterial activity of compounds according to the invention.

Preparation of the Compounds and Biological Activity:
Abbreviations or symbols used herein include:
ACN: acetonitrile
AcOH: acetic acid
Bn: benzyl
Boc: tert-butoxycarbonyl
Boc₂O: tert-butoxycarbonyl anhydride
br: broad (NMR signal)
Cbz: carboxybenzyl
CbzCl: benzyl chloroformate
CFU: colony-forming units
CLSI: clinical laboratory standards institute
d: doublet
DBU: 1,8-diazabicyclo[5.4.0]undec-7-ene
DCM: dichloromethane
DCE: 1,2-dichloroethane
dd: doublet of doublet
ddd: doublet of doublet of doublet
ddt: doublet of doublet of triplet
dq: doublet of quartet
dt: doublet of triplet
DIAD: diisopropyl azodicarboxylate
DIPEA: N,N-diisopropylethylamine
DMA: dimethylacetamide
DMAP: N,N-dimethyl-4-aminopyridine
DMCyDA: trans-N,N'-dimethylcyclohexan-1,2-diamine
DMF: N,N-dimethylformamide
DMSO: dimethylsulfoxide
EDC.HCl: N-(3-Dimethylaminopropyl)-N'-ethylcarbodiimide hydrochloride
EtOAc: ethyl acetate
Et₂O: diethyl ether
h: hours
HATU: 1-[Bis(dimethylamino)methylene]-1H-1,2,3-triazolo[4,5-b]pyridinium 3-oxid hexafluorophosphate
HOBt: 1-Hydroxybenzotriazole hydrate
iPrOH: isopropanol
m: multiplet
min: minutes
MeOH: methanol
MeONa: sodium methoxide
MIC: minimum inhibitory concentration
MS: mass spectrometry
MsCl: methanesulfonyl chloride
NMR: nuclear magnetic resonance spectroscopy
Nos: nosyl, nitrobenzenesulfonyl
Pd(Ph₃)₄: tetrakis(triphenylphosphine)palladium(0)
PG: protective group
PhSH: thiophenol
PhSiH₃: Phenylsilane
PPh₃: triphenylphosphine
Ppm: parts per million
q: quartet
rt: room temperature
s: singlet
t: triplet
td: triplet of doublet
TBDMSCl: tert-Butyldimethylsilyl chloride
TBDPSCl: tert-Butyldiphenylchlorosilane
tBuOH: tert-butanol
tBuOK: potassium tert-butoxide
TEA: triethylamine
Tf: trifluoromethanesulfonate
TFA: trifluoroacetic acid
THF: tetrahydrofuran
TLC: thin layer chromatography
Tr: trityl (triphenylmethyl)

Example 1: Synthesis of Sodium [7-oxo-3-(2-oxo-thiazol-3-yl)-1,6-diaza-bicyclo[3.2.1]oct-3-en-6-yl] sulfate

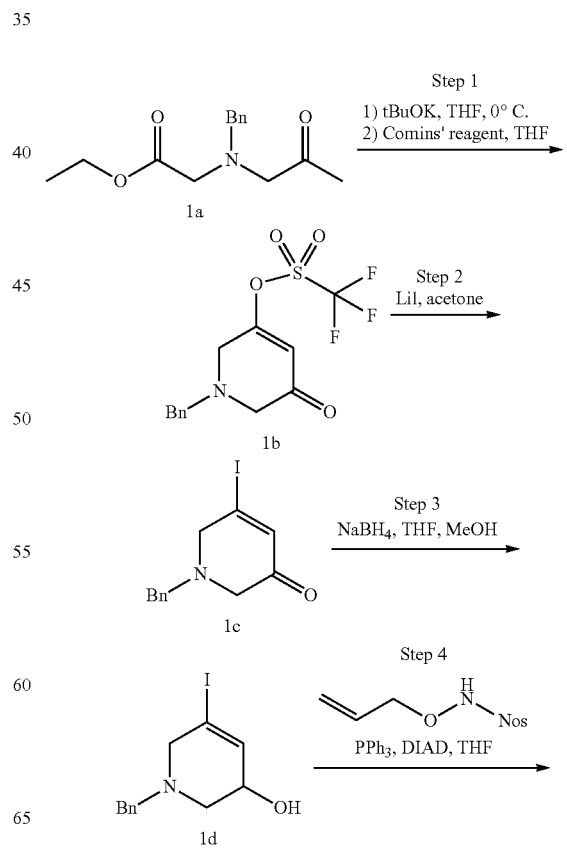

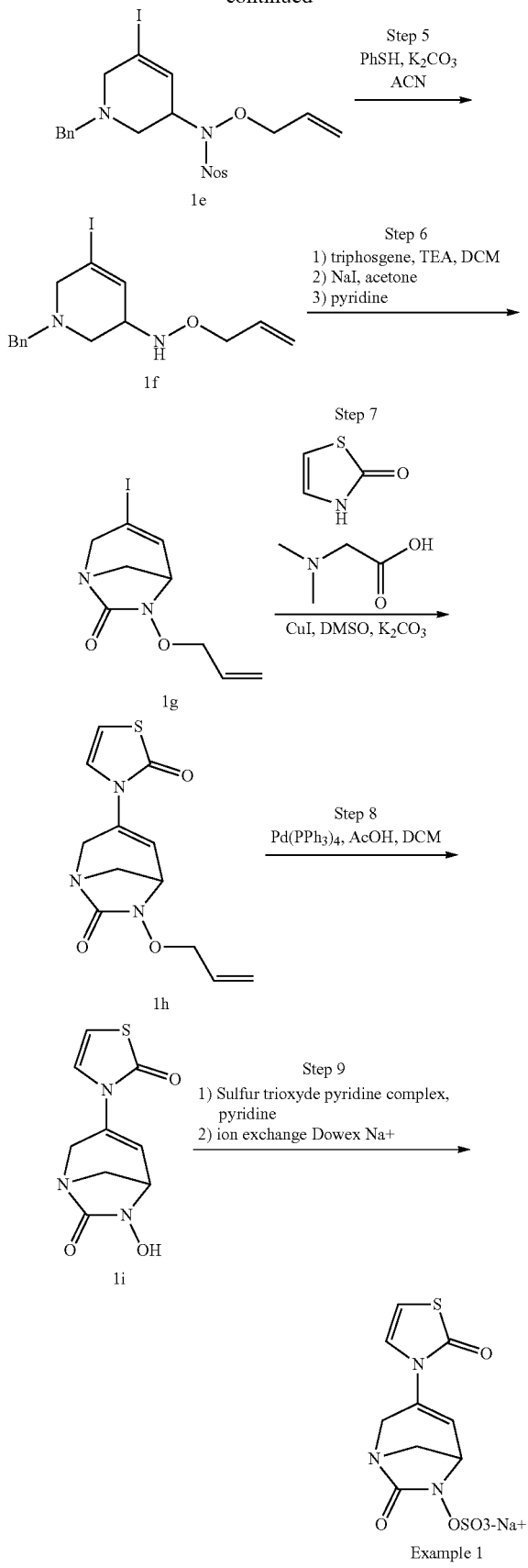

Step 1: Preparation of Intermediate (1-benzyl-5-oxo-2,6-dihydropyridin-3-yl) trifluoromethanesulfonate (1b)

In a 500 mL round bottom flask, under nitrogen atmosphere, tBuOK (2.7 g, 24.07 mmol) was dissolved in anhydrous THF (180 mL) and the resulting solution was cooled at 0° C. Ethyl N-benzyl-N-acetonylglycinate (1a) (synthesized according to the procedures described in the literature (J. Org. Chem. 2006, 71 (21), 8256, J. Med. Chem. 2012, 55 (11), 5403, WO2013/181741) (6 g, 24.07 mmol) dissolved in anhydrous THF (60 mL) was added with a dropping funnel over 5 min. The resulting viscous solution was stirred for 30 min at 0° C. (LC/MS showed the formation of the corresponding dione m/z ([M+H]$^+$ 204, [M+H$_2$O+H]$^+$222, [M−H]$^-$ 202).

At 0° C., N-(5-Chloro-2-pyridyl)bis(trifluoromethanesulfonimide) (Comins reagent) (9.7 g, 24.07 mmol) dissolved in THF (20 mL) was added and the reaction was stirred for an additional 30 min. The reaction mixture was diluted with Et$_2$O and the solution was washed with H$_2$O. The organic layer was dried over Na$_2$SO$_4$, filtered and concentrated in vacuo. The residue was purified by flash chromatography on silica gel (toluene/acetone 100/0 to 95/5 or cyclohexane/EtOAc 100/0 to 50/50) to provide intermediate (1b) which was triturated in a mixture of petroleum ether and diethyl ether (9/1) at −78° C. After filtration, intermediate (1b) was obtained as a white solid (5.80 g, 17.29 mmol, 71%) and stored in the freezer.

MS m/z ([M+H]$^+$) 336.

$^1$H NMR (300 MHz, CDCl$_3$): δ (ppm) 3.27 (s, 2H), 3.49 (s, 2H), 3.73 (s, 2H), 6.17 (t, J=1.3 Hz, 1H), 7.27-7.40 (m, 5H).

Step 2: Preparation of Intermediate 1-benzyl-5-iodo-2,6-dihydropyridin-3-one (1c)

In a 1 L round bottom flask under nitrogen atmosphere, intermediate (1b) (16.1 g, 48.02 mmol) was dissolved in acetone (480 mL). Anhydrous LiI was added (12.9 g, 96.03 mmol) and the resulting pale yellow solution was stirred for 3.5 h at 45° C. The mixture was concentrated to dryness under reduced pressure. The residue was diluted with DCM (350 mL) making salts precipitate which were filtered over a pad of Celite®. The filtrate was washed with H$_2$O (2×100 mL), dried over Na$_2$SO$_4$ and concentrated in vacuo to provide intermediate (1c) (15.3 g, 15.0 g expected) as pale yellow solid.

MS m/z ([M+H]$^+$) 314.

$^1$H NMR (300 MHz, CDCl$_3$): δ (ppm) 3.29 (br s, 2H), 3.66 (br s, 2H), 3.73 (br s, 2H), 6.89 (t, J=1.7 Hz, 1H), 7.29-7.37 (m, 5H).

Step 3: Preparation of Intermediate 1-benzyl-5-iodo-3,6-dihydro-2H-pyridin-3-ol (1d)

In a 1 L three-neck round bottom flask under nitrogen atmosphere, intermediate (1c) (15.3 g, 48.02 mmol theoretically) was dissolved in a 5/1 MeOH/THF mixture (0.16 M) and cooled down to 0° C. After 15 min, NaBH$_4$ (2.1 g, 55.2 mmol) was added by small portions over 10 min. The reaction was completed within 10 min. The solvents were removed in vacuo at ambient temperature to a volume of approximately 60 mL. The mixture was then diluted with DCM (500 mL) and washed with crushed ice/H$_2$O (100 mL). Aqueous layer was extracted with DCM (2×30 mL). The combined organic layers were dried over Na$_2$SO$_4$, evaporated to dryness and the crude intermediate (1d) (15.4 g, 15.1 g expected) was obtained as a solid which was used without further purification.

MS m/z ([M+H]$^+$) 316.

$^1$H NMR (400 MHz, CDCl$_3$): δ (ppm) 2.36 (br s, 1H), 2.57 (dd, J=12.0, 2.4 Hz, 1H), 2.86 (dd, J=12.0, 2.4 Hz, 1H), 3.04 (d, J=16.3 Hz, 1H), 3.43 (d, J=16.3 Hz, 1H), 3.61 (d, J=11.5 Hz, 1H), 3.66 (d, J=11.5 Hz, 1H), 3.99-4.06 (m, 1H), 6.52-6.57 (m, 1H), 7.28-7.38 (m, 5H).

Step 4: Preparation of Intermediate N-allyloxy-N-(1-benzyl-5-iodo-3,6-dihydro-2H-pyridin-3-yl)-2-nitro-benzenesulfonamide (1e)

To a solution of intermediate (Id) (15.4 g, 48.02 mmol theoretically) in anhydrous THF (400 mL) were successively added PPh$_3$ (15.1 g, 57.6 mmol), N-allyloxy-2-nitro-benzenesulfonamide (18.6 g, 72.0 mmol) and DIAD (11.3 mL, 57.6 mmol). After stirring at room temperature for 15 min, the mixture was concentrated in vacuo. The residue was purified by flash chromatography on silica gel (petroleum ether/Et$_2$O 100/0 to 40/60) to provide intermediate (1e) (39.0 g, 26.7 g expected) contaminated by an excess of unreacted N-allyloxy-2-nitro-benzenesulfonamide and reduced DIAD. The oily residue was covered with cold diisopropyl ether making reduced DIAD precipitate partially. After filtration of the white solid, intermediate (1e) (34 g) was recovered and used without further purification in the next step.

MS m/z ([M+H]$^+$) 556.

Step 5: Preparation of Intermediate N-allyloxy-1-benzyl-5-iodo-3,6-dihydro-2H-pyridin-3-amine (1f)

Under nitrogen atmosphere, K$_2$CO$_3$ (50.0 g, 360.1 mmol) was added to a solution of intermediate (1e) (48.02 mmol theoretically) in ACN (400 mL) in the presence of PhSH (25.0 mL, 240.1 mmol). After stirring for 3 h at rt, the reaction mixture was filtered on Celite® and the cake was washed with DCM (3×150 mL). The filtrate was concentrated and the crude yellow slurry (60 g) was poured in heptane (500 mL) making reduced DIAD precipitate. After filtration and concentration of the filtrate, a clear yellow oil was obtained (51 g). A first purification by flash chromatography on silica gel (petroleum ether/Et$_2$O 100/0 to 40/60) followed by a second purification (DCM 100% then DCM/EtOAc 15/85) provided intermediate (1f) as a pale yellow solid after trituration (12.2 g, 68% over 4 steps).

MS m/z ([M+H]$^+$) 371.

$^1$H NMR (400 MHz, CDCl$_3$): δ(ppm) 2.48 (dd, J=11.7, 3.4 Hz, 1H), 2.96-3.08 (m, 2H), 3.34 (d, J=16.5 Hz, 1H), 3.57 (br s, 1H), 3.60 (d, J=13.5 Hz, 1H), 3.65 (d, J=13.5 Hz, 1H), 4.09-4.22 (m, 2H), 5.15-5.30 (m, 2H), 5.73 (br s, 1H), 5.84-5.96 (m, 1H), 6.37-6.43 (m, 1H), 7.25-7.38 (m, 5H).

Step 6: Preparation of Intermediate 6-allyloxy-3-iodo-1,6-diazabicyclo[3.2.1]oct-3-en-7-one (1g)

In a 2 L three neck round bottom flask under inert atmosphere with an addition funnel and a H$_2$O condenser, intermediate (1f) (12.2 g, 32.96 mmol) was diluted in anhydrous DCE (350 mL). A solution of triphosgene (12.7 g, 42.84 mmol) in DCE (150 mL) was added at rt over 5 min and the solution was stirred until the pale yellow solution turned to a white suspension. The reaction mixture was then heated at 55° C. for 20 min.

A solution of dry NaI (49.2 g, 329.6 mmol) in dry acetone (170 mL) was then added dropwise and the yellow suspension turned to a brown slurry which was heated at 65° C. for 25 min. Pyridine (66 mL, 823.9 mmol) was carefully added dropwise over 10 min. The reaction was stirred for 30 min at 65° C. The reaction was cooled down to 0° C., diluted with DCM (600 mL), filtered on Celite® and concentrated to dryness in vacuo. The brown residue was diluted with DCM (600 mL), filtered on Celite® and washed with an aqueous 0.2M solution of NaH$_2$PO$_4$ (2×200 mL) and a Na$_2$S$_2$O$_3$ 1M aqueous solution (2×200 mL). The organic layer was dried over Na$_2$SO$_4$, concentrated in vacuo. The residue (14.5 g) was purified by flash chromatography on silica gel (petroleum ether/Et$_2$O 100/0 to 40/60) to provide intermediate (1g) (7.1 g, 23.2 mmol, 70%) as an orange oil.

MS m/z ([M+H]$^+$) 307.

$^1$H NMR (300 MHz, CDCl$_3$): δ (ppm) 3.21 (d, J=10.8 Hz, 1H), 3.51-3.58 (m, 1H), 3.83-3.86 (m, 1H), 3.90 (dd, J=18.0, 2.2 Hz, 1H), 4.07 (dd, J=18.0, 1.4 Hz, 1H), 4.36-4.53 (m, 2H), 5.28-5.46 (m, 2H), 5.95-6.13 (m, 1H), 6.87-6.97 (m, 1H).

Step 7: Preparation of Intermediate 6-allyloxy-3-(2-oxo-thiazol-3-yl)-1,6-diaza-bicyclo[3.2.1]oct-3-en-7-one (1 h)

A mixture of intermediate (1g) (0.1 g, 0.33 mmol), 3H-thiazol-2-one (0.05 g, 0.49 mmol), N,N-dimethylglycine hydrochloride (0.007 g, 0.05 mmol), CuI (0.006 g, 0.033 mmol) and dry K$_2$CO$_3$ (0.137 g, 0.99 mmol) in DMSO (6 mL) under argon was heated (80-100° C.) for a couple of hours (from 1 to 18 h). The mixture was poured in H$_2$O then extracted with DCM. The organic layer was dried over Na$_2$SO$_4$, filtered and concentrated in vacuo. The residue was purified on silica gel (DCM/acetone: 100/0 to 90/10) to provide intermediate (1 h) (0.092 g, 0.33 mmol, quantitative yield).

MS m/z ([M+H]$^+$) 280

$^1$H NMR (400 MHz, CDCl$_3$): δ (ppm) 3.18 (d, J=11.1 Hz, 1H), 3.48 (dd, J=2.6, 10.9 Hz, 1H), 4.04 (d, J=17.6 Hz, 1H), 4.07-4.08 (m, 1H), 4.25 (dd, J=2.0, 17.6 Hz, 1H), 4.37-4.48 (m, 2H), 5.31-5.42 (m, 2H), 5.91-6.09 (m, 1H), 6.16 (d, J=5.6 Hz, 1H), 6.44-6.50 (m, 1H), 6.58 (d, J=5.6 Hz, 1H).

Step 8: Preparation of Intermediate 6-hydroxy-3-(2-oxo-thiazol-3-yl)-1,6-diaza-bicyclo[3.2.1]oct-3-en-7-one (1i)

A solution of intermediate (1 h) (0.098 g, 0.35 mmol) in anhydrous DCM (3.5 mL) was degazed for 10 min under argon atmosphere. AcOH (0.040 mL, 0.7 mmol) and Pd(PPh$_3$)$_4$ (0.203 g, 0.175 mmol) were successively added. After stirring for 30 min at rt, the mixture was concentrated in vacuo. The residue was purified by flash chromatography on C-18 reverse phase (H$_2$O/ACN 99/1 to 80/20). The fractions containing the desired compound were combined, freezed and lyophilized to provide intermediate (1i) (0.083 g, 0.35 mmol, quantitative yield).

MS m/z ([M+H]$^+$) 240

$^1$H NMR (400 MHz, CDCl$_3$): δ (ppm) 3.05 (d, J=10.6 Hz, 1H), 3.42 (dd, J=2.4, 10.6 Hz, 1H), 3.94 (d, J=17.7 Hz, 1H), 4.13 (dd, J=2.7, 5.4 Hz, 1H), 4.19 (dd, J=1.9, 17.7 Hz, 1H), 6.11 (d, J=5.5 Hz, 1H), 6.49 (d, J=5.3 Hz, 1H), 6.70 (d, J=5.5 Hz, 1H).

Step 9: Preparation of sodium [7-oxo-3-(2-oxo-thiazol-3-yl)-1,6-diaza-bicyclo[3.2.1]oct-3-en-6-yl] sulfate (Example 1)

To a solution of intermediate (1i) (0.083 g, 0.35 mmol) in anhydrous pyridine (4 mL) under inert atmosphere was added sulfur trioxide pyridine complex (0.225 g, 1.42 mmol). After stirring for 18 h, the heterogeneous mixture was concentrated in vacuo. DCM was added to the residue and the solids were filtered. The filtrate was purified by flash chromatography on silica gel (DCM/MeOH: 100/0 to 80/20) to give 0.017 g of a solid which was applied on a Dowex sodium form column (Dowex® 50WX8 hydrogen form stored with an aqueous solution of 2N NaOH and washed until neutral pH with $H_2O$). The fractions containing the desired compound were combined, freezed and lyophilized to provide example (1) (0.0074 g, 0.02 mmol, 6%).

MS m/z ([M–H]⁻) 318.

$^1$H NMR (400 MHz, $D_2O$): δ(ppm) 3.45 (d, J=11.3 Hz, 1H), 3.65 (dd, J=2.6, 11.4 Hz, 1H), 4.13 (d, J=17.8 Hz, 1H), 4.27 (dd, J=2.1, 17.8 Hz, 1H), 4.55 (dd, J=2.7, 5.5 Hz, 1H), 6.48 (d, J=5.4 Hz, 1H), 6.55-6.70 (m, 1H), 6.87 (d, J=5.4 Hz, 1H).

Example 2: Synthesis of sodium [7-oxo-3-(triazol-1-yl)-1,6-diazabicyclo[3.2.1]oct-3-en-6-yl]sulfate

Step 1a: Preparation of Intermediates 6-allyloxy-3-(triazol-1-yl)-1,6-diazabicyclo[3.2.1]oct-3-en-7-one (2a) and 6-allyloxy-3-(triazol-2-yl)-1,6-diazabicyclo[3.2.1]oct-3-en-7-one (2b)

A mixture of intermediate (1g) (629 mg, 2.05 mmol), 1H-1,2,3-triazol (237 μL, 4.10 mmol), dipivaloylmethane (86 μL, 0.41 mmol), CuI (37 mg, 0.20 mmol) and dry $K_2CO_3$ (567 mg, 4.40 mmol) in DMSO (20 mL) under argon was heated (80-100° C.) for a couple of hours (from 1 to 30 h). The mixture was concentrated to dryness under nitrogen flux. The residue was purified on silica gel (DCM/EtOAc: 100/0 to 0/100) to provide intermediate (2a) (243 mg, 0.982 mmol, 48%) as a yellow oil and intermediate (2b) (131 mg, 0.530 mmol, 26%) as a yellow oil.

6-allyloxy-3-(triazol-1-yl)-1,6-diazabicyclo[3.2.1]oct-3-en-7-one (2a)

MS m/z ([M+H]⁺) 248, ([2M+H]⁺) 495.

$^1$H-NMR (300 MHz, $CDCl_3$): δ (ppm) 3.20 (dd, J=11.0, 0.7 Hz, 1H), 3.58 (ddd, J=11.0, 2.9, 1.1 Hz, 1H), 4.16 (dd, J=5.4, 2.8 Hz, 1H), 4.30-4.55 (m, 4H), 5.30-5.41 (m, 2H), 5.95-6.08 (m, 1H), 6.64-6.68 (m, 1H), 7.72 (d, J=1.2 Hz, 1H), 7.76 (d, J=1.2 Hz, 1H).

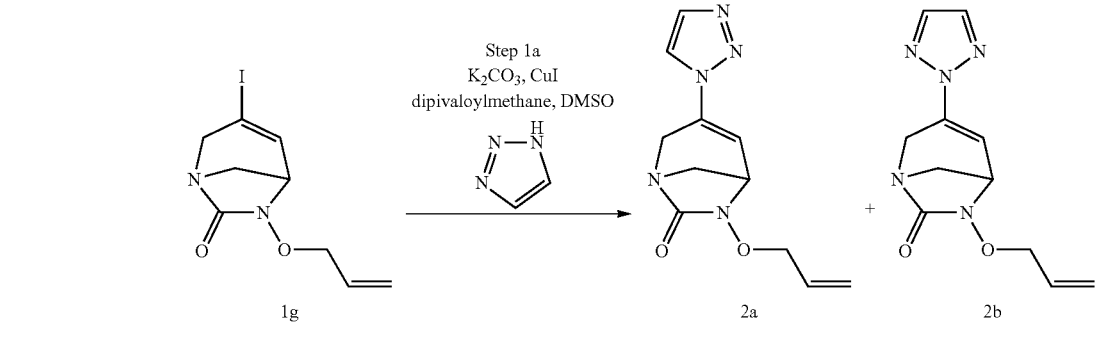

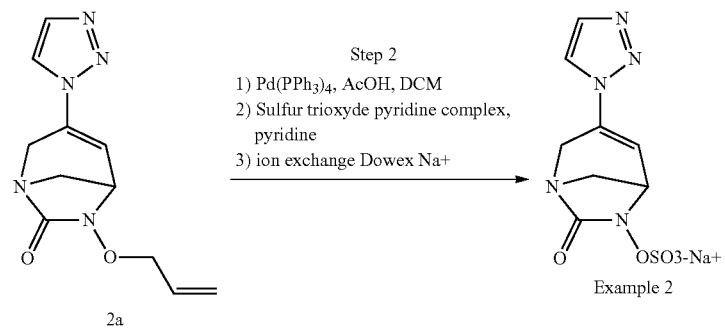

$^{13}$C-NMR (75 MHz, CDCl$_3$): δ (ppm) 134.1, 133.7, 132.5, 120.6, 120.4, 116.4, 77.3, 75.5, 56.7, 53.1, 49.8.

6-allyloxy-3-(triazol-2-yl)-1,6-diazabicyclo[3.2.1]oct-3-en-7-one (2b)

MS m/z ([M+H]$^+$) 248.
$^1$H NMR (400 MHz, CDCl$_3$): δ (ppm) 3.17 (d, J=10.9 Hz, 1H), 3.52-3.60 (m, 1H), 4.16 (dd, J=5.6, 2.7 Hz, 1H), 4.26 (dd, J=17.9, 2.0 Hz, 1H), 4.44 (qd, J=12.3, 6.3 Hz, 2H), 4.63 (d, J=17.8 Hz, 1H), 5.27-5.43 (m, 2H), 6.03 (ddt, J=16.9, 10.3, 6.4 Hz, 1H), 6.99 (d, J=5.5 Hz, 1H), 7.69 (s, 2H).
$^{13}$C NMR (75 MHz, CDCl$_3$): δ (ppm) 170.1, 135.6, 135.3, 132.8, 120.3, 114.2, 76.7, 60.4, 56.8, 52.7, 50.1.

Step 1b: Preparation of Intermediate 6-allyloxy-3-(triazol-1-yl)-1,6-diazabicyclo[3.2.1]oct-3-en-7-one (2a)

In a 100 mL sealed flask under inert atmosphere, intermediate (1g) (4g, 13.07 mmol) was diluted with anhydrous DMSO (40 mL). CuI (249 mg, 1.31 mmol), sodium azide (1.27g, 19.60 mmol), sodium ascorbate (259 mg, 1.31 mmol) and DMCyDA (309 µL, 1.96 mmol) were successively added. The green solution turned rapidly to brown. The mixture was stirred to rt for 30 min until total conversion of starting material. Ethynyltrimethylsilane (2.21 mL, 15.68 mmol) was then added to the mixture which was stirred to rt for 30 min until total conversion of intermediate azide. The mixture was diluted with H$_2$O (400 mL) and extracted with EtOAc (3×200 mL). The combined organic layers were dried (Na$_2$SO$_4$) and concentrated in vacuo to give 4.50 g of a brown oil. This oil was dissolved in anhydrous THF (87 mL) and 3HF.TEA (2.13 mL, 13.07 mmol) was added to the solution which was stirred 1 h at 50° C. The mixture was concentrated in vacuo and the crude (6.35 g) was purified by flash chromatography on silica gel (Cyclohexane/EtOAc: 100/0 to 0/100) to give intermediate (2a) (1.30 g, 5.25 mmol, 40%) as a yellow oil which crystallized as a yellow solid.

MS m/z ([M+H]$^+$) 248, ([2M+H]$^+$) 495.
$^1$H-NMR (300 MHz, CDCl$_3$): δ (ppm) 3.20 (dd, J=11.0, 0.7 Hz, 1H), 3.58 (ddd, J=11.0, 2.9, 1.1 Hz, 1H), 4.16 (dd, J=5.4, 2.8 Hz, 1H), 4.30-4.55 (m, 4H), 5.30-5.41 (m, 2H), 5.95-6.08 (m, 1H), 6.64-6.68 (m, 1H), 7.72 (d, J=1.2 Hz, 1H), 7.76 (d, J=1.2 Hz, 1H).

Step 2: Preparation of sodium [7-oxo-3-(triazol-1-yl)-1,6-diazabicyclo[3.2.1]oct-3-en-6-yl]sulfate (Example 2)

To a solution of intermediate (2a) (150 mg, 0.607 mmol) in anhydrous DCM (6.1 mL) were added glacial AcOH (69 µL, 1.21 mmol) and Pd(PPh$_3$)$_4$ (351 mg, 0.303 mmol). After 45 min of stirring at rt, pyridine (6.1 mL) and sulfur trioxide pyridine complex (483 mg, 3.03 mmol) were added to the reaction mixture. The resulting suspension was protected from light and stirred overnight until the reaction was completed. The reaction mixture was concentrated, then diluted with DCM and filtered. The filtrate was concentrated under vacuum and then purified by flash chromatography on silica gel (DCM/acetone: 100/0 to 0/100) to afford triphenyl-(propenyl)-phosphonium 7-oxo-3-(triazol-1-yl)-1,6-diazabicyclo[3.2.1]oct-3-en-6-yl]sulfate (215.7 mg) as a pale yellow foam. This foam was dissolved in a minimum of a mixture H$_2$O/ACN 20/80 and applied on a Dowex sodium form column (Dowex® 50WX8 hydrogen form stored with an aqueous solution of 2N NaOH and washed until neutral pH with H$_2$O). The fractions containing the desired compound were combined and concentrated (bath temperature <30° C.). The compound was diluted in H$_2$O, filtered on Millipore 0.22 µM, frozen and lyophilized to afford example (2) (96 mg, 0.310 mmol, 51% over 3 steps, purity 95%) as a beige amorphous solid.

MS m/z ([M−H]$^−$) 286.
$^1$H-NMR (300 MHz, D$_2$O): δ(ppm) 3.52 (d, J=11.4 Hz, 1H), 3.73 (dd, J=11.5, 2.8 Hz, 1H), 4.42-4.56 (m, 2H), 4.65 (dd, J=5.6, 2.9 Hz, 1H), 6.91-6.93 (m, 1H), 7.85 (d, J=1.3 Hz, 1H), 8.26 (d, J=1.3 Hz, 1H).

Example 3: Synthesis of sodium [7-oxo-3-(triazol-2-yl)-1,6-diazabicyclo[3.2.1]oct-3-en-6-yl]sulfate

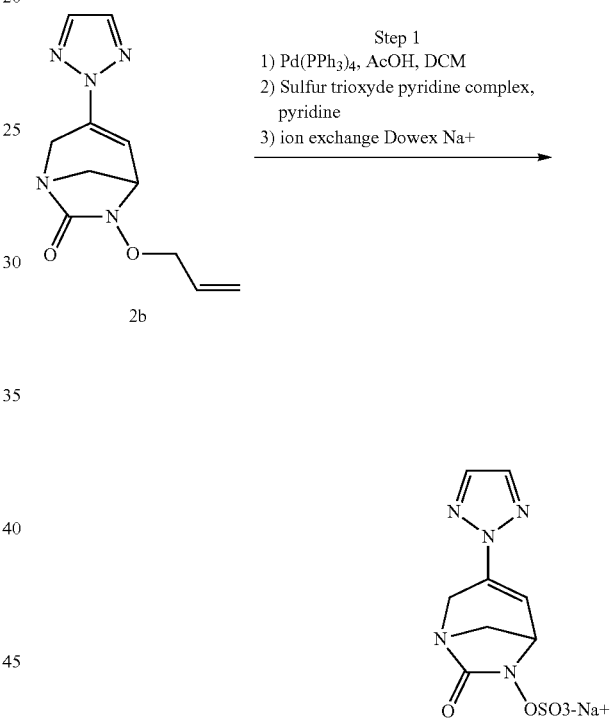

Example 3

Step 1: Preparation of sodium [7-oxo-3-(triazol-2-yl)-1,6-diazabicyclo[3.2.1]oct-3-en-6-yl]sulfate (example 3)

Using the procedure described in example 2 (step 2), intermediate (2b) (180 mg, 0.725 mmol) was converted into example (3) (102 mg, 0.330 mmol, 46%) as a white solid after lyophilization.

MS m/z ([M+H]$^+$) 288.
MS m/z ([M−H]$^−$) 286.
$^1$H-NMR (300 MHz, D$_2$O): δ(ppm) 3.39 (d, J=11.3 Hz, 1H), 3.58-3.66 (m, 1H), 4.40 (d, J=1.6 Hz, 2H), 4.54 (dd, J=5.7, 2.7 Hz, 1H), 6.89 (dd, J=5.4, 1.5 Hz, 1H), 7.81 (s, 2H).

Example 4: Synthesis of lithium difluoro-(7-oxo-3-pyrazol-1-yl-1,6-diaza-bicyclo[3.2.1]oct-3-en-6-yloxy)-acetate

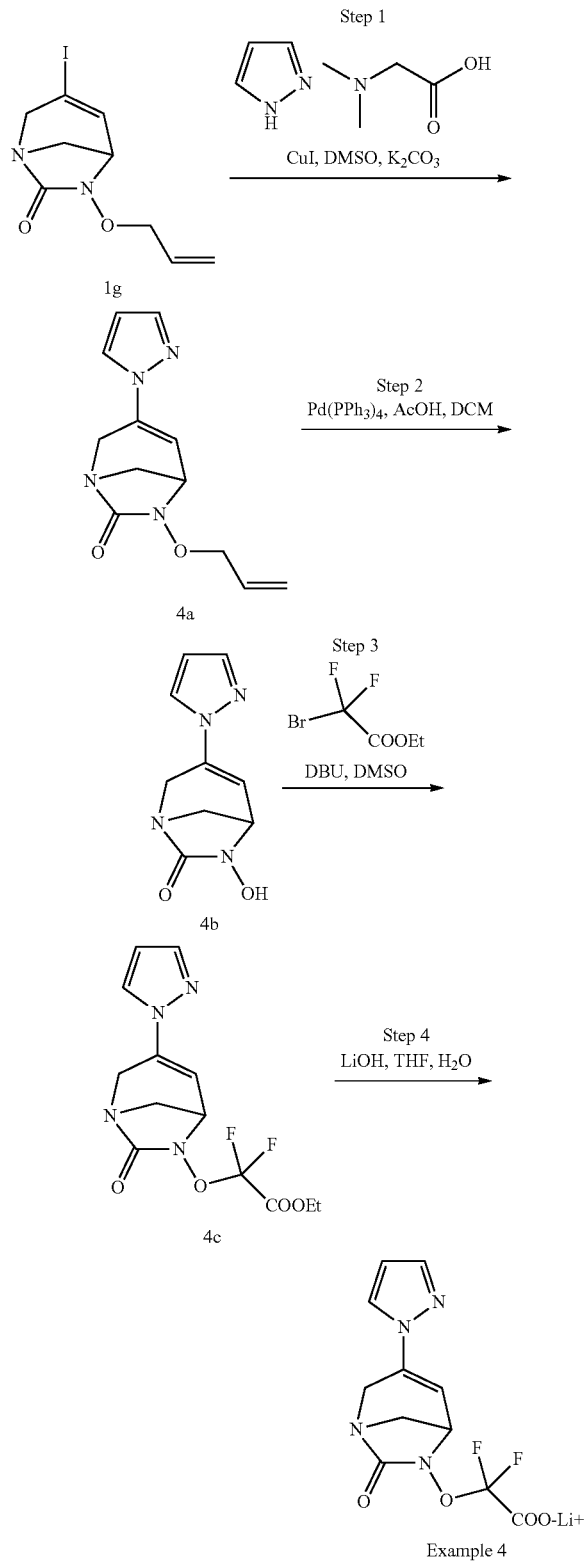

Step 1: Preparation of Intermediate 6-allyloxy-3-pyrazol-1-yl-1,6-diaza-bicyclo[3.2.1]oct-3-en-7-one (4a)

Using the procedure described in example 1 (step 7), intermediate (1g) (0.5 g, 1.63 mmol) was converted by reaction with 1H-pyrazole (0.169 g, 2.45 mmol) into intermediate (4a) (0.349 g, 1.42 mmol, 86%) after purification by flash chromatography on silica gel (DCM/acetone: 100/0 to 90/10).

MS m/z ([M+H]$^+$) 247.

$^1$H NMR (400 MHz, CDCl$_3$): δ (ppm): 3.15 (d, J=10.8 Hz, 1H), 3.53 (dd, J=2.1, 10.8 Hz, 1H), 4.10 (dd, J=2.5, 5.5 Hz, 1H), 4.21 (dd, J=1.9, 17.6 Hz, 1H), 4.34-4.53 (m, 3H), 5.28-5.33 (m, 1H), 5.37 (dq, J=1.3, 17.2 Hz, 1H), 6.02 (ddt, J=6.4, 10.3, 17.0 Hz, 1H), 6.32-6.37 (m, 1H), 6.46 (d, J=5.5 Hz, 1H), 7.57 (d, J=1.5 Hz, 1H), 7.61 (d, J=2.5 Hz, 1H).

Step 2: Preparation of Intermediate 6-hydroxy-3-pyrazol-1-yl-1,6-diaza-bicyclo[3.2.1]oct-3-en-7-one (4b)

A solution of intermediate (4a) (0.100 g, 0.41 mmol) in anhydrous DCM (4 mL) was degazed 10 min under argon atmosphere. AcOH (0.047 mL, 0.81 mmol) and Pd(PPh$_3$)$_4$ (0.237 g, 0.205 mmol) were successively added. After stirring for 30 min at rt, the precipitate was filtered and washed with DCM to afford 0.05 mg of white solid. The filtrate was purified by preparative TLC on silica gel (DCM/acetone 60/40) to give additional 0.013 g. The solids were combined to provide intermediate (4b) (0.063 g, 0.31 mmol, 75%).

MS m/z ([M+H]$^+$) 207.

$^1$H NMR (400 MHz, DMSO-d$_6$): δ(ppm): 3.22 (d, J=10.7 Hz, 1H), 3.36 (dd, J=2.0, 10.8 Hz, 1H), 4.02 (dd, J=2.5, 5.6 Hz, 1H), 4.18 (d, J=1.1 Hz, 2H), 6.43-6.47 (m, 1H), 6.65 (d, J=5.0 Hz, 1H), 7.64 (d, J=1.5 Hz, 1H), 8.18 (d, J=2.4 Hz, 1H), 9.65 (s, 1H).

Step 3: Preparation of Intermediate ethyl difluoro-(7-oxo-3-pyrazol-1-yl-1,6-diaza-bicyclo[3.2.1]oct-3-en-6-yloxy)-acetate (4c)

Intermediate (4b) (0.154 g, 0.75 mmol) was solubilised in DMSO (7.5 mL) with DBU (0.123 mL, 0.825 mmol) and ethyl bromo-difluoro-acetate (0.250 mL, 1.94 mmol) and stirred for 30 min. The mixture was washed with NaH$_2$PO$_4$ 2M and the product was extracted with EtOAc. The organic layer was filtered on a pad of silica then concentrated in vacuo. The residue was triturated in Et$_2$O and filtered on a PTFE membrane to provide intermediate (4c) (0.155 g, 0.47 mmol, 63%).

MS m/z ([M+H]$^+$) 329.

$^1$H NMR (300 MHz, CDCl$_3$): δ (ppm): 1.38 (t, J=7.2 Hz, 3H), 3.25 (d, J=11.1 Hz, 1H), 3.66 (dd, J=1.7, 11.1 Hz, 1H), 4.24-4.44 (m, 4H), 4.59 (dd, J=0.9, 17.7 Hz, 1H), 6.39 (dd, J=1.8, 2.5 Hz, 1H), 6.40-6.45 (m, 1H), 7.60 (d, J=1.7 Hz, 1H), 7.64 (d, J=2.6 Hz, 1H).

Step 4: Preparation of lithium difluoro-(7-oxo-3-pyrazol-1-yl-1,6-diaza-bicyclo[3.2.1]oct-3-en-6-yloxy)-acetate (Example 4)

To a solution of intermediate (4c) (0.143 g, 0.435 mmol) in THF (4 mL) and H$_2$O (0.4 mL) at 0° C. was dropwise added a 0.1 N LiOH solution (4.8 mL, 0.48 mmol). When monitoring indicated the reaction was completed, the mixture was neutralized with HCl (0.1 N) (0.7 mL) at 0° C. The solution was freezed to evaporate THF on vacuum and lyophilize the aqueous solution. The residue was triturated in Et$_2$O and filtered on a PTFE membrane. Then the solid was purified on silica gel (iPrOH). The fractions containing the desired product were concentrated in vacuo. The solid was triturated in Et$_2$O and the result solid was solubilized on H$_2$O to lyophilize and provide example (4 (0.88 g, 0.286 mmol, 66%).

MS m/z ([M+H]$^+$) 301.

$^1$H NMR (300 MHz, D$_2$O) δ (ppm): 3.44 (d, J=11.4 Hz, 1H), 3.66 (ddd, J=0.9, 2.7, 11.3 Hz, 1H), 4.38 (d, J=1.4 Hz, 2H), 4.49 (dd, J=2.5, 5.6 Hz, 1H), 6.48 (dd, J=2.0, 2.6 Hz, 1H), 6.56-6.61 (m, 1H), 7.69 (d, J=1.8 Hz, 1H), 7.92 (d, J=2.6 Hz, 1H).

Example 5: Synthesis of sodium [7-oxo-3-(1,2,4-triazol-1-yl)-1,6-diazabicyclo[3.2.1]oct-3-en-6-yl] sulfate

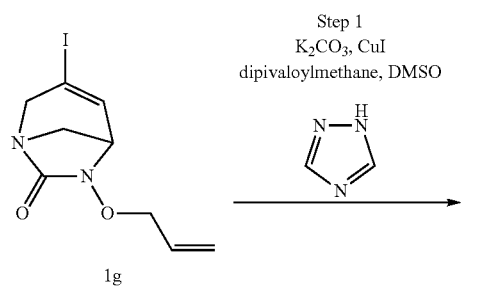

1g

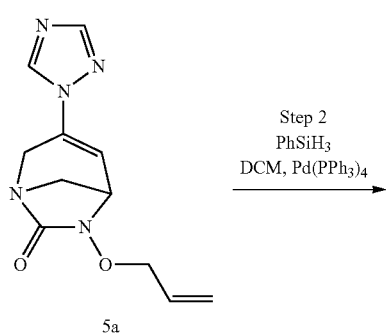

5a

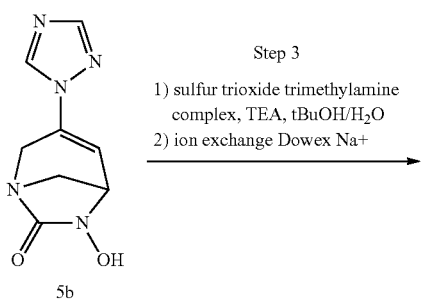

5b

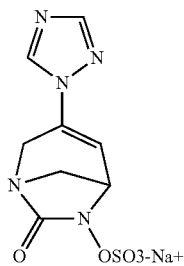

Example 5

Step 1: Preparation of Intermediate 6-allyloxy-3-(1,2,4-triazol-1-yl)-1,6-diazabicyclo[3.2.1]oct-3-en-7-one (5a)

Using the procedure described in example 2 (step 1a), intermediate (1g) (200 mg, 0.65 mmol) was converted by reaction with 1,2,4-triazol (54 mg, 0.78 mmol) into intermediate (5a) (110 mg, 0.44 mmol, 48%) as an orange oil after purification by flash chromatography on silica gel (DCM/acetone: 100/0 to 50/50).

MS m/z ([M+H]$^+$) 248.

$^1$H NMR (400 MHz, CDCl$_3$): δ (ppm) 3.17 (d, J=10.9 Hz, 1H), 3.57 (dd, J=10.9, 2.0 Hz, 1H), 4.14 (dd, J=5.5, 2.6 Hz, 1H), 4.18 (dd, J=17.6, 2.6 Hz, 1H), 4.35-4.50 (m, 3H), 5.30-5.34 (m, 1H), 5.37 (dq, J=17.2, 1.4 Hz, 1H), 5.96-6.07 (m, 1H), 6.68 (d, J=5.4 Hz, 1H), 7.97 (s, 1H), 8.26 (s, 1H).

Step 2: Preparation of Intermediate 6-hydroxy-3-(1,2,4-triazol-1-yl)-1,6-diazabicyclo[3.2.1]oct-3-en-7-one (5b)

Under inert atmosphere, PhSiH$_3$ (32 μL, 0.308 mmol) and Pd(PPh$_3$)$_4$ (7 mg, 0.006 mmol) were added to a solution of intermediate (5a) (51 mg, 0.154 mmol) in anhydrous DCM (2 mL). The reaction mixture was stirred at rt for 1 h and filtered. The precipitate was washed with DCM (2 mL) to give intermediate (5b) (26 mg, 0.125 mmol, 81%) which was used without further purification.

MS m/z ([M+H]$^+$) 208.

Step 3: Preparation of sodium [7-oxo-3-(1,2,4-triazol-1-yl)-1,6-diazabicyclo[3.2.1]oct-3-en-6-yl]sulfate (Example 5)

Intermediate (5b) (13 mg, 0.063 mmol) was dissolved in a mixture of tBuOH (0.3 mL) and H$_2$O (0.3 mL). TEA (2.2 μL, 0.016 mmol) and sulfur trioxide trimethylamine complex (10 mg, 0.075 mmol) was added. The mixture was stirred at rt for 2 h then concentrated in vacuo. The reaction mixture was filtered and the filtrate was concentrated in vacuo. The residue was purified by flash chromatography on silica gel (DCM/Acetone: 100/0 to 0/100). The fractions containing the expected intermediate were combined and concentrated in vacuo. The residue was dissolved in H$_2$O and converted after ion exchange with Dowex sodium form column (Dowex® 50WX8 hydrogen form stored with an aqueous solution of 2N NaOH and washed until neutral pH with H$_2$O) to example (5 (5 mg, 0.016 mmol, 26%).

MS m/z ([M−H]$^−$) 286.

$^1$H NMR (400 MHz, D$_2$O): δ(ppm): 3.47 (d, J=11.4 Hz, 1H), 3.71 (dd, J=11.4, 2.8 Hz, 1H), 4.33 (d, J=17.5 Hz, 1H), 4.41 (dd, J=17.5, 1.9 Hz, 1H), 4.61 (dd, J=5.6, 2.8 Hz, 1H), 6.85 (d, J=5.6 Hz, 1H), 8.12 (s, 1H), 8.71 (s, 1H).

Example 6: Synthesis of sodium [(5R)-7-oxo-3-(triazol-1-yl)-1,6-diazabicyclo[3.2.1]oct-3-en-6-yl] sulfate

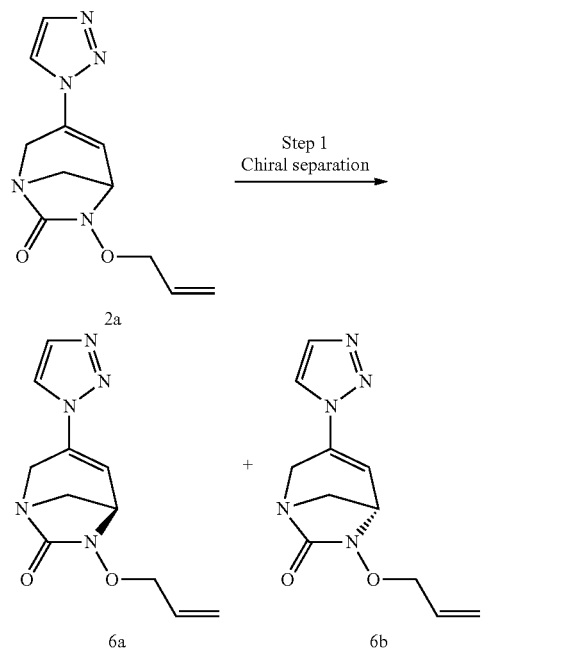

Step 1: Preparation of Intermediate (5R)-6-allyloxy-3-(triazol-1-yl)-1,6-diazabicyclo[3.2.1]oct-3-en-7-one (6a) and (5S)-6-allyloxy-3-(triazol-1-yl)-1,6-diazabicyclo[3.2.1]oct-3-en-7-one (6b)

Both enantiomers of intermediate (2a) (1021 mg, 4.13 mmol) were separated using Supercritical fluid chromatography (LUX C4 5 μm, 250×21.2 mm, iPrOH/CO$_2$ 35/65, 50 mL/min) to provide intermediate (6a) (455 mg, 1.84 mmol, 44%, 98.9% ee, retention time 2.23 min) and intermediate (6b) (482 mg, 1.95 mmol, 47%, 97.6% ee, retention time 2.48 min).

MS m/z ([M+H]$^+$) 248.

$^1$H NMR (400 MHz, CDCl$_3$): δ (ppm) 3.20 (d, J=11.0 Hz, 1H), 3.54-3.63 (m, 1H), 4.16 (dd, J=5.5, 2.7 Hz, 1H), 4.34 (dd, J=17.9, 2.0 Hz, 1H), 4.38-4.57 (m, 3H), 5.30-5.35 (m, 1H), 5.38 (dq, J=17.2, 1.4 Hz, 1H), 5.95-6.10 (m, 1H), 6.62-6.70 (m, 1H), 7.73 (d, J=1.2 Hz, 1H), 7.76 (d, J=1.2 Hz, 1H).

$^1$H NMR (300 MHz, D$_2$O): δ(ppm) 3.49 (d, J=11.4 Hz, 1H), 3.71 (dd, J=11.4, 2.8 Hz, 1H), 4.42 (dd, J=17.7, 1.3 Hz, 1H), 4.51 (dd, J=17.7, 1.9 Hz, 1H), 4.63 (dd, J=5.6, 2.7 Hz, 1H), 6.90 (d, J=5.7 Hz, 1H), 7.82 (d, J=1.3 Hz, 1H), 8.24 (d, J=1.3 Hz, 1H).

Preparative Method
Column: Lux C$_4$ (21.2 mm×250 mm, 5 μm)
Isocratic Conditions 35:65 IPA:CO$_2$
Flow rate: 50 ml/min
Detection: UV 242 nm
BPR 125 BarG Analytical Method:
Column: Lux C$_4$ (4.6 mm×250 mm, 5 μm)
Isocratic Conditions 35:65 IPA:CO$_2$
Flow rate: 4 ml/min
Detection: 210-400 nm
BPR 125 BarG
Column Temperature 40° C.

Step 2: Preparation of sodium [(5R)-7-oxo-3-(triazol-1-yl)-1,6-diazabicyclo[3.2.1]oct-3-en-6-yl]sulfate (Example 6)

Using the procedure described in example 2 (step 2), intermediate (6a) (422 mg, 1.70 mmol) was converted into example (6 (0.243 g, 0.785 mmol, 46%) after lyophilization.

MS m/z ([M−H]$^-$) 286.

$^1$H NMR (300 MHz, D$_2$O): δ(ppm) 3.49 (d, J=11.4 Hz, 1H), 3.71 (dd, J=11.4, 2.8 Hz, 1H), 4.42 (dd, J=17.7, 1.3 Hz, 1H), 4.51 (dd, J=17.7, 1.9 Hz, 1H), 4.63 (dd, J=5.6, 2.7 Hz, 1H), 6.90 (d, J=5.7 Hz, 1H), 7.82 (d, J=1.3 Hz, 1H), 8.24 (d, J=1.3 Hz, 1H).

Example 7: Synthesis of sodium [3-(4-carbamoylpyrazol-1-yl)-7-oxo-1,6-diazabicyclo[3.2.1]oct-3-en-6-yl]sulfate

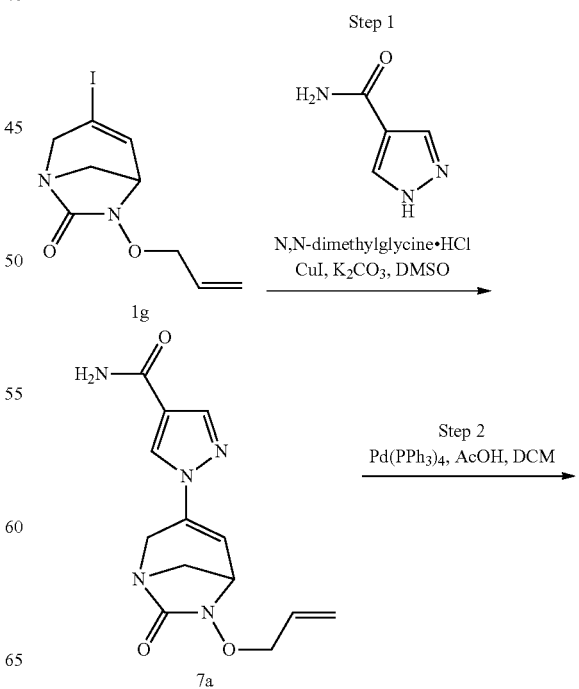

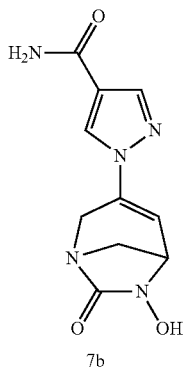

Step 3
1) Sulfur trioxyde pyridine complex, pyridine
2) ion exchange Dowex Na+

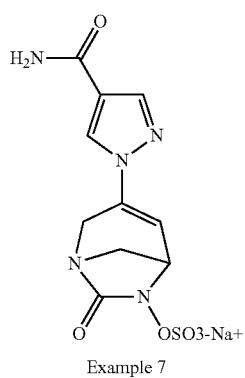

Example 7

Step 1: Preparation of Intermediate 1-(6-allyloxy-7-oxo-1,6-diazabicyclo[3.2.1]oct-3-en-3-yl)pyrazole-4-carboxamide (7a)

A mixture of intermediate (1g) (0.250 g, 0.817 mmol), 1H-pyrazole-4-carboxylic acid amide (0.182 g, 1.633 mmol), N,N-dimethylglycine hydrochloride (0.017 g, 0.122 mmol), CuI (0.016 g, 0.082 mmol) and $K_2CO_3$ (0.339 g, 2.45 mmol) in DMSO (8.2 mL) under argon was heated at 80° C. for 18 h. The mixture was then diluted with $H_2O$ and the product was extracted with DCM and n-BuOH. The organic layer was concentrated in vacuo. The crude product was solubilized in IPA. The insoluble were filtered on PTFE membrane and the filtrate was concentrated in vacuo to provide intermediate (7a) (0.220 g, 0.760 mmol, 93%).

MS m/z ([M+H]$^+$) 290.

1H NMR (400 MHz, DMSO-$d_6$) δ(ppm): 3.27 (d, J=10.9 Hz, 1H), 3.32-3.35 (m, 1H), 4.15 (d, J=17.4 Hz, 1H), 4.26 (dd, J=1.9, 17.4 Hz, 1H), 4.30 (dd, J=2.4, 5.7 Hz, 1H), 4.39 (d, J=6.0 Hz, 2H), 5.27 (d, J=10.5 Hz, 1H), 5.33-5.41 (m, 1H), 5.90-6.01 (m, 1H), 6.68 (d, J=5.4 Hz, 1H), 7.17 (s, 1H), 7.62 (s, 1H), 8.01 (s, 1H), 8.54 (s, 1H).

Step 2: Preparation of Intermediate 1-(6-hydroxy-7-oxo-1,6-diazabicyclo[3.2.1]oct-3-en-3-yl)pyrazole-4-carboxamide (7b)

A solution of intermediate (7a) (0.100 g, 0.345 mmol) in anhydrous DCM (5 mL) was degazed for 10 min under argon atmosphere. AcOH (0.040 mL, 0.69 mmol) and Pd(PPh$_3$)$_4$ (0.090 g, 0.345 mmol) were successively added. After stirring for 30 min at rt, the mixture was concentrated. The residue was triturated in Et$_2$O and filtered to provide intermediate (7b) (0.558 g, 0.224 mmol, 64%).

MS m/z ([M+H]$^+$) 250.

1H NMR (400 MHz, DMSO-$d_6$) δ(ppm): 3.22 (d, J=10.8 Hz, 1H), 3.34-3.38 (m, 1H), 4.05 (dd, J=2.5, 5.5 Hz, 1H), 4.11 (d, J=17.4 Hz, 1H), 4.21 (dd, J=1.7, 17.4 Hz, 1H), 6.72 (d, J=5.4 Hz, 1H), 7.17 (br s, 1H), 7.63 (br s, 1H), 8.00 (s, 1H), 8.54 (s, 1H), 9.72 (br s, 1H).

Step 3: Preparation of sodium [3-(4-carbamoylpyrazol-1-yl)-7-oxo-1,6-diazabicyclo[3.2.1]oct-3-en-6-yl]sulfate (Example 7)

To a solution of intermediate (7b) (0.537 g, 0.215 mmol) in anhydrous pyridine (2.5 mL) under inert atmosphere was added sulfur trioxide pyridine complex (0.139 g, 0.872 mmol). After stirring for 18 h, the heterogeneous mixture was concentrated in vacuo. DCM was added to the residue and the insoluble were filtered. The filtrate was concentrated in vacuo and the product was applied on a Dowex sodium form column (Dowex® 50WX8 hydrogen form stored with an aqueous solution of 2N NaOH and washed until neutral pH with water). The fractions containing the desired compound were combined, freezed and lyophilized to give a solid which was purified on C18-reversed phase silica gel ($H_2O$/ACN: 98/2) and applied again on a Dowex sodium form column to provide example (7) (0.117 g, 0.033 mmol, 15%).

MS m/z ([M−H]$^−$) 328.

1H NMR (400 MHz, D2O) δ(ppm): 3.46 (d, J=11.3 Hz, 1H), 3.70 (dd, J=2.5, 11.2 Hz, 1H), 4.35 (d, J=17.6 Hz, 1H), 4.41 (dd, J=1.6, 17.6 Hz, 1H), 4.60 (dd, J=2.5, 5.6 Hz, 1H), 6.74 (d, J=5.6 Hz, 1H), 8.03 (s, 1H), 8.37 (s, 1H).

Example 8: Synthesis of sodium [3-(4-cyanopyrazol-1-yl)-7-oxo-1,6-diazabicyclo[3.2.1]oct-3-en-6-yl]sulfate

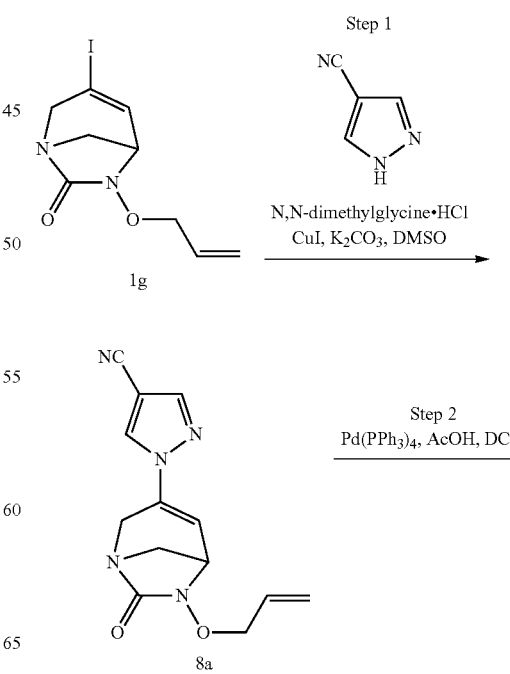

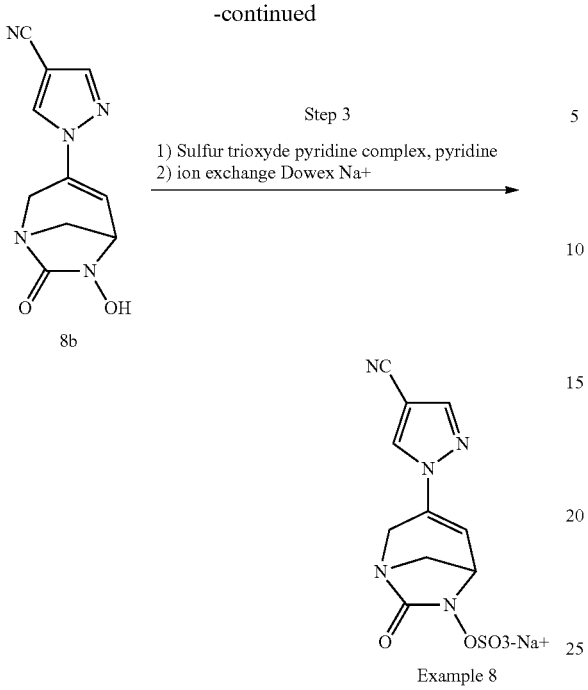

8b

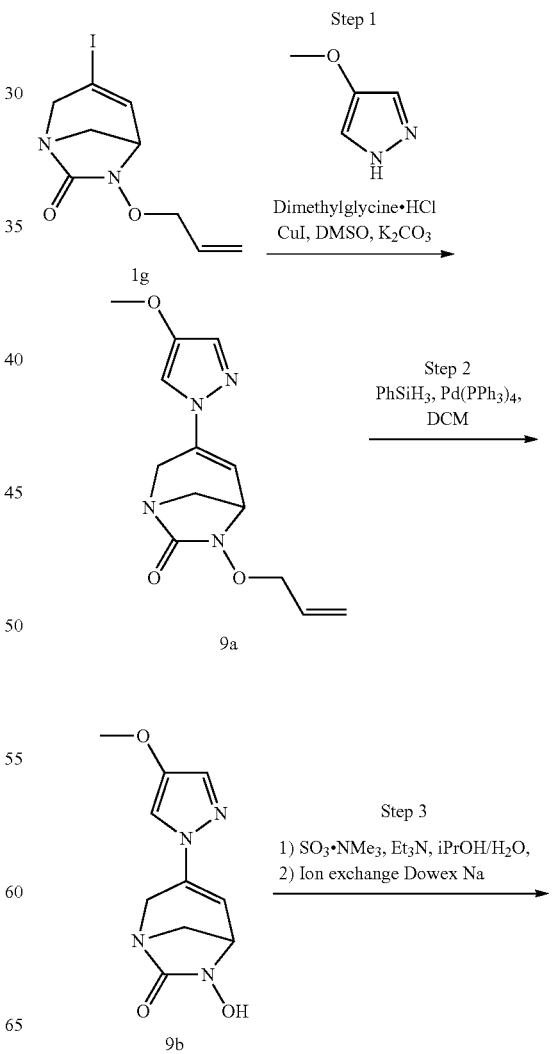

added sulfur trioxide pyridine complex (0.368 g, 3.31 mmol). After stirring for 18 h at rt, the heterogeneous mixture was concentrated in vacuo. DCM was added to the residue and the solids were filtered off. The filtrate was purified by flash chromatography on silica gel (DCM/acetone 100/0 to 0/100) to give a solid which is applied on a Dowex sodium form column (Dowex® 50WX8 hydrogen form stored with an aqueous solution of 2N NaOH and washed until neutral pH with water). The fractions containing the desired compound were combined, freezed and lyophilized to provide example (8) (0.334 g, 0.010 mmol, 17%).

MS m/z ([M−H]$^-$) 310.

$^1$H NMR (400 MHz, D$_2$O) δ(ppm): 3.45 (d, J=11.4 Hz, 1H), 3.70 (dd, J=2.4, 11.4 Hz, 1H), 4.33 (d, J=17.5 Hz, 1H), 4.40 (d, J=17.5 Hz, 1H), 4.61 (dd, J=2.6, 5.6 Hz, 1H), 6.79 (d, J=5.4 Hz, 1H), 8.05 (s, 1H), 8.50 (s, 1H).

Example 9: Synthesis of sodium [7-oxo-3-(4-methoxypyrazol-1-yl)-1,6-diazabicyclo[3.2.1]oct-3-en-6-yl]sulfate Step 1: Preparation of Intermediate 1-(6-allyloxy-7-oxo-1,6-diaza-bicyclo[3.2.1]oct-3-en-3-yl)-1H-pyrazole-4-carbonitrile (8a)

Using the procedure described in example 1 (step 7), intermediate (1g) (0.2 g, 0.653 mmol) was converted by reaction with 1H-pyrazole-4-carbonitrile (0.122 g, 1.307 mmol) into intermediate (8a) (0.177 g, 0.653 mmol, quantitative yield) containing about 30% 1H-pyrazole-4-carbonitrile after purification by flash chromatography on silica gel (i-PrOH).

MS m/z ([M+H]$^+$) 272.

$^1$H NMR (400 MHz, CDCl$_3$) δ(ppm): 3.13 (d, J=11.0 Hz, 1H), 3.54 (dd, J=2.2, 11.0 Hz, 1H), 4.12-4.19 (m, 2H), 4.31-4.51 (m, 3H), 5.21-5.45 (m, 2H), 5.88-6.11 (m, 1H), 6.63 (d, J=5.5 Hz, 1H), 7.82 (s, 1H), 8.05 (s, 1H).

Step 2: Preparation of Intermediate 1-(6-Hydroxy-7-oxo-1,6-diaza-bicyclo[3.2.1]oct-3-en-3-yl)-1H-pyrazole-4-carbonitrile (8b)

Using the procedure described in example 7 (step 2), intermediate (8a) (177 mg, 0.65 mmol) was converted into intermediate (8b) (0.132 g, 0.57 mmol, 88%) containing about 30% triphenylphosphine oxide after purification on silica gel (DCM/Acetone 100/0 to 70/30) followed by a trituration in Et$_2$O.

MS m/z ([M+H]$^+$) 232.

$^1$H NMR (400 MHz, CDCl$_3$) δ(ppm): 3.10 (d, J=10.9 Hz, 1H), 3.42-3.53 (m, 1H), 4.08 (dd, J=2.6, 5.5 Hz, 1H), 4.15 (dd, J=17.7, 1.8 Hz, 1H), 4.34 (d, J=17.7 Hz, 1H), 6.67 (d, J=5.4 Hz, 1H), 7.83 (s, 1H), 8.09 (s, 1H).

Step 3: Preparation of sodium [3-(4-cyanopyrazol-1-yl)-7-oxo-1,6-diazabicyclo[3.2.1]oct-3-en-6-yl]sulfate (Example 8)

To a solution of intermediate (8b) (0.132 g, 0.57 mmol) in anhydrous pyridine (5.7 mL) under inert atmosphere was

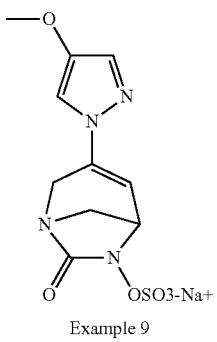

Example 9

Step 1: Preparation of Intermediate 6-allyloxy-3-(4-methoxypyrazol-1-yl)-1,6-diazabicyclo[3.2.1]oct-3-en-7-one (9a)

Using the procedure described in example 1 (step 7), intermediate (1g) (0.26 g, 0.85 mmol) was converted by reaction with 4-methoxy-1H-pyrazole (125 mg, 1.27 mmol) into intermediate (9a) (114 mg, 0.41 mmol, 49%) as a yellow solid after purification by flash chromatography on silica gel (DCM/acetone: 100/0 to 0/100).

MS m/z ([M+H]$^+$) 277.

$^1$H NMR (300 MHz, acetone-d$_6$) δ3.26 (dd, J=10.8, 0.7 Hz, 1H), 3.39-3.44 (m, 1H), 3.74 (s, 3H), 4.17 (dd, J=17.5, 1.9 Hz, 1H), 4.24 (ddd, J=5.6, 2.7, 0.7 Hz, 1H), 4.34 (dd, J=0.7, 17.4 Hz, 1H), 4.37-4.41 (m, 2H), 5.20-5.25 (m, 1H), 5.32-5.39 (m, 1H), 5.93-6.07 (m, 1H), 6.40-6.44 (m, 1H), 7.34 (d, J=0.8 Hz, 1H), 7.76 (d, J=0.8 Hz, 1H).

Step 2: Preparation of Intermediate 6-hydroxy-3-(4-methoxypyrazol-1-yl)-1,6-diazabicyclo[3.2.1]oct-3-en-7-one (9b)

Under inert atmosphere, PhSiH$_3$ (100 μL, 0.80 mmol) and Pd(PPh$_3$)$_4$ (18.6 mg, 0.02 mmol) were successively added to a solution of intermediate (9a) (111 mg, 0.40 mmol) in anhydrous DCM (3.7 mL). The reaction mixture was stirred at rt for 30 min. Then the mixture was concentrated under flux of argon and the residue purified by flash chromatography on silica gel (DCM/acetone: 100/0 to 0/100) to provide intermediate (9b) (142 mg, 0.60 mmol).

MS m/z ([M+H]$^+$) 237.

Step 3: Preparation of sodium [7-oxo-3-(4-methoxypyrazol-1-yl)-1,6-diazabicyclo[3.2.1]oct-3-en-6-yl]sulfate (Example 9)

To a solution of intermediate (9b) (142 mg, 0.60 mmol) in iPrOH/H$_2$O (3.2 mL/1.2 mL) under inert atmosphere were added sulfur trioxide trimethylamine complex (67 mg, 0.48 mmol) and TEA (14 μL, 0.1 mmol). The mixture was stirred overnight. The reaction mixture was concentrated under a flux of argon. The residue was dissolved in a minimum of H$_2$O/ACN (1:1) and passed through an ion exchange column charged with Dowex sodium form (Dowex® 50WX8 hydrogen form stored with an aqueous solution of 2N NaOH and washed until neutral pH with H$_2$O). The fractions containing the desired compound were lyophilized and the residue was then purified by flash chromatography on C18-reversed phase silica gel (H$_2$O/MeCN 99/1) to provide example (9) (28 mg, 0.06 mmol, 20%) as a white solid.

MS m/z ([M+H]$^+$) 317
MS m/z ([M−H]$^−$) 315.

$^1$H NMR (400 MHz, D$_2$O) δ3.45 (d, J=11.3 Hz, 1H), 3.69 (dd, J=11.3, 2.9 Hz, 1H), 3.81 (s, 3H), 4.36 (s, 2H), 4.57 (dd, J=5.7, 2.7 Hz, 1H), 6.49 (d, J=5.7 Hz, 1H), 7.50 (s, 1H), 7.73 (s, 1H).

Example 10: Synthesis of [3-[3-(2-aminoethyl)pyrazol-1-yl]-7-oxo-1,6-diazabicyclo[3.2.1]oct-3-en-6-yl]hydrogen sulfate

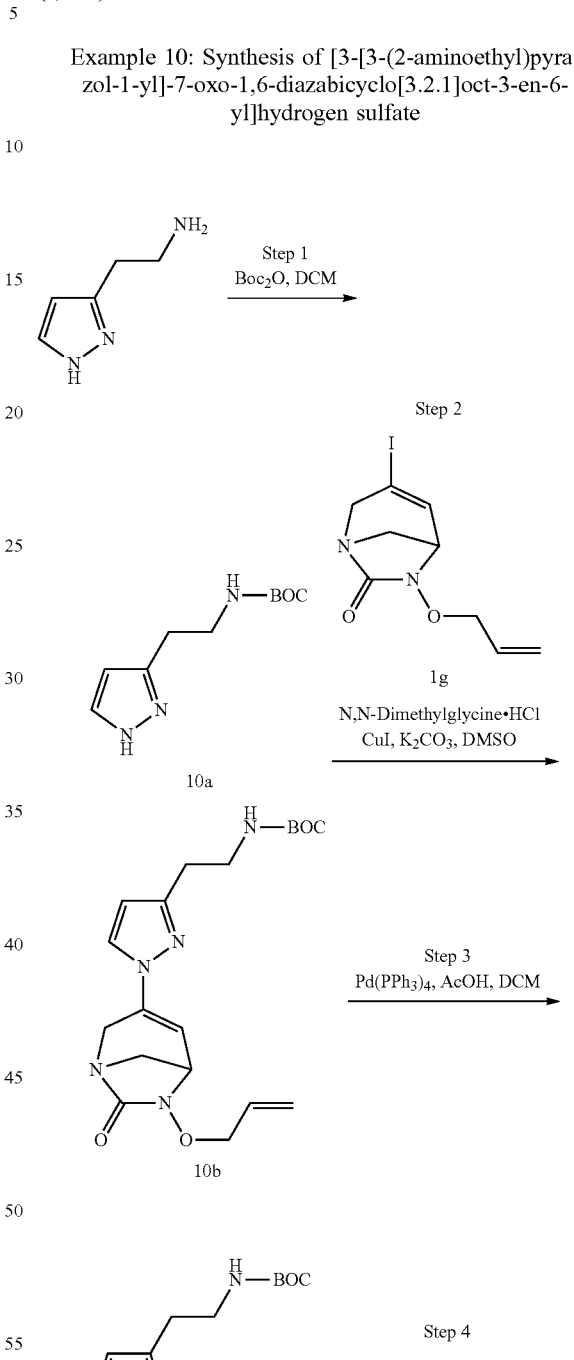

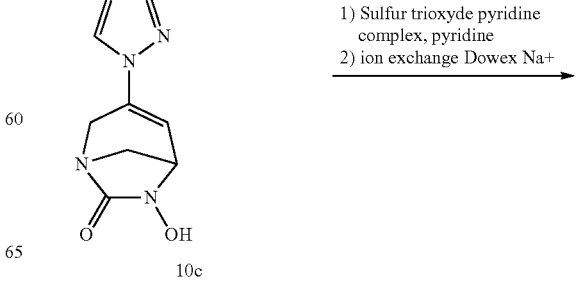

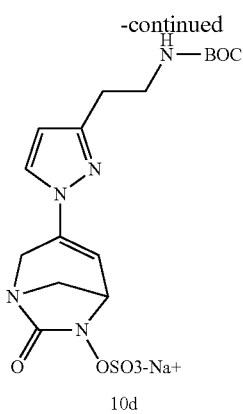

10d

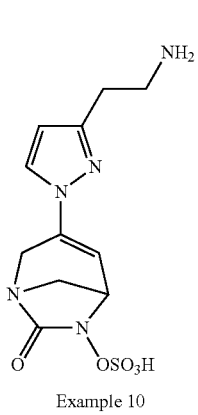

Example 10

Step 1: Preparation of Intermediate tert-butyl N-[2-(1H-pyrazol-3-yl)ethyl]carbamate (10a)

To a solution of 2-(1H-pyrazol-3-yl)ethanamine (0.15 g, 1.35 mmol) in DCM (15 mL) under argon was added Boc$_2$O (0.295 g, 1.35 mmol). The mixture was stirred for 18 h then washed with water and brine. The residue was purified on silica gel (DCM/acetone 100/0 to 0/100) to provide intermediate (10a) (0.186 g, 0.88 mmol, 65%).

MS m/z ([M+H]$^+$) 212.

$^1$H NMR (400 MHz, CDCl$_3$): δ (ppm) 1.43 (s, 9H), 2.88 (t, J=6.7 Hz, 2H), 3.31-3.56 (m, 2H), 4.94 (br s, 1H), 6.13 (d, J=2.1 Hz, 1H), 7.51 (d, J=2.1 Hz, 1H).

Step 2: Preparation of Intermediate tert-butyl N-[2-[1-(6-allyloxy-7-oxo-1,6-diazabicyclo[3.2.1]oct-3-en-3-yl)pyrazol-3-yl]ethyl]carbamate (10b)

Using the procedure described in example 1 (step 7), intermediate (1g) (0.207 g, 0.68 mmol) was converted by reaction with intermediate (10a) (0.186 g, 0.88 mmol) into intermediate (10b) (0.158 g, 0.405 mmol, 59%) after purification by flash chromatography on silica gel (DCM/acetone 100/0 to 90/10).

MS m/z ([M+H]$^+$) 390.

$^1$H NMR (400 MHz, CDCl$_3$): δ (ppm) 1.44 (s, 9H), 2.78 (t, J=6.6 Hz, 2H), 3.14 (d, J=10.7 Hz, 1H), 3.42 (q, J=6.6 Hz, 2H), 3.53 (dd, J=2.1, 10.8 Hz, 1H), 4.09 (dd, J=2.5, 5.5 Hz, 1H), 4.16 (dd, J=1.8, 17.5 Hz, 1H), 4.37-4.50 (m, 3H), 4.84 (br s, 1H), 5.27-5.41 (m, 2H), 5.96-6.08 (m, 1H), 6.17 (d, J=2.5 Hz, 1H), 6.42 (d, J=5.4 Hz, 1H), 7.49 (d, J=2.5 Hz, 1H).

Step 3: Preparation of Intermediate tert-butyl N-[2-[1-(6-hydroxy-7-oxo-1,6-diazabicyclo[3.2.1]oct-3-en-3-yl)pyrazol-3-yl]ethyl]carbamate (10c)

Using the procedure described in example 8 (step 2), intermediate (10b) (158 mg, 0.405 mmol) was converted into intermediate (10c) (118 mg, 0.338 mmol, 83%) after purification on silica gel (DCM/Acetone 100/0 to 70/30).

MS m/z ([M+H]$^+$) 350.

$^1$H NMR (400 MHz, CDCl$_3$): δ (ppm) 1.39 (s, 9H), 2.75 (t, J=6.6 Hz, 2H), 3.07 (d, J=10.7 Hz, 1H), 3.30-3.48 (m, 3H), 4.02 (dd, J=2.6, 5.5 Hz, 1H), 4.10 (dd, J=1.5, 17.6 Hz, 1H), 4.36 (d, J=17.6 Hz, 1H), 5.00 (br s, 1H), 6.14 (d, J=2.5 Hz, 1H), 6.44 (d, J=5.5 Hz, 1H), 7.50 (d, J=2.5 Hz, 1H).

Step 4: Preparation of Intermediate sodium [3-[3-[2-(tert-butoxycarbonylamino)ethyl]pyrazol-1-yl]-7-oxo-1,6-diazabicyclo[3.2.1]oct-3-en-6-yl]sulfate (10d)

Using the procedure described in example 8 (step 3), intermediate (10c) (118 mg, 0.338 mmol) was converted into intermediate (10d) (57 mg, 0.126 mmol, 37%) after purification on silica gel (DCM/MeOH 100/0 to 90/10) and passage through a Dowex sodium form column.

$^1$H NMR (300 MHz, D$_2$O): δ(ppm) 1.35 (br s, 9H), 2.77 (t, J=6.4 Hz, 2H), 3.34 (t, J=6.4 Hz, 2H), 3.42 (d, J=11.3 Hz, 1H), 3.68 (dd, J=2.2, 11.3 Hz, 1H), 4.33 (s, 2H), 4.56 (dd, J=2.5, 5.6 Hz, 1H), 6.36 (d, J=2.2 Hz, 1H), 6.54 (d, J=4.6 Hz, 1H), 7.78 (s, 1H).

Step 5: Preparation of [3-[3-(2-aminoethyl)pyrazol-1-yl]-7-oxo-1,6-diazabicyclo[3.2.1]oct-3-en-6-yl] hydrogen sulfate (Example 10)

Intermediate (10d) (57 mg, 0.126 mmol) was solubilised in TFA (1 mL) under inert atmosphere at 0° C. After stirring for 15 min, the mixture was dry under a flux of azote. The solid was triturated with ACN, filtered on a PTFE membrane and dried under vacuum in the presence of P$_2$O$_5$ to provide example (10) (25.7 mg, 0.078 mmol, 82%).

MS m/z ([M−H]$^−$) 328.

$^1$H NMR (300 MHz, DMSO-d$_6$): δ(ppm) 2.86 (t, J=7.2 Hz, 2H), 3.10 (t, J=7.2 Hz, 2H), 3.23 (d, J=11.0 Hz, 1H), 3.39 (dd, J=2.5, 11.0 Hz, 1H), 4.21 (s, 2H), 4.35 (dd, J=2.4, 5.6 Hz, 1H), 6.38 (d, J=2.5 Hz, 1H), 6.61 (d, J=5.4 Hz, 1H), 7.72 (br s, 3H), 8.14 (d, J=2.5 Hz, 1H).

Example 11: Synthesis of sodium [3-[3-(2-hydroxyethylcarbamoyl)pyrazol-1-yl]-7-oxo-1,6-diazabicyclo[3.2.1]oct-3-en-6-yl]sulfate

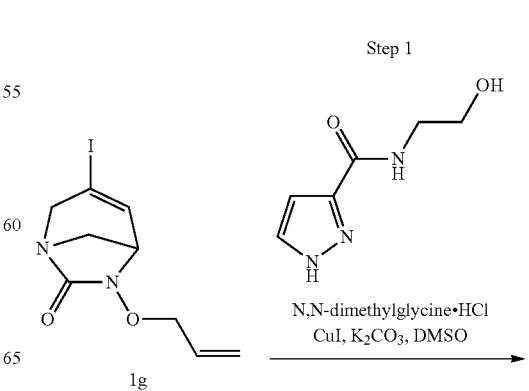

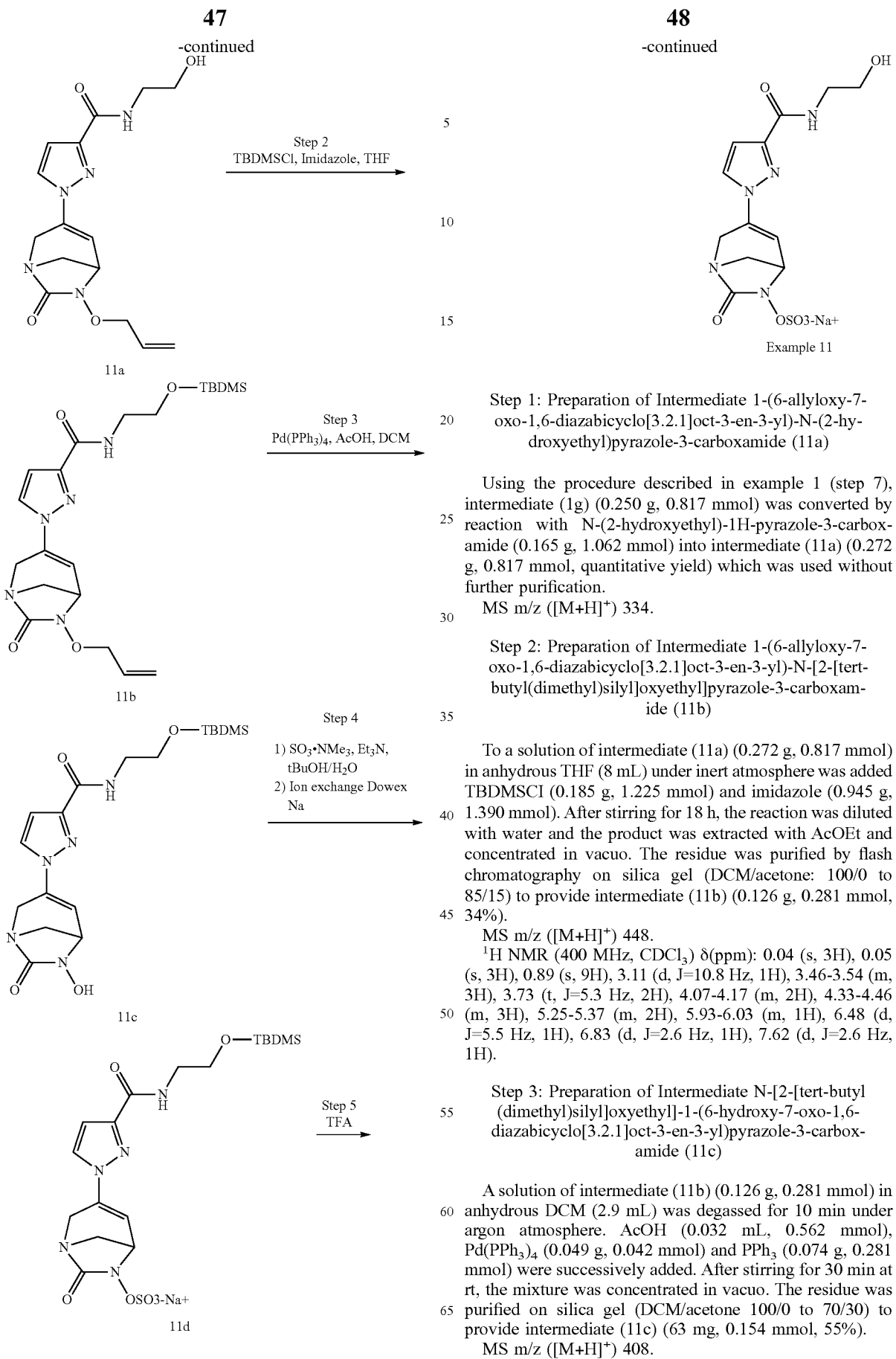

Step 1: Preparation of Intermediate 1-(6-allyloxy-7-oxo-1,6-diazabicyclo[3.2.1]oct-3-en-3-yl)-N-(2-hydroxyethyl)pyrazole-3-carboxamide (11a)

Using the procedure described in example 1 (step 7), intermediate (1g) (0.250 g, 0.817 mmol) was converted by reaction with N-(2-hydroxyethyl)-1H-pyrazole-3-carboxamide (0.165 g, 1.062 mmol) into intermediate (11a) (0.272 g, 0.817 mmol, quantitative yield) which was used without further purification.

MS m/z ([M+H]$^+$) 334.

Step 2: Preparation of Intermediate 1-(6-allyloxy-7-oxo-1,6-diazabicyclo[3.2.1]oct-3-en-3-yl)-N-[2-[tert-butyl(dimethyl)silyl]oxyethyl]pyrazole-3-carboxamide (11b)

To a solution of intermediate (11a) (0.272 g, 0.817 mmol) in anhydrous THF (8 mL) under inert atmosphere was added TBDMSCl (0.185 g, 1.225 mmol) and imidazole (0.945 g, 1.390 mmol). After stirring for 18 h, the reaction was diluted with water and the product was extracted with AcOEt and concentrated in vacuo. The residue was purified by flash chromatography on silica gel (DCM/acetone: 100/0 to 85/15) to provide intermediate (11b) (0.126 g, 0.281 mmol, 34%).

MS m/z ([M+H]$^+$) 448.

$^1$H NMR (400 MHz, CDCl$_3$) δ(ppm): 0.04 (s, 3H), 0.05 (s, 3H), 0.89 (s, 9H), 3.11 (d, J=10.8 Hz, 1H), 3.46-3.54 (m, 3H), 3.73 (t, J=5.3 Hz, 2H), 4.07-4.17 (m, 2H), 4.33-4.46 (m, 3H), 5.25-5.37 (m, 2H), 5.93-6.03 (m, 1H), 6.48 (d, J=5.5 Hz, 1H), 6.83 (d, J=2.6 Hz, 1H), 7.62 (d, J=2.6 Hz, 1H).

Step 3: Preparation of Intermediate N-[2-[tert-butyl(dimethyl)silyl]oxyethyl]-1-(6-hydroxy-7-oxo-1,6-diazabicyclo[3.2.1]oct-3-en-3-yl)pyrazole-3-carboxamide (11c)

A solution of intermediate (11b) (0.126 g, 0.281 mmol) in anhydrous DCM (2.9 mL) was degassed for 10 min under argon atmosphere. AcOH (0.032 mL, 0.562 mmol), Pd(PPh$_3$)$_4$ (0.049 g, 0.042 mmol) and PPh$_3$ (0.074 g, 0.281 mmol) were successively added. After stirring for 30 min at rt, the mixture was concentrated in vacuo. The residue was purified on silica gel (DCM/acetone 100/0 to 70/30) to provide intermediate (11c) (63 mg, 0.154 mmol, 55%).

MS m/z ([M+H]$^+$) 408.

Step 4: Preparation of Intermediate sodium [3-[3-[2-[tert-butyl(dimethyl)silyl]oxyethyl carbamoyl]pyrazol-1-yl]-7-oxo-1,6-diazabicyclo[3.2.1]oct-3-en-6-yl]sulfate (1 d)

To a solution of intermediate (11c) (63 mg, 0.155 mmol) in the mixture of tBuOH/H$_2$O: 1/1 (1.7 mL) was added sulfur trioxide triethylamine complex (26 mg, 0.185 mmol) and Et$_3$N (6 µL, 0.039 mmol). After stirring for 2 h, the mixture was concentrated in vacuo. The residue was purified by flash chromatography on silica gel (DCM/acetone 100/0 to 0/100) to give a solid which are applied on a Dowex sodium form column (Dowex® 50WX8 hydrogen form stored with an aqueous solution of 2N NaOH and washed until neutral pH with water). The fractions containing the desired compound were combined, freezed and lyophilized to provide intermediate (11d) (37 mg, 0.072 mmol, 46%).

MS m/z ([M+H]$^+$) 488.

Step 5: Preparation of sodium [3-[3-(2-hydroxyethylcarbamoyl)pyrazol-1-yl]-7-oxo-1,6-diazabicyclo[3.2.1]oct-3-en-6-yl]sulfate (Example 11)

Intermediate (11d) was solubilized in TFA (0.037 g, 0.072 mmol) at 0° C. under inert atmosphere. After stirring for 1 h, the mixture was dry on nitrogen flux. The residue was triturated in Et$_2$O then purified by flash chromatography on C18-reversed phase silica gel (Water/ACN: 98/2). The fractions containing the desired compound were combined, freezed and lyophilized. The solid was applied on a Dowex sodium form column (Dowex® 50WX8 hydrogen form stored with an aqueous solution of 2N NaOH and washed until neutral pH with water). The fractions containing the desired compound were combined, freezed and lyophilized to provide example (11) (15 mg, 0.029 mmol, 40%).

MS m/z ([M−H]$^-$) 372.

$^1$H RMN (300 MHz, D$_2$O): δ(ppm) 3.44 (d, J=11.2 Hz, 1H), 3.51 (t, J=5.5 Hz, 2H), 3.70 (dd, J=2.8, 11.2 Hz, 1H), 3.74 (t, J=5.5 Hz, 2H), 4.40 (s, 2H), 4.58 (dd, J=2.5, 5.5 Hz, 1H), 6.72 (d, J=5.5 Hz, 1H), 6.83 (d, J=2.7 Hz, 1H), 7.96 (d, J=2.7 Hz, 1H).

Example 12: Synthesis of triethylammonium [3-[3-(hydroxymethyl)pyrazol-1-yl]-7-oxo-1,6-diazabicyclo[3.2.1]oct-3-en-6-yl]sulfate

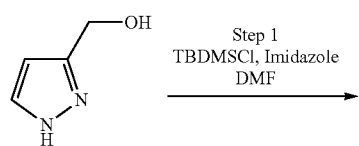

Step 1
TBDMSCl, Imidazole
DMF

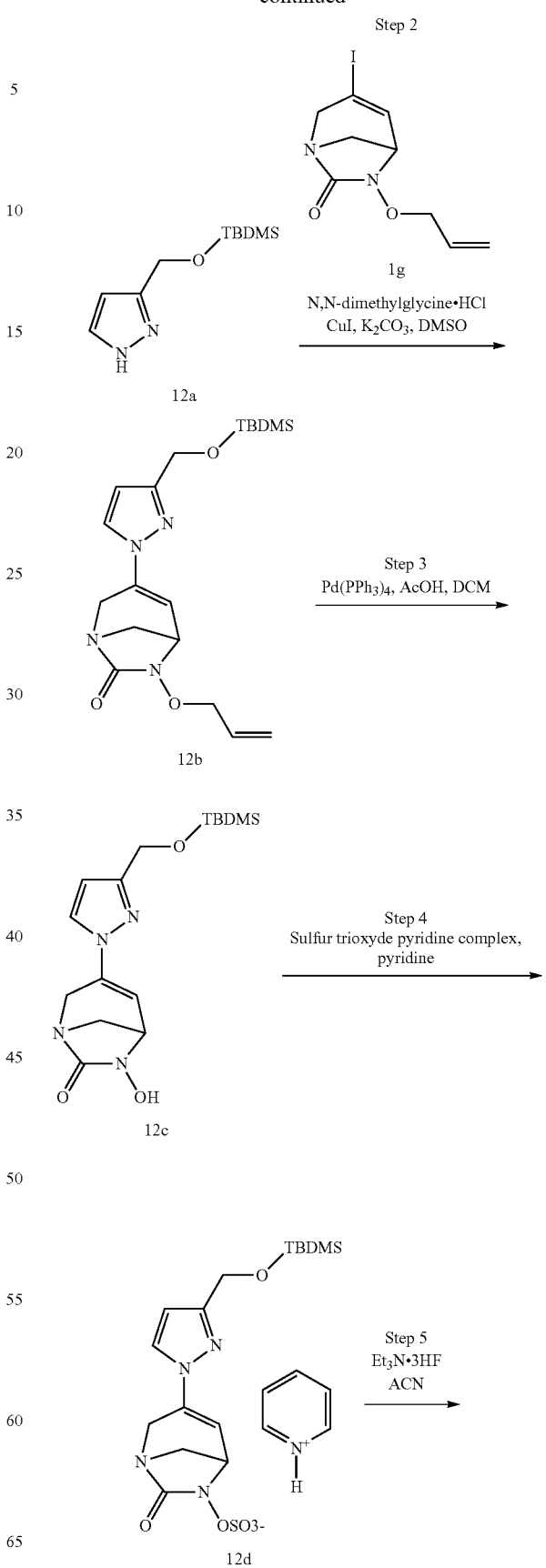

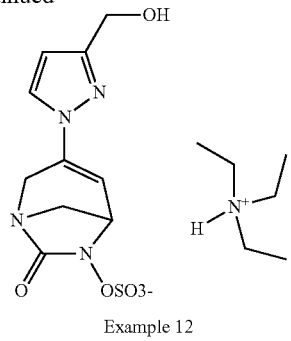

Example 12

Step 1: Preparation of Intermediate 3-(tert-Butyl-dimethyl-silanyloxymethyl)-1H-pyrazole 12a)

To a solution of (1H-pyrazol-3-yl)-methanol (0.150 g, 1.53 mmol) in anhydrous DMF (8 mL) under argon were added TBDMSCI (0.345 g, 2.29 mmol) and imidazole (0.177 g, 2.60 mmol). The mixture was stirred at rt for 18 h. The mixture was extracted with a mixture of EtOAc/Et$_2$O: 1/1 and washed with water to provide intermediate (12a) (0.324 g, 1.53 mmol, quantitative yield) which was used without further purification.

MS m/z ([M+H]$^+$) 213.

Step 2: Preparation of Intermediate 6-allyloxy-3-[3-[[tert-butyl(dimethyl)silyl]oxymethyl]pyrazol-1-yl]-1,6-diazabicyclo[3.2.1]oct-3-en-7-one (12b)

Using the procedure described in example 1 (step 7), intermediate (1g) (0.292 g, 0.95 mmol) was converted by reaction with intermediate (12a) (0.324 g, 1.526 mmol) into intermediate (12b) (0.124 g, 0.317 mmol, 33%) after purification by flash chromatography on silica gel (DCM/acetone 100/0 to 95/5).

MS m/z ([M+H]$^+$) 391.

$^1$H NMR (400 MHz, CDCl$_3$): δ (ppm) 0.08 (s, 6H), 0.90 (s, 9H), 3.13 (d, J=10.7 Hz, 1H), 3.52 (dd, J=2.2, 10.7 Hz, 1H), 4.08 (dd, J=2.4, 5.5 Hz, 1H), 4.17 (dd, J=1.8, 17.6 Hz, 1H), 4.36-4.49 (m, 3H), 4.69 (s, 2H), 5.22-5.44 (m, 2H), 5.96-6.07 (m, 1H), 6.35 (d, J=2.5 Hz, 1H), 6.40 (d, J=5.5 Hz, 1H), 7.52 (d, J=2.5 Hz, 1H).

Step 3: Preparation of Intermediate 3-[3-[[tert-butyl(dimethyl)silyl]oxymethyl]pyrazol-1-yl]-6-hydroxy-1,6-diazabicyclo[3.2.1]oct-3-en-7-one (12c)

Using the procedure described in Example 11 (step 3), intermediate (12b) (124 mg, 0.317 mmol) was converted into intermediate (12c) (111 mg, 0.317 mmol, quantitative yield) after purification on silica gel (DCM/Acetone 100/0 to 70/30).

MS m/z ([M+H]$^+$) 351.

$^1$H NMR (400 MHz, CDCl$_3$) δ(ppm): 0.08 (s, 6H), 0.91 (s, 9H), 3.12 (d, J=10.7 Hz, 1H), 3.50 (dd, J=2.3, 10.7 Hz, 1H), 4.05 (dd, J=2.5, 5.5 Hz, 1H), 4.16 (dd, J=1.8, 17.6 Hz, 1H), 4.39 (d, J=17.6 Hz, 1H), 4.70 (s, 2H), 6.36 (d, J=2.5 Hz, 1H), 6.43 (d, J=5.5 Hz, 1H), 7.54 (d, J=2.5 Hz, 1H).

Step 4: Preparation of Intermediate pyridinium [3-[3-[[tert-butyl(dimethyl)silyl]oxymethyl]pyrazol-1-yl]-7-oxo-1,6-diazabicyclo[3.2.1]oct-3-en-6-yl]sulfate (12d)

To a solution of intermediate (12c) (0.111 g, 0.317 mmol) in anhydrous pyridine (3.2 mL) under inert atmosphere was added sulfur trioxide pyridine complex (0.204 g, 1.28 mmol). After stirring for 18 h, the heterogeneous mixture was concentrated in vacuo. DCM was added to the residue and the solids were filtered off. The filtrate was purified by flash chromatography on silica gel (DCM/acetone 100/0 to 0/100) to provide intermediate (12d) (0.067 g, 0.131 mmol, 41%).

MS m/z ([M+H]$^+$) 431.

$^1$H NMR (300 MHz, CDCl$_3$): δ (ppm) 0.08 (s, 6H), 0.90 (s, 9H), 3.17 (d, J=10.9 Hz, 1H), 3.72 (dd, J=2.1, 10.9 Hz, 1H), 4.19 (dd, J=1.7, 17.9 Hz, 1H), 4.43 (d, J=17.9 Hz, 1H), 4.57 (dd, J=2.5, 5.6 Hz, 1H), 4.67 (s, 2H), 6.34 (d, J=2.5 Hz, 1H), 6.40 (d, J=5.5 Hz, 1H), 7.61 (d, J=2.5 Hz, 1H), 7.96 (dd, J=6.7, 6.7 Hz, 2H), 8.43 (ddd, J=1.5, 6.7, 6.7 Hz, 1H), 9.02 (dd, J=1.5, 6.7 Hz, 2H).

Step 5: Preparation of triethylammonium [3-[3-(hydroxymethyl)pyrazol-1-yl]-7-oxo-1,6-diazabicyclo[3.2.1]oct-3-en-6-yl]sulfate (Example 12)

To a solution of intermediate (12d) (0.067 g, 0.131 mmol) in anhydrous ACN (1.3 mL) under inert atmosphere was added triethylamine trihydrofluoride (0.022 mL, 0.131 mmol). After stirring for 140 min at 40° C., the mixture was concentrated on nitrogen flux. The residue was purified by flash chromatography on silica gel (DCM/acetone 100/0 to 0/100) to provide example (12) (0.031 g, 0.074 mmol, 56%).

MS m/z ([M+H]$^+$) 317.

$^1$H NMR (400 MHz, acetone-d$_6$): δ(ppm) 1.32 (t, J=7.3 Hz, 9H), 3.30 (qd, J=4.8, 14.6 Hz, 6H), 3.33 (d, J=11.0 Hz, 1H), 3.51 (dd, J=2.1, 11.0 Hz, 1H), 4.16-4.28 (m, 2H), 4.34 (d, J=17.6 Hz, 1H), 4.45 (dd, J=2.5, 5.6 Hz, 1H), 4.56 (d, J=5.6 Hz, 2H), 6.42 (d, J=2.5 Hz, 1H), 6.56 (d, J=5.5 Hz, 1H), 7.98 (d, J=2.5 Hz, 1H), 8.44 (br s, 1H).

Example 13: Synthesis of sodium [3-[3-[(2-aminothiazole-5-carbonyl)amino]pyrazol-1-yl]-7-oxo-1,6-diazabicyclo[3.2.1]oct-3-en-6-yl]sulfate

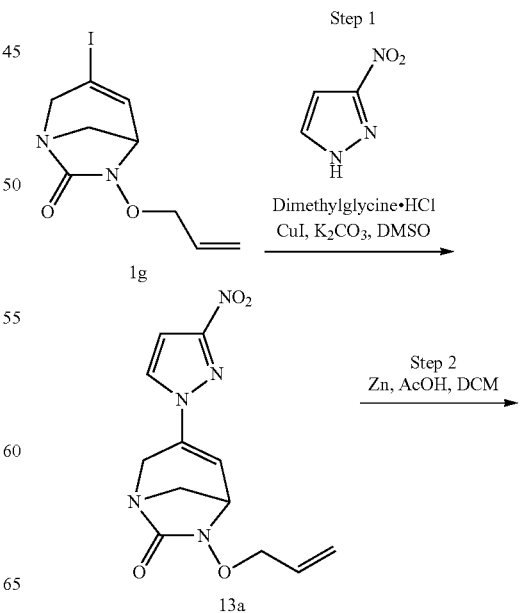

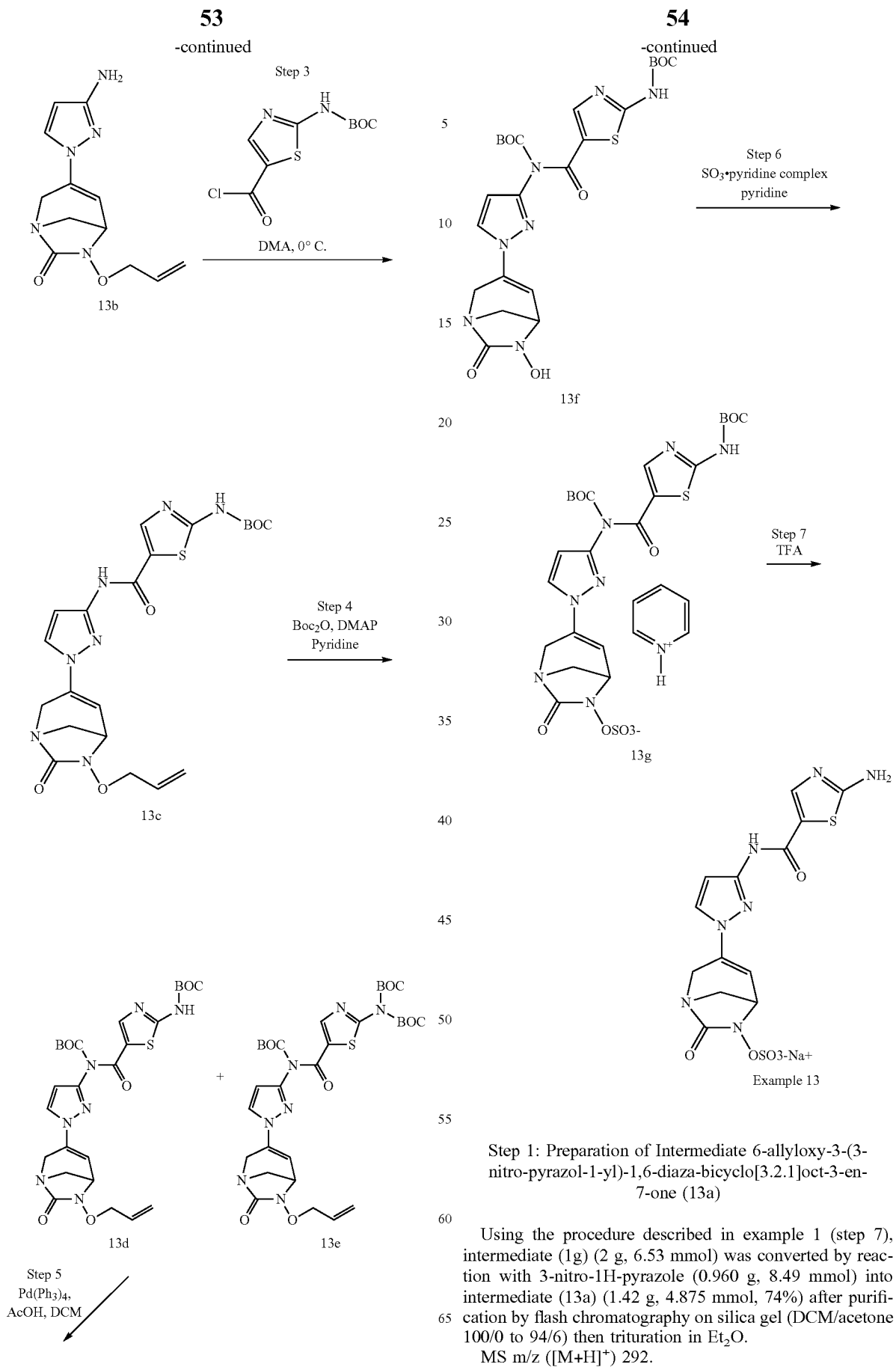
Step 1: Preparation of Intermediate 6-allyloxy-3-(3-nitro-pyrazol-1-yl)-1,6-diaza-bicyclo[3.2.1]oct-3-en-7-one (13a)
Using the procedure described in example 1 (step 7), intermediate (1g) (2 g, 6.53 mmol) was converted by reaction with 3-nitro-1H-pyrazole (0.960 g, 8.49 mmol) into intermediate (13a) (1.42 g, 4.875 mmol, 74%) after purification by flash chromatography on silica gel (DCM/acetone 100/0 to 94/6) then trituration in Et$_2$O.
MS m/z ([M+H]$^+$) 292.

¹H NMR (400 MHz, CDCl₃) δ(ppm): 3.15 (d, J=11.0 Hz, 1H), 3.56 (dd, J=2.1, 11.0 Hz, 1H), 4.16 (dd, J=2.4, 5.5 Hz, 1H), 4.24 (dd, J=1.9, 17.7 Hz, 1H), 4.34-4.49 (m, 3H), 5.28-5.41 (m, 2H), 5.94-6.06 (m, 1H), 6.71 (d, J=5.5 Hz, 1H), 6.98 (d, J=2.7 Hz, 1H), 7.70 (d, J=2.7 Hz, 1H).

Step 2: Preparation of Intermediate 6-allyloxy-3-(3-amino-pyrazol-1-yl)-1,6-diaza-bicyclo[3.2.1]oct-3-en-7-one (13b)

To a solution of intermediate (13a) (1.42 g, 4.875 mmol) in anhydrous DCM (48 mL) at 0° C. were added zinc (3.19 g, 48.75 mmol) and AcOH (2.8 mL, 48.75 mmol). After stirring for 1 h at 0° C., the mixture was filtered on Celite cake and the filtrate immediately poured in cyclohexane at 10° C. The DCM of the mixture was evaporated under a flux of nitrogen and the precipitate was filtered on PTFE membrane to provide intermediate (13b) (1.27 g, 4.87 mmol, quantitative yield).
MS m/z ([M+H]⁺) 262.
¹H NMR (400 MHz, CDCl₃): δ (ppm) 3.11 (d, J=10.7 Hz, 1H), 3.50 (dd, J=2.2, 10.7 Hz, 1H), 3.77 (br s, 2H), 4.03-4.11 (m, 2H), 4.34 (d, J=17.8 Hz, 1H), 4.36-4.48 (m, 2H), 5.27-5.39 (m, 2H), 5.73 (d, J=2.6 Hz, 1H), 5.96-6.06 (m, 1H), 6.28 (d, J=5.5 Hz, 1H), 7.28 (d, J=2.6 Hz, 1H).

Step 3: Preparation of Intermediate tert-butyl N-[5-[[1-[6-allyloxy-7-oxo-1,6-diazabicyclo[3.2.1]oct-3-en-3-yl]pyrazol-3-yl]carbamoyl]thiazol-2-yl]carbamate (13c)

To a solution of intermediate (13b) (0.214 g, 0.818 mmol) in DMA (8 mL) under inert atmosphere at 0° C. was dropwise added a solution of tert-butyl N-(5-chlorocarbonylthiazol-2-yl)carbamate (prepared as described in patent WO2014102759) (0.215 g, 0.818 mmol) in DMA (1.5 mL). After stirring for 35 min, the mixture was concentrated under a flux of nitrogen. The residue was purified by flash chromatography on silica gel (DCM/EtOAc 100/0 to 0/100) and triturated with Et₂O to provide intermediate (13c) (0.399 g, 0.818 mmol, quantitative yield).
MS m/z ([M+H]⁺) 488.
¹H NMR (400 MHz, DMSO-d₆): δ(ppm) 1.50 (s, 9H), 3.27 (d, J=10.8 Hz, 1H), 3.30-3.36 (m, 1H), 4.16-4.29 (m, 3H), 4.39 (d, J=6.0 Hz, 2H), 5.23-5.26 (m, 1H), 5.32-5.40 (m, 1H), 5.90-6.01 (m, 1H), 6.53 (d, J=5.4 Hz, 1H), 6.77 (d, J=2.6 Hz, 1H), 8.08 (d, J=2.6 Hz, 1H), 8.33 (s, 1H), 11.11 (s, 1H), 11.80 (s, 1H).

Step 4: Preparation of Intermediate tert-butyl N-[1-(6-allyloxy-7-oxo-1,6-diazabicyclo[3.2.1]oct-3-en-3-yl)pyrazol-3-yl]-N-[2-(tert-butoxycarbonylamino)thiazole-5-carbonyl]carbamate (13d) and tert-butyl N-[1-(6-allyloxy-7-oxo-1,6-diazabicyclo[3.2.1]oct-3-en-3-yl)pyrazol-3-yl]-N-[2-[bis(tert-butoxycarbonyl)amino]thiazole-5-carbonyl]carbamate (13e)

To a solution of intermediate (13c) (0.030 g, 0.061 mmol) in anhydrous pyridine (0.3 mL) under inert atmosphere at 0° C. were added Boc₂O (0.133 g, 0.61 mmol) and DMAP (0.008 g, 0.006 mmol). After stirring for 1 h, the mixture was concentrated under flux of nitrogen. The residue was purified by flash chromatography on silica gel (DCM/acetone: 100/0 to 90/10) to provide intermediate (13d) (0.014 g, 0.024 mmol, 39%) and intermediate (13e) (0.020 g, 0.029 mmol, 47%).
MS m/z ([M+H]⁺) 588.

Intermediate (13d)

¹H NMR (300 MHz, CDCl₃) δ(ppm): 1.45 (s, 9H), 1.56 (s, 9H), 3.10 (d, J=10.8 Hz, 1H), 3.49 (dd, J=2.7, 10.7 Hz, 1H), 4.06 (dd, J=2.4, 5.6 Hz, 1H), 4.12 (dd, J=1.8, 17.7 Hz, 1H), 4.32 (dd, J=1.1, 17.7 Hz, 1H), 4.33-4.49 (m, 2H), 5.26-5.39 (m, 2H), 5.93-6.08 (m, 1H), 6.40 (d, J=2.6 Hz, 1H), 6.42 (br s, 1H), 7.57 (d, J=2.6 Hz, 1H), 7.88 (s, 1H), 11.03 (br s, 1H).

Intermediate (13e)

¹H NMR (300 MHz, CDCl₃) δ(ppm): 1.45 (s, 9H), 1.47 (s, 9H), 1.53 (s, 9H), 1.56 (s, 9H), 1.59 (s, 9H), 1.61 (s, 9H), 3.10 (2d, J=10.7 Hz, 1H), 3.47-3.54 (m, 1H), 4.04-4.16 (m, 2H), 4.28-4.49 (m, 3H), 5.27-5.40 (m, 2H), 5.93-6.08 (m, 1H), 6.36 (d, J=2.6 Hz, 1H), 6.37 (d, J=2.6 Hz, 1H), 6.42 (d, J=5.6 Hz, 1H), 6.46 (d, J=5.6 Hz, 1H), 7.55 (d, J=2.6 Hz, 1H), 7.60 (d, J=2.6 Hz, 1H), 7.81 (s, 1H), 7.93 (s, 1H).

Step 5: Preparation of Intermediate tert-butyl N-[1-(6-hydroxy-7-oxo-1,6-diazabicyclo[3.2.1]oct-3-en-3-yl)pyrazol-3-yl]-N-[2-(tert-butoxycarbonylamino)thiazole-5-carbonyl]carbamate (13f)

Using the procedure described in example 7 (step 2), intermediate (13d) (132 mg, 0.225 mmol) was converted into intermediate (13f) (0.59 mg, 0.108 mmol, 48%) after purification on silica gel (DCM/Acetone 100/0 to 70/30).
MS m/z ([M+H]⁺) 548.

Step 6: Preparation of Intermediate pyridinium [3-[3-[tert-butoxycarbonyl-[2-(tert-butoxycarbonylamino)thiazole-5-carbonyl]amino]pyrazol-1-yl]-7-oxo-1,6-diazabicyclo[3.2.1]oct-3-en-6-yl]sulfate (13q)

To a solution of intermediate (13f) (0.224 g, 0.346 mmol) in anhydrous pyridine (3.5 mL) under inert atmosphere was added sulfur trioxide pyridine complex (0.223 g, 1.40 mmol). After stirring for 16 h, the heterogeneous mixture was concentrated in vacuo. DCM was added to the residue and the solids were filtered off. The filtrate was purified by flash chromatography on silica gel (DCM/acetone 100/0 to 0/100) to provide intermediate (13g) (0.141 g, 0.199 mmol, 57%).
MS m/z ([M+H]⁺) 628.
¹H NMR (400 MHz, acetone-d₆) δ(ppm): 1.45 (s, 9H), 1.54 (s, 9H), 3.31 (d, J=10.8 Hz, 1H), 3.48 (dd, J=2.2, 10.8 Hz, 1H), 4.17 (dd, J=1.8, 17.6 Hz, 1H), 4.22 (dd, J=1.2, 17.6 Hz, 1H), 4.43 (dd, J=2.6, 5.6 Hz, 1H), 6.53 (d, J=2.7 Hz, 1H), 6.60 (d, J=5.6 Hz, 1H), 7.79 (s, 1H), 8.15-8.20 (m, 1H), 8.68-8.73 (m, 2H), 9.06 (dd, J=1.6, 6.8 Hz, 2H), 10.69 (br s, 1H).

Step 7: Preparation of sodium [3-[3-[(2-aminothiazole-5-carbonyl)amino]pyrazol-1-yl]-7-oxo-1,6-diazabicyclo[3.2.1]oct-3-en-6-yl]sulfate (Example 13)

A solution of intermediate (13g) (0.064 g, 0.090 mmol) in TFA (0.5 mL) under inert atmosphere was stirred at −14° C. for 30 min then at 0° C. for 4 h. The mixture was concentrated under a flux of nitrogen. The solid was triturated with Et₂O and ACN to provide a yellow solid which was applied on a Dowex sodium form column (Dowex® 50WX8 hydrogen form stored with an aqueous solution of 2N NaOH and washed until neutral pH with water). The fractions containing the desired compound were combined, freezed and lyophilized. The solid was purified by flash chromatography on C18-reversed phase silica gel (Water to ACN). The fractions containing the desired compound were combined, freezed and lyophilized to provide example (13) (2.7 mg, 0.006 mmol, 6%).

MS m/z ([M−H]⁻) 428.

¹H NMR (300 MHz, D₂O) δ(ppm): 3.45 (d, J=11.2 Hz, 1H), 3.71 (d, J=10.8 Hz, 1H), 4.36 (s, 2H), 4.58 (dd, J=2.1, 5.7 Hz, 1H), 6.55 (d, J=5.7 Hz, 1H), 6.62 (d, J=2.7 Hz, 1H), 7.73 (s, 1H), 7.79 (d, J=2.7 Hz, 1H).

Example 14: Synthesis of sodium (7-oxo-3-(4-fluoropyrazol-1-yl)-1,6-diazabicyclo[3.2.1]oct-3-en-6-yl) sulfate

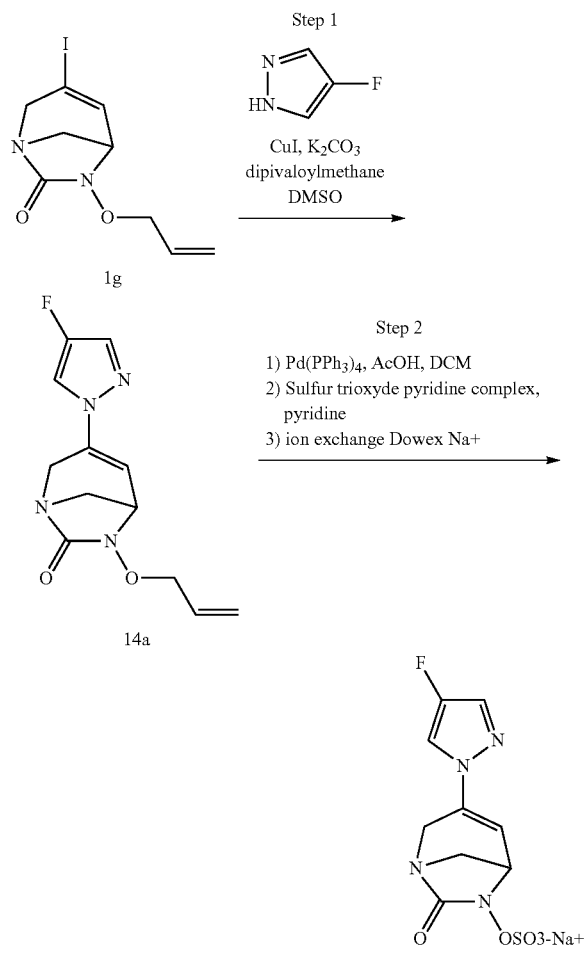

Step 1: Preparation of Intermediate 6-allyloxy-3-(4-fluoropyrazol-1-yl)-1,6-diazabicyclo[3.2.1]oct-3-en-7-one (14a)

Using the procedure described in example 2 (step 1a), intermediate (1g) (250 mg, 0.817 mmol) was converted by reaction with 4-fluoro-1H-pyrazole (84.4 mg, 0.980 mmol) into intermediate (14a) (179 mg, 0.678 mmol, 83%) as an oil after purification by flash chromatography on silica gel (cyclohexane/EtOAc: 100/0 to 50/50).

MS m/z ([M+H]⁺) 264, ([2M+H]⁺) 529.

¹H NMR (300 MHz, CDCl₃): δ (ppm) 3.12 (d, J=10.9 Hz, 1H), 3.52 (ddd, J=11.0, 2.9, 1.1 Hz, 1H), 4.09 (dd, J=5.6, 2.8 Hz, 1H), 4.16 (dd, J=17.7, 1.9 Hz, 1H), 4.36-4.50 (m, 3H), 5.29-5.40 (m, 2H), 5.95-6.08 (m, 1H), 6.31-6.33 (m, 1H), 7.42 (dd, J=4.2, 0.7 Hz, 1H), 7.51 (dd, J=4.8, 0.7 Hz, 1H).

Step 2: Preparation of sodium (7-oxo-3-(4-fluoropyrazol-1-yl)-1,6-diazabicyclo[3.2.1]oct-3-en-6-yl) sulfate (Example 14)

Using the procedure described in example 2 (step 2), intermediate (14a) (179 mg, 0.678 mmol) was converted into example (14) (115 mg, 0.352 mmol, 52%) as a white solid after lyophilization.

MS m/z ([M−H]⁻) 303.

¹H-NMR (300 MHz, D₂O): δ(ppm) 3.44 (dd, J=11.3, 0.7 Hz, 1H), 3.69 (ddd, J=11.3, 2.9, 1.1 Hz, 1H), 4.35 (d, J=1.5 Hz, 2H), 4.58-4.60 (m, 1H), 6.53-6.57 (m, 1H), 7.62 (dd, J=4.0, 0.7 Hz, 1H), 7.93 (dd, J=4.4, 0.8 Hz, 1H).

¹⁹F-NMR (282 MHz, D₂O): δ(ppm) −174.56 (t, J=4.2 Hz, 1F).

Example 15: Synthesis of sodium and 2,2,2-trifluoroacetate [3-(4-methyleneammoniumpyrazol-1-yl)-7-oxo-1,6-diazabicyclo[3.2.1]oct-3-en-6-yl]sulfate

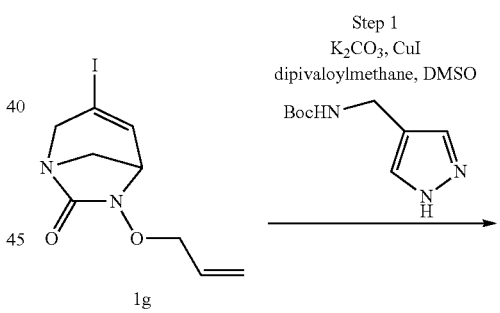

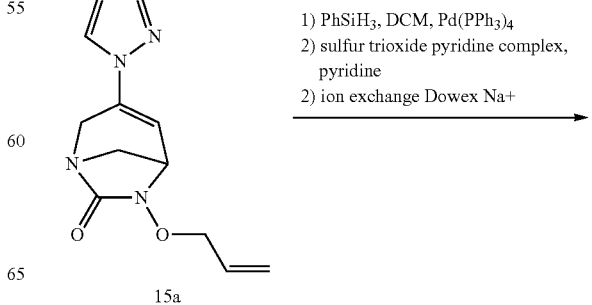

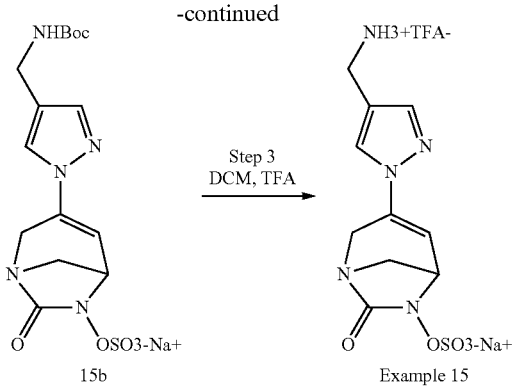

Step 1: Preparation of Intermediate tert-butyl N—[N-(6-allyloxy-7-oxo-1,6-diazabicyclo[3.2.1]oct-3-en-3-yl)pyrazol-4-ylmethyl]carbamate (15a)

Using the procedure described in example 2 (step 1a), intermediate (1g) (500 mg, 1.63 mmol) was converted by reaction with tert-butyl N-(1H-pyrazol-4-ylmethyl)carbamate (387 mg, 1.96 mmol) into intermediate (15a) (362 mg, 0.869 mmol, 53%) as a yellow oil after purification by flash chromatography on silica gel (cyclohexane/EtOAc: 100/0 to 50/50).

MS m/z ([M+H]$^+$) 376.
$^1$H NMR (300 MHz, CDCl$_3$) δ 1.45 (s, 9H), 3.13 (d, J=10.8 Hz, 1H), 3.53 (dd, J=10.8, 2.3 Hz, 1H), 4.07-4.21 (m, 5H), 4.38-4.46 (m, 2H), 4.74 (br s, 1H), 5.28-5.40 (m, 2H), 5.95-6.08 (m, 1H), 6.40 (d, J=5.5 Hz, 1H), 7.50 (s, 1H), 7.56 (s, 1H).

Step 2: Preparation of Intermediate sodium [3-[4-[(tert-butoxycarbonylamino) methyl]pyrazol-1-yl]-7-oxo-1,6-diazabicyclo[3.2.1]oct-3-en-6-yl]sulfate (15b)

Under inert atmosphere, PhSiH$_3$ (238 µL, 1.93 mmol) and Pd(PPh$_3$)$_4$ (45 mg, 0.039 mmol) were added to a solution of intermediate (15a) (362 mg, 0.869 mmol) in anhydrous DCM (35 mL). The reaction mixture was stirred at rt for 2 h. Pyridine (35 mL) and sulfur trioxide pyridine complex (769 mg, 4.83 mmol) were added to reaction mixture. The resulting suspension was protected from light and stirred overnight until the reaction was completed. The reaction mixture was concentrated under reduced pressure, then diluted with DCM and filtered. The filtrate was concentrated under reduced pressure and then purified by flash chromatography on silica gel (DCM/acetone: 100/0 to 80/20). Fractions containing the expected intermediate were combined and concentrated to give a brown solid. This solid was dissolved in a minimum of a mixture H$_2$O/ACN and converted after ion exchange with Dowex sodium form column (Dowex® 50WX8 hydrogen form stored with an aqueous solution of 2N NaOH and washed until neutral pH with H$_2$O) to intermediate (15b) (142 mg, 0.300 mmol, 31%) as a brown solid.

MS m/z ([M–H]$^-$) 414.
$^1$H NMR (300 MHz, D$_2$O) δ 1.41 (s, 9H), 3.43 (d, J=11.3 Hz, 1H), 3.67 (dd, J=11.3, 2.6 Hz, 1H), 4.12-4.15 (m, 2H), 4.32-4.36 (m, 2H), 4.55 (dd, J=5.7, 2.6 Hz, 1H), 6.55 (d, J=5.7 Hz, 1H), 7.62 (s, 1H), 7.84 (s, 1H).

Step 3: Preparation of sodium and 2,2,2-trifluoroacetate [3-(4-methyleneammoniumpyrazol-1-yl)-7-oxo-1,6-diazabicyclo[3.2.1]oct-3-en-6-yl]sulfate Example 15

Intermediate (15b) (10 mg, 0.021 mmol) was dissolved in a mixture of DCM/TFA (2:1) (0.5 mL). The mixture was stirred at 0° C. for 30 min. The residue was triturated in Et$_2$O and DCM. The solid was diluted in H$_2$O and lyophilized to afford example (15) (1.4 mg, 0.003 mmol, 12%) as a white solid.

MS m/z ([M–H]$^-$) 314.
$^1$H NMR (400 MHz, D$_2$O) δ3.46 (d, J=11.3 Hz, 1H), 3.70 (dd, J=11.3, 2.0 Hz, 1H), 4.12-4.18 (m, 2H), 4.36-4.40 (m, 2H), 4.59 (dd, J=5.7, 2.7 Hz, 1H), 6.66 (d, J=5.7 Hz, 1H), 7.78 (s, 1H), 8.08 (s, 1H).
$^{19}$F NMR (367 MHz, D$_2$O) δ−75.54 (s, 3F).

Example 16: Synthesis of sodium [7-oxo-3-(4-sulfamoylpyrazol-1-yl)-1,6-diazabicyclo[3.2.1]oct-3-en-6-yl]sulfate

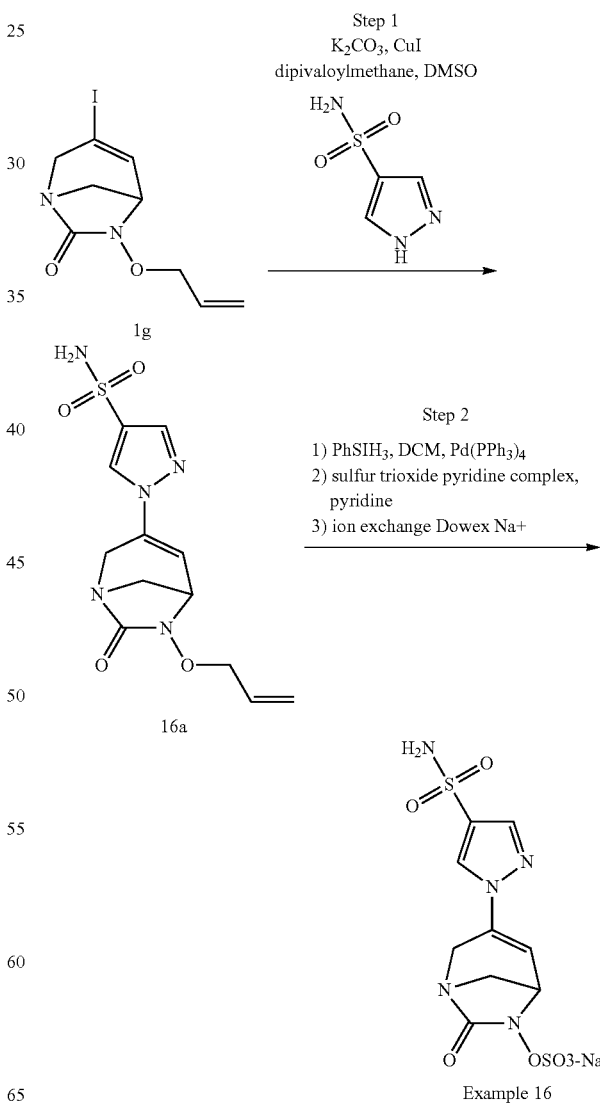

Step 1: Preparation of Intermediate N-(6-allyloxy-7-oxo-1,6-diazabicyclo[3.2.1]oct-3-en-3-yl)pyrazole-4-sulfonamide (16a)

Using the procedure described in example 2 (step 1a), intermediate (1g) (400 mg, 1.31 mmol) was converted by reaction with 1H-pyrazole-4-sulfonamide (231 mg, 1.57 mmol) into intermediate (16a) (362 mg, 0.869 mmol, 53%) as a yellow oil after purification by flash chromatography on silica gel (DCM/Acetone: 100/0 to 80/20).

MS m/z ([M+H]$^+$) 326.
MS m/z ([M−H]$^−$) 324.
$^1$H NMR (400 MHz, CDCl$_3$) δ3.15 (d, J=10.9 Hz, 1H), 3.53 (dd, J=10.9, 2.0 Hz, 1H), 4.13-4.18 (m, 2H), 4.35 (d, J=17.4 Hz, 1H), 4.37-4.48 (m, 2H), 5.30-5.34 (m, 2H), 5.33-5.40 (m, 2H), 5.95-6.05 (m, 1H), 6.62 (d, J=4.9 Hz, 1H), 7.85 (s, 1H), 8.10 (s, 1H).

Step 2: Preparation of sodium [7-oxo-3-(4-sulfamoylpyrazol-1-yl)-1,6-diazabicyclo[3.2.1]oct-3-en-6-yl]sulfate (Example 16)

Under inert atmosphere, PhSiH$_3$ (99 μL, 0.805 mmol) and Pd(PPh$_3$)$_4$ (19 mg, 0.016 mmol) were added to a solution of intermediate (16a) (131 mg, 0.403 mmol) in anhydrous DCM (13 mL). The reaction mixture was stirred at rt for 2 h. The resulting suspension was filtered to give the intermediate N-(6-hydroxy-7-oxo-1,6-diazabicyclo[3.2.1]oct-3-en-3-yl)pyrazole-4-sulfonamide as a brown solid. Under inert atmosphere, this intermediate N-(6-hydroxy-7-oxo-1,6-diazabicyclo[3.2.1]oct-3-en-3-yl)pyrazole-4-sulfonamide (31 mg, 0.109 mmol) was diluted in anhydrous pyridine (4 mL). Sulfur trioxide pyridine complex (87 mg, 0.543 mmol) was added to the reaction mixture. The resulting suspension was protected from light and stirred overnight until the reaction was completed. The reaction mixture was concentrated and the residue was purified by flash chromatography on C18-reversed phase silica gel (H$_2$O/ACN: 100/0 to 98/2). Fractions containing the expected compound were assembled and converted after ion exchange with Dowex sodium form column (Dowex® 50WX8 hydrogen form stored with an aqueous solution of 2N NaOH and washed until neutral pH with H$_2$O) to example 16 (1.4 mg, 0.003 mmol, 3%) as a white solid.

MS m/z ([M+H]$^+$) 366.
MS m/z ([M−H]$^−$) 364.
$^1$H NMR (400 MHz, D$_2$O) δ3.48 (d, J=11.4 Hz, 1H), 3.72 (dd, J=11.4, 2.7 Hz, 1H), 4.37 (d, J=17.5 Hz, 1H), 4.43 (dd, J=17.5, 1.9 Hz, 1H), 4.63 (dd, J=5.6, 2.7 Hz, 1H), 6.82 (d, J=5.7 Hz, 1H), 8.05 (s, 1H), 8.51 (s, 1H).

Example 17: Synthesis of sodium [3-(3-carbonitrilepyrazol-1-yl)-7-oxo-1,6-diazabicyclo[3.2.1]oct-3-en-6-yl]sulfate Step 1

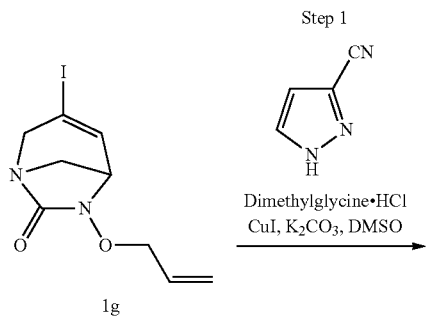

Dimethylglycine•HCl
CuI, K$_2$CO$_3$, DMSO

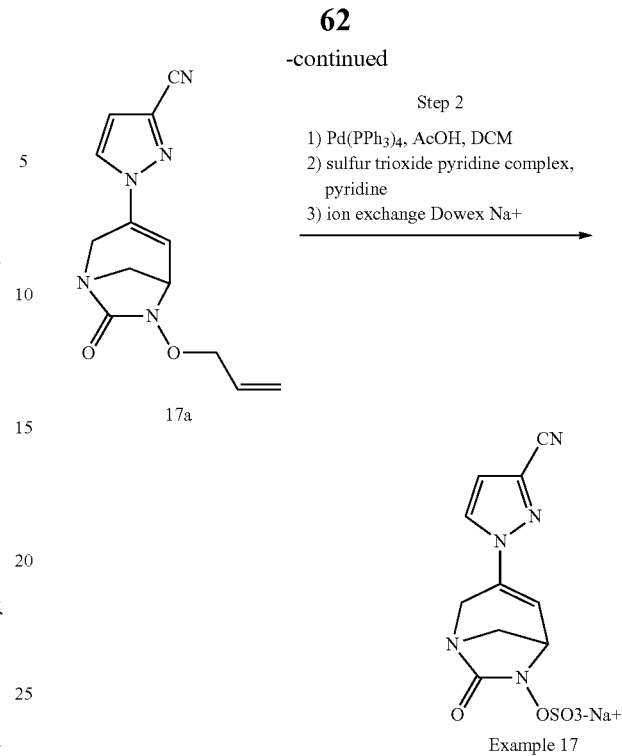

Example 17

Step 1: Preparation of Intermediate N-(6-allyloxy-7-oxo-1,6-diazabicyclo[3.2.1]oct-3-en-3-yl)-3-carbonitrilepyrazole (17a)

Under inert atmosphere, intermediate (1g) (200 mg, 0.653 mmol) was diluted with anhydrous DMSO (6.5 mL). NH-pyrazole-3-carbonitrile (122 mg, 1.31 mmol), dry K$_2$CO$_3$ (271 mg, 1.96 mmol), CuI (12 mg, 0.065 mmol) and N,N-dimethylglycine hydrochloride (14 mg, 0.098 mmol) were successively added. The blue suspension was heated at 100° C. After 18 h, the mixture was diluted in H$_2$O (10 mL) and EtOAc (20 mL) was added. The aqueous layer was extracted with EtOAc (3×20 mL) and the combined organic layers were dried over Na$_2$SO$_4$, filtered and concentrated. The crude compound was purified by flash chromatography on silica gel (cyclohexane/EtOAc: 100/0 to 50/50) to give intermediate (17a) (66 mg, 0.243 mmol, 37%) as a yellow oil.

Using the procedure described in example 1 (step 7), intermediate (1g) (0.2 g, 0.653 mmol) was converted by reaction with NH-pyrazole-3-carbonitrile (122 mg, 1.31 mmol) into intermediate (17a) (66 mg, 0.243 mmol, 37%) as a yellow oil after purification by flash chromatography on silica gel (cyclohexane/EtOAc 100/0 to 50/50).

MS m/z ([M+H]$^+$) 272.
MS m/z ([M−H]$^−$) 270.
$^1$H NMR (400 MHz, CDCl$_3$) 53.14 (d, J=10.9 Hz, 1H), 3.56 (ddd, J=10.9, 2.7, 1.1 Hz, 1H), 4.14 (dd, J=5.6, 2.7 Hz, 1H), 4.20 (dd, J=17.8, 2.0 Hz, 1H), 4.38-4.49 (m, 3H), 5.32 (ddd, J=10.3, 1.4, 1.1 Hz, 1H), 5.38 (ddd, J=17.2, 1.4, 1.1 Hz, 1H), 5.96-6.08 (m, 1H), 6.62 (d, J=5.5 Hz, 1H), 6.75 (d, J=2.7 Hz, 1H), 7.70 (d, J=2.7 Hz, 1H).

Step 2: Preparation of sodium [3-(3-carbonitrilepyrazol-1-yl)-7-oxo-1,6-diazabicyclo[3.2.1]oct-3-en-6-yl]sulfate (Example 17)

Under inert atmosphere, intermediate (17a) (66 mg, 0.243 mmol) was diluted in anhydrous DCM (2.5 mL). AcOH (28

μL, 0.487 mmol) and Pd(PPh$_3$)$_4$ (141 mg, 0.122 mmol) were successively added. The reaction mixture was stirred at rt for 2 h. The mixture was concentrated and purified on silica gel (DCM/acetone: 100/0 to 70/30) to provide the intermediate N-(6-hydroxy-7-oxo-1,6-diazabicyclo[3.2.1]oct-3-en-3-yl)-3-carbonitrilepyrazole. Under inert atmosphere, this intermediate N-(6-hydroxy-7-oxo-1,6-diazabicyclo[3.2.1]oct-3-en-3-yl)-3-carbonitrilepyrazole was diluted in anhydrous pyridine (2.5 mL). Sulfur trioxide pyridine complex (194 mg, 1.21 mmol) was added to the reaction mixture. The resulting suspension was protected from light and stirred overnight until the reaction was completed. The reaction mixture was concentrated then dissolved in a minimum of H$_2$O (and a few of ACN) and converted after ion exchange with Dowex sodium form column (Dowex® 50WX8 hydrogen form stored with an aqueous solution of 2N NaOH and washed until neutral pH with H$_2$O) to example (17) (12.5 mg, 0.038 mmol, 15%) as a white solid.

MS m/z ([M+H]$^+$) 312.

MS m/z ([M−H]$^−$) 310.

$^1$H NMR (400 MHz, D$_2$O) δ3.47 (d, J=11.4 Hz, 1H), 3.71 (dd, J=11.4, 2.8 Hz, 1H), 4.37 (d, J=17.4 Hz, 1H), 4.42 (dd, J=17.4, 1.4 Hz, 1H), 4.62 (dd, J=5.7, 2.8 Hz, 1H), 6.82 (d, J=5.6 Hz, 1H), 6.97 (d, J=2.7 Hz, 1H), 8.11 (d, J=2.7 Hz, 1H).

Example 18: Synthesis of sodium [7-oxo-3-(3-fluoropyrazol-1-yl)-1,6-diazabicyclo[3.2.1]oct-3-en-6-yl]sulfate Step 1

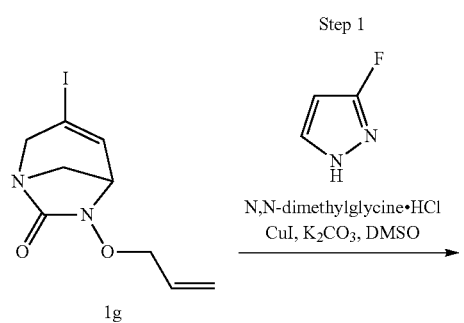

1g

N,N-dimethylglycine·HCl
CuI, K$_2$CO$_3$, DMSO

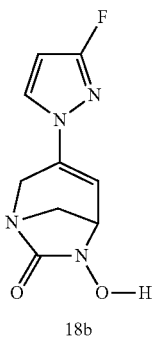

Step 2
PhSiH$_3$, Pd(PPh$_3$)$_4$, DCM

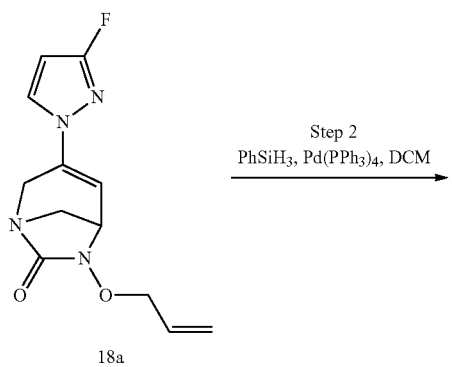

18a

-continued

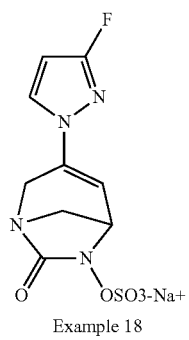

18b

Step 3
1) SO$_3$·pyridine complex, pyridine
2) ion exchange Dowex Na

Example 18

Step 1: Preparation of Intermediate 6-allyloxy-3-(3-fluoropyrazol-1-yl)-1,6-diazabicyclo[3.2.1]oct-3-en-7-one (18a)

Using the procedure described in example 1 (step 7), intermediate (1g) (0.26 g, 0.85 mmol) was converted by reaction with 3-fluoro-1H-pyrazole (110 mg, 1.27 mmol) into intermediate (18a) (186 mg, 0.70 mmol, 82%) as a yellow oil after purification by flash chromatography on silica gel (petroleum ether/acetone: 100/0 to 0/100).

MS m/z ([M+H]$^+$) 265.

$^1$H NMR (400 MHz, acetone) 53.27 (d, J=10.9 Hz, 1H), 3.43 (ddd, J=0.6, 2.6, 10.9 Hz, 1H), 4.17 (dd, J=17.4, 1.8 Hz, 1H), 4.21-4.30 (m, 2H), 4.36-4.45 (m, 2H), 5.20-5.26 (m, 1H), 5.32-5.39 (m, 1H), 5.95-6.06 (m, 1H), 6.10 (dd, J=5.8, 2.7 Hz, 1H), 6.57 (d, J=5.6 Hz, 1H), 7.91 (t, J=2.6 Hz, 1H).

Step 2: Preparation of Intermediate 3-(3-fluoropyrazol-1-yl)-6-hydroxy-1,6-diazabicyclo[3.2.1]oct-3-en-7-one (18b)

Using the procedure described in example 9 (step 2), intermediate (18a) (190 mg, 0.73 mmol) was converted into intermediate (18b) (56 mg, 0.25 mmol, 34%) after purification on silica gel (DCM/acetone: 100/0 to 0/100).

MS m/z ([M+H]$^+$) 225.

Step 3: Preparation of sodium [7-oxo-3-(3-fluoropyrazol-1-yl)-1,6-diazabicyclo[3.2.1]oct-3-en-6-yl]sulfate (Example 18)

To a solution of intermediate (18b) (56 mg, 0.25 mmol) in anhydrous pyridine (5.68 mL) under inert atmosphere was added sulfur trioxide pyridine complex (193 mg, 3.27 mmol). The resulting suspension was stirred overnight. The mixture was concentrated under a flux of argon. The residue was dissolved in a minimum of H$_2$O/ACN (1:1) and passed through an ion exchange column charged with Dowex sodium form column (Dowex® 50WX8 hydrogen form stored with an aqueous solution of 2N NaOH and washed until neutral pH with H₂O). The fractions containing the desired compound were lyophilized and the residue was purified by flash chromatography on C18-reversed phase silica gel (H₂O/MeCN 99/1) to provide example (18) (19 mg, 0.06 mmol, 8%) as a white solid.

MS m/z ([M−H]⁻) 303.

$^1$H NMR (400 MHz, D₂O) δ3.43 (d, J=11.3 Hz, 1H), 3.68 (dd, J=11.3, 2.4 Hz, 1H), 4.26-4.36 (m, 2H), 4.56 (dd, J=5.7, 2.7 Hz, 1H), 6.11 (dd, J=5.7, 2.7 Hz, 1H), 6.54 (d, J=4.6 Hz, 1H), 7.78 (t, J=2.7 Hz, 1H).

Example 19: Synthesis of sodium [3-(3-carbamoylpyrazol-1-yl)-7-oxo-1,6-diazabicyclo[3.2.1]oct-3-en-6-yl]sulfate

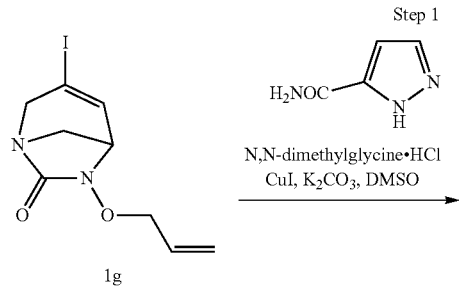

Step 1

1g

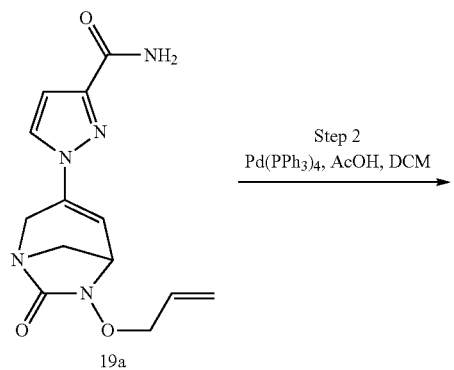

Step 2
Pd(PPh₃)₄, AcOH, DCM

19a

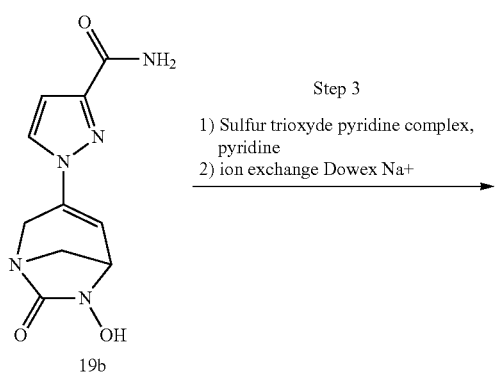

Step 3
1) Sulfur trioxyde pyridine complex, pyridine
2) ion exchange Dowex Na+

19b

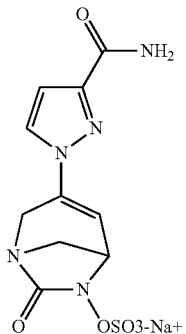

Example 19

Step 1: Preparation of Intermediate 1-(6-allyloxy-7-oxo-1,6-diazabicyclo[3.2.1]oct-3-en-3-yl)pyrazole-3-carboxamide (19a)

Using the procedure described in example 1 (step 7), intermediate (1g) (100 mg, 0.33 mmol) was converted by reaction with 1H-pyrazole-3-carboxamide (44 mg, 0.39 mmol) into intermediate (19a) (30 mg, 0.10 mmol, 31%) as a white solid after purification by recrystallization in acetone.

MS m/z ([M+H]⁺) 290.

$^1$H NMR (400 MHz, DMSO-d₆) δ3.25-3.36 (m, 2H), 4.16-4.35 (m, 3H), 4.39 (d, J=6.1 Hz, 2H), 5.27 (d, J=10.6, 1H), 5.32-5.42 (m, 1H), 5.92-6.00 (m, 1H), 6.63-6.84 (m, 2H), 7.36 (s, 1H), 7.64 (s, 1H), 8.23 (d, J=2.6 Hz, 1H).

Step 2: Preparation of Intermediate 1-(6-hydroxy-7-oxo-1,6-diazabicyclo[3.2.1]oct-3-en-3-yl)pyrazole-3-carboxamide (19b)

To a degassed suspension of intermediate (19a) (26 mg, 0.09 mmol) in anhydrous DCM (1 mL) were added PhSiH₃ (22 µL, 0.18 mmol) and Pd(PPh₃)₄ (4 mg, 0.0034 mmol). The mixture was stirred at rt for 5 h and the solid filtered. The solid was washed with iPr₂O to provide pure intermediate (19b) (19 mg, 0.076 mmol, 86%).

$^1$H NMR (400 MHz, DMSO-d₆) δ3.23 (d, J=10.8 Hz, 1H), 3.37 (dd, J=10.8, 2.8 Hz, 1H), 4.05 (dd, J=5.6, 2.6 Hz, 1H), 4.18 (dd, J=17.6, 1.9 Hz, 1H), 4.27 (d, J=17.6 Hz, 1H), 6.69-6.86 (m, 2H), 7.36 (s, 1H), 7.63 (s, 1H), 8.23 (d, J=2.6 Hz, 1H), 9.68 (s, 1H).

Step 3: Preparation of sodium [3-(3-carbamoylpyrazol-1-yl)-7-oxo-1,6-diazabicyclo[3.2.1]oct-3-en-6-yl]sulfate (Example 19)

To a solution of intermediate (19b) (14 mg, 0.056 mmol) in anhydrous pyridine (0.4 mL) under inert atmosphere was added sulfur trioxide pyridine complex (45 mg, 0.28 mmol). After stirring for 18 h at rt, the heterogeneous mixture was concentrated in vacuo. THF was added to the residue and the solids were filtered. The solid was triturated in acetonitrile and the filtrate was then concentrated in vacuo to provide a solid which solubilized in a mixture of water and acetonitrile and applied on a Dowex sodium form column (Dowex® 50WX8 hydrogen form stored with an aqueous solution of 2N NaOH and washed until neutral pH with water). The fractions containing the desired compound were combined, freezed and lyophilized. The solid was then purified by column chromatography on C18-reversed silica gel (water/acetonitrile 98/2 to 0/100) to provide example (19) (4.1 mg, 0.011 mmol, 20%).

MS m/z ([M−H]⁻) 328

$^1$H NMR (400 MHz, D$_2$O) δ 1.89 (s, 1H), 3.45 (d, J=11.3 Hz, 1H), 3.61-3.75 (m, 1H), 4.31-4.49 (m, 2H), 4.58 (dd, J=5.7, 2.7 Hz, 1H), 6.74 (d, J=5.6 Hz, 1H), 6.85 (d, J=2.7 Hz, 1H), 7.99 (d, J=2.7 Hz, 1H).

Example 20: Synthesis of sodium [7-oxo-3-[4-(N-morpholine)-pyrazol-1-yl)]-1,6-diaza-bicyclo[3.2.1]oct-3-en-6-yl]sulfate

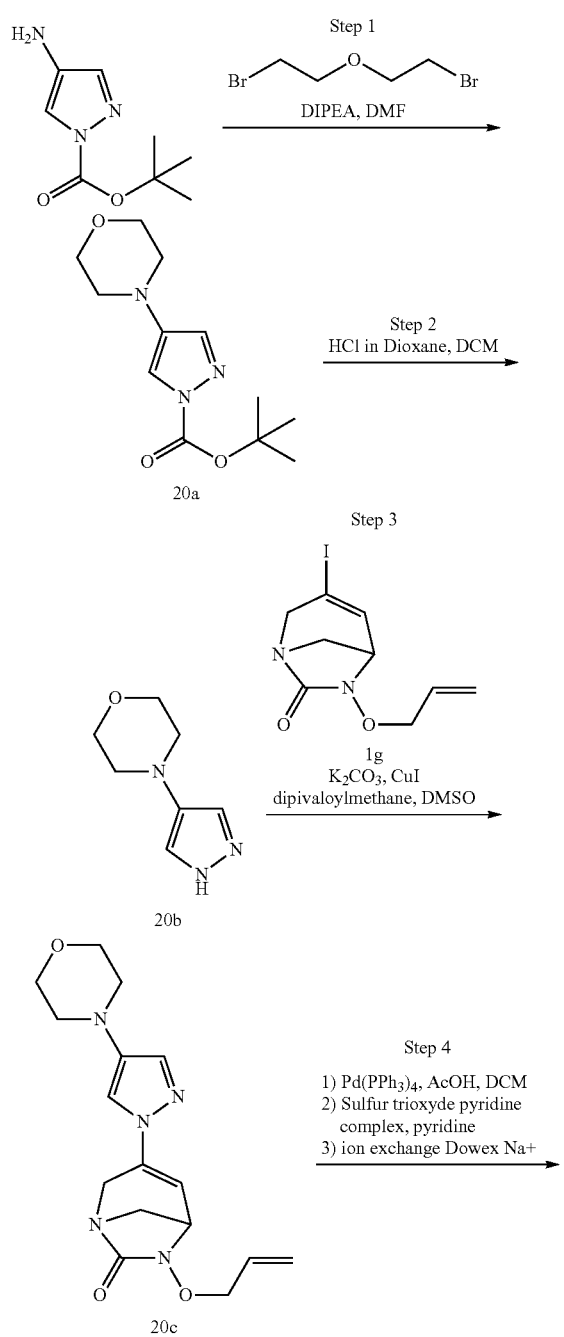

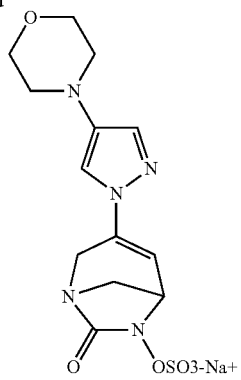

Example 20

Step 1: Preparation of Intermediate tert-butyl 4-(N-morpholine)-1H-pyrazole-1-carboxylate (20a)

To a stirred mixture of tert-butyl 4-amino-1H-pyrazole-1-carboxylate (512 mg, 2.795 mmol) and bis(2-bromoethyl) ether (778 mg, 3.354 mmol) in DMF (28 mL) was added DIPEA (1.46 mL, 8.384 mmol) and the resulting solution was stirred at 90° C. for 16 h. The reaction mixture was diluted with AcOEt, washed twice with water and then with brine, dried over sodium sulphate and concentrated under reduced pressure. The residue was purified on silica gel (DCM/acetone: 100/0 to 80/20) to provide intermediate (20a) (282 mg, 1.113 mmol, 40%) as a light-brown solid.

MS m/z ([M+H]⁺) 254.

$^1$H NMR (400 MHz, DMSO-d$_6$): δ(ppm) 1.55 (s, 9H), 2.93 (dd, J=5.1, 4.2 Hz, 4H), 3.69 (dd, J=5.1, 4.2 Hz, 4H), 7.62 (d, J=0.7 Hz, 1H), 7.74 (d, J=0.7 Hz, 1H).

Step 2: Preparation of Intermediate 4-(N-morpholine)-1H-pyrazole (20b)

To a stirred mixture of intermediate (20a) (282 mg, 1.113 mmol) in DCM (5.6 mL) was added a solution of 4M HCl in dioxane (2.78 mL, 11.13 mmol) and the resulting mixture was stirred at room temperature for 1 h. The formed precipitate was concentrated by evaporation with air flow. The residue was washed with DCM, Et$_2$O, acetone and then AcOEt to obtain a light-brown solid (113 mg). The pyrazole hydrochloride salt was partitioned between AcOEt and saturated aqueous NaHCO$_3$ solution and stirred 5 min at room temperature. The organic was layer was then isolated and the aqueous one was extracted with AcOEt three times. The combined organic layers were dried over Na2SO4 and concentrated under reduced pressure to afford intermediate (20b) (90 mg, 0.588 mmol, 53%) as a light-brown solid.

MS m/z ([M+H]⁺) 154.

$^1$H NMR (400 MHz, CDCl$_3$): δ (ppm) 2.91-2.95 (m, 4H), 3.80-3.84 (m, 4H), 7.74 (s, 2H).

Step 3: Preparation of Intermediate 6-allyloxy-3-[4-(N-morpholine)-pyrazol-1-yl]-1,6-diaza-bicyclo[3.2.1]oct-3-en-7-one (20c)

Using the procedure described in example 2 (step 1a), intermediate (1g) (171 mg, 0.559 mmol) was converted by reaction with intermediate (20b) (90 mg, 0.587 mmol) into intermediate (20c) (181 mg, 0.546 mmol, 98%) as a brown foam after purification by flash chromatography on silica gel (DCM/acetone: 100/0 to 70/30).

MS m/z ([M+H]$^+$) 332.

$^1$H NMR (400 MHz, CDCl$_3$): δ(ppm): 2.88-2.93 (m, 4H), 3.11 (d, J=10.7 Hz, 1H), 3.49 (dd, J=10.7, 2.2 Hz, 1H), 3.78-3.82 (m, 4H), 4.06 (dd, J=5.6, 2.4 Hz, 1H), 4.16 (dd, J=17.6, 1.8 Hz, 1H), 4.34-4.48 (m, 3H), 5.26-5.30 (m, 1H), 5.31-5.38 (m, 1H), 5.93-6.06 (m, 1H), 6.22 (d, J=5.5 Hz, 1H), 7.09 (s, 1H), 7.28 (s, 1H).

Step 4: Preparation of sodium [7-oxo-3-[4-(N-morpholine)-pyrazol-1-yl)]-1,6-diaza-bicyclo[3.2.1]oct-3-en-6-yl]sulfate (Example 20)

Using the procedure described in example 2 (step 2), intermediate (20c) (181 mg, 0.546 mmol) was converted into example (20) (40 mg, 0.102 mmol, 19% over 3 steps) as a light-brown solid after lyophilization.

MS m/z ([M+H]$^+$) 372.

MS m/z ([M−H]$^−$) 370.

$^1$H NMR (400 MHz, D$_2$O): δ(ppm) 2.98-3.03 (m, 4H), 3.43 (d, J=11.4 Hz, 1H), 3.68 (d, J=11.4 Hz, 1H), 3.84-3.89 (m, 4H), 4.34 (s, 2H), 4.57 (dd, J=5.9, 2.5 Hz, 1H), 6.48 (d, J=0.9 Hz, 1H), 7.56 (s, 1H), 7.65 (s, 1H).

Example 21: Synthesis of sodium [3-(4-acetamidepyrazol-1-yl)-7-oxo-1,6-diazabicyclo[3.2.1]oct-3-en-6-yl]sulfate

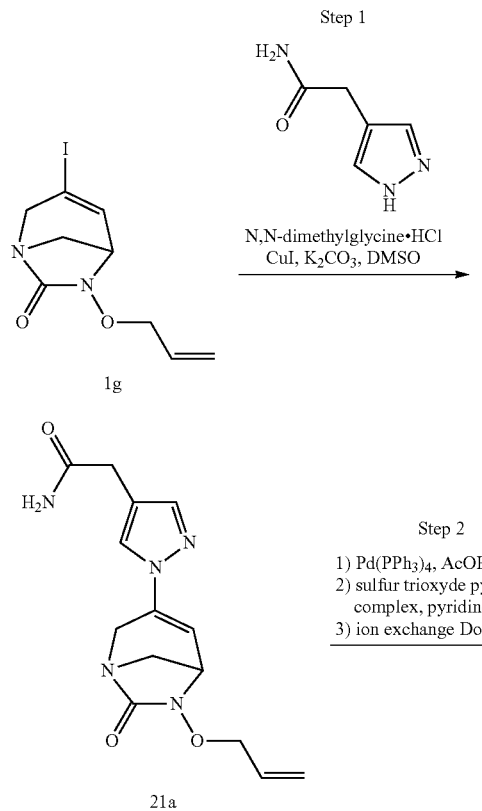

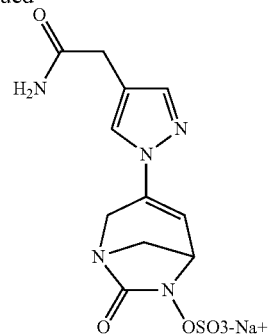

Example 21

Step 1: Preparation of Intermediate N-(6-allyloxy-7-oxo-1,6-diazabicyclo[3.2.1]oct-3-en-3-yl)-4-acetamidepyrazole (21a)

Using the procedure described in example 1 (step 7), intermediate (1g) (121 g, 0.395 mmol) was converted by reaction with 1H-pyrazole-4-acetamide (99 mg, 0.791 mmol) into intermediate (21a) (50.5 mg, 0.166 mmol, 42%) as a yellow oil after purification by flash chromatography on silica gel (DCM/acetone: 100/0 to 40/60).

MS m/z ([M+H]$^+$) 304.

$^1$H NMR (400 MHz, CDCl$_3$) δ 3.14 (d, J=10.8 Hz, 1H), 3.43 (s, 2H), 3.53 (dd, J=10.8, 2.9 Hz, 1H), 4.10 (dd, J=5.6, 2.6 Hz, 1H), 4.19 (dd, J=17.6, 1.9 Hz, 1H), 4.37-4.49 (m, 3H), 5.31 (ddd, J=10.3, 1.5, 1.4 Hz, 1H), 5.37 (ddd, J=17.2, 1.5, 1.4 Hz, 1H), 5.42 (br s, 1H), 5.57 (br s, 1H), 5.96-6.06 (m, 1H), 6.43 (d, J=5.5 Hz, 1H), 7.49 (s, 1H), 7.62 (s, 1H).

Step 2: Preparation of sodium [3-(4-acetamidepyrazol-1-yl)-7-oxo-1,6-diazabicyclo[3.2.1]oct-3-en-6-yl]sulfate (Example 21)

Under inert atmosphere intermediate (21a) (50 mg, 0.165 mmol) was diluted in anhydrous DCM (1.7 mL). AcOH (19 µL, 0.330 mmol) and Pd(PPh$_3$)$_4$ (95 mg, 0.082 mmol) were successively added. The reaction mixture was stirred at rt for 2 h. The mixture was concentrated under reduced pressure. The crude product was triturated with DCM and filtered to provide the intermediate N-(6-hydroxy-7-oxo-1,6-diazabicyclo[3.2.1]oct-3-en-3-yl)-4-acetamidepyrazole. Under inert atmosphere, this intermediate (20 mg, 0.076 mmol) was diluted in anhydrous pyridine (0.8 mL). Sulfur trioxide pyridine complex (60.5 mg, 0.380 mmol) was added to the reaction mixture. The resulting suspension was protected from light and stirred overnight until the reaction was completed. The reaction mixture was concentrated and then purified by flash chromatography on C18-reversed phase silica gel (H$_2$O/ACN: 100/0 to 98/2). Fractions containing the product were combined and concentrated. The residue was dissolved in a minimum of H$_2$O and converted after ion exchange with Dowex sodium form column (Dowex® 50WX8 hydrogen form stored with an aqueous solution of 2N NaOH and washed until neutral pH with H$_2$O) to example (21) (3 mg, 0.008 mmol, 5% over 3 steps) as a white solid.

MS m/z ([M+H]$^+$) 344.

MS m/z ([M−H]$^−$) 342.

$^1$H NMR (400 MHz, D$_2$O) δ 3.46 (d, J=11.3 Hz, 1H), 3.52 (s, 2H), 3.69 (dd, J=11.3, 2.7 Hz, 1H), 4.35 (dd, J=17.4, 1.1

Hz, 1H), 4.39 (dd, J=17.4, 1.6 Hz, 1H), 4.58 (dd, J=5.6, 2.7 Hz, 1H), 6.60 (d, J=5.8 Hz, 1H), 7.64 (s, 1H), 7.90 (s, 1H).

Example 22: Synthesis of sodium [7-oxo-3-[4-(trifluoromethyl)pyrazol-1-yl]-1,6-diazabicyclo[3.2.1]oct-3-en-6-yl]sulfate

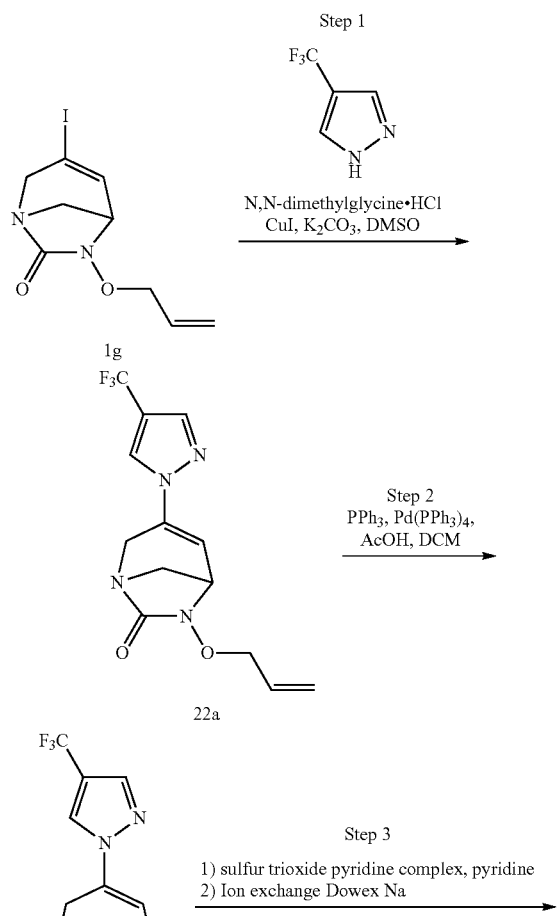

Step 1: Preparation of Intermediate 6-allyloxy-3-[4-(trifluoromethyl)pyrazol-1-yl]-1,6-diazabicyclo[3.2.1]oct-3-en-7-one (22a)

Using the procedure described in example 1 (step 7), intermediate (1g) (0.26 g, 0.85 mmol) was converted by reaction with 4-(trifluoromethyl)-1H-pyrazole (165 mg, 1.19 mmol) into intermediate (22a) (0.181 g, 0.58 mmol, 68%) as a white solid after purification by flash chromatography on silica gel (Heptane/AcOEt 100/0 to 0/100).

MS m/z ([M+H]$^+$) 315.

$^1$H NMR (400 MHz, acetone) δ3.62 (dd, J=11.0, 0.7 Hz, 1H), 3.46 (ddd, J=10.9, 2.8, 1.0 Hz, 1H), 4.28 (dd, J=17.5, 1.9 Hz, 1H), 4.31-4.43 (m, 4H), 5.22-5.26 (m, 1H), 5.34-5.39 (m, 1H), 5.96-6.06 (m, 1H), 6.83-6.86 (m, 1H), 7.95 (s, 1H), 8.56 (s, 1H).

Step 2: Preparation of Intermediate 6-hydroxy-3-[4-(trifluoromethyl)pyrazol-1-yl]-1,6-diazabicyclo[3.2.1]oct-3-en-7-one (22b)

Under inert atmosphere, to a solution of intermediate (22a) (119 mg, 0.38 mmol) in anhydrous DCM (3.8 mL) were successively added AcOH (43 μL, 0.76 mmol), PPh$_3$ (99 mg, 0.38 mmol) and Pd(PPh$_3$)$_4$ (66 mg, 0.06 mmol). The reaction mixture was stirred at rt for 30 min. Then the mixture was concentrated under a flux of argon and the residue purified by flash chromatography on silica gel (DCM/acetone: 100/0 to 0/100) to provide intermediate (22b) (105 mg, 0.38 mmol).

MS m/z ([M+H]$^+$) 275.

Step 3: Preparation of sodium [7-oxo-3-[4-(trifluoromethyl)pyrazol-1-yl]-1,6-diazabicyclo[3.2.1]oct-3-en-6-yl]sulfate (Example 22)

Using the procedure described in example 1 (step 9), intermediate (22b) (100 mg, 0.36 mmol) was converted into example (22) (0.181 g, 0.58 mmol, 78%) as a white solid after passing through the ion exchange column and purification on C18-reversed phase silica gel (H$_2$O/MeCN 99/1).

MS m/z ([M+H]$^+$) 355.

$^1$H NMR (400 MHz, D$_2$O) δ3.44 (d, J=11.4 Hz, 1H), 3.68 (dd, J=11.4, 2.8 Hz, 1H), 4.33 (d, J=17.5 Hz, 1H), 4.39 (dd, J=1.2, 17.5 Hz, 1H), 4.58 (dd, J=5.7, 2.7 Hz, 1H), 6.72 (d, J=5.6 Hz, 1H), 7.96 (s, 1H), 8.40 (s, 1H).

Example 23: Synthesis of sodium (7-oxo-3-(3-carboxamide-5-methyl-pyrazol-1-yl)-1,6-diazabicyclo[3.2.1]oct-3-en-6-yl) sulfate

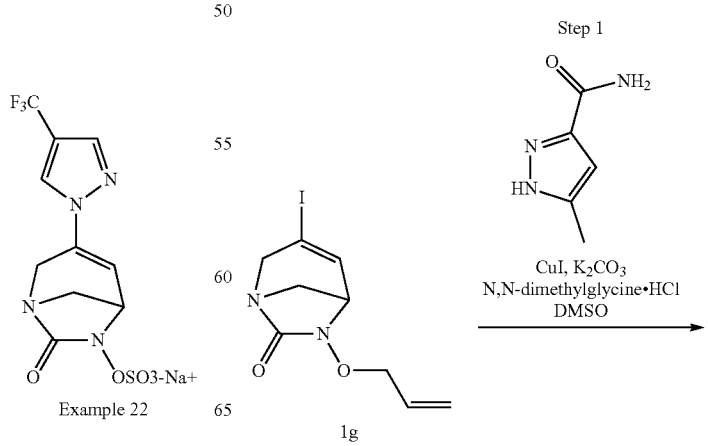

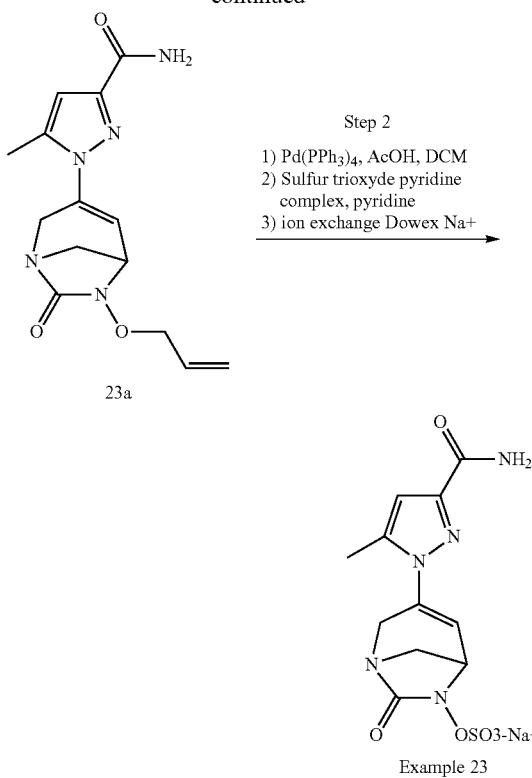

Example 24: Synthesis of sodium and 2,2,2-trifluoroacetate [7-oxo-3-[4-carboxamide,N-(2-ammoniumethoxy)-pyrazol-1-yl]-1,6-diazabicyclo[3.2.1]oct-3-en-6-yl]sulfate

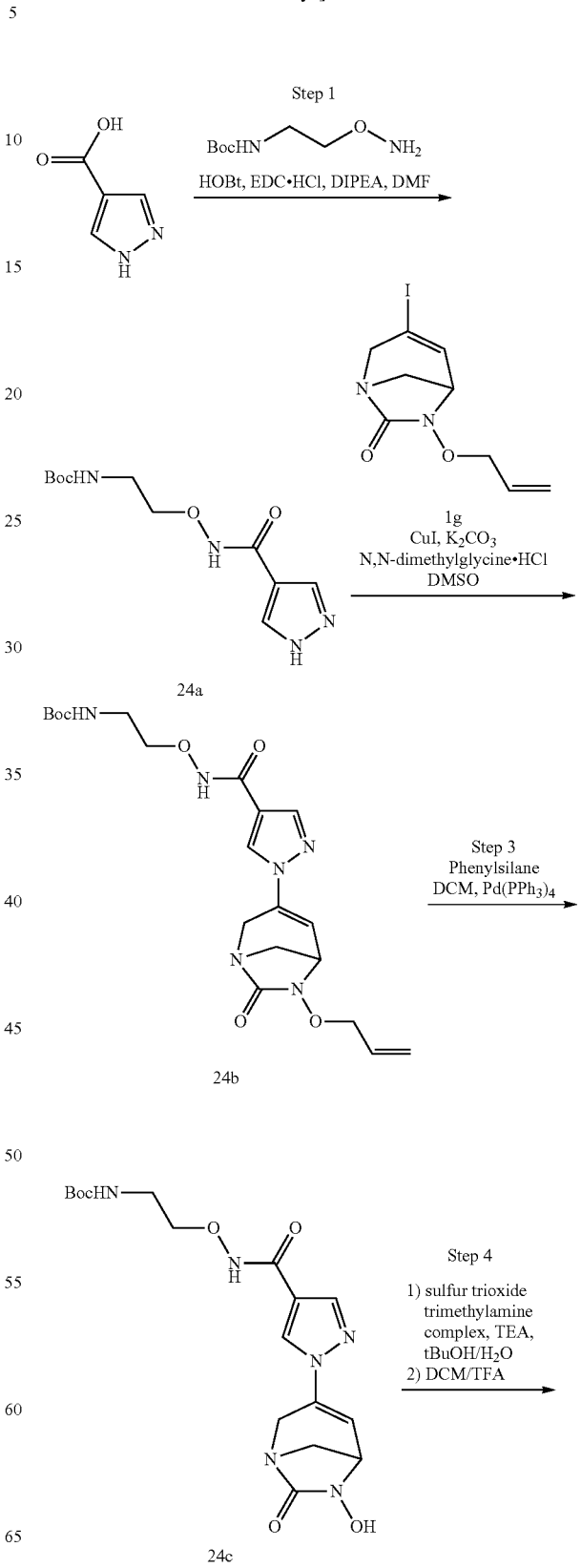

Step 1: Preparation of Intermediate 6-allyloxy-3-(3-carboxamide-5-methyl-pyrazol-1-yl)-1,6-diazabicyclo[3.2.1]oct-3-en-7-one (23a)

Using the procedure described in example 1 (step 7), intermediate (1g) (0.25 g, 0.817 mmol) was converted by reaction with 5-methyl-1H-pyrazole-3-carboxamide (123 mg, 0.98 mmol) into intermediate (23a) (95.7 mg, 0.315 mmol, 39%) as a beige solid after purification by flash chromatography on silica gel (DCM/acetone: 100/0 to 50/50) then trituration in acetone.

MS m/z ([M+H]$^+$) 304, ([2M+H]$^+$) 607.

$^1$H NMR (300 MHz, DMSO-d$_6$): δ(ppm) 2.33 (s, 3H), 3.28-3.36 (m, 2H), 4.01 (dd, J=17.6, 2.0 Hz, 1H), 4.19 (d, J=17.6 Hz, 1H), 4.31 (dd, J=5.6, 2.3 Hz, 1H), 4.38-4.40 (m, 2H), 5.24-5.39 (m, 2H), 5.91-6.01 (m, 1H), 6.46 (d, J=5.4 Hz, 1H), 6.52 (d, J=0.9 Hz, 1H), 7.24 (s, 1H), 7.56 (s, 1H).

Step 2: Preparation of sodium (7-oxo-3-(3-carboxamide-5-methyl-pyrazol-1-yl)-1,6-diazabicyclo[3.2.1]oct-3-en-6-yl) sulfate (Example 23)

Using the procedure described in example 2 (step 2), intermediate (23a) (76 mg, 0.251 mmol) was converted into example (23) (58.4 mg, 0.160 mmol, 52%) as a white solid after lyophilization.

MS m/z ([M−H]$^-$) 342, ([2M−H]$^-$) 685.

$^1$H-NMR (300 MHz, D$_2$O): δ(ppm) 2.32 (s, 3H), 3.51 (d, J=11.4 Hz, 1H), 3.69 (dd, J=11.5, 2.8 Hz, 1H), 4.12-4.29 (m, 2H), 4.61 (dd, J=5.5, 2.6 Hz, 1H), 6.50-6.59 (m, 2H).

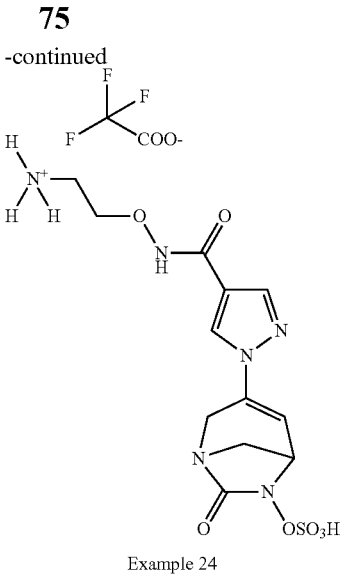

Example 24

Step 1: Preparation of Intermediate tert-butyl [4-carboxamide, N-(2-aminoethoxy)-pyrazole]carbamate (24a)

Under inert atmosphere NH-pyrazol-4-carboxylic acid (207 mg, 1.87 mmol) was diluted in anhydrous DMF (19 mL). HOBt H$_2$O (367 mg, 2.40 mmol) and EDC.HCl (460 mg, 2.40 mmol) were successively added. The reaction mixture was stirred at rt for 10 min. tert-Butyl N-(2-aminoxyethyl)carbamate (325 mg, 1.87 mmol) and DIPEA (420 µL, 2.40 mmol) were added. The reaction mixture was stirred at rt for 16 h. The reaction mixture was concentrated in vacuo and purified by flash chromatography on silica gel (DCM/acetone: 100/0 to 20/80) to give intermediate (24a) (198 mg, 0.72 mmol, 39%) as a white solid.

MS m/z ([M+H]$^+$) 271.

MS m/z ([M−H]$^−$) 269.

$^1$H NMR (400 MHz, CDCl$_3$) δ 1.42 (s, 9H), 3.38-3.41 (m, 2H), 3.92-3.95 (m, 2H), 5.56 (br s, 1H), 8.02 (s, 2H), 10.52 (s, 1H).

Step 2: Preparation of Intermediate tert-butyl [1-(6-allyloxy-7-oxo-1,6-diazabicyclo[3.2.1]oct-3-en-3-yl)]pyrazole-4-carboxamide, N-(2-aminoethoxy)] oxybutanoate (24b)

Using the procedure described in example 1 (step 7), intermediate (1g) (112 mg, 0.37 mmol) was converted by reaction with intermediate (24a) (198 mg, 0.73 mmol) into intermediate (24b) (83 mg, 0.18 mmol, 49%) as a yellow oil after purification by flash chromatography on silica gel (DCM/acetone: 100/0 to 30/70).

MS m/z ([M+H]$^+$) 449.

MS m/z ([M−H]$^−$) 447.

$^1$H NMR (400 MHz, CDCl$_3$) δ1.46 (s, 9H), 3.15 (d, J=11.2 Hz, 1H), 3.43 (dd, J=5.7, 5.7 Hz, 2H), 3.54 (dd, J=11.2, 2.0 Hz, 1H), 3.93 (dd, J=4.9, 4.9 Hz, 2H), 4.13 (dd, J=5.6, 2.6 Hz, 1H), 4.18 (dd, J=17.8, 1.9 Hz, 1H), 4.37-4.49 (m, 3H), 5.21 (br s, 1H), 5.31 (dd, J=10.2, 1.5 Hz, 1H), 5.37 (ddt, J=17.2, 1.5, 1.4 Hz, 1H), 5.96-6.06 (m, 1H), 6.59 (t, J=5.5 Hz, 1H), 7.92 (s, 1H), 8.14 (s, 1H), 10.05 (s, 1H).

Step 3: Preparation of Intermediate tert-butyl [1-(6-hydroxy-7-oxo-1,6-diazabicyclo[3.2.1]oct-3-en-3-yl)]pyrazole-4-carboxamide, N-(2-aminoethoxy)] oxybutanoate (24c)

Under inert atmosphere, PhSiH$_3$ (45 µL, 0.368 mmol) and Pd(PPh$_3$)$_4$ (11 mg, 0.009 mmol) were added to a solution of intermediate (24b) (83 mg, 0.181 mmol) in DCM (1.8 mL). The reaction mixture was stirred at rt for 2 h. The mixture was concentrated and then purified by flash chromatography on silica gel (DCM/acetone: 100/0 to 20/80). Fractions containing the expected intermediate were combined and concentrated to give intermediate (24c) (30 mg, 0.074 mmol, 41%).

MS m/z ([M+H]$^+$) 409.

$^1$H NMR (400 MHz, CDCl$_3$) δ 1.41 (s, 9H), 3.09 (d, J=10.9 Hz, 1H), 3.27-3.41 (m, 2H), 3.46 (d, J=8.8 Hz, 1H), 3.86-4.00 (m, 2H), 4.03-4.10 (m, 2H), 4.03-4.34 (m, 1H), 5.79 (br s, 1H), 6.60 (d, J=5.1 Hz, 1H), 7.89 (s, 1H), 8.21 (s, 1H), 10.69 (s, 1H).

Step 4: Preparation of sodium and 2,2,2-trifluoroacetate [7-oxo-3-[4-carboxamide,N-(2-ammoniumethoxy)-pyrazol-1-yl]-1,6-diazabicyclo[3.2.1]oct-3-en-6-yl]sulfate (Example 24)

Intermediate (24c) (30 mg, 0.074 mmol) was diluted in water/tBuOH (1:1) (0.74 mL). Sulfur trioxide trimethylamine complex (12 mg, 0.089 mmol) and TEA (3 µL, 0.043 mmol) were successively added. The reaction mixture was stirred at rt overnight. The crude compound was concentrated in vacuo and purified by flash chromatography on silica gel (DCM/acetone: 100/0 to 0/100) to give the corresponding sulfate intermediate as a colorless oil. This intermediate (10 mg, 0.020 mmol) was dissolved in a mixture of DCM/TFA (5:1) (0.4 mL) at 0° C. and the mixture was stirred at 0° C. for 30 min. The residue was triturated in Et$_2$O and DCM. The solid was diluted in H$_2$O and lyophilized to afford example (24) (3.4 mg, 0.007 mmol, 9% over 2 steps).

MS m/z ([M+H]$^+$) 389.

MS m/z ([M−H]$^−$) 387.

$^1$H NMR (400 MHz, D$_2$O) δ 3.31-3.35 (m, 2H), 3.45 (d, J=11.5 Hz, 1H), 3.69 (dd, J=11.5, 2.1 Hz, 1H), 4.22-4.26 (m, 2H), 4.34 (d, J=17.6 Hz, 1H), 4.40 (dd, J=17.6, 1.8 Hz, 1H), 4.60 (dd, J=5.7, 2.6 Hz, 1H), 6.75 (d, J=5.7 Hz, 1H), 8.00 (s, 1H), 8.37 (s, 1H). $^{19}$F NMR (367 MHz, D$_2$O) δ-75.56 (s, 3F).

Example 25: Synthesis of sodium [7-oxo-3-[3-(thiazol-2-ylcarbamoyl)pyrazol-1-yl]-1,6-diazabicyclo[3.2.1]oct-3-en-6-yl]sulfate

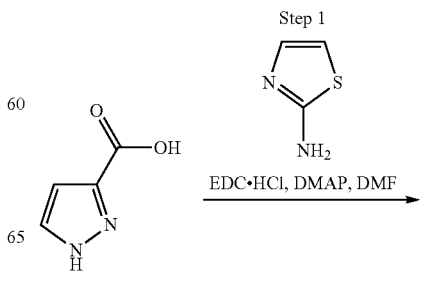

Step 1

Step 2

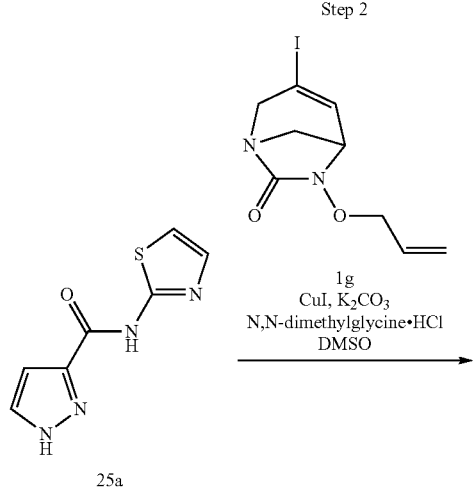

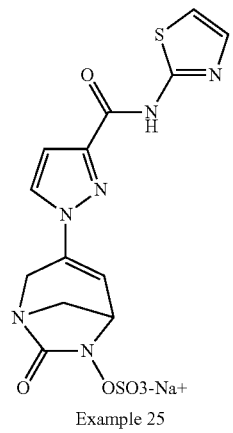

Example 25

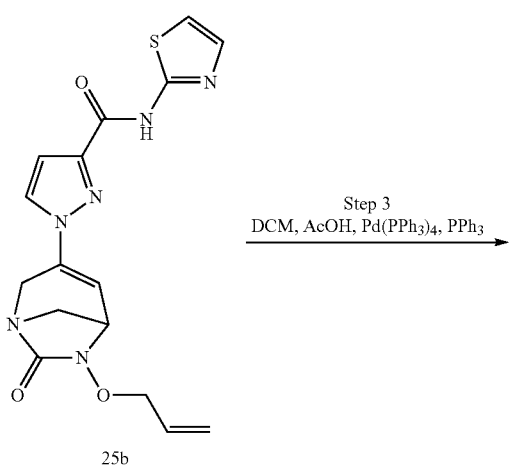

25b

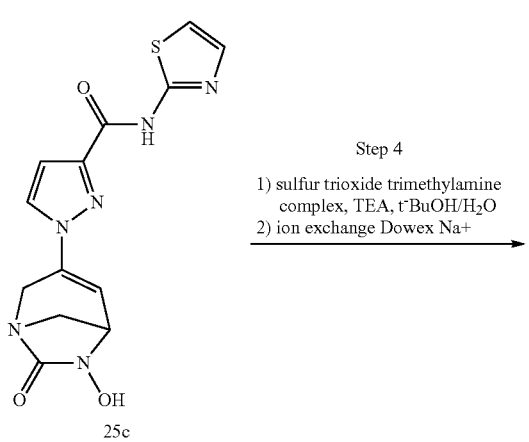

25c

Step 1: Preparation of Intermediate N-thiazol-2-yl-1H-pyrazole-3-carboxamide (25a)

Under inert atmosphere 1H-pyrazol-3-carboxylic acid (245 mg, 2.19 mmol) and DMAP (668 mg, 5.46 mmol) were diluted in anhydrous DMF (10 mL). EDC.HCl (1.05 g, 5.46 mmol) was added in portions. The reaction mixture was stirred at rt for 10 min. A mixture of 2-aminothiazol (219 mg, 2.19 mmol) in DMF (5 mL) was dropewisely added. The reaction mixture was stirred at rt for 16 h. The reaction mixture was concentrated and triturated with DCM to give intermediate (25a) (168 mg, 0.865 mmol, 39%) as a white solid.

MS m/z ([M+H]$^+$) 195.
MS m/z ([M−H]$^−$) 193.
$^1$H NMR (400 MHz, DMSO-d$_6$) δ 6.98 (br s, 1H), 7.26 (d, J=3.6 Hz, 1H), 7.53 (d, J=3.6 Hz, 1H), 7.91 (br s, 1H), 12.02 (br s, 1H), 13.58 (br s, 1H).

Step 2: Preparation of Intermediate N-(6-allyloxy-7-oxo-1,6-diazabicyclo[3.2.1]oct-3-en-3-yl)-3-(N-thiazol-2-yl-carboxamide)pyrazole (25b)

Using the procedure described in example 1 (step 7), intermediate (1g) (123 mg, 0.402 mmol) was converted by reaction with intermediate (25a) (156 mg, 0.804 mmol) into intermediate (25b) (71 mg, 0.191 mmol, 48%) as a white solid after purification by flash chromatography on silica gel (DCM/acetone: 100/0 to 0/100).

MS m/z ([M+H]$^+$) 373.
MS m/z ([M−H]$^−$) 371.
$^1$H NMR (400 MHz, CDCl$_3$) δ3.18 (d, J=11.0 Hz, 1H), 3.58 (ddd, J=11.0, 2.9, 1.1 Hz, 1H), 4.16 (dd, J=5.5, 2.6 Hz, 1H), 4.23 (dd, J=17.6, 1.9 Hz, 1H), 4.39-4.51 (m, 3H), 5.33 (dd, J=10.3, 1.6 Hz, 1H), 5.39 (ddd, J=17.6, 1.6, 1.4 Hz, 1H), 5.98-6.08 (m, 1H), 6.63 (d, J=5.5 Hz, 1H), 7.02 (d, J=3.5 Hz, 1H), 7.02 (d, J=2.7 Hz, 1H), 7.50 (d, J=3.5 Hz, 1H), 7.71 (d, J=2.7 Hz, 1H), 10.04 (br s, 1H).

Step 3: Preparation of Intermediate N-(6-hydroxy-7-oxo-1,6-diazabicyclo[3.2.1]oct-3-en-3-yl)-3-(N-thiazol-2-yl-carboxamide)pyrazole (25c)

Under inert atmosphere intermediate (25b) (71 mg, 0.191 mmol) was diluted in anhydrous DCM (2.3 mL). AcOH (27 μL, 0.466 mmol), Pd(PPh$_3$)$_4$ (40 mg, 0.035 mmol) and PPh$_3$ (61 mg, 0.233 mmol) were successively added. The reaction mixture was stirred at rt for 3 h. The mixture was concentrated under reduced pressure and then purified by flash chromatography on silica gel (DCM/acetone: 100/0 to 30/70). Fractions containing the expected intermediate were combined and concentrated to give intermediate (25c) (51 mg, 0.153 mmol, 80%) as a white solid.

MS m/z ([M+H]$^+$) 333.

MS m/z ([M−H]$^-$) 331.

$^1$H NMR (400 MHz, DMSO-d$_6$) δ 3.24 (d, J=11.0 Hz, 1H), 3.38 (dd, J=11.0, 2.6 Hz, 1H), 4.07 (dd, J=5.6, 2.6 Hz, 1H), 4.22 (dd, J=17.7, 2.0 Hz, 1H), 4.37 (dd, J=17.7, 1.0 Hz, 1H), 6.91 (d, J=5.6 Hz, 1H), 7.09 (d, J=2.7 Hz, 1H), 7.28 (d, J=3.6 Hz, 1H), 7.55 (d, J=3.6 Hz, 1H), 8.37 (d, J=2.7 Hz, 1H), 9.70 (s, 1H), 12.36 (s, 1H).

Step 4: Preparation of sodium [7-oxo-3-[3-(thiazol-2-ylcarbamoyl)pyrazol-1-yl]-1,6-diazabicyclo[3.2.1]oct-3-en-6-yl]sulfate (Example 25)

Intermediate (25c) (45.5 mg, 0.137 mmol) was diluted in water/tBuOH (1:1) (1.4 mL). Sulfur trioxide trimethylamine complex (23 mg, 0.164 mmol) and TEA (5 µL, 0.034 mmol) were successively added. The reaction mixture was stirred at rt overnight. The crude compound was concentrated in vacuo and purified by flash chromatography on C18-reversed phase silica gel (H$_2$O/ACN: 100/0 to 80/20). Fractions containing the expected intermediate were combined and concentrated to give a white solid. This solid was dissolved in a minimum of H$_2$O and converted after ion exchange with Dowex sodium form column (Dowex® 50WX8 hydrogen form stored with an aqueous solution of 2N NaOH and washed until neutral pH with H$_2$O) to example (25) (25 mg, 0.056 mmol, 41%) as a white solid.

MS m/z ([M+H]$^+$) 413.

MS m/z ([M−H]$^-$) 411.

$^1$H NMR (400 MHz, D$_2$O) δ 3.44 (d, J=11.4 Hz, 1H), 3.71 (dd, J=11.4, 2.6 Hz, 1H), 4.36 (dd, J=17.6, 1.6 Hz, 1H), 4.42 (d, J=17.6 Hz, 1H), 4.60 (dd, J=5.7, 2.6 Hz, 1H), 6.66 (d, J=5.7 Hz, 1H), 6.90 (d, J=2.7 Hz, 1H), 7.17 (d, J=3.6 Hz, 1H), 7.43 (d, J=3.6 Hz, 1H), 7.85 (d, J=2.7 Hz, 1H).

Example 26: Synthesis of sodium (7-oxo-3-(3-carboxamide-4-fluoro-pyrazol-1-yl)-1,6-diazabicyclo[3.2.1]oct-3-en-6-yl) sulfate Step 1

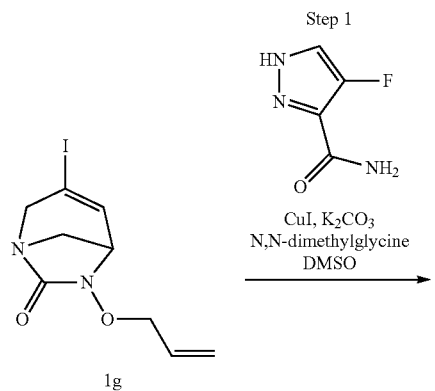

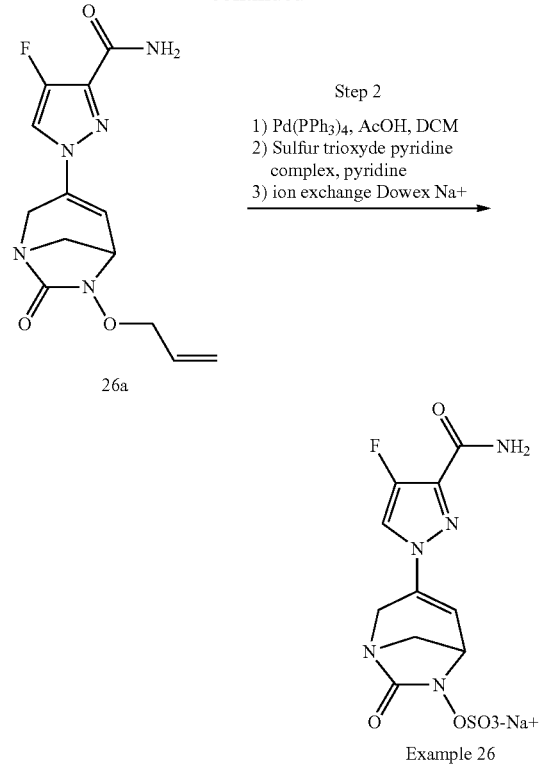

Step 1: Preparation of Intermediate 6-allyloxy-3-(3-carboxamide-4-fluoro-pyrazol-1-yl)-1,6-diazabicyclo[3.2.1]oct-3-en-7-one (26a)

Using the procedure described in example 1 (step 7), intermediate (1g) (220 mg, 0.719 mmol) was converted by reaction with 3-carboxamide-4-fluoro-1H-pyrazole (111 mg, 0.862 mmol) into intermediate (26a) (63 mg, 0.206 mmol, 29%) as a white solid after purification by flash chromatography on silica gel (DCM/acetone: 100/0 to 50/50) then trituration in acetone.

MS m/z ([M+H]$^+$) 308, ([2M+H]$^+$) 615.

$^1$H NMR (300 MHz, DMSO-d$_6$): δ(ppm) 3.24-3.35 (m, 2H), 4.17-4.40 (m, 5H), 5.25-5.40 (m, 2H), 5.91-6.01 (m, 1H), 6.71-6.73 (m, 1H), 7.49 (br s, 1H), 7.66 (br s, 1H), 8.50 (d, J=4.4 Hz, 1H).

$^{19}$F-NMR (282 MHz, DMSO-d$_6$): δ(ppm) −169.53 (d, J=4.4 Hz, 1F).

Step 2: Preparation of sodium (7-oxo-3-(3-carboxamide-4-fluoro-pyrazol-1-yl)-1,6-diazabicyclo[3.2.1]oct-3-en-6-yl) sulfate (Example 26)

Using the procedure described in example 2 (step 2), intermediate (26a) (63 mg, 0.203 mmol) was converted into example (26) (20.6 mg, 0.056 mmol, 27%) as a white solid after lyophilization.

MS m/z ([M+H]$^+$) 348.

MS m/z ([M−H]$^-$) 346, ([2M−H]$^-$) 693.

$^1$H-NMR (300 MHz, D$_2$O): δ(ppm) 3.42 (d, J=11.3 Hz, 1H), 3.66-3.71 (m, 1H), 4.35-4.39 (m, 2H), 4.59 (dd, J=5.6, 2.6 Hz, 1H), 6.66-6.68 (m, 1H), 7.99 (d, J=4.4 Hz, 1H).

$^{19}$F-NMR (282 MHz, D$_2$O): δ(ppm) −168.25 (d, J=4.6 Hz, 1F).

Example 27: Synthesis of sodium (7-oxo-3-(3-(methoxycarbamoyl)-pyrazol-1-yl)-1,6-diazabicyclo[3.2.1]oct-3-en-6-yl) sulfate and sodium (7-oxo-3-(5-(methoxycarbamoyl)-pyrazol-1-yl)-1,6-diazabicyclo[3.2.1]oct-3-en-6-yl) sulfate

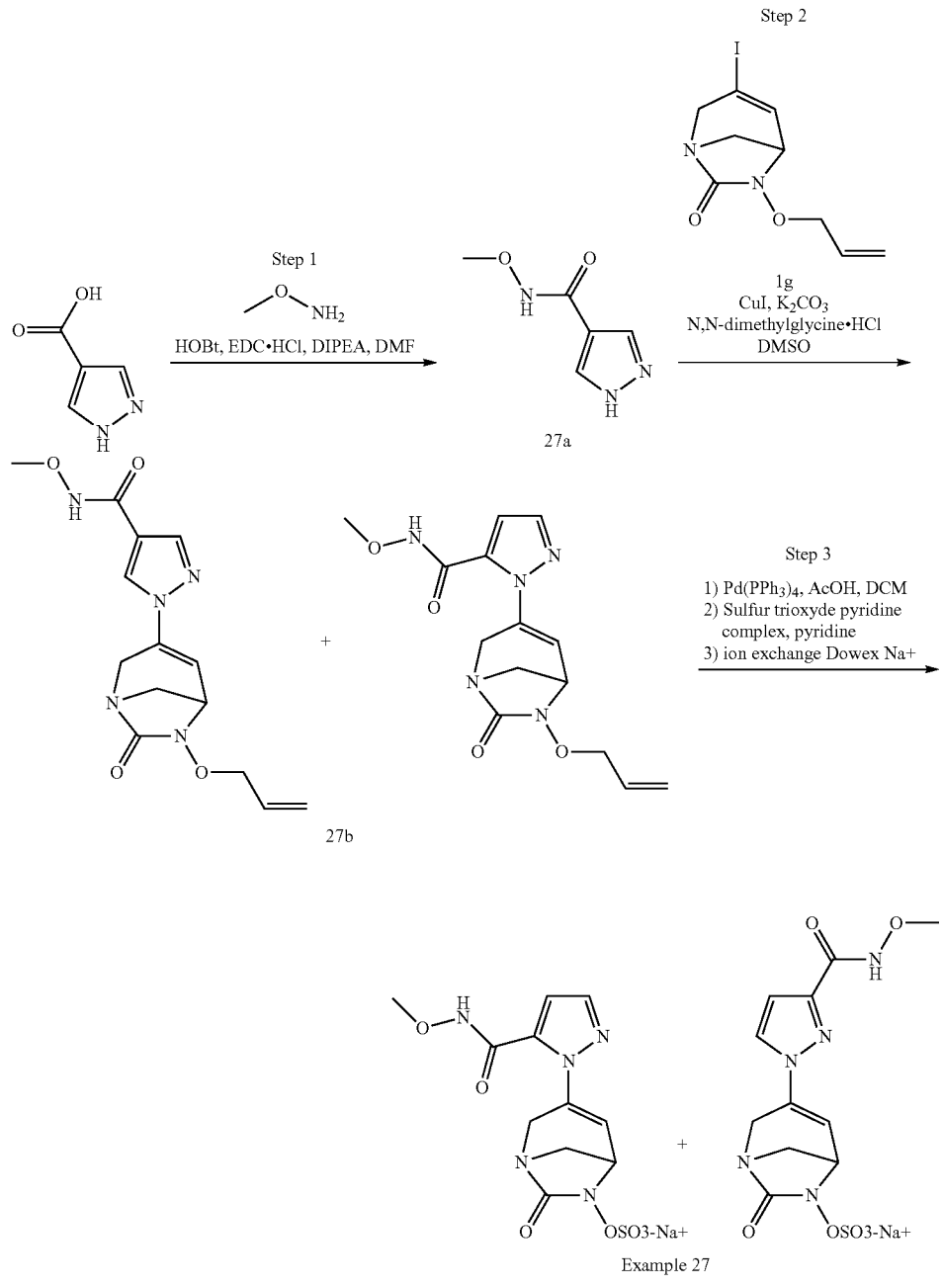

Example 27

Step 1: Preparation of Intermediate N-methoxy-1H-pyrazole-3-carboxamide (27a)

Under inert atmosphere 1H-pyrazol-3-carboxylic acid (250 mg, 2.23 mmol) was diluted in anhydrous DMF (7.4 mL) and HOBt H₂O (444 mg, 2.90 mmol) and EDC.HCl (556 mg, 2.90 mmol) were successively added. The reaction mixture was stirred at rt for 10 min. Methoxyamine hydrochloride (335 mg, 4.01 mmol) and DIPEA (1.17 mL, 6.69 mmol) were added and the reaction mixture was stirred at rt for 16 h. The reaction mixture was concentrated in vacuo and purified by flash chromatography on silica gel (DCM/methanol: 100/0 to 90/10) then by C-18 reverse phase (H₂O/ACN: 98/2 to 50/50) to give intermediate (27a) (297.5 mg, 2.11 mmol, 94%) as a white solid.

MS m/z ([M+H]$^+$) 142.
MS m/z ([M−H]$^−$) 140.
$^1$H NMR (300 MHz, DMSO-d$_6$): δ(ppm) 3.65 (s, 3H), 6.63 (t, J=2.2 Hz, 1H), 7.82 (dd, J=2.4, 1.4 Hz, 1H), 11.49 (s, 1H), 13.27 (s, 1H).

Step 2: Preparation of Intermediate 6-allyloxy-3-(3-(methoxycarbamoyl)-pyrazol-1-yl)-1,6-diazabicyclo[3.2.1]oct-3-en-7-one and 6-allyloxy-3-(5-(methoxycarbamoyl)-pyrazol-1-yl)-1,6-diazabicyclo[3.2.1]oct-3-en-7-one (27b)

Using the procedure described in example 1 (step 7), intermediate (1g) (250 mg, 0.817 mmol) was converted by reaction with intermediate (27a) (127 mg, 0.898 mmol) into an inseparable mixture of regioisomers (27b) (58 mg, 0.181 mmol, 22%, regioisomers ratio: 55/45) as a yellow gum after purification by flash chromatography on silica gel (DCM/Acetone: 100/0 to 0/100).

MS m/z ([M+H]$^+$) 320, ([2M+H]$^+$) 639.

MS m/z ([M−H]$^−$) 318.

$^1$H NMR (300 MHz, CDCl$_3$): δ (ppm) 3.13 (d, J=11.0 Hz, 0.45H), 3.28 (d, J=10.8 Hz, 0.55H), 3.43-3.61 (m, 1H), 3.83 (s, 1.35H), 3.86 (s, 1.65H), 4.02-4.31 (m, 2H), 4.32-4.53 (m, 3H), 5.15-5.46 (m, 2H), 5.79-6.16 (m, 1H), 6.39 (d, J=5.5 Hz, 0.55H), 6.52 (d, J=5.6 Hz, 0.45H), 6.61 (d, J=1.9 Hz, 0.55H), 6.89 (d, J=2.6 Hz, 0.45H), 7.50 (d, J=1.8 Hz, 0.55H), 7.65 (d, J=2.6 Hz, 0.45H), 9.37 (br s, 0.55H), 9.51 (s, 0.45H).

Step 3: Preparation of sodium (7-oxo-3-(3-(methoxycarbamoyl)-pyrazol-1-yl)-1,6-diazabicyclo[3.2.1]oct-3-en-6-yl) sulfate and sodium (7-oxo-3-(5-(methoxycarbamoyl)-pyrazol-1-yl)-1,6-diazabicyclo[3.2.1]oct-3-en-6-yl) sulfate (Example 27)

Using the procedure described in example 2 (step 2), intermediates (27b) (58 mg, 0.181 mmol) were converted into example (36) as a mixture of regioisomers (25.4 mg, 0.067 mmol, 37%, regioisomer ratio: 56/44) as a white solid after lyophilization.

MS m/z ([M−H]$^−$) 358, ([2M−H]$^−$) 717.

MS m/z ([M+H−SO$_3$H]$^+$) 280, ([M+H]$^+$) 360.

$^1$H-NMR (400 MHz, D$_2$O): δ(ppm) 3.35 (d, J=8.6 Hz, 0.44H), 3.38 (d, J=8.7 Hz, 0.56H), 3.59 (dt, J=2.9, 1.6 Hz, 0.56H), 3.62 (dt, J=2.9, 1.8 Hz, 0.44H), 3.74 (s, 1.68H), 3.76 (s, 1.32H), 4.01-4.21 (m, 1H), 4.29 (d, J=1.5 Hz, 1H), 4.48 (dd, J=5.5, 2.6 Hz, 0.44H), 4.51 (dd, J=5.7, 2.6 Hz, 0.56H), 6.41 (d, J=5.3 Hz, 0.44H), 6.63 (dt, J=5.6, 1.3 Hz, 0.56H), 6.67 (d, J=2.1 Hz, 0.44H), 6.72 (d, J=2.7 Hz, 0.56H), 7.62 (d, J=2.1 Hz, 0.44H), 7.88 (d, J=2.7 Hz, 0.56H).

Example 28: Synthesis of sodium (7-oxo-3-(3-acetylpyrazol-1-yl)-1,6-diazabicyclo[3.2.1]oct-3-en-6-yl) sulfate

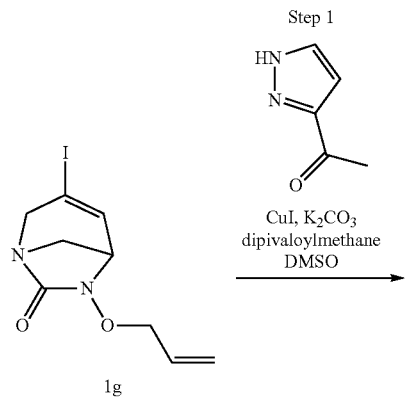

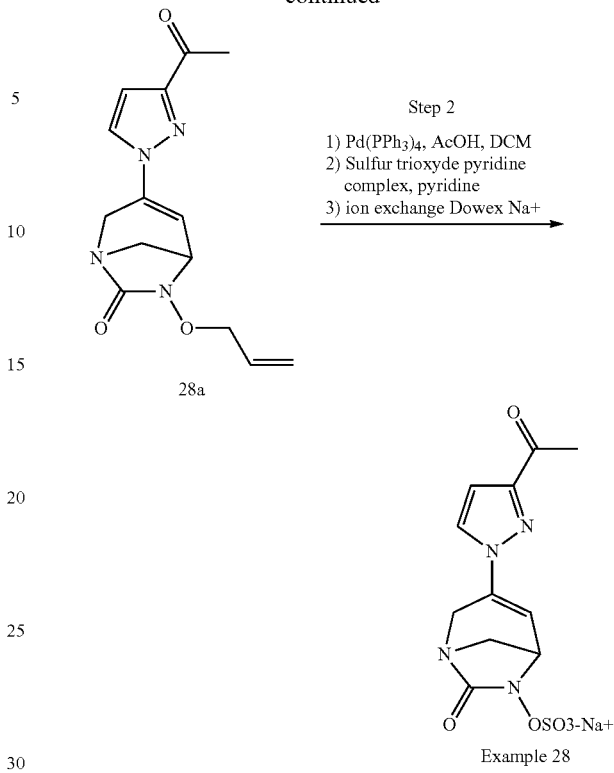

Step 1: Preparation of Intermediate 6-allyloxy-3-(3-acetylpyrazol-1-yl)-1,6-diazabicyclo[3.2.1]oct-3-en-7-one (28a)

Using the procedure described in example 2 (step 1a), intermediate (1g) (450 mg, 1.47 mmol) was converted by reaction with 1-(1H-pyrazol-3-yl)ethanone (194 mg, 1.76 mmol) into intermediate (28a) (336 mg, 1.17 mmol, 79%) as an oil after purification by flash chromatography on silica gel (DCM/Acetone: 100/0 to 50/50).

MS m/z ([M+H]$^+$) 289, ([2M+H]$^+$) 577.

$^1$H NMR (300 MHz, CDCl$_3$): δ (ppm) 2.55 (s, 3H), 3.16 (d, J=10.9 Hz, 1H), 3.54-3.58 (m, 1H), 4.11-4.17 (m, 1H), 4.22 (dd, J=17.8, 1.9 Hz, 1H), 4.37-4.57 (m, 3H), 5.30-5.41 (m, 2H), 6.02 (dddd, J=17.1, 10.3, 6.7, 6.1 Hz, 1H), 6.55-6.58 (m, 1H), 6.84 (d, J=2.6 Hz, 1H), 7.64 (d, J=2.6 Hz, 1H).

Step 2: Preparation of sodium (7-oxo-3-(3-acetylpyrazol-1-yl)-1,6-diazabicyclo[3.2.1]oct-3-en-6-yl) sulfate (Example 28)

Using the procedure described in example 2 (step 2), intermediate (28a) (50 mg, 0.173 mmol) was converted into example (28) (31.7 mg, 0.090 mmol, 52%) as a white solid after lyophilization.

MS m/z ([M−H]$^−$) 327, ([2M−H]$^−$) 655.

MS m/z ([M+H−SO$_3$H]$^{+)}$ 249, ([M+H]$^+$) 329.

$^1$H-NMR (300 MHz, D$_2$O): δ(ppm) 2.59 (s, 3H), 3.46 (d, J=11.4 Hz, 1H), 3.67-3.72 (m, 1H), 4.42 (d, J=1.5 Hz, 2H), 4.60 (dd, J=5.7, 2.6 Hz, 1H), 6.79 (dd, J=5.8, 1.3 Hz, 1H), 6.93 (d, J=2.7 Hz, 1H), 7.99 (d, J=2.7 Hz, 1H).

Example 29: Synthesis of (7-oxo-3-(3-[(Z,E)-N-(2-aminoethoxy)-C-methyl-carbonimidoyl]-pyrazol-1-yl)-1,6-diazabicyclo[3.2.1]oct-3-en-6-yl) hydrogen sulfate

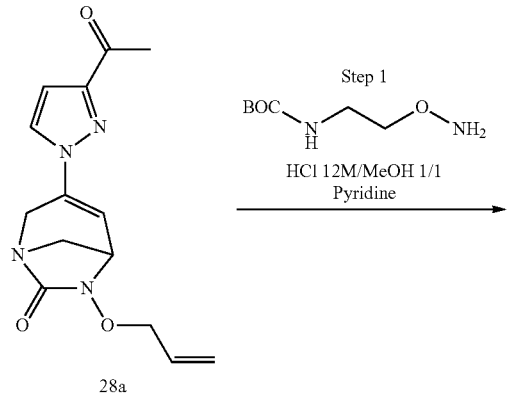

28a

Step 1
BOC–NH–CH2CH2–O–NH2
HCl 12M/MeOH 1/1
Pyridine

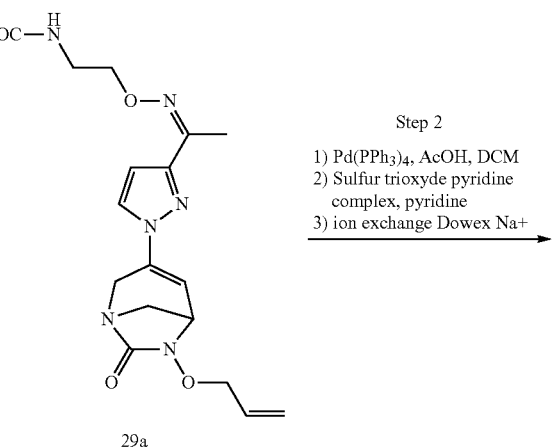

29a

Step 2
1) Pd(PPh3)4, AcOH, DCM
2) Sulfur trioxyde pyridine complex, pyridine
3) ion exchange Dowex Na+

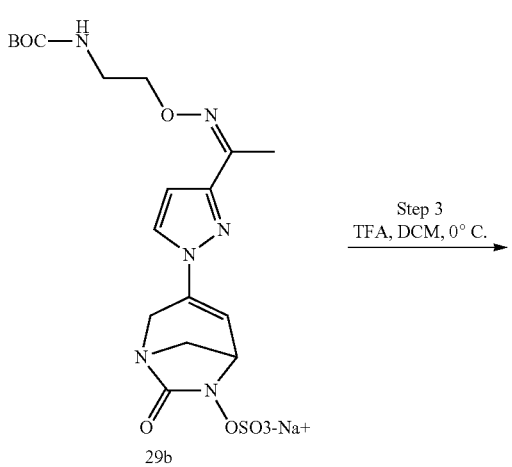

29b

Step 3
TFA, DCM, 0° C.

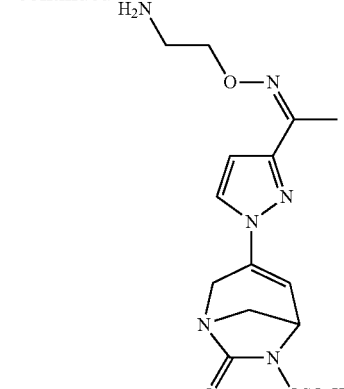

Example 29

Step 1: Preparation of Intermediate 6-allyloxy-3-(3-[(Z,E)-N-[2-(tert-butoxycarbonylamino)ethoxy]-C-methyl-carbonimidoyl]-pyrazol-1-yl)-1,6-diazabicyclo[3.2.1]oct-3-en-7-one (29a)

In a 50 mL flask under inert atmosphere, intermediate (28a) (282 mg, 0.978 mmol) and tert-butyl[2-(aminooxy)ethyl]carbamate (189.6 mg, 1.076 mmol) were dissolved in anhydrous pyridine (9.8 mL). A drop of a mixture of HCl 12M/MeOH 1/1 was added and the reaction mixture was stirred overnight ar rt. The mixture was concentrated under vacuum and purified by flash chromatography on silica gel (Cyclohexane/EtOAc: 100/0 to 30/70) to give intermediate (29a) (419 mg, 0.938 mmol, 96%, Z/E: 15/85) as a viscous gum.

MS m/z ([M+H-Boc]$^+$) 347, ([M+H-tBu]$^+$) 391, ([M+H]$^+$) 447.

$^1$H NMR (300 MHz, CDCl$_3$): δ (ppm) 1.49 (s, 9H), 2.26 (s, 3H), 3.19 (d, J=10.8 Hz, 1H), 3.50-3.60 (m, 3H), 4.12-4.27 (m, 4H), 4.39-4.60 (m, 3H), 4.97 (br s, 1H), 5.33-5.45 (m, 2H), 6.07 (dddd, J=17.0, 10.3, 6.7, 6.0 Hz, 1H), 6.50 (dd, J=5.5, 1.2 Hz, 1H), 6.70 (d, J=2.6 Hz, 1H), 7.59 (d, J=2.6 Hz, 1H).

Step 2: Preparation of Intermediate sodium (7-oxo-3-(3-[(Z,E)-N-[2-(tert-butoxycarbonylamino)ethoxy]-C-methyl-carbonimidoyl]-pyrazol-1-yl)-1,6-diazabicyclo[3.2.1]oct-3-en-6-yl) sulfate (29b)

Using the procedure described in example 2 (step 2), intermediate (29a) (441 mg, 0.988 mmol) was converted into intermediate (29b) (129.7 mg, 0.255 mmol, 26%, ratio Z/E: 17/83) as a white solid after lyophilization.

MS m/z ([M–H]$^-$) 485.
MS m/z ([M+H-Boc-SO$_3$H]$^+$) 307, ([M+H-Boc]$^+$) 387, ([M+H]$^+$) 487.

$^1$H-NMR (300 MHz, D$_2$O): δ(ppm) 1.33 (s, 9H), 2.21 (s, 3H), 3.30-3.48 (m, 3H), 3.67 (d, J=9.5 Hz, 1H), 4.18-4.22 (m, 2H), 4.36 (br s, 2H), 4.55 (dd, J=5.6, 2.6 Hz, 1H), 6.64 (d, J=5.7 Hz, 1H), 6.70 (d, J=2.7 Hz, 1H), 7.87 (d, J=2.7 Hz, 1H).

Step 3: Preparation of (7-oxo-3-(3-[(Z,E)-N-(2-aminoethoxy)-C-methyl-carbonimidoyl]-pyrazol-1-yl)-1,6-diazabicyclo[3.2.1]oct-3-en-6-yl) hydrogen sulfate (Example 29)

Intermediate (29b) (117 mg, 0.230 mmol) was dissolved in a mixture 2.5/1 of DCM/TFA (2.8 mL, 0.08M) at 0° C.

under inert atmosphere. After stirring for 45 min (conversion of starting material monitored by LC/MS), cold Et$_2$O (3 mL) was added at 0° C. After stirring for 10 min at 0° C., the precipitate was filtered (Pall VWR 514-4084, 045 µm, GH polypro, Nanosep®MF) and washed with cold Et$_2$O. The solid was then triturated in ACN to form the zwitterionic compound. The white solid was filtered and washed with ACN. The solid was dissolved in water MilliQ® and lyophilized to provide example (29) (58.8 mg, 0.177 mmol, 77%, ratio Z/E: 14/86) as a white solid.

MS m/z ([M–H]$^-$) 385, ([2M–H]$^-$) 771.

MS m/z ([M+H—SO$_3$H]$^+$) 307, ([M+H]$^+$) 387.

$^1$H-NMR (300 MHz, D$_2$O): δ(ppm) 2.17 (s, 3H), 3.30-3.45 (m, 3H), 3.64 (dd, J=11.5, 2.6 Hz, 1H), 4.26-4.43 (m, 4H), 4.52 (dd, J=5.8, 2.6 Hz, 1H), 6.56 (d, J=5.6 Hz, 1H), 6.63 (d, J=2.7 Hz, 1H), 7.77 (d, J=2.7 Hz, 1H).

Example 30: Synthesis of sodium (7-oxo-3-(3-carboxamide-5-fluoro-pyrazol-1-yl)-1,6-diazabicyclo[3.2.1]oct-3-en-6-yl) sulfate

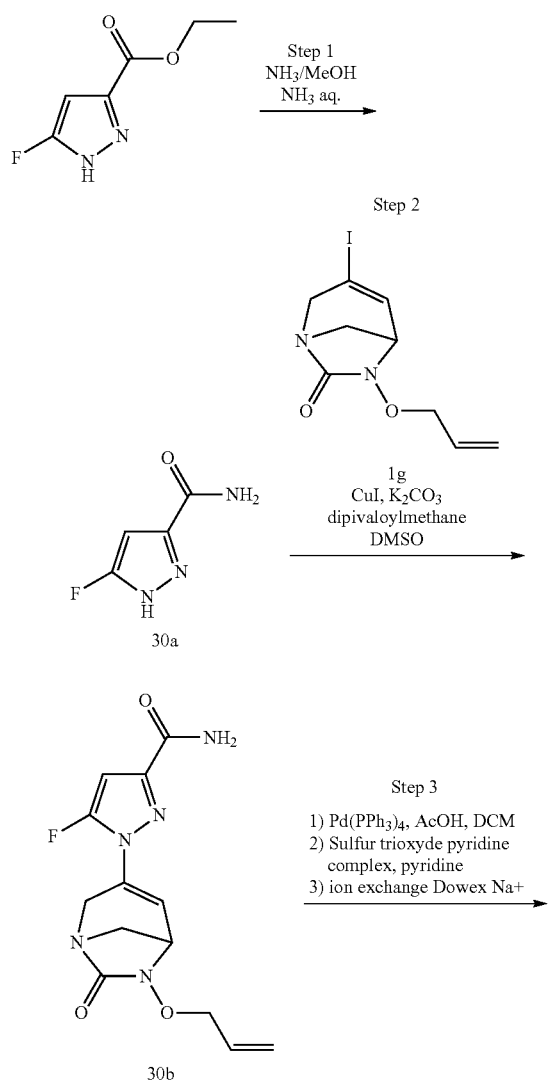

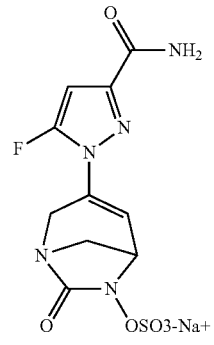

Example 30

Step 1: Preparation of Intermediate 5-fluoro-1H-pyrazole-3-carboxamide (30a)

Ethyl 5-fluoro-1H-pyrazole-3-carboxylate (200 mg, 1.26 mmol) was dissolved in a 7 M NH$_3$ in MeOH (3.6 mL) and concentrated ammonium hydroxide solution (3.6 mL) and the mixture was stirred at rt overnight. The solvent was evaporated under reduced pressure to give intermediate (30a) (150 mg, 0.920 mmol, 92%) as a white solid which was used for the next step without further purification.

MS m/z ([M+H]$^+$) 130.

MS m/z ([M–H]$^-$) 128.

$^1$H NMR (300 MHz, DMSO-d$_6$): δ(ppm) 6.49 (d, J=6.2 Hz, 1H), 7.63 (s, 1H), 7.98 (s, 1H), 13.10 (br s, 1H).

$^{19}$F-NMR (282 MHz, DMSO-d$_6$): δ(ppm) –131.06 (s, 1F).

Step 2: Preparation of Intermediate 6-allyloxy-3-(3-carboxamide-5-fluoro-pyrazol-1-yl)-1,6-diazabicyclo[3.2.1]oct-3-en-7-one (30b)

Using the procedure described in example 2 (step 1a), intermediate (1g) (225 mg, 0.735 mmol) was converted by reaction with intermediate (30a) (123 mg, 0.956 mmol) into intermediate (30b) (19 mg, 0.061 mmol, 8%) as a beige solid after purification by flash chromatography on silica gel (DCM/acetone: 100/0 to 0/100).

MS m/z ([M+H]$^+$) 308, ([2M+H]$^+$) 615.

MS m/z ([M–H]$^-$) 306.

$^1$H NMR (300 MHz, MeOD): δ(ppm) 3.33 (m, 1H), 3.48 (d, J=10.1 Hz, 1H), 4.04-4.53 (m, 5H), 5.25-5.45 (m, 2H), 6.03 (ddt, J=16.7, 10.4, 6.3 Hz, 1H), 6.40 (d, J=5.2 Hz, 1H), 6.66 (d, J=5.5 Hz, 1H).

$^{19}$F-NMR (282 MHz, MeOD): δ(ppm) –128.49 (s, 1F).

Step 3: Preparation of sodium (7-oxo-3-(3-carboxamide-5-fluoro-pyrazol-1-yl)-1,6-diazabicyclo[3.2.1]oct-3-en-6-yl) sulfate (Example 30)

Using the procedure described in example 2 (step 2), intermediate (30b) (18 mg, 0.059 mmol) was converted into example (30) (7.2 mg, 0.019 mmol, 33%) as a white solid after lyophilization.

MS m/z ([M+H]$^+$) 348, ([M+H—SO$_3$H]$^+$) 268.

MS m/z ([M–H]$^-$) 347, ([2M–H]$^-$) 693.

$^1$H-NMR (300 MHz, DMSO-d$_6$): δ(ppm) 3.20-3.46 (m, 2H), 4.18 (br s, 2H), 4.41 (dd, J=5.7, 2.5 Hz, 1H), 6.50 (d, J=5.2 Hz, 1H), 6.56-6.65 (m, 1H), 7.45 (s, 1H), 7.80 (s, 1H).

$^{19}$F-NMR (282 MHz, DMSO-d$_6$): δ(ppm) –126.94 (s, 1F).

Example 31: Synthesis of sodium (7-oxo-3-[3-(morpholine-4-carbonyl)pyrazol-1-yl]-1,6-diazabicyclo[3.2.1]oct-3-en-6-yl)

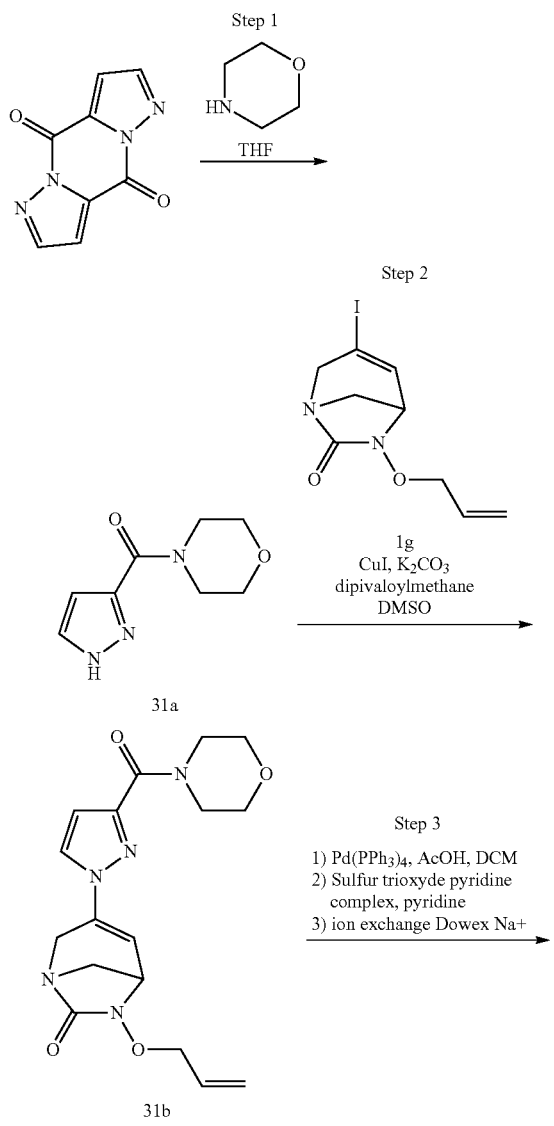

Step 1: Preparation of Intermediate morpholino(1H-pyrazol-3-yl)methanone (31a)

Dipyrazolo[3,1-a: 3',1'-d]pyrazine-4,9-dione (prepared according to *Bioorganic & Medicinal Chemistry Letters*, 2015, 25 (15), 3024-3029) (300 mg, 1.59 mmol) and morpholine (293 µL, 3.35 mmol) were dissolved in anhydrous THF (8 mL) and stirred at 80° C. for 1 h30. The reaction mixture was filtered and the filtrate was evaporated under reduced pressure to yield intermediate (31a) (500 mg, 2.75 mmol, 87%) as a beige solid which was used for the next step without further purification.

MS m/z ([M+H]$^+$) 182.

$^1$H NMR (300 MHz, CDCl$_3$): δ (ppm) 3.49-4.17 (m, 8H), 6.67 (d, J=2.3 Hz, 1H), 7.59 (d, J=2.3 Hz, 1H).

Step 2: Preparation of Intermediate 6-allyloxy-3-[3-(morpholine-4-carbonyl)pyrazol-1-yl]-1,6-diazabicyclo[3.2.1]oct-3-en-7-one (31b)

Using the procedure described in example 2 (step 1a), intermediate (1g) (250 mg, 0.817 mmol) was converted by reaction with intermediate (31a) (192 mg, 1.062 mmol) into intermediate (31b) (271 mg, 0.753 mmol, 92%) as an orange gum after purification by flash chromatography on silica gel (DCM/acetone: 100/0 to 0/100).

MS m/z ([M+H]$^+$) 360, ([2M+H]$^+$) 719.

$^1$H NMR (300 MHz, CDCl$_3$): δ (ppm) 3.14 (d, J=10.8 Hz, 1H), 3.49-3.61 (m, 1H), 3.68-3.80 (m, 6H), 4.02 (t, J=4.8 Hz, 2H), 4.08-4.23 (m, 2H), 4.35-4.53 (m, 3H), 5.25-5.44 (m, 2H), 6.02 (dddd, J=17.1, 10.3, 6.7, 6.1 Hz, 1H), 6.49 (dt, J=5.5, 1.2 Hz, 1H), 6.80 (d, J=2.6 Hz, 1H), 7.63 (d, J=2.6 Hz, 1H).

Step 3: Preparation of sodium (7-oxo-3-[3-(morpholine-4-carbonyl)pyrazol-1-yl]-1,6-diazabicyclo[3.2.1]oct-3-en-6-yl) sulfate (Example 31)

Using the procedure described in example 2 (step 2), intermediate (31b) (246 mg, 0.683 mmol) was converted into example (31) (173 mg, 0.409 mmol, 60%) as a white solid after lyophilization.

MS m/z ([M+H]$^+$) 400, ([M+H—SO$_3$H]$^+$) 320.

MS m/z ([M−H]$^-$) 398, ([2M−H]$^-$) 797.

$^1$H-NMR (400 MHz, D$_2$O): δ(ppm) 3.44 (d, J=11.3 Hz, 1H), 3.64-3.86 (m, 9H), 4.29-4.44 (m, 2H), 4.58 (dd, J=5.7, 2.6 Hz, 1H), 6.70-6.71 (m, 2H), 7.99 (d, J=2.7 Hz, 1H).

Example 32: Synthesis of (7-oxo-3-[3-(4-piperidylcarbamoyl)pyrazol-1-yl]-1,6-diazabicyclo[3.2.1]oct-3-en-6-yl) hydrogen sulfate

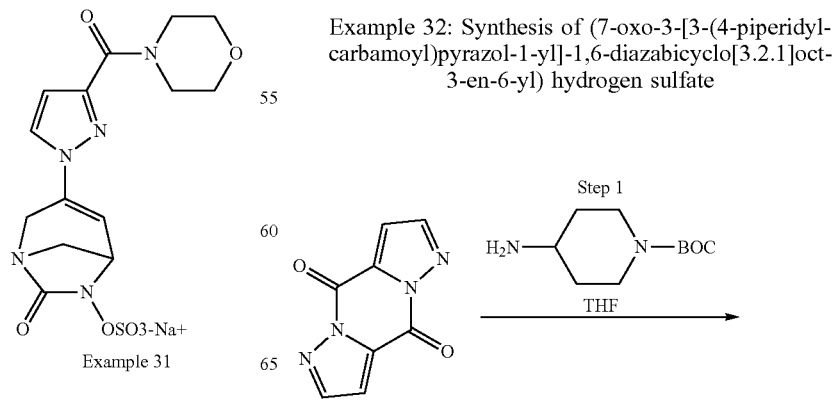

91

-continued

Step 2

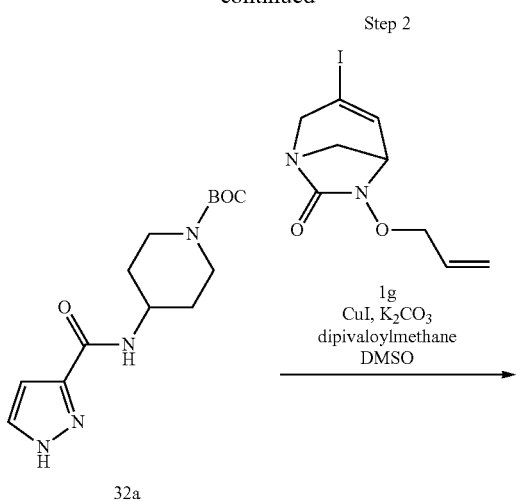

32a

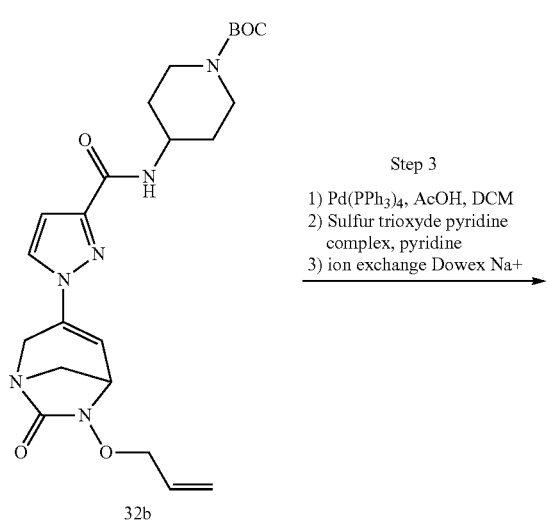

32b

Step 3
1) Pd(PPh₃)₄, AcOH, DCM
2) Sulfur trioxyde pyridine complex, pyridine
3) ion exchange Dowex Na+

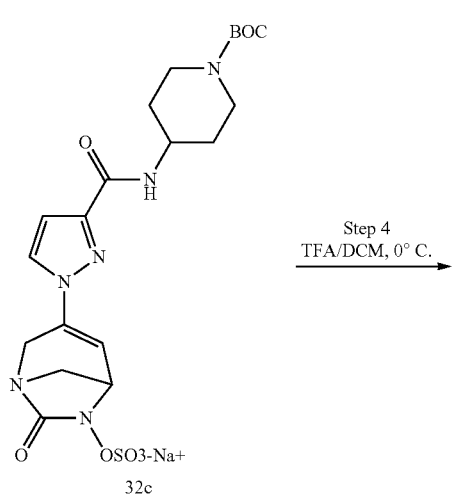

32c

Step 4
TFA/DCM, 0° C.

92

-continued

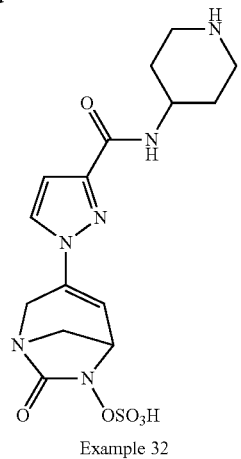

Example 32

Step 1: Preparation of Intermediate tert-butyl 4-(1H-pyrazole-3-carbonylamino)piperidine-1-carboxylate (32a)

Dipyrazolo[3,1-a: 3',1'-d]pyrazine-4,9-dione (prepared according to *Bioorganic & Medicinal Chemistry Letters*, 2015, 25 (15), 3024-3029) (250 mg, 1.33 mmol) and tert-butyl 4-aminopiperidine-1-carboxylate (532.2 mg, 2.66 mmol) were dissolved in anhydrous THF (6.6 mL) and stirred at 80° C. for 1 h10. The reaction mixture was evaporated under reduced pressure and purified on a pad of silica gel (DCM/Acetone: 50/50) to yield intermediate (32a) (755 mg, 2.56 mmol, 97%) as a beige solid.

MS m/z ([M+H-Boc]⁺) 195, ([M+H-tBu]⁺) 239, ([M+H]⁺) 295.

MS m/z ([M−H]⁻) 293.

¹H NMR (300 MHz, MeOD): δ(ppm) 1.46 (s, 9H), 1.47-1.56 (m, 2H), 1.92 (d, J=11.4 Hz, 2H), 2.92 (br s, 2H), 3.88-4.22 (m, 3H), 6.75 (s, 1H), 7.69 (s, 1H).

Step 2: Preparation of Intermediate 6-allyloxy-3-[3-[(1-tert-butoxycarbonyl-4-piperidyl)carbamoyl]pyrazol-1-yl]-1,6-diazabicyclo[3.2.1]oct-3-en-7-one (32b)

Using the procedure described in example 2 (step 1a), intermediate (1g) (250 mg, 0.817 mmol) was converted by reaction with intermediate (32a) (313 mg, 1.06 mmol) into intermediate (32b) (289 mg, 0.611 mmol, 75%) as an orange gum as an orange gum after purification by flash chromatography on silica gel (DCM/acetone: 100/0 to 0/100).

MS m/z ([M+H-tBu]⁺) 417, ([M+H-Boc]⁺) 373, ([2M+H]⁺) 945.

¹H NMR (400 MHz, CDCl₃): δ (ppm) 1.46 (s, 9H), 1.46-1.48 (m, 2H), 1.97 (dd, J=12.7, 3.7 Hz, 2H), 2.90 (t, J=12.5 Hz, 2H), 3.14 (d, J=10.9 Hz, 1H), 3.55 (ddd, J=10.8, 2.8, 1.1 Hz, 1H), 3.98-4.21 (m, 5H), 4.36-4.55 (m, 2H), 5.23-5.47 (m, 2H), 6.01 (dddd, J=17.1, 10.3, 6.7, 6.1 Hz, 1H), 6.53 (d, J=5.5 Hz, 1H), 6.69 (d, J=8.2 Hz, 1H), 6.87 (d, J=2.6 Hz, 1H), 7.61 (d, J=2.6 Hz, 1H).

Step 3: Preparation of Intermediate sodium (7-oxo-3[3-[(1-tert-butoxycarbonyl-4-piperidyl)carbamoyl]pyrazol-1-yl]-1,6-diazabicyclo[3.2.1]oct-3-en-6-yl) sulfate (32c)

Using the procedure described in example 2 (step 2), intermediate (32b) (279 mg, 0.590 mmol) was converted into intermediate (32c) (131.2 mg, 0.245 mmol, 41%) as a white solid after lyophilization.

MS m/z ([M−H]⁻) 511.

MS m/z ([M+H-tBu-SO₃H]⁺) 377, ([M+H—SO₃H]⁺) 457

¹H-NMR (300 MHz, D₂O): δ(ppm) 1.34-1.48 (m, 2H), 1.42 (s, 9H), 1.89 (d, J=12.7 Hz, 2H), 2.90 (t, J=12.6 Hz, 2H), 3.42 (d, J=11.3 Hz, 1H), 3.60-3.72 (m, 1H), 3.90-4.10 (m, 3H), 4.37 (br s, 2H), 4.55 (dd, J=5.7, 2.6 Hz, 1H), 6.72 (d, J=5.6 Hz, 1H), 6.82 (d, J=2.6 Hz, 1H), 7.96 (d, J=2.6 Hz, 1H).

Step 4: Preparation of (7-oxo-3-[3-(4-piperidylcarbamoyl)pyrazol-1-yl]-1,6-diazabicyclo[3.2.1]oct-3-en-6-yl) hydrogen sulfate (Example 32)

Intermediate (32c) (40 mg, 0.075 mmol) was dissolved in a mixture 2.5/1 of DCM/TFA (0.93 mL, 0.08M) at 0° C. under inert atmosphere. After stirring for 45 min (conversion of starting material monitored by LC/MS), cold Et₂O (1 mL) was added at 0° C. After stirring for 10 min at 0° C., the precipitate was filtered (Pall VWR 514-4084, 045 µm, GH polypro, Nanosep®MF) and washed with cold Et₂O. The solid was then triturated in ACN to form the zwitterionic compound. The white solid was filtered and washed with ACN. The solid was purified by C-18 reverse phase (H₂O/ACN: 98/2 to 30/70) to afford after lyophilization example (32) (18 mg, 0.044 mmol, 59%) as a white solid.

MS m/z ([M+H]⁺) 413, ([M+H—SO₃H]⁺) 333.

MS m/z ([M−H]⁻) 411.

¹H-NMR (300 MHz, D₂O): δ(ppm) 1.71-1.95 (m, 2H), 2.09-2.28 (m, 2H), 3.13 (td, J=12.9, 3.1 Hz, 2H), 3.40 (d, J=11.3 Hz, 1H), 3.44-3.56 (m, 2H), 3.60-3.73 (dd, J=11.6, 3.7 Hz, 1H), 4.09 (m, 1H), 4.34 (d, J=1.4 Hz, 2H), 4.55 (dd, J=5.7, 2.5 Hz, 1H), 6.63-6.71 (d, J=5.6 Hz 1H), 6.76 (d, J=2.6 Hz, 1H), 7.88 (d, J=2.6 Hz, 1H).

Example 33: Synthesis of triethylammonium {[3-(N-acetamido)pyrazol-1-yl]-7-oxo-1,6-diazabicyclo[3.2.1]oct-3-en-6-yl}sulfate Step 1

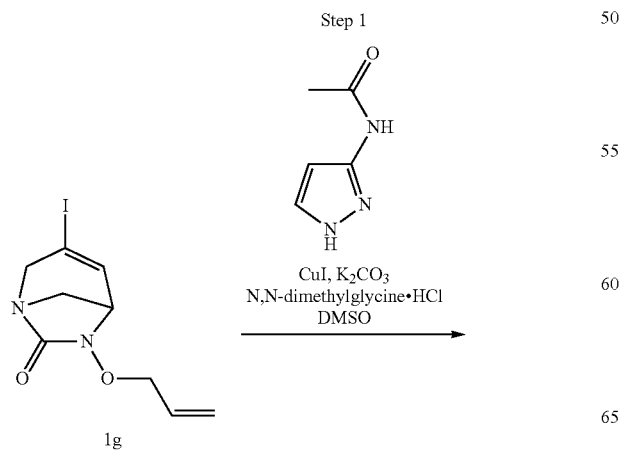

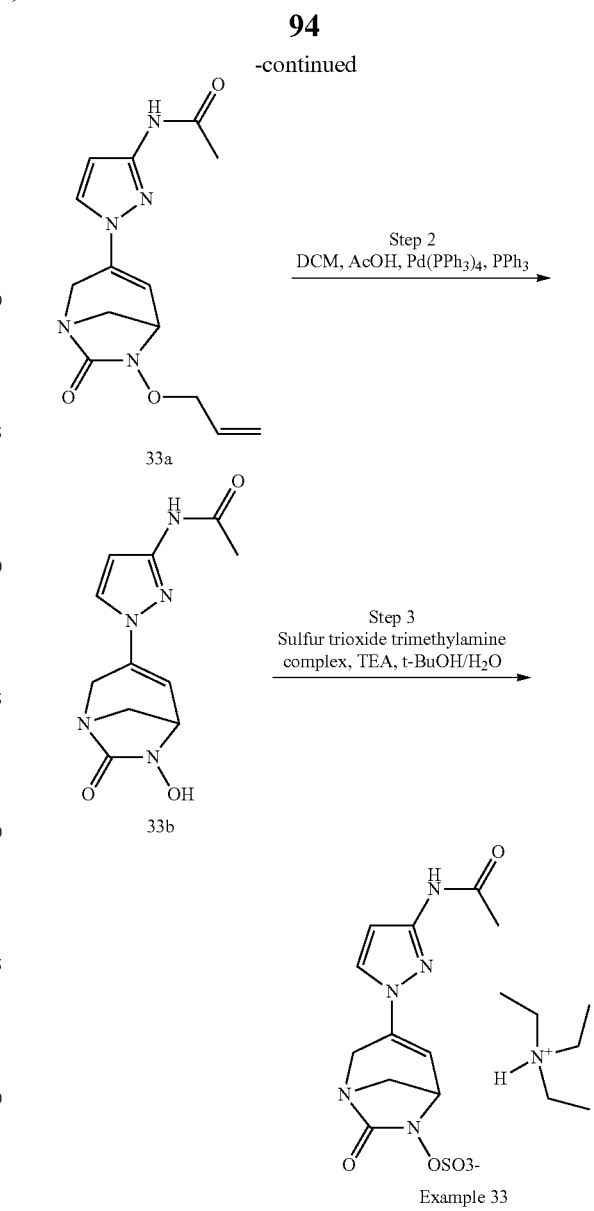

Example 33

Step 1: Preparation of Intermediate N-(6-allyloxy-7-oxo-1,6-diazabicyclo[3.2.1]oct-3-en-3-yl)-3-(N-acetamido)pyrazole (33a)

Using the procedure described in example 1 (step 7), intermediate (1g) (200 mg, 0.653 mmol) was converted by reaction with N-(1H-pyrazol-3-yl)acetamide (164 mg, 1.31 mmol) into intermediate (33a) (72 mg, 0.237 mmol, 36%) as an orange oil after purification by flash chromatography on silica gel (DCM/Acetone: 100/0 to 50/50).

MS m/z ([M+H]⁺) 304.

MS m/z ([M−H]⁻) 302.

¹H NMR (400 MHz, CDCl₃) δ 2.10 (s, 3H), 3.10 (d, J=10.8 Hz, 1H), 3.47 (dd, J=10.8, 2.2 Hz, 1H), 4.06 (dd, J=5.6, 2.6 Hz, 1H), 4.13 (dd, J=17.7, 1.9 Hz, 1H), 4.34-4.44 (m, 3H), 5.27 (dd, J=10.4, 1.1 Hz, 1H), 5.33 (ddd, J=17.2, 1.4, 1.1 Hz, 1H), 5.92-6.02 (m, 1H), 6.28 (d, J=5.6 Hz, 1H), 6.82 (d, J=2.6 Hz, 1H), 7.49 (d, J=2.6 Hz, 1H), 8.90 (s, 1H).

Step 2: Preparation of Intermediate N-(6-hydroxy-7-oxo-1,6-diazabicyclo[3.2.1]oct-3-en-3-yl)-3-(N-acetamido)pyrazole (33b)

Under inert atmosphere intermediate (33a) (72 mg, 0.237 mmol) was diluted in anhydrous DCM (2.4 mL). AcOH (29 μL, 0.477 mmol), Pd(PPh$_3$)$_4$ (41 mg, 0.036 mmol) and PPh$_3$ (63 mg, 0.238 mmol) were successively added. The reaction mixture was stirred at rt for 2 h. The mixture was filtered to provide intermediate (33b) (50 mg, 0.190 mmol, 80%) as an off-white solid.

MS m/z ([M+H]$^+$) 264.

MS m/z ([M–H]$^-$) 262.

$^1$H NMR (400 MHz, DMSO-d$_6$) δ2.00 (s, 3H), 3.20 (d, J=10.7 Hz, 1H), 3.34 (dd, J=10.7, 2.9 Hz, 1H), 4.00 (dd, J=5.6, 2.6 Hz, 1H), 4.10 (dd, J=17.5, 1.1 Hz, 1H), 4.15 (dd, J=17.5, 1.6 Hz, 1H), 6.51 (d, J=5.6 Hz, 1H), 6.67 (d, J=2.6 Hz, 1H), 8.01 (d, J=2.6 Hz, 1H), 9.64 (br s, 1H), 10.63 (s, 1H).

Step 3: Preparation triethylammonium {[3-(N-acetamido)pyrazol-1-yl]-7-oxo-1,6-diazabicyclo[3.2.1]oct-3-en-6-yl}sulfate (Example 33)

Intermediate (33b) (46 mg, 0.175 mmol) was diluted in water/tBuOH (1:1) (1.7 mL). Sulfur trioxide trimethylamine complex (29 mg, 0.208 mmol) and TEA (6 μL, 0.043 mmol) were successively added. The reaction mixture was stirred at rt overnight. The crude compound was concentrated and purified by flash chromatography on C18-reversed phase silica gel (H$_2$O/ACN: 100/0 to 90/10) to give example (33) (24 mg, 0.054 mmol, 31%) as an off-white solid.

MS m/z ([M+H]$^+$) 344.

MS m/z ([M–H]$^-$) 342.

$^1$H NMR (400 MHz, D$_2$O) δ 1.24 (t, J=7.3 Hz, 9H), 2.14 (s, 3H), 3.16 (q, J=7.3 Hz, 6H), 3.40 (d, J=11.2 Hz, 1H), 3.65 (dd, J=11.2, 2.5 Hz, 1H), 4.31 (m, 2H), 4.53 (dd, J=5.7, 2.7 Hz, 1H), 6.54 (d, J=5.7 Hz, 1H), 6.55 (d, J=2.8 Hz, 1H), 7.79 (d, J=2.8 Hz, 1H).

Example 34: Synthesis of sodium {7-oxo-3-[3-(thiazole-2-carbonylamino)pyrazol-1-yl]-1,6-diazabicyclo[3.2.1]oct-3-en-6-yl}sulfate

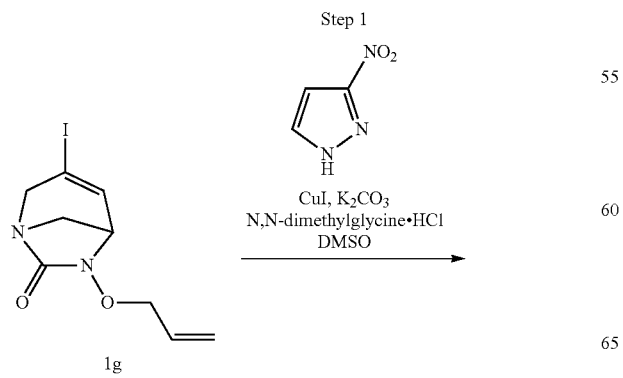

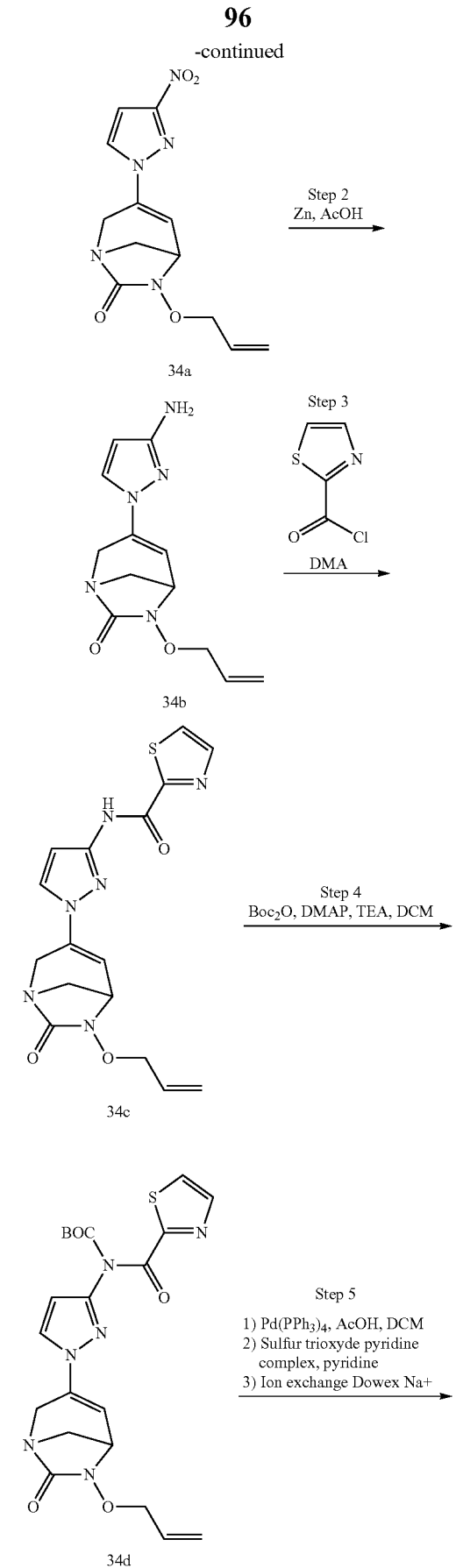

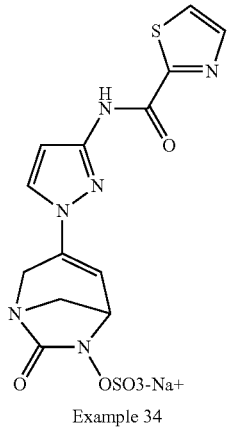

Example 34

Step 1: Preparation of intermediate 6-allyloxy-3-(3-nitropyrazol-1-yl)-1,6-diazabicyclo[3.2.1]oct-3-en-7-one (34a)

Using the procedure described in example 1 (step 7), intermediate (1g) (2.00 g, 6.53 mmol) was converted by reaction with 3-nitro-1H-pyrazole (961 mg, 8.49 mmol) into intermediate (34a) (1.07 g, 3.61 mmol, 55%) as a white solid after purification by flash chromatography on silica gel (DCM/Acetone: 100/0 to 70/30) then trituration in Et$_2$O.

MS m/z ([M+H]$^+$) 292.

$^1$H NMR (400 MHz, CDCl$_3$) δ 3.15 (d, J=11.0 Hz, 1H), 3.57 (dd, J=11.0, 2.8 Hz, 1H), 4.16 (dd, J=5.5, 2.5 Hz, 1H), 4.25 (dd, J=17.7, 1.9 Hz, 1H), 4.38-4.49 (m, 3H), 5.33 (ddd, J=10.3, 1.7, 0.9 Hz, 1H), 5.38 (ddd, J=17.2, 1.7, 1.4 Hz, 1H), 5.96-6.06 (m, 1H), 6.72 (d, J=5.5 Hz, 1H), 6.99 (d, J=2.7 Hz, 1H), 7.69 (d, J=2.7 Hz, 1H).

Step 2: Preparation of intermediate 6-allyloxy-3-(3-aminopyrazol-1-yl)-1,6-diazabicyclo[3.2.1]oct-3-en-7-one (34b)

Under inert atmosphere, intermediate (34a) (1.07 g, 3.61 mmol) and AcOH (2.1 mL, 36.84 mmol) were diluted in DCM (37 mL). The solution was cooled at 0° C. and then Zn powder (2.4 g, 36.84 mmol) was added. The reaction mixture was stirred at 0° C. for 1.5 h. The mixture was filtered and the filtrate was concentrated. The residue was triturated with Et$_2$O to give intermediate (34b) (958 mg, 2.75 mmol, 76%).

MS m/z ([M+H]$^+$) 262.

$^1$H NMR (400 MHz, CDCl$_3$) δ 3.16 (d, J=10.7 Hz, 1H), 3.50 (dd, J=10.7, 2.6 Hz, 1H), 4.04-4.06 (m, 1H), 4.08 (dd, J=12.8, 2.2 Hz, 1H), 4.30 (d, J=17.2 Hz, 1H), 4.36-4.48 (m, 2H), 5.30 (ddd, J=10.3, 1.6, 1.3 Hz, 1H), 5.36 (ddd, J=17.2, 1.6, 1.4 Hz, 1H), 5.74 (d, J=2.6 Hz, 1H), 5.96-6.06 (m, 1H), 6.30 (d, J=5.9 Hz, 1H), 7.28 (d, J=2.6 Hz, 1H).

Step 3: Preparation of intermediate N—[N-(6-allyloxy-7-oxo-1,6-diazabicyclo[3.2.1]oct-3-en-3-yl)pyrazol-3-yl]thiazole-2-carboxamide (34c)

Under inert atmosphere, intermediate (34b) (500 mg, 1.91 mmol) was diluted in DMA (19 mL). 1,3-Thiazole-2-carbonyl chloride (565 mg, 3.83 mmol) was added. The mixture was stirred at rt for 2 h. The formed precipitate was filtered and washed with Et$_2$O to give intermediate (34c) (386 mg, 1.01 mmol, 53%) as a off-white solid.

MS m/z ([M+H]$^+$) 373.
MS m/z ([M−H]$^-$) 371.

$^1$H NMR (400 MHz, DMSO-d$_6$) δ3.27 (d, J=10.9 Hz, 1H), 3.33 (dd, J=10.9, 2.4 Hz, 1H), 4.19 (dd, J=17.4, 1.2 Hz, 1H), 4.24 (dd, J=17.4, 1.5 Hz, 1H), 4.29 (dd, J=5.7, 2.4 Hz, 1H), 4.39 (d, J=5.5 Hz, 2H), 5.26 (ddd, J=10.4, 1.6, 1.4 Hz, 1H), 5.37 (ddd, J=17.3, 1.6, 1.6 Hz, 1H), 5.91-6.01 (m, 1H), 6.57 (d, J=5.7 Hz, 1H), 6.76 (d, J=2.6 Hz, 1H), 8.10 (d, J=3.1 Hz, 1H), 8.12 (d, J=2.6 Hz, 1H), 8.14 (d, J=3.1 Hz, 1H), 10.99 (br s, 1H).

Step 4: Preparation of intermediate tert-butyl N—[N-(6-allyloxy-7-oxo-1,6-diazabicyclo[3.2.1]oct-3-en-3-yl)pyrazol-3-yl]thiazole-2-carbonyl carbamate (34d)

Under inert atmosphere, intermediate (34c) (226 mg, 0.61 mmol) was diluted in DCM (6 mL). Boc$_2$O (154 μL, 0.67 mmol), TEA (93 μL, 0.67 mmol) and DMAP (7 mg, 0.06 mmol) were added. The mixture reaction was stirred at rt for 16 h. The crude compound was purified by flash chromatography on silica gel (DCM/acetone: 100/0 to 70/30) to give intermediate (34d) (295 mg, 0.54 mmol, 88%) as a colorless oil.

MS m/z ([M+H]$^+$) 473.

$^1$H NMR (400 MHz, CDCl$_3$) δ 1.39 (s, 9H), 3.10 (d, J=10.8 Hz, 1H), 3.50 (dd, J=10.8, 2.8 Hz, 1H), 4.07 (dd, J=5.6, 2.6 Hz, 1H), 4.14 (dd, J=17.6, 1.8 Hz, 1H), 4.32 (dd, J=17.6, 1.0 Hz, 1H), 4.38-4.48 (m, 2H), 5.30 (ddd, J=10.3, 1.6, 1.4 Hz, 1H), 5.36 (dd, J=17.2, 1.4 Hz, 1H), 5.96-6.06 (m, 1H), 6.41 (d, J=5.6 Hz, 1H), 6.42 (d, J=2.6 Hz, 1H), 7.61 (d, J=2.6 Hz, 1H), 7.62 (d, J=3.1 Hz, 1H), 7.92 (d, J=3.1 Hz, 1H).

Step 5: Preparation of sodium {7-oxo-3-[3-(thiazole-2-carbonylamino)pyrazol-1-yl]-1,6-diazabicyclo[3.2.1]oct-3-en-6-yl}sulfate (Example 34)

Under inert atmosphere, intermediate (34d) (290 mg, 0.61 mmol) was diluted in anhydrous DCM (6 mL). AcOH (70 μL, 1.23 mmol) and Pd(PPh$_3$)$_4$ (354 mg, 0.31 mmol) were successively added. The reaction mixture was stirred at rt for 2 h. After 2 h, anhydrous pyridine (6 mL) and sulfur trioxide pyridine complex (488 mg, 3.06 mmol) were added to the reaction mixture. The resulting suspension was protected from light and stirred overnight until the reaction was completed. The reaction mixture was concentrated and then purified by flash chromatography on silica gel (DCM/acetone: 100/0 to 0/100). Fractions containing the product were combined and concentrated. The intermediate obtained (195 mg, 0.24 mmol) was dissolved in a minimum of H$_2$O/acetone (1:1) and converted after ion exchange with Dowex sodium form column (Dowex® 50WX8 hydrogen form stored with an aqueous solution of 2N NaOH and washed until neutral pH with H$_2$O). Fractions containing the product were combined and lyophilized. The solid obtained was triturated in water (5 mL) and stirred at 0° C. for 8 h. The mixture was filtered and purified by flash chromatography on C18-reversed phase silica gel (H$_2$O/ACN: 100/0 to 60/40). Fractions containing the product were combined and lyophilized to give example (34) (5 mg, 0.11 mmol, 18% over 3 steps) as a yellow solid.

MS m/z ([M+H]$^+$) 413.
MS m/z ([M−H]$^-$) 411.

$^1$H NMR (300 MHz, DMSO-d$_6$) δ3.27 (d, J=11.0 Hz, 1H), 3.39 (dd, J=11.0, 2.3 Hz, 1H), 4.19-4.23 (m, 2H), 4.37 (dd, J=5.7, 2.4 Hz, 1H), 6.60 (d, J=5.7 Hz, 1H), 6.78 (d, J=2.6 Hz, 1H), 8.11 (d, J=3.1 Hz, 1H), 8.14 (d, J=3.1 Hz, 1H), 8.17 (d, J=2.6 Hz, 1H), 11.02 (br s, 1H).
Example 35: Synthesis of sodium and 2,2,2-trifluoroacetate [7-oxo-3-[3-(methylene-2-ammoniumthiazole)pyrazol-1-yl]-1,6-diazabicyclo[3.2.1]oct-3-en-6-yl]sulfate
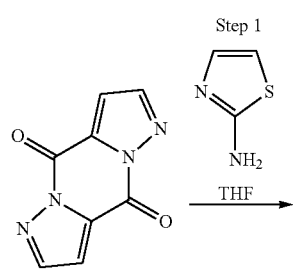
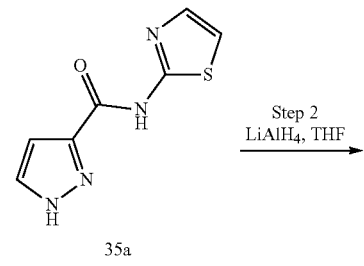
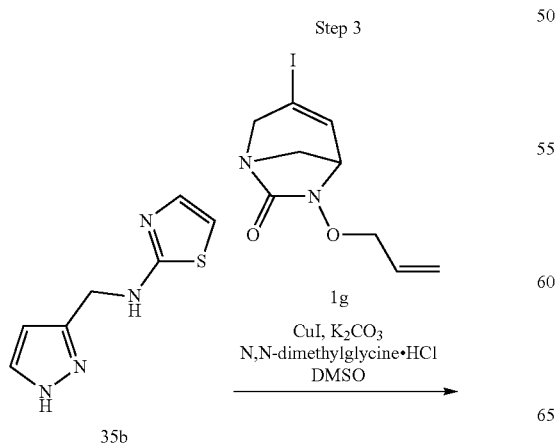
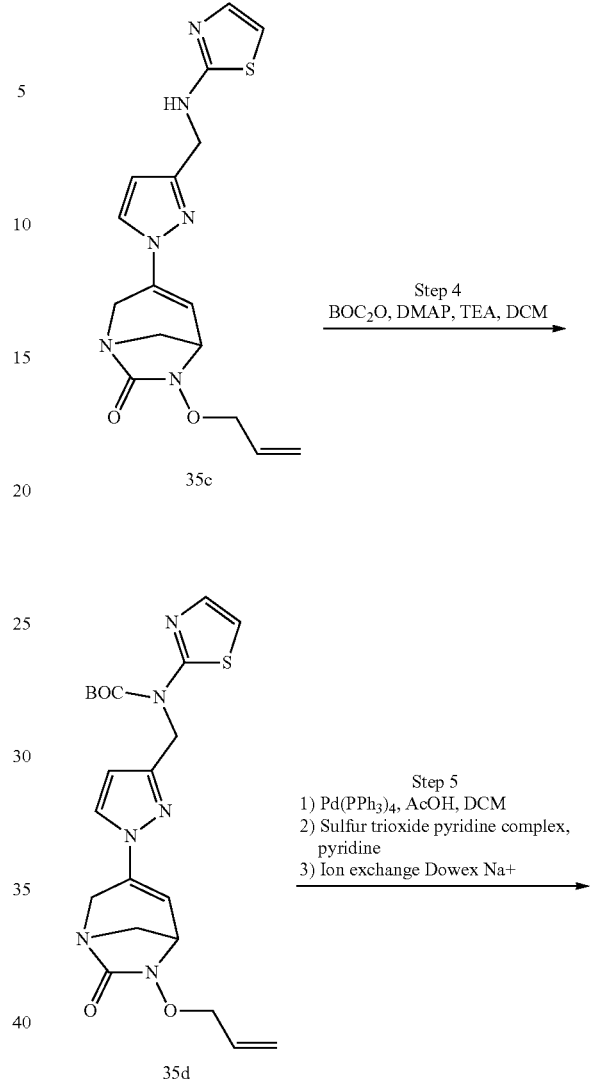

-continued

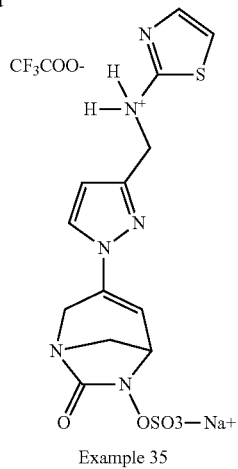

Example 35

Step 1: Preparation of Intermediate N-thiazol-2-yl-1H-pyrazole-3-carboxamide (35a)

Dipyrazolo[3,1-a: 3',1'-d]pyrazine-4,9-dione (prepared according to *Bioorganic & Medicinal Chemistry Letters*, 2015, 25 (15), 3024-3029) (500 mg, 2.66 mmol) and 2-aminothiazole (532 mg, 5.32 mmol) were diluted in THF (5 mL). The mixture reaction was heated at 60° C. for 2 h. After cooling down to rt, the mixture was filtered, washed with ACN and Et$_2$O to give intermediate (35a) (843 mg, 4.34 mmol, 82%) as an off-white solid.

MS m/z ([M+H]$^+$) 195.
MS m/z ([M–H]$^-$) 193.
$^1$H NMR (300 MHz, DMSO-d$_6$) δ7.00 (s, 1H), 7.26 (d, J=3.6 Hz, 1H), 7.53 (d, J=3.6 Hz, 1H), 7.88 (s, 1H), 12.04 (br s, 1H), 13.57 (br s, 1H).

Step 2: Preparation of Intermediate N-(1H-pyrazol-3-ylmethyl)thiazol-2-amine (35b)

Under inert atmosphere, to a solution of intermediate (35a) (750 mg, 3.86 mmol) in THF (8 mL) at 0° C., a solution of LiAlH$_4$ in THF (2M, 3.9 mL, 7.72 mmol) was added dropwise. The mixture was heated under reflux for 4 h. After cooling down to rt, the reaction mixture was cooled at 0° C. and then quenched with water and filtered. The filtrate was extracted with EtOAc (5×50 mL). The organic layer was dried with Na$_2$SO$_4$, filtered and concentrated to give intermediate (35b) (342 mg, 1.89 mmol, 49%) as an off-white solid.

MS m/z ([M+H]$^+$) 181.
MS m/z ([M–H]$^-$) 179.
$^1$H NMR (400 MHz, DMSO-d$_6$) δ4.40 (m, 2H), 6.18 (d, J=2.1 Hz, 1H), 6.61 (d, J=3.7 Hz, 1H), 7.02 (d, J=3.7 Hz, 1H), 7.63 (s, 1H), 7.84 (s, 1H), 12.62 (br s, 1H).

Step 3: Preparation of Intermediate 6-allyloxy-3-[3-[(thiazol-2-ylamino)methyl]pyrazol-1-yl]-1,6-diazabicyclo[3.2.1]oct-3-en-7-one (35c)

Using the procedure described in example 1 (step 7), intermediate (1g) (420 mg, 1.37 mmol) was converted by reaction with N-(1H-pyrazol-3-ylmethyl)thiazol-2-amine (35b) (322 mg, 1.78 mmol) into intermediate (35c) (194 mg, 0.49 mmol, 35%) as an orange oil after purification by flash chromatography on silica gel (DCM/Acetone: 100/0 to 0/100).

MS m/z ([M+H]$^+$) 359.
MS m/z ([M–H]$^-$) 357.

$^1$H NMR (400 MHz, CDCl$_3$) δ 3.14 (d, J=10.8 Hz, 1H), 3.53 (dd, J=10.8, 1.9 Hz, 1H), 4.10 (dd, J=5.6, 2.6 Hz, 1H), 4.17 (dd, J=17.6, 1.9 Hz, 1H), 4.37-4.54 (m, 3H), 4.50 (m, 2H), 5.31 (m, 1H), 3.37 (ddd, J=17.2, 1.6, 1.4 Hz, 1H), 5.97-6.07 (m, 1H), 6.35 (d, J=2.5 Hz, 1H) 6.46 (d, J=5.6 Hz, 1H), 6.54 (s, 1H), 7.14 (s, 1H), 7.55 (d, J=2.5 Hz, 1H).

Step 4: Preparation of Intermediate tert-butyl {[1-(6-allyloxy-7-oxo-1,6-diazabicyclo[3.2.1]oct-3-en-3-yl)pyrazol-3-yl]methyleneamino}-N-thiazol-2-yl-carbamate (35d)

Under inert atmosphere, intermediate (35c) (166 mg, 0.46 mmol) was diluted in DCM (5 mL). Boc$_2$O (117 μL, 0.51 mmol), TEA (71 μL, 0.51 mmol) and DMAP (6 mg, 0.05 mmol) were added. The mixture reaction was stirred at rt for 16 h. The crude compound was purified by flash chromatography on silica gel (DCM/acetone: 100/0 to 20/80) to give intermediate (35d) (137 mg, 0.29 mmol, 62%) as a yellow oil.

MS m/z ([M+H]$^+$) 459.
$^1$H NMR (400 MHz, CDCl$_3$) δ 1.53 (s, 9H), 3.11 (d, J=10.7 Hz, 1H), 3.51 (dd, J=10.7, 1.9 Hz, 1H), 4.06 (dd, J=5.6, 2.6 Hz, 1H), 4.15 (dd, J=17.6, 1.9 Hz, 1H), 4.36-4.48 (m, 3H), 5.30 (dd, J=10.3, 1.3 Hz, 1H), 5.33-5.35 (m, 2H), 5.38 (ddd, J=17.2, 1.6, 1.4 Hz, 1H), 6.01 (dddd, J=17.6, 10.3, 6.7, 6.0 Hz, 1H), 6.24 (d, J=2.6 Hz, 1H), 6.37 (d, J=5.6 Hz, 1H), 6.93 (d, J=3.7 Hz, 1H), 7.42 (d, J=3.7 Hz, 1H), 7.48 (d, J=2.6 Hz, 1H).

Step 5: Preparation of Intermediate sodium {3-[tert-butoxycarbonyl-N-(thiazol-2-yl)-3-aminomethyl-pyrazol-1-yl]-7-oxo-1,6-diazabicyclo[3.2.1]oct-3-en-6-yl}sulfate (35e)

Under inert atmosphere, intermediate (35d) (127 mg, 0.28 mmol) was diluted in anhydrous DCM (2.8 mL). AcOH (32 μL, 0.55 mmol) and Pd(PPh$_3$)$_4$ (160 mg, 0.14 mmol) were successively added. The reaction mixture was stirred at rt for 2 h. Then anhydrous pyridine (2.8 mL) and sulfur trioxide pyridine complex (220 mg, 1.38 mmol) were added to the reacting mixture. The resulting suspension was protected from light and stirred overnight until the reaction was completed. The reaction mixture was concentrated and then purified by flash chromatography on silica gel (DCM/acetone: 100/0 to 0/100). Fractions containing the product were combined and concentrated. The residue was dissolved in a minimum of H$_2$O/ACN (1:1) and converted after ion exchange with Dowex sodium form column (Dowex® 50WX8 hydrogen form stored with an aqueous solution of 2N NaOH and washed until neutral pH with H$_2$O) to give intermediate (35e) (68 mg, 0.13 mmol, 47%) as a yellow solid.

MS m/z ([M+H]$^+$) 499.
MS m/z ([M–H]$^-$) 497.
$^1$H NMR (400 MHz, DMSO-d$_6$) δ 1.48 (s, 9H), 3.24 (d, J=10.9 Hz, 1H), 3.35 (dd, J=10.9, 2.5 Hz, 1H), 4.12-4.16 (m, 2H), 4.32 (dd, J=5.7, 2.5 Hz, 1H), 5.23 (s, 2H), 6.20 (d, J=2.6 Hz, 1H), 6.54 (d, J=5.7 Hz, 1H), 7.24 (d, J=3.6 Hz, 1H), 7.43 (d, J=3.6 Hz, 1H), 8.10 (d, J=2.6 Hz, 1H).

Step 6: Preparation of sodium and 2,2,2-trifluoroacetate [7-oxo-3-[3-(methylene-2-ammoniumthiazole)pyrazol-1-yl]-1,6-diazabicyclo[3.2.1]oct-3-en-6-yl] sulfate (Example 35)

Intermediate (35e) (57 mg, 0.11 mmol) was dissolved in a mixture of DCM/TFA (3:2) (2.2 mL) and stirred at 0° C.

After 48 h at 0° C., the mixture was concentrated. The residue was purified by flash chromatography on C18-reversed phase silica gel (H₂O/ACN: 100/0 to 70/30). Fractions containing the desired compound were combined and lyophilized to afford example (35) (1.7 mg, 0.003 mmol, 3%) as a light-pink solid.

MS m/z ([M+H]⁺) 399.

MS m/z ([M−H]⁻) 397.

$^1$H NMR (300 MHz, D$_2$O) δ 3.44 (d, J=11.4 Hz, 1H), 3.68 (dd, J=11.4, 2.1 Hz, 1H), 4.34-4.37 (m, 2H), 4.49-4.51 (m, 2H), 4.56 (dd, J=5.7, 2.6 Hz, 1H), 6.45 (d, J=2.7 Hz, 1H), 6.58 (d, J=5.7 Hz, 1H), 6.68 (d, J=3.8 Hz, 1H), 7.07 (d, J=3.8 Hz, 1H), 7.38 (br s, 1H), 7.84 (d, J=2.7 Hz, 1H), 8.45 (br s, 1H). $^{19}$F NMR (367 MHz, D$_2$O) δ-75.55 (s, 3F).

Example 37: Synthesis of sodium [7-oxo-3-[3-(oxazol-2-ylcarbamoyl)pyrazol-1-yl]-1,6-diazabicyclo[3.2.1]oct-3-en-6-yl]sulfate

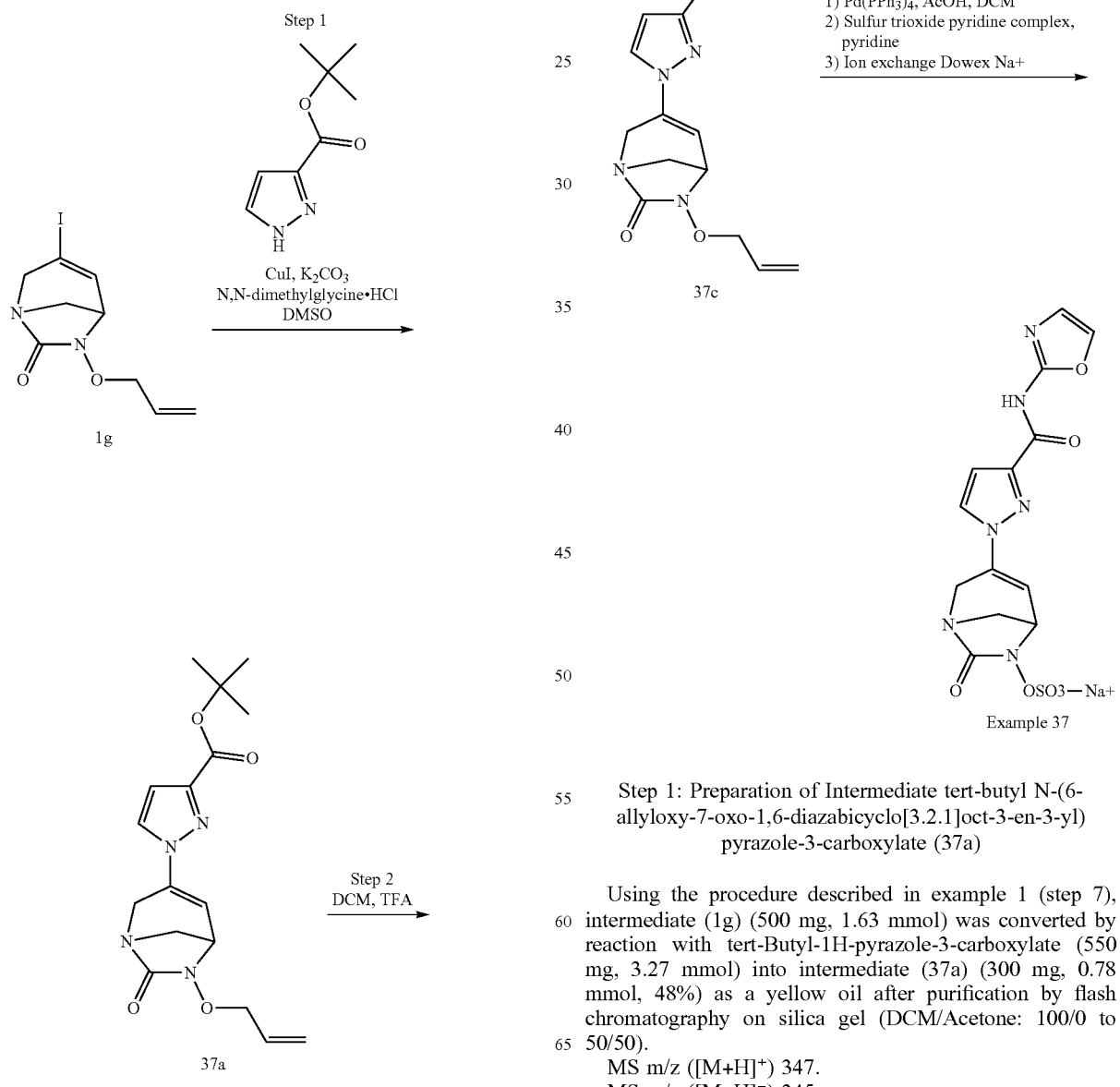

Step 1: Preparation of Intermediate tert-butyl N-(6-allyloxy-7-oxo-1,6-diazabicyclo[3.2.1]oct-3-en-3-yl)pyrazole-3-carboxylate (37a)

Using the procedure described in example 1 (step 7), intermediate (1g) (500 mg, 1.63 mmol) was converted by reaction with tert-Butyl-1H-pyrazole-3-carboxylate (550 mg, 3.27 mmol) into intermediate (37a) (300 mg, 0.78 mmol, 48%) as a yellow oil after purification by flash chromatography on silica gel (DCM/Acetone: 100/0 to 50/50).

MS m/z ([M+H]⁺) 347.

MS m/z ([M−H]⁻) 345.

¹H NMR (400 MHz, CDCl₃) δ 1.58 (s, 9H), 3.13 (d, J=10.8 Hz, 1H), 3.53 (dd, J=10.8, 1.8 Hz, 1H), 4.11 (dd, J=5.6, 2.6 Hz, 1H), 4.27 (dd, J=17.7, 1.8 Hz, 1H), 4.37-4.49 (m, 3H), 5.31 (dt, J=10.4, 1.6 Hz, 1H), 5.37 (ddd, J=17.2, 1.6, 1.4 Hz, 1H), 5.96-6.06 (m, 1H), 6.58 (d, J=5.6 Hz, 1H), 6.77 (d, J=2.6 Hz, 1H), 7.60 (d, J=2.6 Hz, 1H).

Step 2: Preparation of Intermediate N-(6-allyloxy-7-oxo-1,6-diazabicyclo[3.2.1]oct-3-en-3-yl)pyrazole-3-carboxylic acid (37b)

The intermediate (37a) (300 mg, 0.78 mmol) was dissolved in a mixture of DCM and TFA (5:1) (4.3 mL). The mixture was stirred at rt for 4 h. The mixture was concentrated and then purified by flash chromatography on silica gel (DCM/acetone: 100/0 to 60/40). Fractions containing the expected intermediate were combined and concentrated to give intermediate (37b) (162 mg, 0.53 mmol, 68%) as a yellow solid.

MS m/z ([M+H]⁺) 291.
MS m/z ([M−H]⁻) 289.
¹H NMR (300 MHz, DMSO-d₆) δ3.27 (d, J=11.0 Hz, 1H), 3.34 (dd, J=11.0, 2.6 Hz, 1H), 4.24 (m, 2H), 4.32 (dd, J=5.6, 2.2 Hz, 1H), 4.39 (d, J=6.3 Hz, 2H), 5.26 (dd, J=10.4, 1.9 Hz, 1H), 5.36 (ddd, J=17.4, 1.9, 1.6 Hz, 1H), 5.89-6.02 (m, 1H), 6.77 (d, J=5.6 Hz, 1H), 6.85 (d, J=2.6 Hz, 1H), 8.29 (d, J=2.6 Hz, 1H), 12.99 (br s, 1H).

Step 3: Preparation of Intermediate N-(6-allyloxy-7-oxo-1,6-diazabicyclo[3.2.1]oct-3-en-3-yl)-3-(N-oxazol-2-yl-carboxamide)pyrazole (37c)

Under inert atmosphere, intermediate (37b) (300 mg, 1.03 mmol) was diluted in anhydrous DMF (10 mL). HOBt H₂O (206 mg, 1.34 mmol) and EDC.HCl (258 mg, 1.34 mmol) were successively added. The reaction mixture was stirred at rt for 10 min. 2-aminooxazole (304 mg, 3.62 mmol) and DIPEA (451 μL, 2.58 mmol) were added. The reaction mixture was stirred at rt for 16 h. Then the mixture was diluted in H₂O (150 mL). The aqueous layer was extracted with EtOAc (3×150 mL). The organic layers were combined, washed with a satured NaHCO₃, dried over Na₂SO₄, filtered and concentrated. The crude compound was purified by flash chromatography on silica gel (DCM/acetone: 100/0 to 40/60) to provide intermediate (37c) (182 mg, 0.42 mmol, 41%) as a colorless oil.

MS m/z ([M+H]⁺) 357.
MS m/z ([M−H]⁻) 355.
¹H NMR (400 MHz, CDCl₃) 3.17 (d, J=10.9 Hz, 1H), 3.57 (dd, J=10.9, 1.9 Hz, 1H), 4.16 (dd, J=5.5, 2.6 Hz, 1H), 4.23 (dd, J=17.6, 1.9 Hz, 1H), 4.29-4.50 (m, 3H), 5.33 (dd, J=10.3, 1.5 Hz, 1H), 5.38 (ddd, J=17.6, 1.5, 1.4 Hz, 1H), 5.98-6.08 (m, 1H), 6.65 (d, J=5.5 Hz, 1H), 7.03 (d, J=2.7 Hz, 1H), 7.08 (d, J=1.1 Hz, 1H), 7.51 (d, J=1.1 Hz, 1H), 7.70 (d, J=2.7 Hz, 1H), 8.02 (br s, 1H).

Step 4: Preparation of sodium [7-oxo-3-[3-(oxazol-2-ylcarbamoyl)pyrazol-1-yl]-1,6-diazabicyclo[3.2.1]oct-3-en-6-yl]sulfate (example 37)

Using the procedure described in example 2 (step 2), intermediate (37c) (106 mg, 0.30 mmol) was converted into example (37) (46 mg, 0.11 mmol, 40% over three steps) as a light-yellow solid after purification by flash chromatography on silica gel (DCM/acetone: 100/0 to 0/100) before the ion exchange on Dowex.

MS m/z ([M+H]⁺) 397.
MS m/z ([M−H]⁻) 395.

¹H NMR (300 MHz, D₂O) δ3.45 (d, J=11.1 Hz, 1H), 3.70 (dd, J=11.1, 1.9 Hz, 1H), 4.40-4.46 (m, 2H), 4.60 (dd, J=5.6, 2.5 Hz, 1H), 6.77 (d, J=5.6 Hz, 1H), 6.98 (d, J=2.7 Hz, 1H), 7.11 (d, J=1.1 Hz, 1H), 7.64 (d, J=1.1 Hz, 1H), 8.03 (d, J=2.7 Hz, 1H).

Example 38: Synthesis of 3[3-[4-(2-aminoethylcarbamoyl)pyrazol-1-yl]-7-oxo-1,6-diazabicyclo[3.2.1]oct-3-en-6-yl]hydrogen sulfate

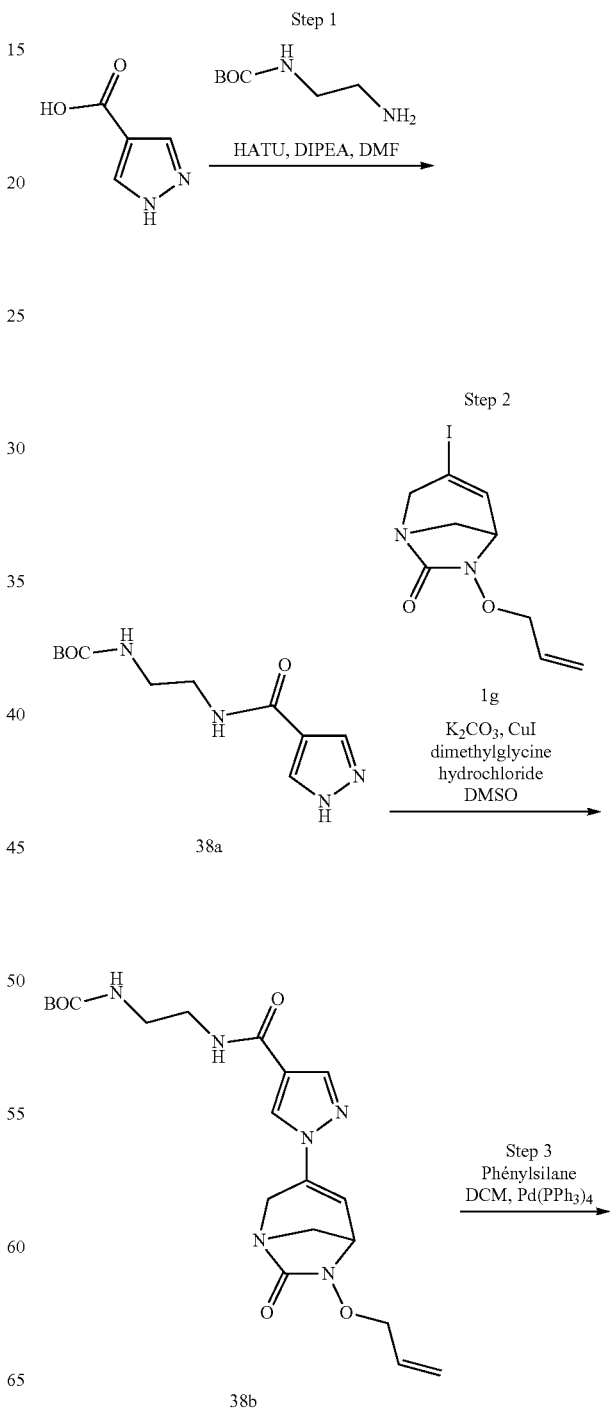

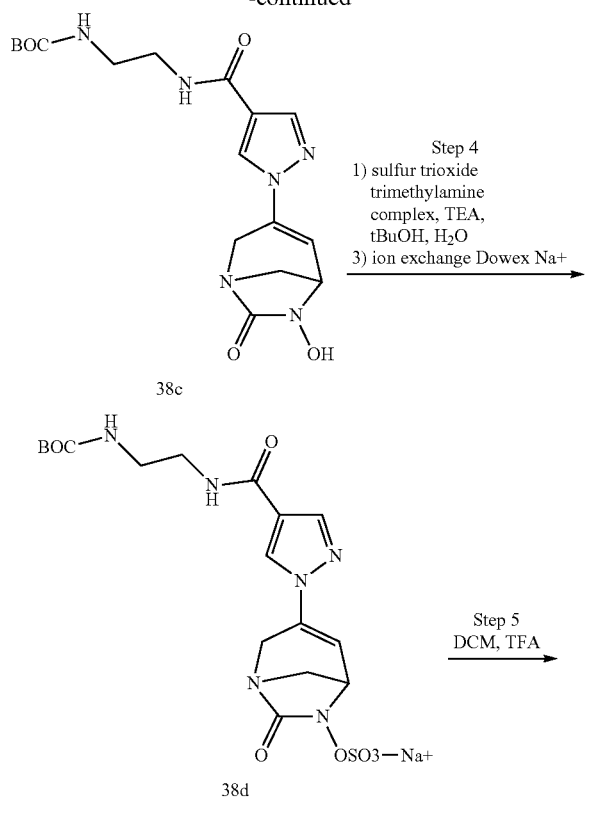

Step 1: Preparation of Intermediate tert-butyl N-[2-(1H-pyrazole-4-carbonylamino)ethyl]carbamate (38a)

1H-pyrazole-4-carboxylic acid (50 mg, 4.46 mmol) was dissolved in DMF (45 mL). Tert-butyl N-(2-aminoethyl)carbamate (1.44 mL, 9.82 mmol), HATU (1.87g, 4.91 mmol) and DIPEA (2.33 mL, 13.4 mmol) were added and mixture was stirred at 50° C. overnight. After concentration, the residue was purified on silica gel (DCM/MeOH: 100/0 to 80/20) to provide intermediate (38a) (408 mg, 1.61 mmol, 36%).

MS m/z ([M+H]$^+$) 255.

$^1$H NMR (400 MHz, CD$_3$OD): δ (ppm) 1.42 (s, 9H), 3.25 (t, J=6.1 Hz, 2H), 3.41 (t, J=6.1 Hz, 2H), 8.04 (s, 2H).

Step 2: Preparation of Intermediate tert-butyl N-[2-[[1-(6-allyloxy-7-oxo-1,6-diazabicyclo[3.2.1]oct-3-en-3-yl)pyrazole-4-carbonyl]amino]ethyl]carbamate (38b)

Using the procedure described in example 1 (step 7), intermediate (1g) (0.15 g, 0.49 mmol) was converted by reaction with intermediate (38a) (0.14 g, 0.55 mmol) into intermediate (38b) (0.138 g, 0.32 mmol, 66%) after purification by flash chromatography on silica gel (DCM/Acetone: 100/0 to 0/100).

MS m/z ([2M+H]$^+$) 865.

$^1$H NMR (300 MHz, CDCl$_3$): δ (ppm) 1.40 (s, 9H), 3.13 (d, J=10.8 Hz, 1H), 3.28-3.38 (m, 2H), 3.39-3.57 (m, 3H), 4.07-4.21 (m, 2H), 4.31-4.51 (m, 3H), 5.20-5.42 (m, 3H), 5.89-6.08 (m, 1H), 6.54 (d, J=5.5 Hz, 1H), 7.35 (s, 1H), 7.85 (s, 1H), 8.07 (s, 1H).

Step 3: Preparation of Intermediate tert-butyl N-[2-[[1-(6-hydroxy-7-oxo-1,6-diazabicyclo[3.2.1]oct-3-en-3-yl)pyrazole-4-carbonyl]amino]ethyl]carbamate (38c)

Under inert atmosphere, phenylsilane (68 µL, 0.546 mmol) and Pd(PPh$_3$)$_4$ (16 mg, 0.014 mmol) were added to a solution of intermediate (38b) (118 mg, 0.273 mmol) in anhydrous DCM (2.8 mL). The reaction mixture was stirred at rt for 1 h30 and concentrated. The crude product was purified on silica gel (DCM/acetone: 100/0 to 0/100) to provide intermediate (38c) (52 mg, 0.132 mmol, 48%).

MS m/z ([M+H]$^+$) 393.

Step 4: Preparation of Intermediate sodium [3-[4-[2-(tert-butoxycarbonylamino) ethylcarbamoyl]pyrazol-1-yl]-7-oxo-1,6-diazabicyclo[3.2.1]oct-3-en-6-yl]sulfate (38d)

Intermediate (38c) (52 mg, 0.132 mmol) was dissolved in a mixture of tBuOH (0.7 mL) and H$_2$O (0.7 mL). TEA (4.6 µL, 0.032 mmol) and sulfur trioxide trimethylamine complex (22 mg, 0.158 mmol) was added. The mixture was stirred at rt for 2 h then concentrated in vacuo. The residue was purified by flash chromatography on C18-reversed phase silica gel (H$_2$O/ACN 98/2 to 0/100). The fractions containing the expected intermediate were combined and concentrated in vacuo. The residue was dissolved in H$_2$O and converted after ion exchange with Dowex sodium form column (Dowex® 50WX8 hydrogen form stored with an aqueous solution of 2N NaOH and washed until neutral pH with H$_2$O) to intermediate (38d) (25 mg, 0.050 mmol, 39%).

MS m/z ([M-H]$^-$) 471.

Step 5: Preparation of [3-[4-(2-aminoethylcarbamoyl)pyrazol-1-yl]-7-oxo-1,6-diazabicyclo[3.2.1]oct-3-en-6-yl]hydrogen sulfate (example 38)

Intermediate (38d) (25 mg, 0.050 mmol) was dissolved in DCM (0.5 mL). At 0° C., TFA (0.25 mL) was added and mixture was stirred at 0° C. for 20 min. Et$_2$O was added to give a precipitate and ethereal phase was removed. Residue was triturated several times in ACN and the obtained solid was dried under azote. The residue was purified by flash chromatography on C18-reversed phase silica gel (H$_2$O/ACN 98/2 to 0/100). The fractions containing desired product were combined and concentrated in vacuo to give example (38) (6.1 mg, 0.016 mmol, 34%).

MS m/z ([M-H]$^+$) 373.

$^1$H NMR (400 MHz, D$_2$O): δ(ppm) 3.24 (t, J=5.8 Hz, 2H), 3.45 (d, J=11.4 Hz, 1H), 3.66 (t, J=5.9 Hz, 2H), 3.67-3.72 (m, 1H), 4.34 (dd, J=17.5, 1.2 Hz, 1H), 4.40 (dd, J=17.5, 1.8 Hz, 1H), 4.60 (dd, J=5.7, 2.6 Hz, 1H), 6.73 (d, J=5.5 Hz, 1H), 8.01 (s, 1H), 8.35 (s, 1H).

Example 39: Synthesis of sodium [3-[4-[(Z,E)-N-hydroxy-C-methyl-carbonimidoyl]pyrazol-1-yl]-7-oxo-1,6-diazabicyclo[3.2.1]oct-3-en-6-yl]sulfate

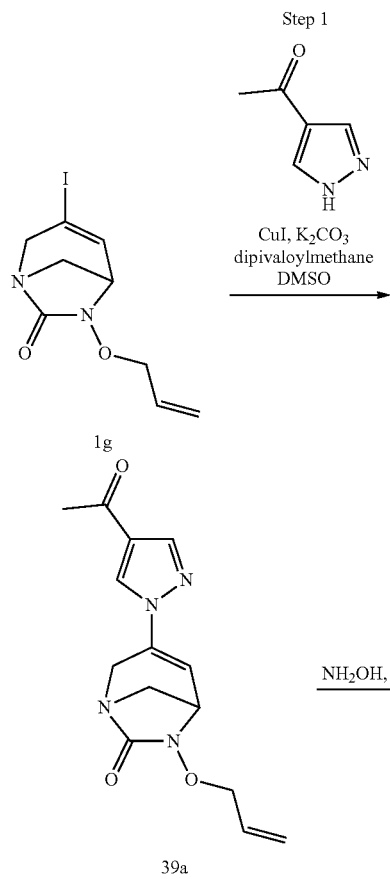

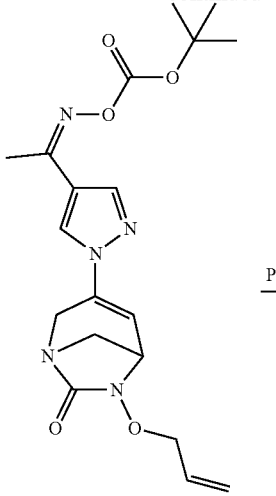

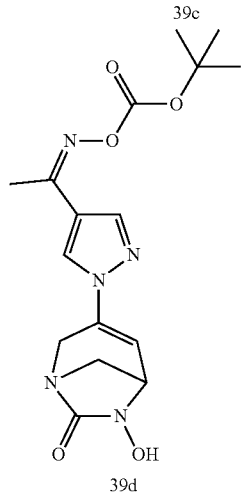

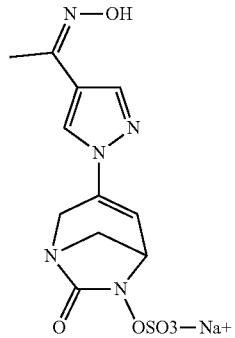

Example 39

Step 1: Preparation of Intermediate 3-(4-acetylpyrazol-1-yl)-6-allyloxy-1,6-diazabicyclo[3.2.1]oct-3-en-7-one (39a)

Using the procedure described in example 2 (step 1a), intermediate (1g) (250 mg, 0.817 mmol) was converted by reaction with 1-(1H-pyrazol-4-yl)ethanone (108 mg, 0.98 mmol) into intermediate (39a) (197 mg, 0.553 mmol, 68%) after purification by flash chromatography on silica gel (cyclohexane/EtOAc: 100/0 to 100/0).

MS m/z ([M+H]$^+$) 289.

¹H NMR (400 MHz, CDCl₃): δ (ppm) 2.46 (s, 3H), 3.17 (d, J=5.6 Hz, 1H), 3.57 (dd, J=1.8, 10.9 Hz, 1H), 4.10-4.25 (m, 2H), 4.39-4.52 (m, 3H), 5.30-5.43 (m, 2H), 5.97-6.09 (m, 1H), 6.65 (d, J=5.6 Hz, 1H), 7.96 (s, 1H), 8.08 (s, 1H).

Step 2: Preparation of Intermediate 6-allyloxy-3-[4-[(Z,E)-N-hydroxy-C-methyl-carbonimidoyl]pyrazol-1-yl]-1,6-diazabicyclo[3.2.1]oct-3-en-7-one (39b)

To a solution of intermediate (39a) (25 mg, 0.867 mmol) in MeOH (8.7 mL) was added hydroxylamine hydrochloride (90 mg, 1.302 mmol) and pyridine (141 µL, 1.735 mmol). After stirring for 2 h at rt, the mixture was concentrated in vacuo. The residue was purified by flash chromatography on silica gel (cyclohexane/EtOAc: 100/0 to 100/0) to provide intermediate (39b) (100 mg, 0.330 mmol, 38%) as yellow oil.

MS m/z ([M+H]⁺) 304.

Step 3: Preparation of Intermediate [(Z,E)-1-[1-(6-allyloxy-7-oxo-1,6-diazabicyclo[3.2.1]oct-3-en-3-yl)pyrazol-4-yl]ethylideneamino]tert-butyl carbonate (39c)

To a solution of intermediate (39b) (100 mg, 0.33 mmol) in DCM (3.3 mL) were added Boc₂O (108 mg, 0.495 mmol), TEA (70 µL, 0.495 mmol) and DMAP (40 mg, 0.33 mmol). After stirring for 1 h at rt, the mixture was concentrated in vacuo. The residue was purified by flash chromatography on silica gel (cyclohexane/EtOAc: 100/0 to 100/0) to provide intermediate (39c) (110 mg, 0.273 mmol, ratio Z/E: 62/38, 83%) as a colorless oil.

MS m/z ([M+H]⁺) 404, ([2M+H]⁺) 807.

¹H NMR (400 MHz, CDCl₃): δ (ppm) 1.58 (s, 9H), 2.30 (s, 1.86H), 2.34 (s, 1.14H), 3.16 (d, J=10.9 Hz, 0.62H), 3.19 (d, J=10.9 Hz, 0.38H), 3.52-3.62 (m, 1H), 4.13-4.27 (m, 2H), 4.38-4.53 (m, 3H), 5.29-5.44 (m, 2H), 5.98-6.10 (m, 1H), 6.56 (d, J=5.4 Hz, 0.62H), 6.64 (d, J=5.4 Hz, 0.38H), 7.90 (s, 0.62H), 7.99 (s, 0.38H), 8.00 (s, 0.62H), 8.21 (s, 0.38H).

Step 4: Preparation of Intermediate tert-butyl [(Z,E)-1-[1-(6-hydroxy-7-oxo-1,6-diazabicyclo[3.2.1]oct-3-en-3-yl)pyrazol-4-yl]ethylideneamino]carbonate (39d)

A solution of intermediate (39c) (110 mg, 0.273 mmol) in anhydrous DCM (2.7 mL) was degazed for 10 min under argon atmosphere. Phenylsilane (67 µL, 0.546 mmol) and Pd(PPh₃)₄ (13 mg, 0.011 mmol) were successively added. After stirring for 2 h at rt, the mixture was concentrated in vacuo. The residue was purified by flash chromatography on silica gel (DCM/acetone: 100/0 to 100/0) to provide intermediate (39d) (31 mg, 0.062 mmol, 22%) as an orange powder contaminated with triphenylphosphine oxide.

MS m/z ([M+H]⁺) 364.

Step 5: Preparation of sodium [3-[4-[(Z,E)-N-hydroxy-C-methyl-carbonimidoyl]pyrazol-1-yl]-7-oxo-1,6-diazabicyclo[3.2.1]oct-3-en-6-yl]sulfate (example 39)

To a solution of intermediate (39d) (31 mg, 0.062 mmol) in tBuOH (0.427 mL) and water (0.427 mL) under inert atmosphere was added sulfur trioxide trimethylamine complex (14.3 mg, 0.102 mmol) and TEA (3.0 µL, 0.021 mmol). After stirring for 2 h, the heterogeneous mixture was concentrated in vacuo. The crude was purified by flash chromatography on C18-reversed phase silica gel (H₂O/ACN: gradient 98/2 to 0/100). The fractions containing the desired compound were combined to provide 14 mg of a solid which was applied on a Dowex sodium form column (Dowex® 50WX8 hydrogen form stored with an aqueous solution of 2N NaOH and washed until neutral pH with H₂O). The fractions containing the desired compound were combined and concentrated in vacuo. The crude was purified by flash chromatography on C18-reversed phase silica gel (H₂O/ACN: gradient 98/2 to 0/100). The fractions containing the desired compound were combined, freezed and lyophilized to provide example (39) (5.8 mg, 0.015 mmol, ratio Z/E 50/50, 18%) as white powder.

MS m/z ([M−H]⁻) 342.

¹H NMR (400 MHz, D₂O): δ(ppm) 2.12 (s, 1.5H), 2.13 (s, 1.5H), 3.39 (dd, J=11.3, 3.9 Hz, 1H), 3.60-3.67 (m, 1H), 4.24-4.37 (m, 2H), 4.50-4.56 (m, 1H), 6.58 (d, J=5.7 Hz, 0.5H), 6.64 (d, J=5.7 Hz, 0.5H), 7.83 (s, 0.5H), 8.11 (s, 1H), 8.47 (s, 0.5H).

Example 40: Synthesis of sodium [3-(4-acetylpyrazol-1-yl)-7-oxo-1,6-diazabicyclo[3.2.1]oct-3-en-6-yl]sulfate

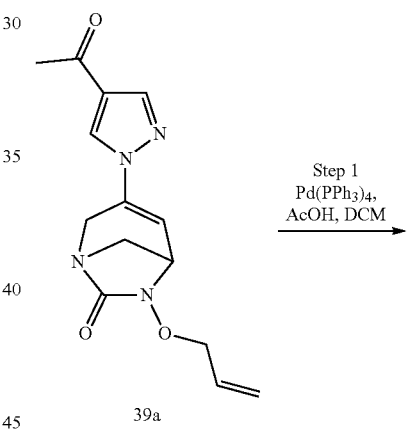

39a

Step 1
Pd(PPh₃)₄, AcOH, DCM

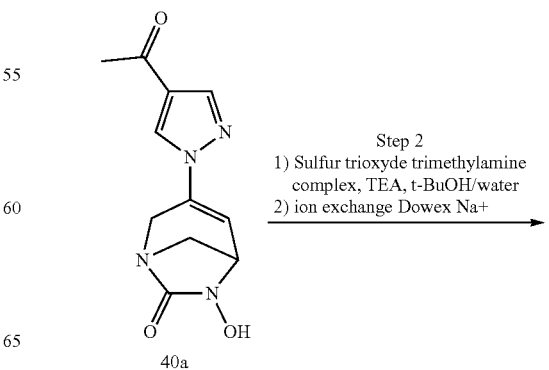

40a

Step 2
1) Sulfur trioxyde trimethylamine complex, TEA, t-BuOH/water
2) ion exchange Dowex Na+

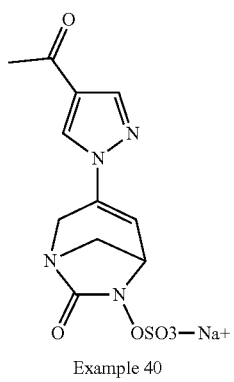

Example 40

Step 1: Preparation of Intermediate 3-(4-acetylpyrazol-1-yl)-6-hydroxy-1,6-diazabicyclo[3.2.1]oct-3-en-7-one (40a)

A solution of intermediate (39a) (145 mg, 0.407 mmol) in anhydrous DCM (4.1 mL) was degazed for 10 min under argon atmosphere. AcOH (47 μL, 0.815 mmol) and Pd(PPh$_3$)$_4$ (236 mg, 0.204 mmol) were successively added. After stirring for 2 h at rt, the mixture was concentrated in vacuo. The residue was purified by flash chromatography on silica gel (DCM/acetone: 100/0 to 100/0) to provide intermediate (40a) (90 mg, 0.150 mmol, 37%) as yellow powder contaminated with triphenylphosphine oxide.

MS m/z ([M+H]$^+$) 249

$^1$H NMR (400 MHz, Acetone-d$_6$): δ(ppm) 2.42 (s, 3H), 3.31 (d, J=10.9 Hz, 1H), 3.47 (dd, J=10.8, 2.8 Hz, 1H), 4.15 (dd, J=5.5, 2.7 Hz, 1H), 4.26 (dd, J=17.4, 1.9 Hz, 1H), 4.35 (d, J=17.3 Hz, 1H), 6.88 (d, J=5.4 Hz, 1H), 8.00 (s, 1H), 8.61 (s, 1H).

Step 2: Preparation of sodium [3-(4-acetylpyrazol-1-yl)-7-oxo-1,6-diazabicyclo[3.2.1]oct-3-en-6-yl] sulfate (example 40)

To a solution of intermediate (40a) (85 mg, 0.20 mmol) in tBuOH (1.01 mL) and H$_2$O (1.01 mL) under inert atmosphere was added sulfur trioxide trimethylamine complex (33.8 mg, 0.243 mmol) and TEA (7.1 μL, 0.051 mmol). After stirring for 1 h, the heterogeneous mixture was concentrated in vacuo. The crude was purified by flash chromatography on C18-reversed phase silica gel (H$_2$O/ACN: 98/2 to 0/100). The fractions containing the desired compound were combined to provide 67 mg of a solid which was applied on a Dowex sodium form column (Dowex® 50WX8 hydrogen form stored with an aqueous solution of 2N NaOH and washed until neutral pH with H$_2$O). The fractions containing the desired compound were combined, freezed and lyophilized to provide 35 mg of a solid which was purified again by flash chromatography on C18-reversed phase silica gel (H$_2$O/ACN: 98/2 to 0/100). The fractions containing the desired compound were combined to provide example (40) (22.8 mg, 0.065 mmol, 30%) as a white powder.

MS m/z ([M−H]$^-$) 327.

$^1$H NMR (400 MHz, D$_2$O): δ(ppm): 2.46 (s, 3H), 3.41 (d, J=11.3 Hz, 1H), 3.65 (dd, J=11.4, 2.1 Hz, 1H), 4.33 (dd, J=7.2, 1.3 Hz, 2H), 4.55 (dd, J=5.6, 2.5 Hz, 1H), 6.74 (d, J=5.5 Hz, 1H), 8.06 (s, 1H), 8.49 (s, 1H).

Example 41: Synthesis of [3-[4-(2-aminoethyl)pyrazol-1-yl]-7-oxo-1,6-diazabicyclo[3.2.1]oct-3-en-6-yl]hydrogen sulfate Step 1

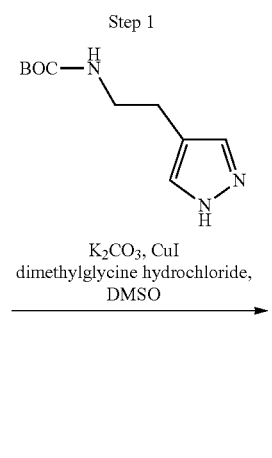

1g

K$_2$CO$_3$, CuI
dimethylglycine hydrochloride,
DMSO

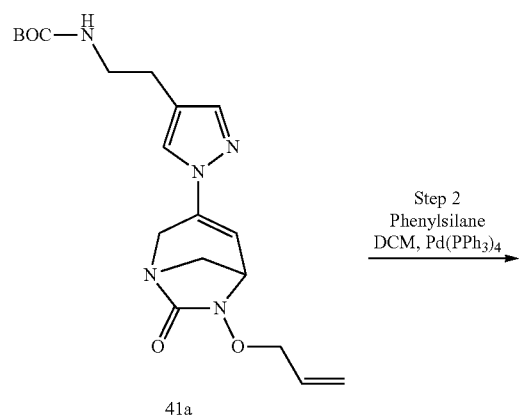

41a

Step 2
Phenylsilane
DCM, Pd-(PPh$_3$)$_4$

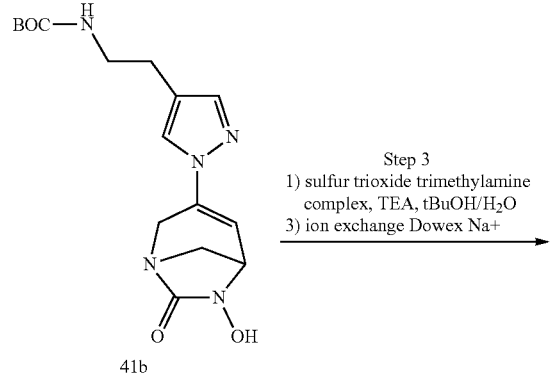

41b

Step 3
1) sulfur trioxide trimethylamine complex, TEA, tBuOH/H$_2$O
3) ion exchange Dowex Na+

-continued

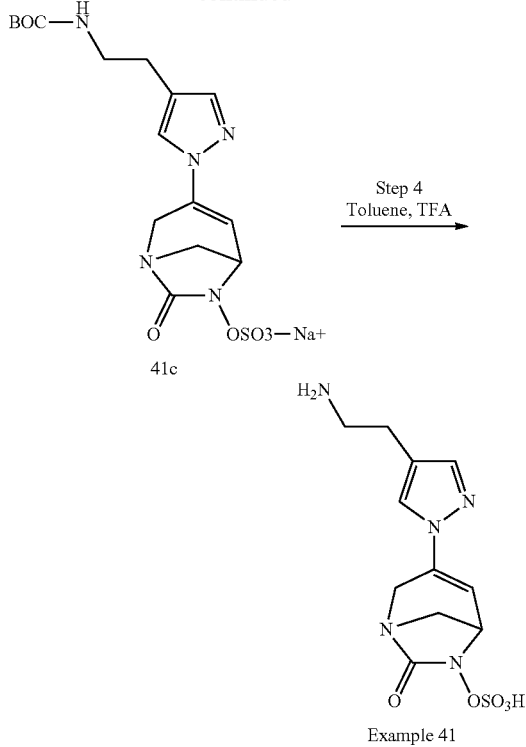

41c

Example 41

Step 1: Preparation of Intermediate tert-butyl N-[2-[1-(6-allyloxy-7-oxo-1,6-diazabicyclo[3.2.1]oct-3-en-3-yl)pyrazol-4-yl]ethyl]carbamate (41a)

Using the procedure described in example 1 (step 7), intermediate (1g) (0.25 g, 0.82 mmol) was converted by reaction with tert-butyl N-[2-(1H-pyrazol-4-yl)ethyl]carbamate (0.275 g, 1.31 mmol) into intermediate (41a) (0.208 g, 0.53 mmol, 66%) after purification by flash chromatography on silica gel (DCM/Acetone: 100/0 to 80/20).

MS m/z ([M+H]$^+$) 390.

1H NMR (400 MHz, CDCl3): δ (ppm) 1.44 (s, 9H), 2.64 (t, J=6.8 Hz, 2H), 3.14 (d, J=10.7 Hz, 1H), 3.25-3.34 (m, 2H), 3.52 (dd, J=10.8, 2.2 Hz, 1H), 4.09 (dd, J=5.5, 2.5 Hz, 1H), 4.19 (dd, J=17.6, 1.8 Hz, 1H), 4.26-4.54 (m, 3H), 4.57 (br s, 1H), 5.27-5.42 (m, 2H), 5.96-6.08 (m, 1H), 6.37 (d, J=5.4 Hz, 1H), 7.41 (s, 1H), 7.45 (s, 1H).

Step 2: Preparation of Intermediate tert-butyl N-[2-[1-(6-hydroxy-7-oxo-1,6-diazabicyclo[3.2.1]oct-3-en-3-yl)pyrazol-4-yl]ethyl]carbamate (41b)

Under inert atmosphere, phenylsilane (123 μL, 1.028 mmol) and Pd(PPh$_3$)$_4$ (30 mg, 0.026 mmol) were added to a solution of intermediate (41a) (200 mg, 0.514 mmol) in anhydrous DCM (3.4 mL). The reaction mixture was stirred at rt for 1 h and concentrated. The crude product was purified on silica gel (DCM/acetone: 100/0 to 80/20) to provide intermediate (41b) (85 mg, 0.244 mmol, 48%) contaminated with triphenylphosphine oxide.

MS m/z ([M+H]$^+$) 350.

Step 3: Preparation of sodium [3-[4-[2-(tert-butoxycarbonylamino)ethyl]pyrazol-1-yl]-7-oxo-1,6-diazabicyclo[3.2.1]oct-3-en-6-yl]sulfate (41c)

Intermediate (41b) (33 mg, 0.094 mmol) was dissolved in a mixture of tBuOH (0.47 mL) and H$_2$O (0.47 mL). TEA (3.3 μL, 0.024 mmol) and sulfur trioxide trimethylamine complex (16 mg, 0.113 mmol) was added. The mixture was stirred at rt for 2 h then concentrated in vacuo. The residue was purified by flash chromatography on C18-reversed phase silica gel (H$_2$O/ACN 98/2 to 0/100). The fractions containing the expected intermediate were combined and concentrated in vacuo. The residue was dissolved in H$_2$O and converted after ion exchange with Dowex sodium form column (Dowex® 50WX8 hydrogen form stored with an aqueous solution of 2N NaOH and washed until neutral pH with H$_2$O) to intermediate (41c) (18 mg, 0.040 mmol, 43%).

MS m/z ([M−H]$^-$) 428.

Step 4: Preparation of [3-[4-(2-aminoethyl)pyrazol-1-yl]-7-oxo-1,6-diazabicyclo[3.2.1]oct-3-en-6-yl] hydrogen sulfate (example 41)

TFA (300 μL) was added to a solution of Intermediate (41c) (18 mg, 0.040 mmol) in toluene (600 μL). The mixture was stirred at rt for 30 min then concentrated under azote. The residue was purified by flash chromatography on C18-reversed phase silica gel (H$_2$O/ACN 98/2 to 0/100). The fractions containing the expected product were combined and concentrated in vacuo to give example (41) (1.6 mg, 0.005 mmol, 13%).

MS m/z ([M−H]$^-$) 328.

1H NMR (400 MHz, D$_2$O): δ (ppm) 2.89 (t, J=7.2 Hz, 2H), 3.21 (t, J=7.2 Hz, 2H), 3.45 (d, J=11.3 Hz, 1H), 3.66-3.73 (m, 1H), 4.33 (d, J=17.5 Hz, 1H), 4.39 (dd, J=17.5, 1.8 Hz, 1H), 4.58 (dd, J=5.7, 2.7 Hz, 1H), 6.58 (d, J=5.5 Hz, 1H), 7.65 (s, 1H), 7.89 (s, 1H).

Example 42: Synthesis of 2,2,2-trifluoroacetate [7-oxo-3-(4-piperazin-4-ium-1-ylpyrazol-1-yl)-1,6-diazabicyclo[3.2.1]oct-3-en-6-yl]hydrogen sulfate

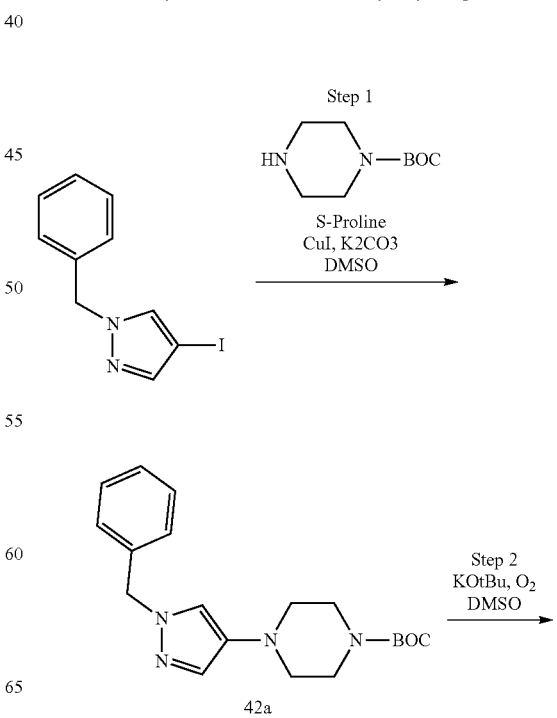

42a

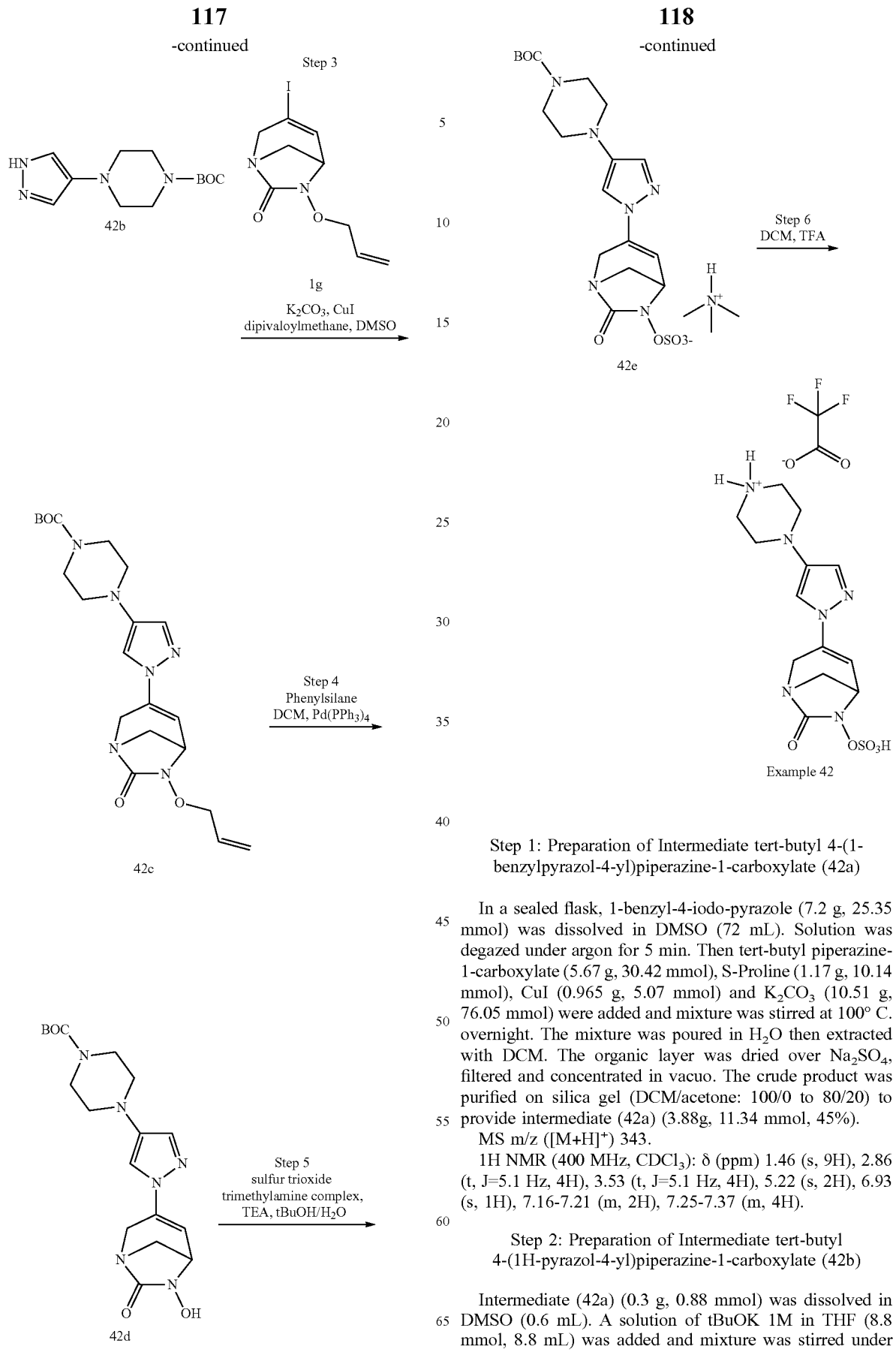

Step 1: Preparation of Intermediate tert-butyl 4-(1-benzylpyrazol-4-yl)piperazine-1-carboxylate (42a)

In a sealed flask, 1-benzyl-4-iodo-pyrazole (7.2 g, 25.35 mmol) was dissolved in DMSO (72 mL). Solution was degazed under argon for 5 min. Then tert-butyl piperazine-1-carboxylate (5.67 g, 30.42 mmol), S-Proline (1.17 g, 10.14 mmol), CuI (0.965 g, 5.07 mmol) and $K_2CO_3$ (10.51 g, 76.05 mmol) were added and mixture was stirred at 100° C. overnight. The mixture was poured in $H_2O$ then extracted with DCM. The organic layer was dried over $Na_2SO_4$, filtered and concentrated in vacuo. The crude product was purified on silica gel (DCM/acetone: 100/0 to 80/20) to provide intermediate (42a) (3.88g, 11.34 mmol, 45%).

MS m/z ([M+H]$^+$) 343.

1H NMR (400 MHz, CDCl$_3$): δ (ppm) 1.46 (s, 9H), 2.86 (t, J=5.1 Hz, 4H), 3.53 (t, J=5.1 Hz, 4H), 5.22 (s, 2H), 6.93 (s, 1H), 7.16-7.21 (m, 2H), 7.25-7.37 (m, 4H).

Step 2: Preparation of Intermediate tert-butyl 4-(1H-pyrazol-4-yl)piperazine-1-carboxylate (42b)

Intermediate (42a) (0.3 g, 0.88 mmol) was dissolved in DMSO (0.6 mL). A solution of tBuOK 1M in THF (8.8 mmol, 8.8 mL) was added and mixture was stirred under oxygen bubbling for 30 min. A solution of tBuOK 1M in THF (5 mmol, 5 mL) was added again and mixture was stirred under oxygen bubbling for 20 min. Reaction mixture was quenched by addition of ammonium chloride solution, diluted with water and was extracted with AcOEt.

The organic layer was dried over $Na_2SO_4$, filtered and concentrated in vacuo. The crude product was purified on silica gel (DCM/acetone: 100/0 to 0/100) to provide intermediate (42b) (156 mg, 0.62 mmol, 71%).
MS m/z ([M+H]$^+$) 253.
$^1$H NMR (400 MHz, CDCl$_3$): δ (ppm) 1.47 (s, 9H), 2.91 (t, J=5.2 Hz, 4H), 3.57 (t, J=5.2 Hz, 4H), 7.25 (s, 2H).

Step 3: Preparation of Intermediate tert-butyl 4-[1-(6-allyloxy-7-oxo-1,6-diazabicyclo[3.2.1]oct-3-en-3-yl)pyrazol-4-yl]piperazine-1-carboxylate (42c)

Using the procedure described in example 2 (step 1a), intermediate (1g) (0.53 g, 1.74 mmol) was converted by reaction with intermediate (42b) (0.53 g, 2.08 mmol) into intermediate (42c) (0.5 g, 1.16 mmol, 67%) after purification by flash chromatography on silica gel (DCM/acetone: 100/0 to 50/50).
MS m/z ([M+H]$^+$) 431.
$^1$H NMR (400 MHz, CDCl$_3$): δ (ppm) 1.47 (s, 9H), 2.87 (t, J=5.2 Hz, 4H), 3.13 (d, J=10.7 Hz, 1H), 3.47-3.59 (m, 5H), 4.07 (dd, J=5.6, 2.6 Hz, 1H), 4.18 (dd, J=17.6, 1.8 Hz, 1H), 4.35-4.50 (m, 3H), 5.26-5.42 (m, 2H), 5.96-6.07 (m, 1H), 6.24 (d, J=5.1 Hz, 1H), 7.10 (br s, 1H), 7.31 (br s, 1H).

Step 4: Preparation of Intermediate tert-butyl 4-[1-(6-hydroxy-7-oxo-1,6-diazabicyclo[3.2.1]oct-3-en-3-yl)pyrazol-4-yl]piperazine-1-carboxylate (42d)

Under inert atmosphere, acetic acid (133 μL, 2.32 mmol) and Pd(PPh$_3$)$_4$ (335 mg, 0.29 mmol) were added to a solution of intermediate (42c) (250 mg, 0.581 mmol) in anhydrous DCM (5.8 mL). The reaction mixture was stirred at rt for 1 h30 and concentrated. The crude product was purified on silica gel (DCM/acetone: 100/0 to 0/100) to provide intermediate (42d) (180 mg, 0.461 mmol, 80%).
MS m/z ([M+H]$^+$) 391.

Step 5: Preparation of trimethylammonium [3-[4-(4-tert-butoxycarbonylpiperazin-1-yl)pyrazol-1-yl]-7-oxo-1,6-diazabicyclo[3.2.1]oct-3-en-6-yl]sulfate (42e)

Intermediate (42d) (180 mg, 0.461 mmol) was dissolved in a mixture of tBuOH (2.3 mL) and H$_2$O (2.3 mL). TEA (16 μL, 0.115 mmol) and sulfur trioxide trimethylamine complex (77 mg, 0.553 mmol) were added. The mixture was stirred at rt overnight then concentrated. The residue was purified by flash chromatography on C18-reversed phase silica gel (H$_2$O/ACN 98/2 to 0/100) to provide intermediate (42e) (154 mg, 0.291 mmol, 64%).
MS m/z ([M–H]$^-$) 469.

Step 6: Preparation of 2,2,2-trifluoroacetate [7-oxo-3-(4-piperazin-4-ium-1-ylpyrazol-1-yl)-1,6-diazabicyclo[3.2.1]oct-3-en-6-yl]hydrogen sulfate (example 42)

Intermediate (42e) (130 mg, 0.245 mmol) was dissolved in DCM (1.2 mL). At 0° C., TFA (0.6 mL) was added and mixture was stirred at 0° C. for 45 min. Et$_2$O was added to give a precipitate, ethereal phase was removed. Residue was triturated several times in ACN and obtained solid was dried under azote. The residue was purified by flash chromatography on C18-reversed phase silica gel (H$_2$O/ACN 98/2 to 0/100). The fractions containing desired product were combined and concentrated in vacuo to give example (42) (5.4 mg, 0.012 mmol, 5%).
MS m/z ([M–H]$^-$) 369.
$^1$H NMR (400 MHz, D$_2$O): δ (ppm) 3.20-3.29 (m, 4H), 3.35-3.46 (m, 5H), 3.61-3.70 (m, 1H), 4.32 (s, 2H), 4.55 (dd, J=5.7, 2.6 Hz, 1H), 6.44 (d, J=5.6 Hz, 1H), 7.52 (s, 1H), 7.62 (s, 1H).

Example 43: Synthesis of sodium [7-oxo-3-(3,4,5-trideuteriopyrazol-1-yl)-1,6-diazabicyclo[3.2.1]oct-3-en-6-yl]sulfate

Step 1: Preparation of Intermediate 6-allyloxy-3-(3,4,5-trideuteriopyrazol-1-yl)-1,6-diazabicyclo[3.2.1]oct-3-en-7-one (43a)

Using the procedure described in example 2 (step 1a), intermediate (1g) (200 mg, 0.65 mmol) was converted by reaction with 3,4,5-trideuterio-1H-pyrazole (prepared as described in Catalysis Communication, 2001, 2: 125-128) (56 mg, 0.78 mmol) into intermediate (43a) (101 mg, 0.41 mmol, 63%) after purification by flash chromatography on silica gel (DCM/acetone: 100/0 to 90/10).

MS m/z ([M+H]$^+$) 250.

$^1$H NMR (400 MHz, CDCl$_3$): δ (ppm) 3.14 (d, J=10.8 Hz, 1H), 3.52 (dd, J=10.8, 2.3 Hz, 1H), 4.09 (dd, J=5.6, 2.7 Hz, 1H), 4.20 (dd, J=17.5, 1.9 Hz, 1H), 4.35-4.50 (m, 3H), 5.27-5.31 (m, 1H), 5.32-5.39 (m, 1H), 5.94-6.06 (m, 1H), 6.45 (d, J=5.5 Hz, 2H).

Step 2: Preparation of sodium [7-oxo-3-(3,4,5-trideuteriopyrazol-1-yl)-1,6-diazabicyclo[3.2.1]oct-3-en-6-yl]sulfate (Example 43)

Using the procedure described in example 2 (step 2), intermediate (43a) (100 mg, 0.40 mmol) was converted into example (43) (43 mg, 0.14 mmol, 35%) after purification by flash chromatography on C18-reversed phase on silica gel (H$_2$O/ACN 98/2 to ACN) followed by lyophilization.

MS m/z ([M−H]$^−$) 288.

$^1$H NMR (400 MHz, D$_2$O): δ (ppm) 3.43 (d, J=11.3 Hz, 1H), 3.66 (dd, J=11.3, 2.1 Hz, 1H), 4.32-4.37 (m, 2H), 4.55 (dd, J=5.6, 2.6 Hz, 1H), 6.57 (d, J=5.6 Hz, 1H).

Example 44: Synthesis of sodium [7-oxo-3-(tetrazol-2-yl)-1,6-diazabicyclo[3.2.1]oct-3-en-6-yl]sulfate

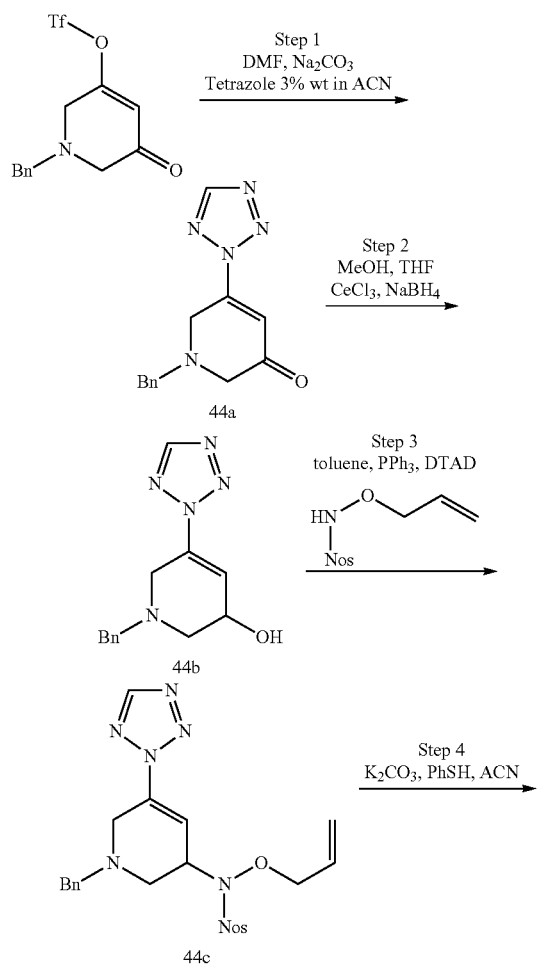

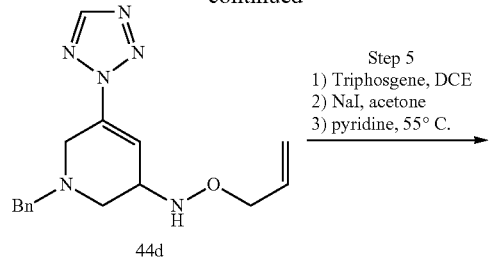

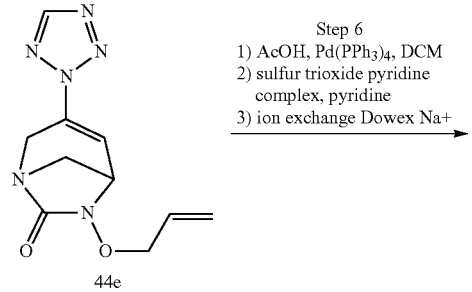

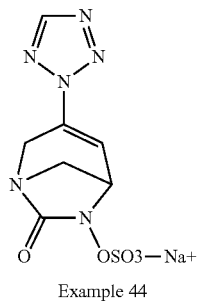

Example 44

Step 1: Preparation of Intermediate 1-benzyl-5-(tetrazol-2-yl)-2,6-dihydropyridin-3-one (44a)

At 0° C., (tetrazole 3% wt in ACN (57.4 g, 32.8 mmol) and Na$_2$CO$_3$ (4.14 g, 39.42 mmol) were added to a solution of (1-benzyl-5-oxo-2,6-dihydropyridin-3-yl) trifluoromethanesulfonate (2.2 g, 6.57 mmol) in DMF (16.4 mL). The mixture was stirred at 0° C. for 4 h, then diluted with water and extracted with AcOEt. Organic layer was dried over Na$_2$SO$_4$, filtered and concentrated in vacuo. The crude product was purified by flash chromatography on silica gel (DCM/MeOH: 100/0 to 90/10) to provide intermediate (44a) (370 mg, 1.45 mmol, 22%).

MS m/z ([M−H]$^−$) 254.

$^1$H NMR (400 MHz, CDCl$_3$): δ (ppm) 3.36 (br s, 2H), 3.86 (s, 2H), 4.15 (br s, 2H), 7.00 (t, J=1.5 Hz, 1H), 7.28-7.42 (m, 5H), 8.66 (s, 1H).

Step 2: Preparation of Intermediate 1-benzyl-5-(tetrazol-2-yl)-3,6-dihydro-2H-pyridin-3-ol (44b)

Intermediate (44a) (428 mg, 1.68 mmol) was dissolved in a mixture of MeOH (15 mL) and THF (3 mL). At 0° C., dry CeCl$_3$ (163 mg, 1.68 mmol) and NaBH$_4$ (70 mg, 1.85 mmol) were added. The mixture was stirred at 0° C. for 30 min, then acetone and H$_2$O were successively added. Mixture was concentrated. H$_2$O and NH$_4$Cl solution were added to the residue and desired product was extracted with AcOEt. Organic layer was dried over Na$_2$SO$_4$, filtered and concentrated in vacuo. The crude product was purified on silica gel (DCM/Acetone: 100/0 to 70/30) to intermediate (44b) (407 mg, 1.58 mmol, 95%).

MS m/z ([M+H]$^+$) 258.

¹H NMR (400 MHz, CDCl₃): δ (ppm) 2.40 (br s, 1H), 2.67 (dd, J=11.8, 2.9 Hz, 1H), 2.96 (dd, J=11.9, 3.2 Hz, 1H), 3.44 (d, J=16.6 Hz, 1H), 3.72-3.88 (m, 2H), 4.03 (d, J=16.6 Hz, 1H), 4.38 (br s, 1H), 6.91 (d, J=4.5 Hz, 1H), 7.27-7.41 (m, 5H), 8.53 (s, 1H).

Step 3: Preparation of Intermediate N-allyloxy-N-[1-benzyl-5-(tetrazol-2-yl)-3,6-dihydro-2H-pyridin-3-yl]-2-nitro-benzenesulfonamide (44c)

Under argon atmosphere, intermediate (44b) (400 mg, 1.56 mmol) was dissolved in toluene (16 mL), N-allyloxy-2-nitro-benzenesulfonamide (402 mg, 1.56 mmol) and PPh₃ (409 mg, 1.56 mmol) were added. At 0° C., DTAD (395 mg, 1.71 mmol) was added per portion to the mixture which was stirred at rt for 4 h. After concentration, the residue was purified by flash chromatography on silica gel (DCM/Acetone: 100/0 to 80/20) to provide intermediate (44c) (714 mg, 1.44 mmol, 92%).

MS m/z ([M+H]⁺) 498.

¹H NMR (400 MHz, CDCl₃): δ (ppm) 2.85 (br s, 2H), 3.53-3.90 (m, 4H), 4.46-4.58 (m, 2H), 4.94 (br s, 1H), 5.16-5.29 (m, 2H), 5.82 (ddt, J=16.8, 10.4, 6.4 Hz, 1H), 6.48 (br s, 1H), 7.27-7.38 (m, 5H), 7.49-7.84 (m, 3H), 8.09 (d, J=7.9 Hz, 1H), 8.47 (s, 1H).

Step 4: Preparation of Intermediate N-allyloxy-1-benzyl-5-(tetrazol-2-yl)-3,6-dihydro-2H-pyridin-3-amine (44d)

At 0° C., K₂CO₃ (1.48 g, 10.72 mmol) and thiophenol (732 μL, 7.14 mmol) were added to a solution of intermediate (44c) (710 mg, 1.43 mmol) in ACN (14 mL). The mixture was stirred at rt for 3 h30. Crude product was filtered on celite, washed with ACN and DCM. The filtrate was concentrated and the residue was purified by flash chromatography on silica gel (DCM/Acetone: 100/0 to 70/30) to provide intermediate (44d) (368 mg, 1.18 mmol, 83%).

MS m/z ([M+H]⁺) 313.

¹H NMR (400 MHz, CDCl₃): δ (ppm) 2.58 (d, J=11.7 Hz, 1H), 3.09 (d, J=11.7 Hz, 1H), 3.44 (d, J=16.5 Hz, 1H), 3.70-4.00 (m, 4H), 4.20 (d, J=5.9 Hz, 2H), 5.14-5.33 (m, 2H), 5.75 (br s, 1H), 5.92 (ddt, J=16.5, 11.0, 5.9 Hz, 1H), 6.82 (br s, 1H), 7.28-7.43 (m, 5H), 8.51 (s, 1H).

Step 5: Preparation of Intermediate 6-allyloxy-3-(tetrazol-2-yl)-1,6-diazabicyclo[3.2.1]oct-3-en-7-one (44e)

A solution of triphosgene (455 mg, 1.53 mmol) in DCE (2 mL) was added to a solution of intermediate (44d) (368 mg, 1.18 mmol) in DCE (12 mL). The mixture was stirred at rt for 30 min. A solution of NaI (1.77g, 11.8 mmol) in acetone (7.5 mL) was added and mixture was stirred at rt for 15 min. Then solution was heated at 55° C. for 15 min and pyridine (2.38 mL, 29.5 mmol) was added. The mixture was stirred at 55° C. for 2 h30. After cooling and dilution with DCM, mixture was filtered on celite and filtrate was concentrated. Residue was dissolved in DCM. Organic layer was washed with Na₂S₂O₃ solution, dried over Na₂SO₄, filtered and concentrated in vacuo. The crude product was purified by flash chromatography on silica gel (Toluene/Acetone: 100/0 to 80/20) to provide intermediate (44e) (132 mg, 0.53 mmol, 45%).

MS m/z ([M+H]⁺) 249.

¹H NMR (300 MHz, CDCl₃): δ (ppm) 3.20 (d, J=11.0 Hz, 1H), 3.61 (ddd, J=11.2, 2.9, 1.2 Hz, 1H), 4.23 (dd, J=5.5, 2.3 Hz, 1H), 4.34 (dd, J=18.0, 2.0 Hz, 1H), 4.38-4.52 (m, 2H), 4.65 (dd, J=18.0, 1.2 Hz, 1H), 5.28-5.43 (m, 2H), 5.94-6.10 (m, 1H), 7.25-7.29 (m, 1H), 8.54 (s, 1H).

Step 6: Preparation of sodium [7-oxo-3-(tetrazol-2-yl)-1,6-diazabicyclo[3.2.1]oct-3-en-6-yl]sulfate (Example 44)

Using the procedure described in example 2 (step 2), intermediate (44e) (130 mg, 0.52 mmol) was converted into example (44) (5 mg, 0.02 mmol, 8%) after purification by flash chromatography on C18-reversed phase on silica gel (H₂O/ACN 99/1 to 0/100) followed by lyophilization.

MS m/z ([M–H]⁻) 287.

¹H NMR (400 MHz, D₂O): δ (ppm) 3.52 (d, J=11.5 Hz, 1H), 3.75 (ddd, J=11.5, 2.8, 1.1 Hz, 1H), 4.57 (dd, J=3.6, 1.6 Hz, 2H), 4.70 (dd, J=5.6, 2.7 Hz, 1H), 7.35 (dd, J=5.6, 1.5 Hz, 1H), 8.82 (s, 1H).

Example 45: Synthesis of sodium [3-[3-(2-amino-2-oxo-ethyl)pyrazol-1-yl]-7-oxo-1,6-diazabicyclo[3.2.1]oct-3-en-6-yl]sulfate

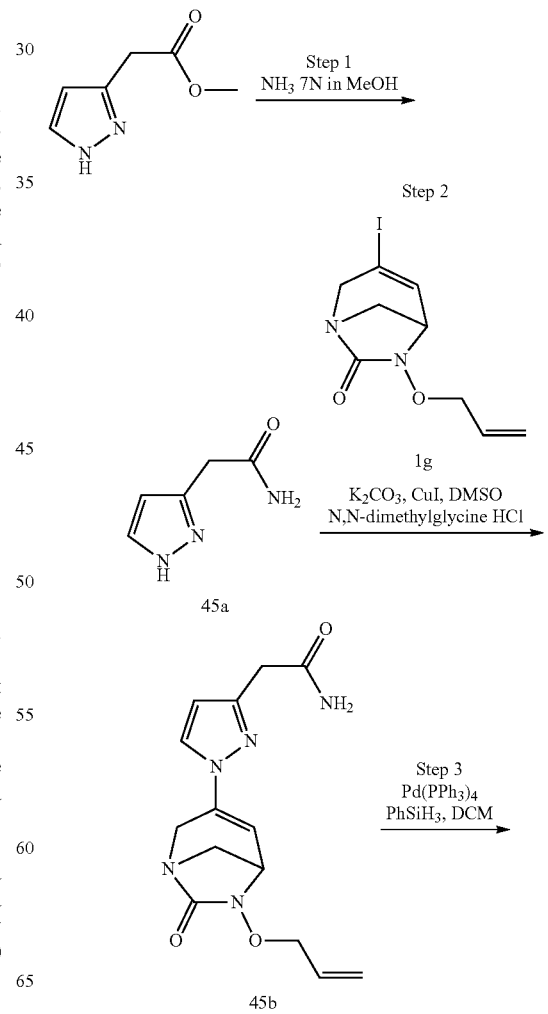

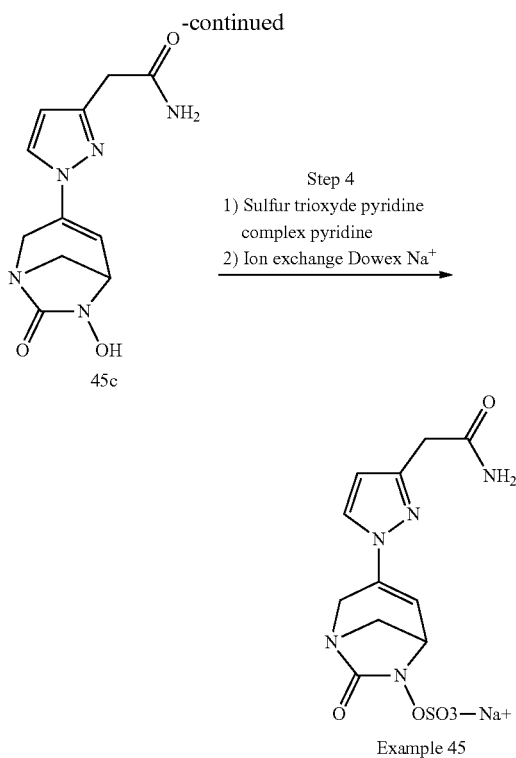

Step 4
1) Sulfur trioxyde pyridine complex pyridine
2) Ion exchange Dowex Na⁺

Example 45

Step 1: Preparation of Intermediate 2-(1H-pyrazol-3-yl)acetamide (45a)

A mixture of (1H-pyrazol-3-yl)-acetic acid methyl ester (0.50 g, 3.57 mmol) in ammonia 7M in MeOH (20 mL, 140 mmol) was heated at 55° C. for 4 days. The reaction mixture was concentrated in vacuo to provide intermediate (45a) (0.44 g, 3.52 mmol, 98%) as a pink powder.

MS m/z ([M+H]$^+$) 126.

$^1$H NMR (400 MHz, DMSO-d$_6$): δ (ppm) 3.39 (s, 2H), 6.10 (d, J=2.0 Hz, 1H), 6.90 (s, 1H), 7.35 (s, 1H), 7.51 (s, 1H), 12.52 (br s, 1H).

Step 2: Preparation of Intermediate 2-[1-(6-allyloxy-7-oxo-1,6-diazabicyclo[3.2.1]oct-3-en-3-yl)pyrazol-3-yl]acetamide (45b)

Using the procedure described in example 1 (step 7), intermediate (1g) (600 mg, 1.96 mmol) was converted by reaction with intermediate (45a) (490 mg, 3.27 mmol) into intermediate (45b) (200 mg, 0.66 mmol, 34%) as major product (ratio 83/16) from the mixture of both regioisomers after purification by flash chromatography on silica gel (DCM/Acetone: 60/40 to 30/70).

MS m/z ([M+H]$^+$) 304.

$^1$H NMR (400 MHz, CDCl$_3$): δ (ppm) 3.15 (d, J=10.8 Hz, 1H), 3.49-3.55 (m, 1H), 3.60 (s, 2H), 4.12 (dd, J=2.6, 5.6 Hz, 1H), 4.17 (dd, J=2.0, 17.5 Hz, 1H), 4.37-4.51 (m, 3H), 5.29-5.44 (m, 2H), 5.53 (s, 1H), 5.97-6.08 (m, 1H), 6.30 (d, J=2.5 Hz, 1H), 6.37 (s, 1H), 6.46-6.48 (m, 1H), 7.57 (d, J=2.6 Hz, 1H).

Step 3: Preparation of Intermediate 2-[1-(6-hydroxy-7-oxo-1,6-diazabicyclo[3.2.1]oct-3-en-3-yl)pyrazol-3-yl]acetamide (45c)

Under inert atmosphere, a solution of intermediate (45b) (130 mg, 0.66 mmol) was diluted in anhydrous DCM (18 mL). PhSiH$_3$ (326 μL, 2.64 mmol) and Pd(PPh$_3$)$_4$ (76 mg, 0.066 mmol) were successively added. After stirring 1 h, DCM was added and the solid was filtered to provide intermediate (45c) (70 mg, 0.26 mmol, 63%).

MS m/z ([M−H]$^−$) 263.

Step 4: Preparation of sodium [3-[3-(2-amino-2-oxo-ethyl)pyrazol-1-yl]-7-oxo-1,6-diazabicyclo[3.2.1]oct-3-en-6-yl]sulfate (Example 45)

To a solution of intermediate (45c) (70 mg, 0.26 mmol) in anhydrous pyridine (3 mL) under inert atmosphere was added sulfur trioxide pyridine complex (212 mg, 1.33 mmol). After stirring for 18 h, DCM was added to the residue and the solid was filtered and washed with DCM/Acetone (50/50). The filtrate was evaporate to give a solid which are applied on a Dowex sodium form column (Dowex® 50WX8 hydrogen form stored with an aqueous solution of 2N NaOH and washed until neutral pH with water). The fractions containing the desired compound were combined, freezed and lyophilized to give a mixture of both regioisomers with example (45) as major product (ratio 91/9) (46 mg, 0.13 mmol, 51%, white powder).

MS m/z ([M−H]$^−$) 342.

$^1$H NMR (400 MHz, D$_2$O): δ (ppm) 3.35 (d, J=11.3 Hz, 1H), 3.56 (s, 3H), 4.26 (t, J=1.7 Hz, 2H), 4.46 (dd, J=5.7, 2.7 Hz, 1H), 6.32 (d, J=2.6 Hz, 1H), 6.46-6.53 (m, 1H), 7.77 (d, J=2.6 Hz, 1H).

Example 46: Synthesis of [3-[3-(2-aminoethoxycarbamoyl)pyrazol-1-yl]-7-oxo-1,6-diazabicyclo[3.2.1]oct-3-en-6-yl]hydrogen sulfate

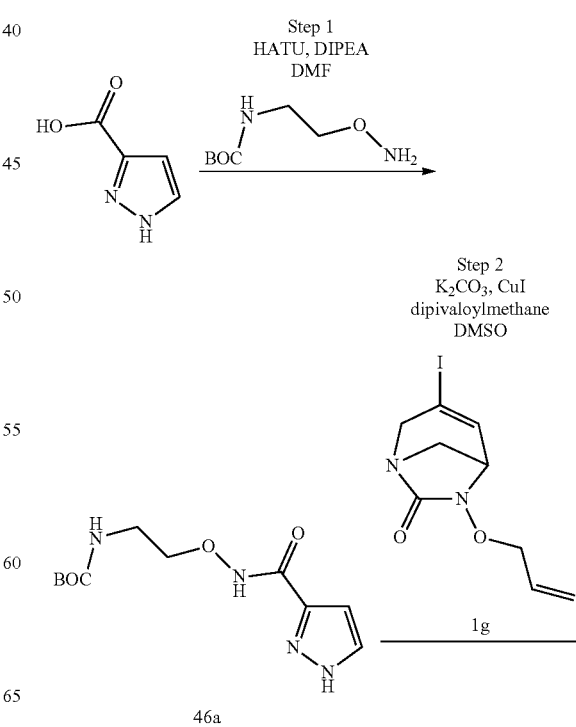

Step 1
HATU, DIPEA
DMF

Step 2
K$_2$CO$_3$, CuI
dipivaloylmethane
DMSO

46a

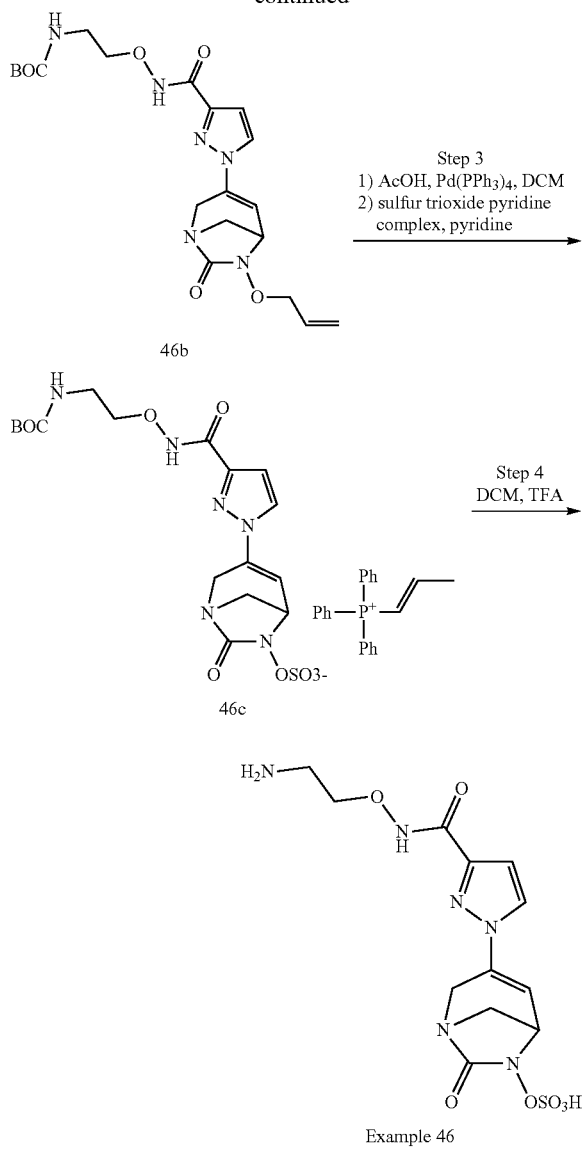

Step 1: Preparation of Intermediate tert-butyl N-[2-(1H-pyrazole-3-carbonylamino)oxyethyl]carbamate (46a)

Tert-butyl N-(2-aminooxyethyl)carbamate (510 mg, 2.90 mmol), HATU (932 mg, 2.45 mmol) and DIPEA (1.16 mL, 6.69 mmol) were added to a solution of 1H-pyrazole-3-carboxylic acid (250 mg, 2.23 mmol) in DMF (11 mL). The mixture was stirred at 40° C. overnight. After concentration, addition of water and extraction with AcOEt, the organic layer was dried over $Na_2SO_4$, filtered and concentrated in vacuo and the residue was purified by flash chromatography on silica gel (DCM/acetone: 100/0 to 70/30) to provide intermediate (46a) (575 mg, 2.13 mmol, 95%).

MS m/z ([M+H]$^+$) 271.

$^1$H NMR (400 MHz, DMSO-d$_6$): δ (ppm) 1.39 (s, 9H), 3.14-3.22 (m, 2H), 3.80 (t, J=5.2 Hz, 2H), 6.66 (s, 1H), 6.82 (t, J=5.5 Hz, 1H), 7.84 (s, 1H), 11.37 (s, 1H), 13.31 (s, 1H).

Step 2: Preparation of Intermediate tert-butyl N-[2-[[1-(6-allyloxy-7-oxo-1,6-diazabicyclo[3.2.1]oct-3-en-3-yl)pyrazole-3-carbonyl]amino]oxyethyl]carbamate (46b)

Using the procedure described in example 2 (step 1a), intermediate (1g) (0.30 g, 0.98 mmol) was converted by reaction with intermediate (46a) (0.32 g, 1.17 mmol) into intermediate (46b) (0.147 g, 0.33 mmol, 25%) with a 8/2 ratio in favor for the desired isomer after purification by flash chromatography on silica gel (DCM/acetone: 100/0 to 60/40).

MS m/z ([M+H]$^+$) 449.

$^1$H NMR (400 MHz, CDCl$_3$): δ (ppm) 1.45 (s, 9H), 3.13 (d, J=10.9 Hz, 1H), 3.27-3.57 (m, 3H), 3.90-4.02 (m, 2H), 4.09-4.21 (m, 2H), 4.35-4.50 (m, 3H), 5.25-5.40 (m, 2H), 5.50-5.72 (m, 1H), 5.90-6.07 (m, 1H), 6.42 (d, J=5.4 Hz, 0.2H), 6.54 (d, J=5.5 Hz, 0.8H), 6.64 (d, J=1.9 Hz, 0.2H), 6.88 (d, J=2.6 Hz, 0.8H), 7.52 (br s, 0.2H), 7.66 (d, J=2.6 Hz, 0.8H), 9.71 (br s, 0.8H), 10.37 (br s, 0.2H).

Step 3: Preparation of Intermediate triphenyl-[(E)-prop-1-enyl]phosphonium [3-[3-[2-(tert-butoxycarbonylamino)ethoxycarbamoyl]pyrazol-1-yl]-7-oxo-1,6-diazabicyclo[3.2.1]oct-3-en-6-yl]sulfate (46c)

Under inert atmosphere, acetic acid (46 μL, 0.80 mmol) and Pd(PPh$_3$)$_4$ (231 mg, 0.20 mmol) were added to a solution of intermediate (46b) (180 mg, 0.40 mmol) in anhydrous DCM (4 mL). The reaction mixture was stirred at rt for 2 h, then pyridine (4 mL) and sulfur trioxide pyridine complex (319 mg, 2.00 mmol) were added. The mixture was stirred at rt overnight in the dark. Mixture was diluted with DCM and filtered. Filtrate was concentrated and the crude product was purified by flash chromatography on silica gel (DCM/acetone: 100/0 to 0/100) to provide intermediate (46c) (135 mg, 0.17 mmol, 43%) with a 8/2 ratio in favor for the desired isomer.

MS m/z ([M−H]$^−$) 487.

Step 5: Preparation of [3-[3-(2-aminoethoxycarbamoyl)pyrazol-1-yl]-7-oxo-1,6-diazabicyclo[3.2.1]oct-3-en-6-yl]hydrogen sulfate (Example 46)

At 0° C., TFA (0.2 mL) was added to a solution of intermediate (46c) (70 mg, 0.063 mmol) in DCM (0.6 mL). The mixture was stirred at 0° C. for 40 min. Et$_2$O was added to give a precipitate, ethereal phase was removed. Residue was triturated several times in ACN and the obtained solid was dried under azote. The residue was purified by flash chromatography on C18-reversed phase silica gel (H$_2$O/ACN 98/2 to 0/100). The fractions containing desired product were combined and concentrated in vacuo to give example (46) (10 mg, 0.026 mmol, 42%).

MS m/z ([M−H]$^−$) 387.

$^1$H NMR (300 MHz, D$_2$O): δ (ppm) 3.25-3.35 (m, 2H), 3.38-3.49 (m, 1H), 3.66 (dd, J=11.4, 2.9 Hz, 1H), 4.05 (d, J=17.7 Hz, 0.2H), 4.18-4.26 (m, 2.2H), 4.36 (d, J=1.5 Hz, 1.6H), 4.49-4.61 (m, 1H), 6.51 (d, J=5.4 Hz, 0.2H), 6.69-6.74 (m, 1H), 6.83 (d, J=2.7 Hz, 0.8H), 7.67 (d, J=2.0 Hz, 0.2H), 7.98 (d, J=2.7 Hz, 0.8H).

Example 47: Synthesis of sodium [3-[3-(2-hydroxy-ethoxycarbamoyl)pyrazol-1-yl]-7-oxo-1,6-diazabicyclo[3.2.1]oct-3-en-6-yl]sulfate

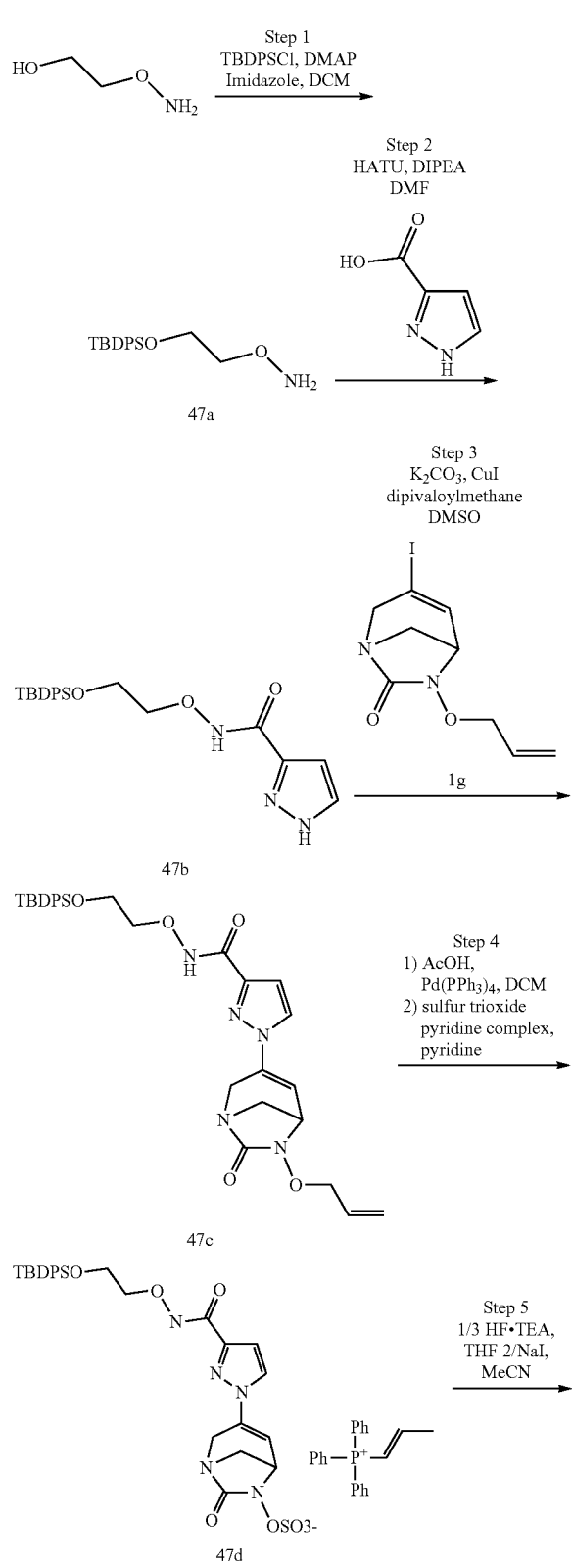

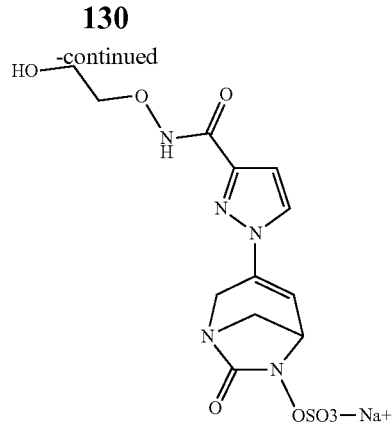

Example 47

Step 1: Preparation of Intermediate O-[2-[tert-butyl (diphenyl)silyl]oxyethyl]hydroxylamine (47a)

DMAP (80 mg, 0.65 mmol), imidazole (1.10 g, 16.22 mmol) and TBDPSCl (2.2 mL, 8.44 mmol) were added successively to a solution of 2-aminooxyethanol (500 mg, 6.49 mmol) in DCM (33 mL). Mixture was stirred at rt for 18 h. Insolubles were filtered and the filtrate was concentrated. The crude product was purified by flash chromatography on silica gel (DCM/MeOH: 100/0 to 80/20) to provide intermediate (47a) (2.1g, 6.49 mmol, 100%).

MS m/z ([M+H]$^+$) 316.

$^1$H NMR (300 MHz, CDCl$_3$): δ (ppm) 1.06 (s, 9H), 3.80-3.91 (m, 4H), 7.34-7.46 (m, 6H), 7.64-7.73 (m, 4H).

Step 2: Preparation of Intermediate N-[2-[tert-butyl (diphenyl)silyl]oxyethoxy]-1H-pyrazole-3-carboxamide) (47b)

Intermediate (47a) (1.052 g, 3.34 mmol), HATU (932 mg, 2.45 mmol) and DIPEA (1.16 mL, 6.69 mmol) were successively added to a solution of 1H-pyrazole-3-carboxylic acid (250 mg, 2.23 mmol) in DMF (11 mL). The mixture was stirred at 40° C. overnight and then concentrated. The residue was solubilized in water and then extracted with AcOEt. The organic layer was dried over Na$_2$SO$_4$, filtered and concentrated in vacuo. The residue was purified by flash chromatography on silica gel (DCM/acetone: 100/0 to 70/30) to provide intermediate (47b) (600 mg, 1.47 mmol, 66%).

MS m/z ([M−H]$^−$) 408.

$^1$H NMR (300 MHz, DMSO-d$_6$): δ (ppm) 1.00 (s, 9H), 3.87 (t, J=5.0 Hz, 2H), 4.01 (t, J=5.0 Hz, 2H), 6.65 (s, 1H), 7.37-7.51 (m, 6H), 7.60-7.69 (m, 4H), 7.83 (s, 1H), 11.47 (s, 1H), 13.27 (s, 1H).

Step 3: Preparation of Intermediate 1-(6-allyloxy-7-oxo-1,6-diazabicyclo[3.2.1]oct-3-en-3-yl)-N-[2-[tert-butyl(diphenyl)silyl]oxyethoxy]pyrazole-3-carboxamide (47c)

Using the procedure described in example 2 (step 1a), intermediate (1g) (0.20 g, 0.65 mmol) was converted by reaction with intermediate (47b) (0.32 g, 0.78 mmol) into intermediate (47c) (0.089 g, 0.15 mmol, 24%) with a ratio 6/4 in favor for the desired isomer after purification by flash chromatography on silica gel (DCM/acetone: 100/0 to 50/50)

MS m/z ([M+H]$^+$) 588.

$^1$H NMR (400 MHz, CDCl$_3$) δ 1.03-1.09 (m, 9H), 2.65-2.87 (m, 2H), 3.06-3.33 (m, 1H), 3.44-3.56 (m, 1H), 3.84-3.98 (m, 2H), 3.98-4.18 (m, 3H), 4.25-4.52 (m, 3H), 5.22-5.42 (m, 2H), 5.89-6.09 (m, 1H), 6.29-6.53 (m, 1H), 6.89 (d, J=2.6 Hz, 0.6H), 7.31-7.49 (m, 6H), 7.62 (d, J=2.6 Hz, 0.4H), 7.64-7.72 (m, 4H), 8.83 (br s, 0.4H), 9.29 (s, 0.6H).

Step 4: Preparation of Intermediate triphenyl-[(E)-prop-1-enyl]phosphonium [3-[3-[2-[tert-butyl(diphenyl)silyl]oxyethoxycarbamoyl]pyrazol-1-yl]-7-oxo-1,6-diazabicyclo[3.2.1]oct-3-en-6-yl]sulfate (47d)

Under inert atmosphere, acetic acid (18 µL, 0.30 mmol) and Pd(PPh$_3$)$_4$ (87 mg, 0.07 mmol) were added to a solution of intermediate (47c) (89 mg, 0.15 mmol) in anhydrous DCM (1.5 mL). The reaction mixture was stirred at rt for 2 h30, then pyridine (1.5 mL) and sulfur trioxide pyridine complex (120 mg, 0.75 mmol) were added and mixture was stirred at rt overnight in the dark. Mixture was diluted with DCM and filtered. The filtrate was concentrated. The crude product was purified by flash chromatography on silica gel (DCM/acetone: 100/0 to 0/100) to provide intermediate (47d) (38 mg, 0.04 mmol, 28%) with a ratio 6/4 in favor for the desired isomer.

MS m/z ([M–H]$^-$) 626.

Step 5: Preparation of sodium [3-[3-(2-hydroxyethoxycarbamoyl)pyrazol-1-yl]-7-oxo-1,6-diazabicyclo[3.2.1]oct-3-en-6-yl]sulfate (Example 47)

At 0° C., 3HF.NEt$_3$ (6.7 µL, 0.041 mmol) was added to a solution of intermediate (47d) (38 mg, 0.041 mmol) in THF (0.2 mL). The mixture was stirred at 0° C. for 1 h. More 3HF.NEt$_3$ (26.8 µL, 0.164 mmol) was added and the mixture was stirred at rt overnight. After concentration, Et$_2$O was added to give a precipitate which was filtered. The precipitate was dissolved in ACN (0.2 mL). A solution of NaI (60 mg, 0.40 mmol) in ACN (0.3 mL) was added and mixture was stirred at rt for 2 h. The precipitate was filtered, washed with ACN and purified by flash chromatography on C18-reversed phase silica gel (H$_2$O/ACN 98/2 to 0/100). The fractions containing desired product were combined and concentrated in vacuo to give example (47) (7.7 mg, 0.019 mmol, 47%) with a ratio 7/3 in favor for the desired isomer.

MS m/z ([M–H]$^-$) 388.

$^1$H NMR (300 MHz, D$_2$O) δ3.38-3.47 (m, 1H), 3.59-3.72 (m, 1H), 3.78-3.85 (m, 2H), 4.03-4.41 (m, 4H), 4.50-4.59 (m, 1H), 6.44-6.85 (m, 2H), 7.68 (d, J=2.1 Hz, 0.3H), 7.97 (d, J=2.7 Hz, 0.7H).

Example 48: Synthesis of sodium and 2,2,2-trifluoroacetate [3-[3-[2-(2-ammoniumethylamino)-2-oxoethyl]pyrazol-1-yl]-7-oxo-1,6-diazabicyclo[3.2.1]oct-3-en-6-yl]sulfate

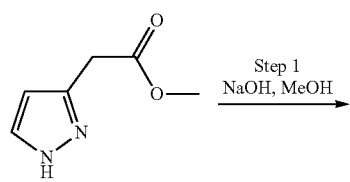

Step 1
NaOH, MeOH

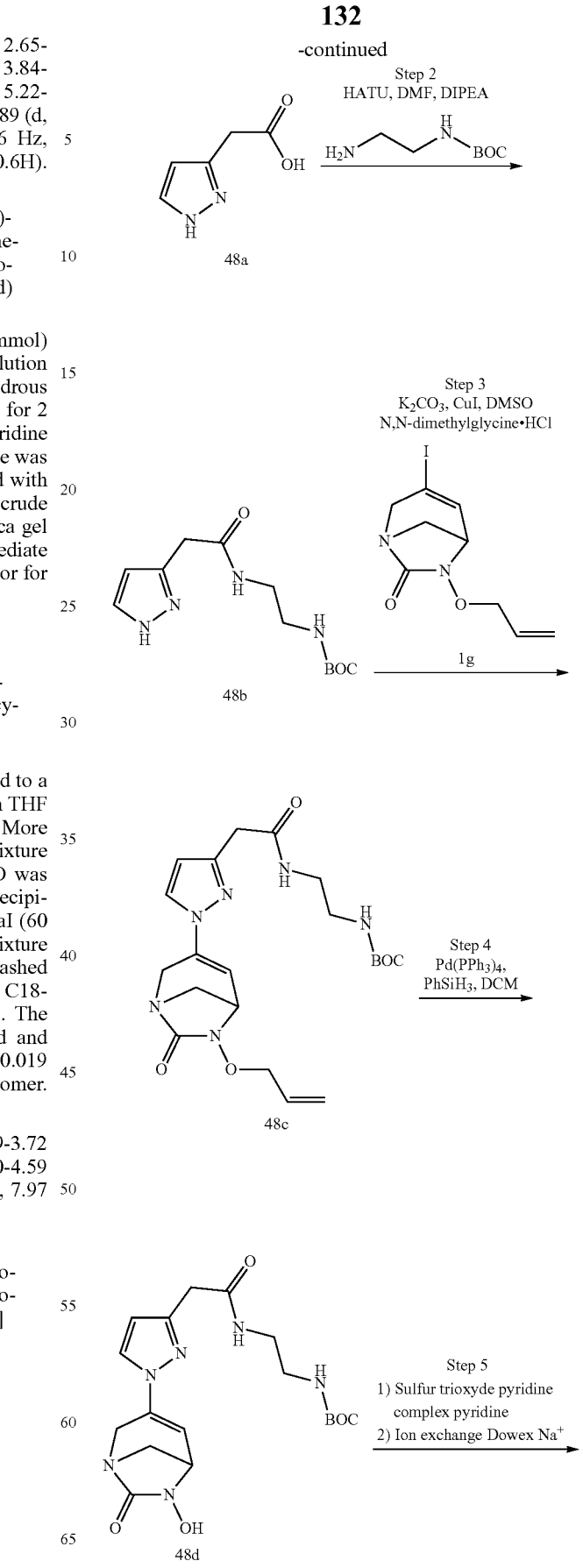

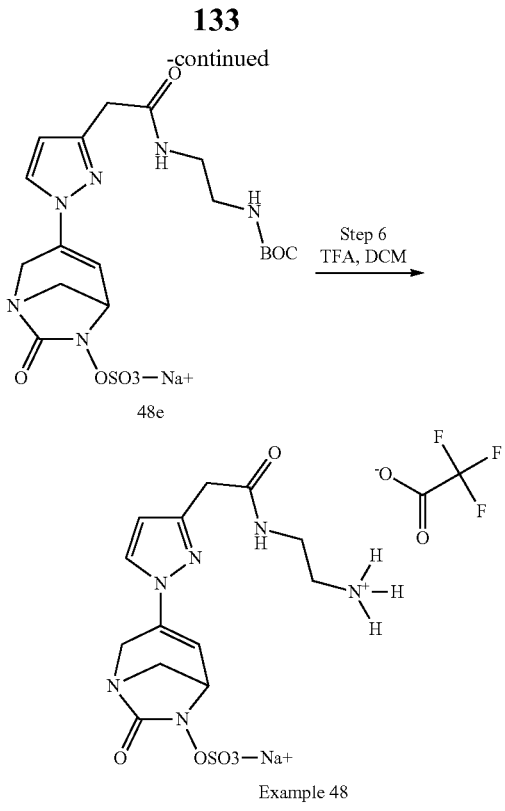

Example 48

Step 1: Preparation of Intermediate 2-(1H-pyrazol-3-yl)acetic acid (48a)

A mixture of (1H-pyrazol-3-yl)-acetic acid methyl ester (0.85 g, 6.07 mmol) and NaOH 6N (1.27 mL, 7.65 mmol) was diluted in MeOH (17 mL). After stirring 1 night, the reaction mixture was concentrated in vacuo. The residue was diluted with water and acidified with HCl 37% until pH 1. The mixture was concentrated under nitrogen flux. ACN was added and the solid was filtered to provide intermediate (48a) (200 mg, 6.07 mmol, 100%).

MS m/z ([M+H]$^+$) 127.

$^1$H NMR (300 MHz, CDCl$_3$): δ (ppm) 4.61 (s, 2H), 6.14 (s, 1H), 7.46 (d, J=2.0 Hz, 1H), 8.02 (s, 1H).

Step 2: Preparation of Intermediate tert-butyl N-[2-[[2-(1H-pyrazol-3-yl)acetyl]amino]ethyl]carbamate (48b)

To a solution of intermediate (48a) (0.75 g, 5.79 mmol) in anhydrous DMF (30 mL) were added HATU (1.7 g, 6.37 mmol), DIPEA (6.1 mL, 34.74 mmol) and tert-butyl N-(2-aminoethyl)carbamate (1.2 mL, 7.52 mmol). The suspension was stirred 1 night at rt. The residue was concentrated in vacuo and purified on silica gel (DCM/Acetone: 70/30 to 30/70) to provide intermediate (XXb) (620 mg, 2.31 mmol, 40%) as a brown powder.

MS m/z ([M+H]$^+$) 269.

$^1$H NMR (400 MHz, CD$_3$OD): δ (ppm) 1.44 (s, 9H), 3.16 (t, J=6.1 Hz, 2H), 3.26-3.30 (m, 2H), 3.58 (s, 2H), 6.26 (d, J=2.2 Hz, 1H), 7.57 (d, J=2.2 Hz, 1H).

Step 3: Preparation of Intermediate tert-butyl N-[2-[[2-[1-(6-allyloxy-7-oxo-1,6-diazabicyclo[3.2.1]oct-3-en-3-yl)pyrazol-3-yl]acetyl]amino]ethyl]carbamate (48c)

Using the procedure described in example 1 (step 7), intermediate (1g) (352 mg, 1.15 mmol) was converted by reaction with intermediate (48b) (620 mg, 2.32 mmol) into intermediate (48c) (220 mg, 0.49 mmol, 43%) after purification by flash chromatography on silica gel (DCM/Acetone: 70/30 to 30/70).

MS m/z ([M+H]$^+$) 347.

$^1$H NMR (400 MHz, CDCl$_3$): δ (ppm) 1.45 (s, 9H), 3.12-3.43 (m, 5H), 3.50-3.66 (m, 3H), 4.14-4.24 (m, 2H), 4.40-4.55 (m, 3H), 4.92 (br s, 1H), 5.33-5.47 (m, 2H), 5.96-6.12 (m, 1H), 6.31 (br s, 1H), 6.49 (br s, 1H), 6.60 (br s, 1H), 7.57 (br s, 1H).

Step 4: Preparation of Intermediate tert-butyl N-[2-[[2-[1-(6-hydroxy-7-oxo-1,6-diazabicyclo[3.2.1]oct-3-en-3-yl)pyrazol-3-yl]acetyl]amino]ethyl]carbamate (48d)

Under inert atmosphere, a solution of intermediate (48c) (50 mg, 0.11 mmol) was diluted in anhydrous DCM (2.8 mL). AcOH (13 μL, 0.22 mmol) and Pd(PPh$_3$)$_4$ (64 mg, 0.055 mmol) were successively added. After stirring 2 h, the residue was concentrated in vacuo and purified by flash chromatography on silica gel (DCM/Acetone: 70/30 to 50/50) to provide intermediate (48d) (30 mg, 0.073 mmol, 67%).

MS m/z ([M+H]$^+$) 407.

Step 5: Preparation of Intermediate sodium [3-[3-[2-[2-(tert-butoxycarbonylamino) ethylamino]-2-oxo-ethyl]pyrazol-1-yl]-7-oxo-1,6-diazabicyclo[3.2.1]oct-3-en-6-yl]sulfate (48e)

To a solution of intermediate (48d) (30 mg, 0.073 mmol) in anhydrous pyridine (3 mL) under inert atmosphere was added sulfur trioxide pyridine complex (58 mg, 0.365 mmol). After stirring for 18 h, DCM was added to the residue and the solid was filtered. The filtrate was evaporated to give a solid which is applied on a Dowex sodium form column (Dowex® 50WX8 hydrogen form stored with an aqueous solution of 2N NaOH and washed until neutral pH with water). Fractions containing the desired compound were combined, freezed and lyophilized to give a mixture of regioisomers with intermediate (48e) as major product (ratio 80/20) (20 mg, 0.039 mmol, 54%).

MS m/z ([M−H]$^−$) 485.

$^1$H NMR (300 MHz, D$_2$O): δ (ppm) 1.33 (s, 9H), 3.13-3.18 (m, 2H), 3.23-3.30 (m, 2H), 3.41 (d, J=11.3 Hz, 1H), 3.57-3.68 (m, 3H), 4.32 (s, 2H), 4.53 (dd, J=2.6, 5.7 Hz, 1H), 6.38 (d, J=2.6 Hz, 1H), 6.56 (d, J=5.8 Hz, 1H), 7.84 (d, J=2.6 Hz, 1H).

Step 6: Preparation of sodium [3-[3-[2-(2-ammoniumethylamino)-2-oxo-ethyl]pyrazol-1-yl]-7-oxo-1,6-diazabicyclo[3.2.1]oct-3-en-6-yl]sulfate 2,2,2-trifluoroacetate (Example 48)

Intermediate (48e) (20 mg, 0.04 mmol) was solubilized in TFA (350 μL) and DCM (1.25 mL) at 0° C. under inert atmosphere. After stirring for 1 h, Et$_2$O was added. The precipitate was triturated several times with Et$_2$O and then with ACN to give example 48 (4.7 mg, 0.011 mmol, 30%) as a yellow powder.

MS m/z ([M−H]$^−$) 385.

$^1$H NMR (400 MHz, D$_2$O): δ (ppm) 3.05-3.08 (m, 2H), 3.35-3.38 (m, 1H), 3.42-3.45 (m, 2H), 3.58-3.63 (m, 2H), 4.15-4.19 (m, 1H), 4.27-4.30 (m, 2H), 4.49 (dd, J=5.6, 2.7 Hz, 1H), 6.34 (d, J=2.6 Hz, 1H), 6.51 (d, J=5.7 Hz, 1H), 7.78 (d, J=2.6 Hz, 1H).

Example 49: Synthesis of sodium and 2,2,2-trifluoroacetate [3-[3-(ammoniummethyl)pyrazol-1-yl]-7-oxo-1,6-diazabicyclo[3.2.1]oct-3-en-6-yl]sulfate

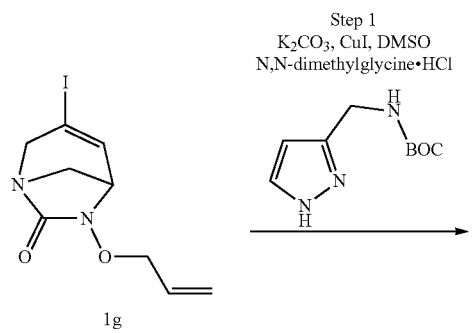

1g

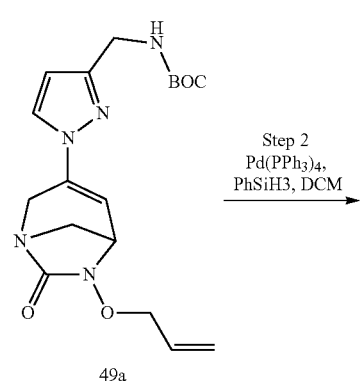

49a

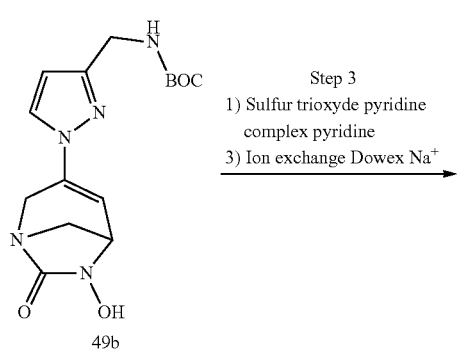

49b

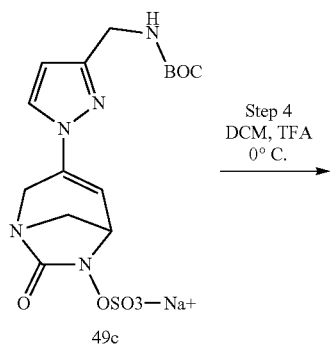

49c

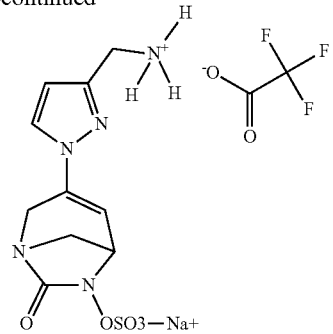

Example 49

Step 1: Preparation of Intermediate tert-butyl N-[[1-(6-allyloxy-7-oxo-1,6-diazabicyclo[3.2.1]oct-3-en-3-yl)pyrazol-3-yl]methyl]carbamate (49a)

Using the procedure described in example 1 (step 7), intermediate (1g) (700 mg, 2.30 mmol) was converted by reaction with tert-butyl N-(1H-pyrazol-3-ylmethyl)carbamate (910 mg, 4.60 mmol) into intermediate (49a) (380 mg, 1.01 mmol, 44%) after purification by flash chromatography on silica gel (DCM/Acetone: 100/0 to 80/20).

MS m/z ([M+H]$^+$) 376.

$^1$H NMR (400 MHz, CDCl$_3$): δ (ppm) δ 1.41 (s, 9H), 3.08 (d, J=10.8 Hz, 1H), 3.46 (dd, J=2.8, 10.9 Hz, 1H), 4.03-4.15 (m, 2H), 4.19-4.24 (m, 2H), 4.32-4.43 (m, 3H), 5.14 (br s, 1H), 5.23-5.35 (m, 2H), 5.96 (ddt, J=6.3, 10.3, 16.8 Hz, 1H), 6.22 (d, J=2.6 Hz, 1H), 6.37 (d, J=5.5 Hz, 1H), 7.49 (d, J=2.6 Hz, 1H).

Step 2: Preparation of Intermediate tert-butyl N-[[1-(6-hydroxy-7-oxo-1,6-diazabicyclo[3.2.1]oct-3-en-3-yl)pyrazol-3-yl]methyl]carbamate (49b)

Under inert atmosphere, a solution of intermediate (49a) (50 mg, 0.11 mmol) was diluted in anhydrous DCM (1 mL). PhSiH$_3$ (7.4 µL, 0.08 mmol) and Pd(PPh$_3$)$_4$ (2.4 mg, 0.002 mmol) were successively added. After stirring 2 h30, the residue was concentrated in vacuo and purified by flash chromatography on silica gel (DCM/Acetone: 100/0 to 70/30) to provide intermediate (49b) (13 mg, 0.038 mmol, 98%).

MS m/z ([M+H]$^+$) 336.

Step 3: Preparation of sodium [3-[3-[(tert-butoxycarbonylamino)methyl]pyrazol-1-yl]-7-oxo-1,6-diazabicyclo[3.2.1]oct-3-en-6-yl]sulfate (49c)

To a solution of intermediate (49b) (13 mg, 0.04 mmol) in anhydrous pyridine (0.5 mL) under inert atmosphere was added sulfur trioxide pyridine complex (26 mg, 0.20 mmol). After stirring for 18 h, DCM was added to the residue and the solid was filtered and washed with DCM. The filtrate was evaporated to give a solid which are applied on a Dowex sodium form column (Dowex® 50WX8 hydrogen form stored with an aqueous solution of 2N NaOH and washed until neutral pH with water). The fractions containing the desired compound were combined, freezed and lyophilized to provide intermediate (49c) (10 mg, 0.02 mmol, 50%).

MS m/z ([M−H]$^-$) 415.

$^1$H NMR (300 MHz, D$_2$O): δ (ppm) 1.38 (s, 9H), 3.40 (d, J=11.2 Hz, 1H), 3.59-3.68 (m, 1H), 4.19 (s, 2H), 4.30 (s, 2H), 4.52 (dd, J=2.6, 5.7 Hz, 1H), 6.35 (s, 1H), 6.52 (d, J=5.7 Hz, 1H), 7.78 (d, J=2.7 Hz, 1H).

Step 4: Preparation of sodium and 2,2,2-trifluoroacetate [3-[3-(ammoniummethyl)pyrazol-1-yl]-7-oxo-1,6-diazabicyclo[3.2.1]oct-3-en-6-yl]sulfate (Example 49)

Intermediate (49c) (10 mg, 0.02 mmol) was solubilized in TFA (250 μL) and DCM (750 μL) at 0° C. under inert atmosphere. After stirring for 1 h, the residue was triturated several times with Et$_2$O and ACN at 0° C. to give example (49) (2.5 mg, 0.0079 mmol, 33%) as a yellow powder.

MS m/z ([M−H]$^−$) 314.

$^1$H NMR (400 MHz, D$_2$O): δ (ppm) δ 3.42-3.48 (m, 1H), 3.67-3.72 (m, 1H), 4.22 (s, 2H), 4.38 (d, J=1.6 Hz, 2H), 4.58 (dd, J=2.5, 5.7 Hz, 1H), 6.27 (s, 1H), 6.53 (d, J=2.7 Hz, 1H), 7.93 (d, J=2.7 Hz, 1H).

Example 50: Synthesis of sodium [3-[3-[(2-hydroxyacetyl)amino]pyrazol-1-yl]-7-oxo-1,6-diazabicyclo[3.2.1]oct-3-en-6-yl]sulfate

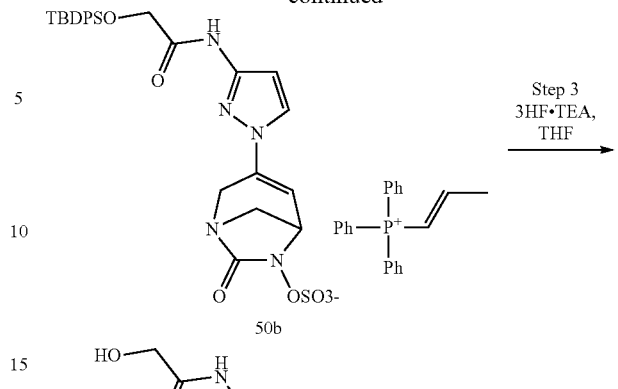

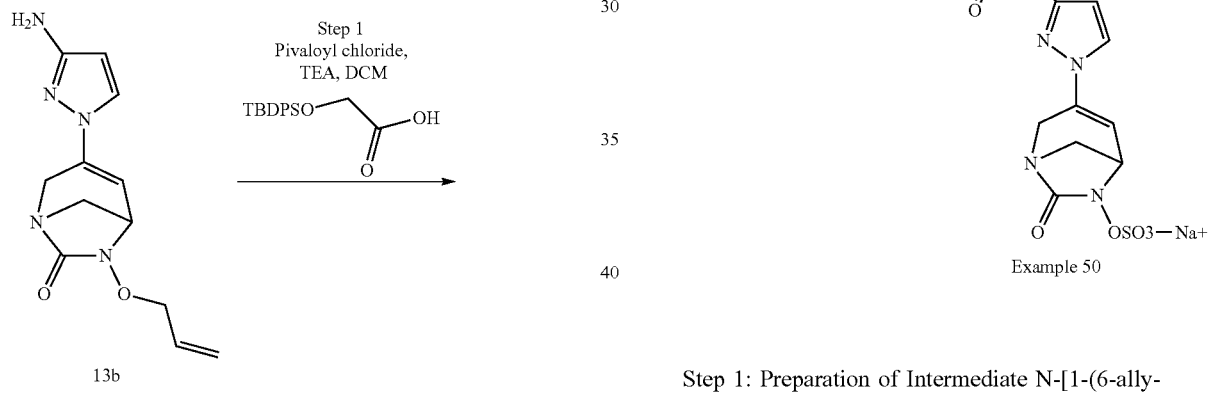

Step 1: Preparation of Intermediate N-[1-(6-allyloxy-7-oxo-1,6-diazabicyclo[3.2.1]oct-3-en-3-yl)pyrazol-3-yl]-2-[tert-butyl(diphenyl)silyl]oxy-acetamide (50a)

At 0° C., TEA (0.24 mL, 1.78 mmol) and Pivaloyl chloride (88 μL, 0.71 mmol) were added to a solution of 2-[tert-butyl(diphenyl)silyl]oxyacetic acid (224 mg, 0.71 mmol) in DCM (6 mL). The mixture was stirred at 0° C. for 45 min. Then, a solution of intermediate (13b) (155 mg, 0.59 mmol) in DCM (2.5 mL) was added and mixture was stirred at rt overnight. After concentration, the crude product was purified by flash chromatography on silica gel (DCM/Acetone: 100/0 to 80/20) to provide intermediate (50a) (260 mg, 0.47 mmol, 79%).

MS m/z ([M+H]$^+$) 558.

$^1$H NMR (300 MHz, CDCl$_3$): δ (ppm) 1.14 (s, 9H), 3.14 (d, J=10.8 Hz, 1H), 3.50-3.58 (m, 1H), 4.07-4.19 (m, 2H), 4.21 (s, 2H), 4.36-4.53 (m, 3H), 5.30-5.43 (m, 2H), 5.95-6.10 (m, 1H), 6.43 (d, J=5.4 Hz, 1H), 6.89 (d, J=2.6 Hz, 1H), 7.37-7.48 (m, 6H), 7.50 (d, J=2.6 Hz, 1H), 7.60-7.69 (m, 4H), 9.03 (s, 1H).

Step 2: Preparation of Intermediate triphenyl-[(E)-prop-1-enyl]phosphonium [3-[3-[[2-[tert-butyl(diphenyl)silyl]oxyacetyl]amino]pyrazol-1-yl]-7-oxo-1,6-diazabicyclo[3.2.1]oct-3-en-6-yl]sulfate (50b)

Under inert atmosphere, acetic acid (52 µL, 0.90 mmol) and Pd(PPh₃)₄ (260 mg, 0.22 mmol) were added to a solution of intermediate (50a) (250 mg, 0.45 mmol) in anhydrous DCM (4.5 mL). The reaction mixture was stirred at rt for 2 h30, then pyridine (4.5 mL) and sulfur trioxide pyridine complex (357 mg, 2.25 mmol) were added and mixture was stirred at rt overnight in the dark. Mixture was diluted with DCM, obtained precipitate was filtered and filtrate was concentrated. The crude product was purified by flash chromatography on silica gel (DCM/acetone: 100/0 to 0/100) to provide intermediate (50b) (269 mg, 0.30 mmol, 67%).

MS m/z ([M−H]⁻) 596.

Step 3: Preparation of triethylammonium [3-[3-[(2-hydroxyacetyl)amino]pyrazol-1-yl]-7-oxo-1,6-diazabicyclo[3.2.1]oct-3-en-6-yl]sulfate (50c)

Intermediate (50b) (269 mg, 0.30 mmol) was dissolved in ACN (1.5 mL). Then, 3HF·NEt₃ (98 µL, 0.59 mmol) was added and mixture was stirred at rt overnight. Obtained solid was filtered to give intermediate (50c) (89 mg, 0.19 mmol, 65%).

MS m/z ([M−H]⁻) 358.

¹H NMR (300 MHz, D₂O): δ (ppm) 1.26 (t, J=7.3 Hz, 9H), 3.18 (q, J=7.3 Hz, 6H), 3.43 (d, J=11.3 Hz, 1H), 3.62-3.72 (m, 1H), 4.24 (s, 2H), 4.34 (d, J=1.5 Hz, 2H), 4.55 (dd, J=5.7, 2.6 Hz, 1H), 6.58 (d, J=5.8 Hz, 1H), 6.62 (d, J=2.7 Hz, 1H), 7.85 (d, J=2.7 Hz, 1H).

Step 4: Preparation of sodium [3-[3-[(2-hydroxyacetyl)amino]pyrazol-1-yl]-7-oxo-1,6-diazabicyclo [3.2.1]oct-3-en-6-yl]sulfate (Example 50)

Intermediate (50c) (75 mg, 0.16 mmol) was dissolved in H₂O and converted after ion exchange with Dowex sodium form column (Dowex® 50WX8 hydrogen form stored with an aqueous solution of 2N NaOH and washed until neutral pH with H₂O) into example (50) (55 mg, 0.14 mmol, 89%).

MS m/z ([M−H]⁻) 358.

¹H NMR (300 MHz, D₂O): δ (ppm) 3.43 (d, J=11.3 Hz, 1H), 3.61-3.73 (m, 1H), 4.24 (s, 2H), 4.34 (d, J=1.5 Hz, 2H), 4.55 (dd, J=5.7, 2.6 Hz, 1H), 6.53-6.61 (m, 1H), 6.61 (d, J=2.7 Hz, 1H), 7.84 (d, J=2.7 Hz, 1H).

Example 51: Synthesis of sodium [3-[3-(3-hydroxypropanoylamino)pyrazol-1-yl]-7-oxo-1,6-diazabicyclo[3.2.1]oct-3-en-6-yl]sulfate

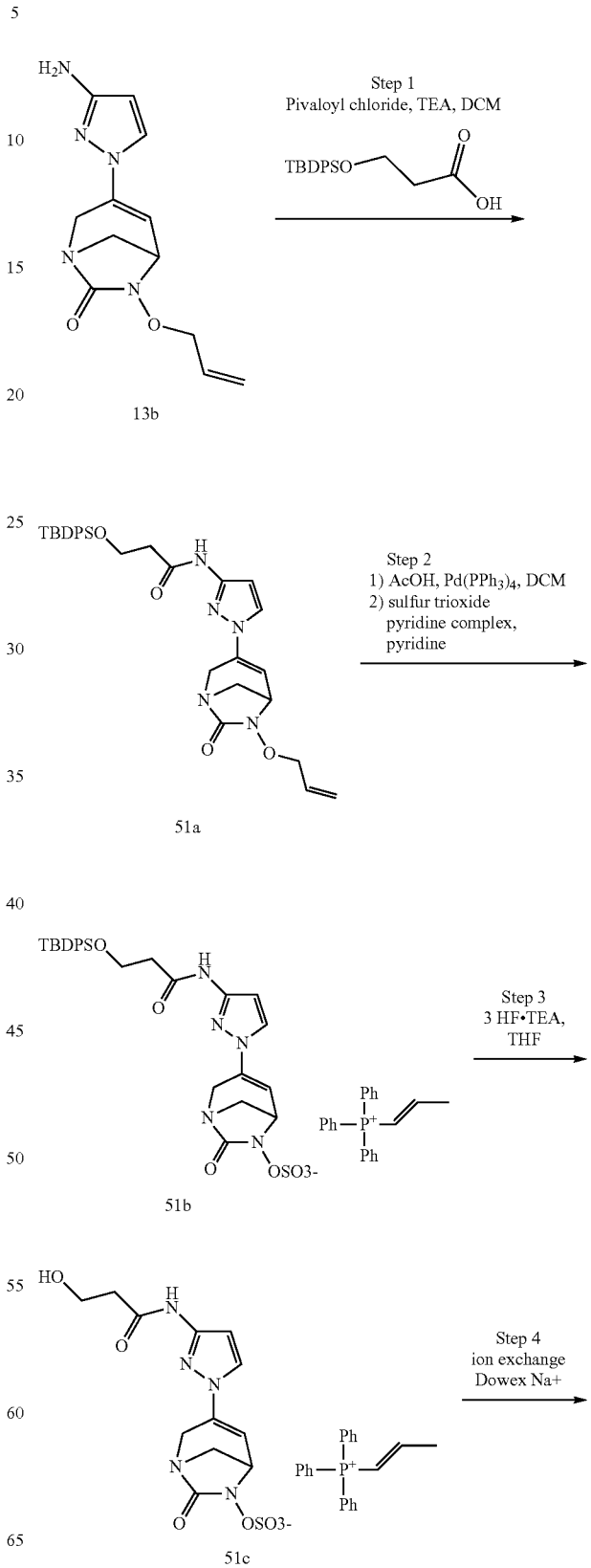

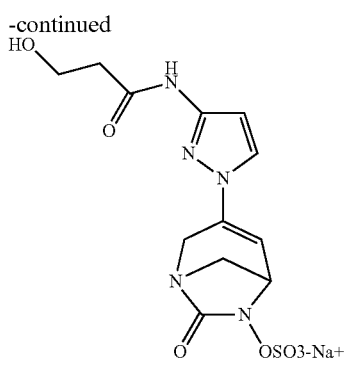

Example 51

Step 1: Preparation of Intermediate N-[1-(6-allyloxy-7-oxo-1,6-diazabicyclo[3.2.1]oct-3-en-3-yl)pyrazol-3-yl]-3-[tert-butyl(diphenyl)silyl]oxy-propanamide (51a)

Using the procedure described in example 50 (step 1), intermediate (13b) (100 mg, 0.38 mmol) was converted by reaction with 3-[tert-butyl(diphenyl)silyl]oxypropanoic acid (151 mg, 0.46 mmol) into intermediate (51a) (130 mg, 0.23 mmol, 50%) after purification by flash chromatography on silica gel (DCM/Acetone: 100/0 to 80/20).

MS m/z ([M+H]$^+$) 572.

$^1$H NMR (300 MHz, CDCl$_3$): δ (ppm) 1.11 (s, 9H), 2.57 (t, J=5.6 Hz, 2H), 3.13 (d, J=10.8 Hz, 1H), 3.52 (dd, J=10.7, 2.7 Hz, 1H), 3.96 (t, J=5.6 Hz, 2H), 4.04-4.18 (m, 2H), 4.34-4.54 (m, 3H), 5.27-5.44 (m, 2H), 5.94-6.11 (m, 1H), 6.34 (d, J=5.5 Hz, 1H), 6.87 (d, J=2.6 Hz, 1H), 7.35-7.49 (m, 6H), 7.51 (d, J=2.7 Hz, 1H), 7.63-7.72 (m, 4H), 9.21 (s, 1H).

Step 2: Preparation of Intermediate triphenyl-[(E)-prop-1-enyl]phosphonium [3-[3-[3-[tert-butyl(diphenyl)silyl]oxypropanoylamino]pyrazol-1-yl]-7-oxo-1,6-diazabicyclo[3.2.1]oct-3-en-6-yl]sulfate (51b)

Using the procedure described in example 50 (step 2), intermediate (51a) (130 mg, 0.23 mmol) was converted into intermediate (51b) (107 mg, 0.12 mmol, 52%) after purification by flash chromatography on silica gel (DCM/Acetone: 100/0 to 0/100).

MS m/z ([M−H]$^−$) 610.

Step 3: Preparation of triphenyl-[(E)-prop-1-enyl]phosphonium [3-[3-(3-hydroxypropanoylamino)pyrazol-1-yl]-7-oxo-1,6-diazabicyclo[3.2.1]oct-3-en-6-yl]sulfate (51c)

Intermediate (51b) (107 mg, 0.12 mmol) was dissolved in ACN (1.2 mL) and 3HF.NEt$_3$ (39 μL, 0.23 mmol) was then added. The mixture was stirred at rt overnight. After concentration, crude product was purified by flash chromatography on C18-reversed phase silica gel (H$_2$O/ACN: 99/1 to 0/100) to provide intermediate (51c) (40 mg, 0.059 mmol, 51%).

MS m/z ([M−H]$^−$) 372.

Step 4: Preparation of sodium [3-[3-(3-hydroxypropanoylamino)pyrazol-1-yl]-7-oxo-1,6-diazabicyclo[3.2.1]oct-3-en-6-yl]sulfate (Example 51)

Intermediate (51c) (40 mg, 0.059 mmol) was converted after ion exchange with Dowex sodium form column (Dowex® 50WX8 hydrogen form stored with an aqueous solution of 2N NaOH and washed until neutral pH with H$_2$O) to Example (51) (12 mg, 0.03 mmol, 52%).

MS m/z ([M−H]$^−$) 372.

$^1$H NMR (300 MHz, D$_2$O): δ (ppm) 2.66 (t, J=6.0 Hz, 2H), 3.42 (d, J=11.3 Hz, 1H), 3.63-3.71 (m, 1H), 3.91 (t, J=6.0 Hz, 2H), 4.33 (d, J=1.5 Hz, 2H), 4.55 (dd, J=5.7, 2.6 Hz, 1H), 6.55 (d, J=5.7 Hz, 1H), 6.60 (d, J=2.7 Hz, 1H), 7.80 (d, J=2.7 Hz, 1H).

Example 52: Synthesis of sodium [3-[3-[(2-amino-2-oxo-ethoxy)carbamoyl]pyrazol-1-yl]-7-oxo-1,6-diazabicyclo[3.2.1]oct-3-en-6-yl]sulfate

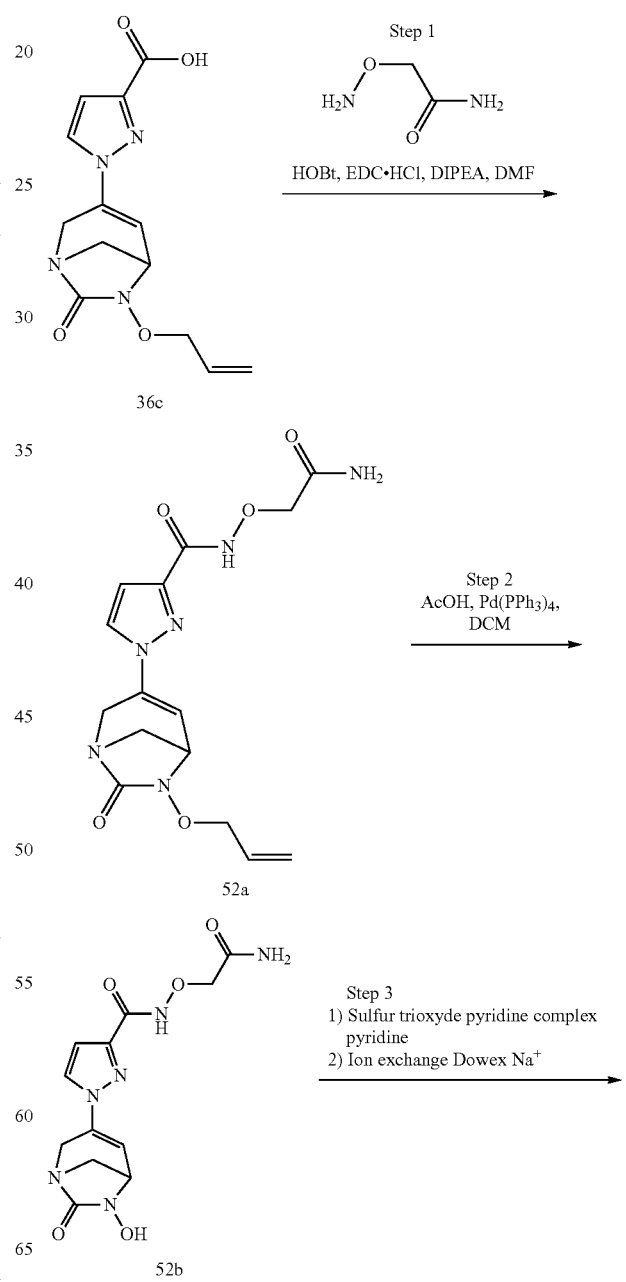

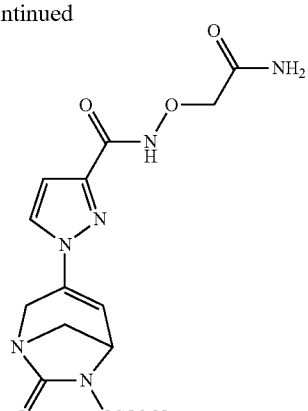

Example 52

Step 1: Preparation of 1-(6-allyloxy-7-oxo-1,6-diazabicyclo[3.2.1]oct-3-en-3-yl)-N-(2-amino-2-oxo-ethoxy)pyrazole-3-carboxamide (52a)

Using procedure described in example 36 (step 4), intermediate (36c) (126 mg, 0.434 mmol) was converted by reaction with 2-aminooxyacetamide hydrochloride (51 mg, 0.659 mmol) into intermediate (52a) (70 mg, 0.193 mmol, 44%) after purification by flash chromatography on silica gel (DCM/acetone 100/0 to 0/100).

MS m/z ([M−H]⁻) 361.
MS m/z ([M+H]⁺) 363.

Step 2: Preparation of N-(2-amino-2-oxo-ethoxy)-1-(6-hydroxy-7-oxo-1,6-diazabicyclo[3.2.1]oct-3-en-3-yl)pyrazole-3-carboxamide (52b)

Intermediate (52a) (70 mg, 0.193 mmol) was dissolved in anhydrous DCM (1.4 mL). The solution was degazed 10 min under argon atmosphere and AcOH (22 μL, 0.386 mmol) and Pd(PPh₃)₄ (111 mg, 0.097 mmol) were successively added. After stirring for 45 min at rt, a white solid was filtered to afford intermediate (52b) (40 mg, 0.122 mmol, 28% on 2 steps).

MS m/z ([M+H]⁺) 323.
MS m/z ([M−H]⁻) 321.

Step 3: Preparation of sodium [3-[3-[(2-amino-2-oxo-ethoxy)carbamoyl]pyrazol-1-yl]-7-oxo-1,6-diazabicyclo[3.2.1]oct-3-en-6-yl]sulfate (Example 52)

To a solution of intermediate (52b) (40 mg, 0.122 mmol) in anhydrous pyridine (0.720 mL) under inert atmosphere was added sulfur trioxide pyridine complex (98 mg, 0.613 mmol). After stirring for 18 h, the heterogeneous mixture was concentrated in vacuo. DCM was added to the residue and the mixture was filtered to remove the salts. The same operation was done with acetone and ACN. The filtrate was then applied on a Dowex sodium form column (Dowex® 50WX8 hydrogen form stored with an aqueous solution of 2N NaOH and washed until neutral pH with water). The fractions containing the desired compound were combined, freezed and lyophilized and purified by chromatography on C18-reversed phase silica gel (water/ACN: 99/1) to give example (52) (2 mg, 0.005 mmol, 4%).

MS m/z ([M−H]⁻) 401.
MS m/z ([M+H]⁺) 403.

¹H NMR (300 MHz, D₂O): δ(ppm) 3.44 (d, J=10.2 Hz, 1H), 3.65-3.72 (m, 1H), 4.39 (d, J=1.4 Hz, 2H), 4.53 (s, 2H), 4.56-4.60 (m, 1H), 6.73-6.75 (m, 1H), 6.85 (d, J=2.7 Hz, 1H), 8.01 (d, J=2.7 Hz, 1H).

Example 55: Synthesis of sodium [7-oxo-3-(4-thiazol-2-yltriazol-1-yl)-1,6-diazabicyclo[3.2.1]oct-3-en-6-yl]sulfate

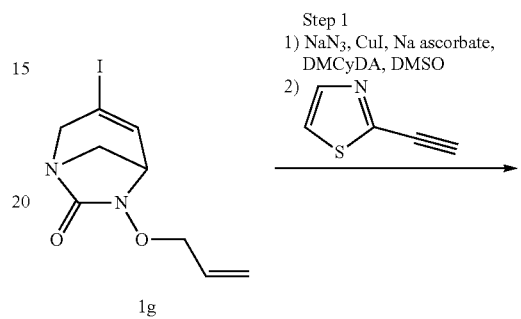

1g

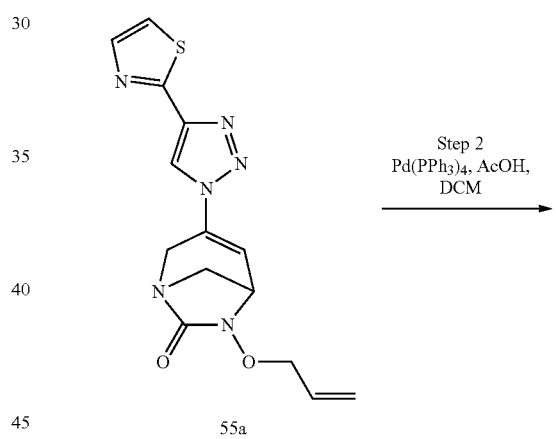

55a

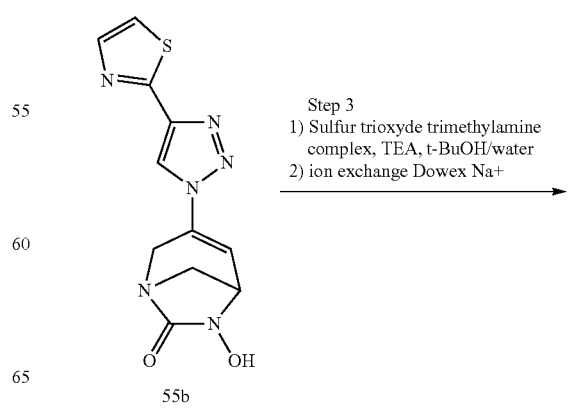

55b

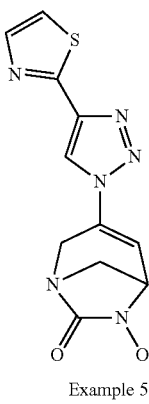

Example 55

Step 1: Preparation of Intermediate 6-allyloxy-3-(4-thiazol-2-yltriazol-1-yl)-1,6-diazabicyclo[3.2.1]oct-3-en-7-one (55a)

In a 5 mL sealed flask under inert atmosphere, intermediate (1g) (250 mg, 0.82 mmol) was diluted with anhydrous DMSO (3 mL). CuI (16 mg, 0.08 mmol), sodium azide (80 mg, 1.22 mmol), sodium ascorbate (16 mg, 0.08 mmol) and DMCyDA (19 μL, 0.12 mmol) were successively added. The green solution turned rapidly to brown. The mixture was stirred at rt until reaction completion. After 1 h, 2-ethynylthiazole (89 μL, 0.98 mmol) was added to the mixture. The mixture was stirred at rt until disappearance of intermediate azide. After 30 min, the mixture was diluted with $H_2O$ (30 mL) and extracted with EtOAc (3×15 mL). The combined organic phases were dried ($Na_2SO_4$) and concentrated in vacuo to give a brown oil which was purified by flash chromatography on silica gel (cyclohexane/EtOAc: 100/0 to 0/100) to give intermediate (55a) (80 mg, 0.24 mmol, 30%) as a brown solid.

MS m/z ([M+H]$^+$) 331, ([2M+H]$^+$) 661.

$^1$H-NMR (300 MHz, CDCl$_3$): δ (ppm) 3.22 (d, J=11.0 Hz, 1H), 3.60 (dd, J=11.0, 2.8 Hz, 1H), 4.19 (dd, J=5.5, 2.6 Hz, 1H), 4.29-4.64 (m, 4H), 5.26-5.45 (m, 2H), 6.03 (ddt, J=16.8, 10.3, 6.4 Hz, 1H), 6.74 (d, J=5.5 Hz, 1H), 7.40 (d, J=3.2 Hz, 1H), 7.87 (d, J=3.2 Hz, 1H), 8.28 (s, 1H).

Step 2: Preparation of Intermediate 6-hydroxy-3-(4-thiazol-2-yltriazol-1-yl)-1,6-diazabicyclo[3.2.1]oct-3-en-7-one (55b)

Using the procedure described in example (4) (step 2), intermediate (55a) (80 mg, 0.24 mmol) was converted into intermediate (55b) (32 mg, 0.11 mmol, 45%) after purification by flash chromatography on silica gel (DCM/Acetone: 100/0 to 0/100).

MS m/z ([M+H]$^+$) 291.

Step 3: Preparation of sodium [7-oxo-3-(4-thiazol-2-yltriazol-1-yl)-1,6-diazabicyclo[3.2.1]oct-3-en-6-yl]sulfate (example 55)

Using the procedure described in example (5) (step 3), intermediate (55b) (32 mg, 0.11 mmol) was converted after ion exchange (Dowex sodium form column) into example (55) (31 mg, 0.08 mmol, 70%) as a white powder.

MS m/z ([M−H]$^−$) 369.

$^1$H-NMR (400 MHz, D$_2$O): δ(ppm) 3.53 (d, J=11.5 Hz, 1H), 3.77 (dd, J=11.6, 2.8 Hz, 1H), 4.39-4.56 (m, 2H), 4.70 (dd, J=5.7, 2.6 Hz, 1H), 6.95 (s, 1H), 7.59-7.69 (m, 1H), 7.77-7.82 (m, 1H), 8.40-8.48 (m, 1H).

Example 56: Synthesis of sodium [3-(4-carbamoyl-triazol-1-yl)-7-oxo-1,6-diazabicyclo[3.2.1]oct-3-en-6-yl]sulfate

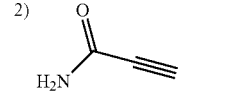

Step 1
1) NaN$_3$, CuI, Na ascorbate, DMCyDA, DMSO
2)

1g

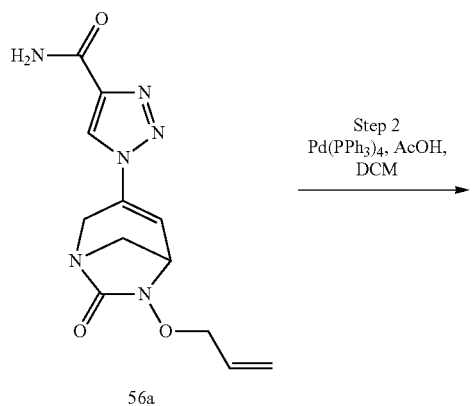

Step 2
Pd(PPh$_3$)$_4$, AcOH, DCM

56a

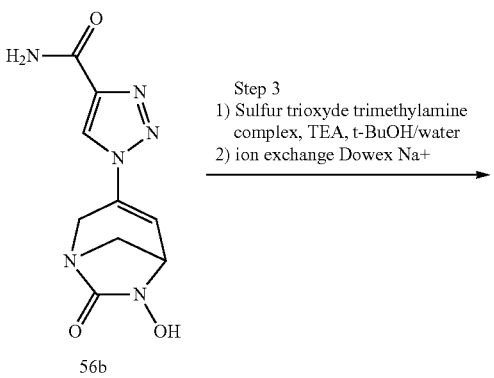

Step 3
1) Sulfur trioxyde trimethylamine complex, TEA, t-BuOH/water
2) ion exchange Dowex Na+

56b

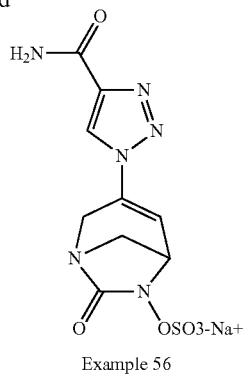

Example 56

Step 1: Preparation of Intermediate 1-(6-allyloxy-7-oxo-1,6-diazabicyclo[3.2.1]oct-3-en-3-yl)triazole-4-carboxamide (56a)

In a 5 mL sealed flask under inert atmosphere, intermediate (1g) (250 mg, 0.82 mmol) was diluted with anhydrous DMSO (3 mL). CuI (16 mg, 0.08 mmol), sodium azide (80 mg, 1.22 mmol), sodium ascorbate (16 mg, 0.08 mmol), and DMCyDA (19 µL, 0.12 mmol) were successively added. The green solution turned rapidly to brown. The mixture was stirred at rt until reaction completion. After 45 min, propiolamide (68 mg, 0.98 mmol) was added and the mixture was stirred at rt until disappearance of intermediate azide. After 1 h, the reaction mixture was concentrated under nitrogen flux. The crude was purified by flash chromatography on silica gel (cyclohexane/EtOAc: 100/0 to 0/100) and triturated with Et₂O to give intermediate (56a) (88 mg, 0.30 mmol, 37%) as a white solid.

MS m/z ([M+H]⁺) 291, ([2M+H]⁺) 581.

¹H-NMR (400 MHz, CDCl₃): δ (ppm) 3.19 (d, J=11.0 Hz, 1H), 3.54-3.63 (m, 1H), 4.19 (dd, J=5.5, 2.6 Hz, 1H), 4.30 (dd, J=17.8, 2.0 Hz, 1H), 4.36-4.50 (m, 2H), 4.54 (dd, J=17.8, 1.1 Hz, 1H), 5.28-5.42 (m, 2H), 5.85-6.09 (m, 2H), 6.74-6.80 (m, 1H), 7.08 (s, 1H), 8.36 (s, 1H).

Step 2: Preparation of Intermediate 1-(6-hydroxy-7-oxo-1,6-diazabicyclo[3.2.1]oct-3-en-3-yl)triazole-4-carboxamide (56b)

A solution of intermediate (56a) (88 mg, 0.30 mmol) in anhydrous DCM (4 mL) was degassed 10 min under argon atmosphere. AcOH (35 µL, 0.61 mmol) and Pd(PPh₃)₄ (0.18 g, 0.15 mmol) were successively added. After stirring for 2 h30 at rt, the precipitate was filtered and washed with DCM to afford a white solid (45 mg). The solid was purified by flash chromatography on C18-reversed phase silica gel (H₂O/ACN: 100/0 to 0/100). Fractions containing the desired compound were combined, freezed and lyophilized to give intermediate (56b) (25 mg, 0.10 mmol, 33%) as white solid.

MS m/z ([M+H]⁺) 251.

Step 3: Preparation of sodium [3-(4-carbamoyltriazol-1-yl)-7-oxo-1,6-diazabicyclo[3.2.1]oct-3-en-6-yl]sulfate (example 56)

Using the procedure described in example (5) (step 3), intermediate (56b) (25 mg, 0.10 mmol) was converted after ion exchange (Dowex sodium form column) and flash chromatography on C18-reversed phase silica gel (H₂O/ACN: 98/2) into example (56) (14 mg, 0.04 mmol, 39%) as a white powder.

MS m/z ([M+H—SO₃H]⁺⁾ 251, ([M+H]⁺) 331.

MS m/z ([M-H]⁻) 329.

¹H-NMR (300 MHz, D₂O): δ(ppm) 3.51 (d, J=11.4 Hz, 1H), 3.73 (dd, J=11.4, 2.8 Hz, 1H), 4.43 (dd, J=17.7, 1.3 Hz, 1H), 4.52 (dd, J=17.7, 1.9 Hz, 1H), (m, 1H), 4.66 (dd, J=5.6, 2.6 Hz, 1H), 7.00 (d, J=5.6 Hz, 1H), 8.70 (s, 1H).

Example 57: Synthesis of sodium and 2,2,2-trifluoroacetate [3-[4-(ammoniummethyl)triazol-1-yl]-7-oxo-1,6-diazabicyclo[3.2.1]oct-3-en-6-yl]sulfate Step 1
1) NaN₃, CuI, Na ascorbate,

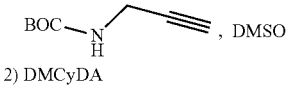, DMSO

2) DMCyDA

1g

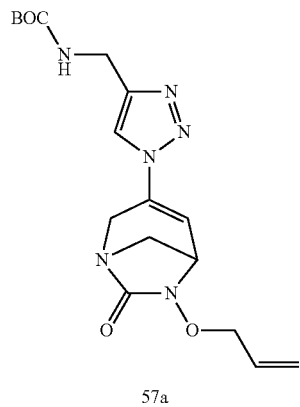

57a

Step 2
Pd(PPh₃)₄, AcOH, DCM

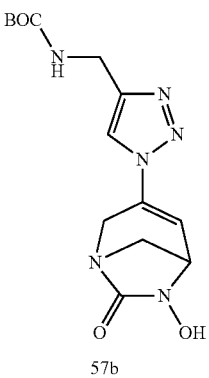

57b

Step 3
1) Sulfur trioxyde trimethylamine complex, TEA, t-BuOH/water
2) ion exchange Dowex Na+

-continued

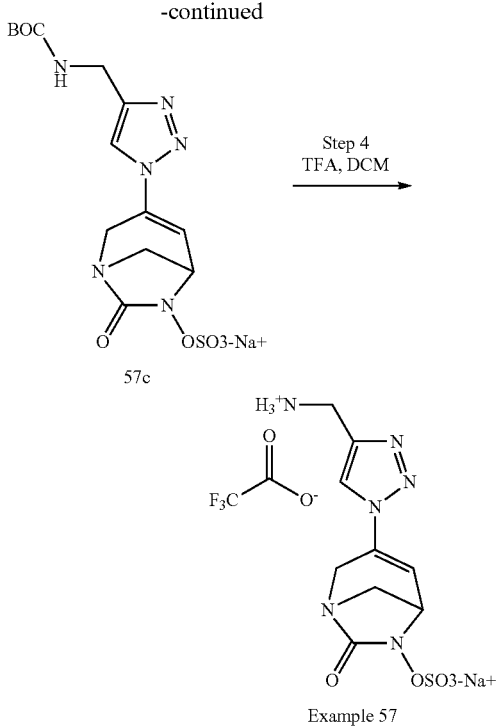

Example 57

Step 1: Preparation of Intermediate tert-butyl N-[[1-(6-allyloxy-7-oxo-1,6-diazabicyclo[3.2.1]oct-3-en-3-yl)triazol-4-yl]methyl]carbamate (57a)

In a 5 mL sealed flask under inert atmosphere, intermediate (1g) (250 mg, 0.82 mmol) was diluted with anhydrous DMSO (3 mL). CuI (16 mg, 0.08 mmol), sodium azide (80 mg, 1.22 mmol), sodium ascorbate (68 mg, 0.34 mmol), N-Boc-propargylamine (152 mg, 0.98 mmol) and DMCyDA (19 µL, 0.12 mmol) were successively added. The green solution turned rapidly to brown. The mixture was stirred at rt until reaction completion. After 1 h, the reaction mixture was diluted in H$_2$O (30 mL) and extracted with EtOAc (3×15 mL). The organic phases were dried (Na$_2$SO$_4$), concentrated and the crude was purified by flash chromatography on silica gel (cyclohexane/EtOAc: 100/0 to 0/100) to give intermediate (57a) (259 mg, 0.69 mmol, 84%) as a yellow oil.

MS m/z ([M+H]$^+$) 377, ([2M+H]$^+$) 753.

$^1$H-NMR (400 MHz, CDCl$_3$): δ (ppm) 1.44 (s, 9H), 3.18 (d, J=11.0 Hz, 1H), 3.52-3.61 (m, 1H), 4.15 (dd, J=5.5, 2.6 Hz, 1H), 4.30 (dd, J=17.9, 2.0 Hz, 1H), 4.36-4.55 (m, 5H), 5.11 (br s, 1H), 5.28-5.43 (m, 2H), 6.01 (ddt, J=16.9, 10.3, 6.4 Hz, 1H), 6.57-6.65 (m, 1H), 7.73 (s, 1H).

Step 2: Preparation of Intermediate tert-butyl N-[[1-(6-hydroxy-7-oxo-1,6-diazabicyclo[3.2.1]oct-3-en-3-yl)triazol-4-yl]methyl]carbamate (57b)

Using the procedure described in example (4) (step 2), intermediate (57a) (259 mg, 0.69 mmol) was converted into intermediate (57b) (104 mg, 0.31 mmol, 45%) as an orange oil contaminated with triphenylphosphine oxide.

MS m/z ([M+H]$^+$) 337.

Step 3: Preparation of sodium [3-[4-[(tert-butoxycarbonylamino)methyl]triazol-1-yl]-7-oxo-1,6-diazabicyclo[3.2.1]oct-3-en-6-yl]sulfate (57c)

Intermediate (57b) (104 mg, 0.31 mmol) was dissolved in a mixture of tBuOH (1.5 mL) and H$_2$O (1.5 mL). TEA (11 µL, 0.08 mmol) and sulfur trioxide trimethylamine complex (52 mg, 0.37 mmol) was added and the mixture was stirred overnight at rt. The reaction mixture was concentrated in vacuo and directly purified by chromatography on C-18 reverse phase (H$_2$O/ACN: 98/2 to 0/100). Fractions containing the expected intermediate were combined and concentrated in vacuo. The residue was dissolved in H$_2$O and converted after ion exchange with Dowex sodium form column (Dowex® 50WX8 hydrogen form stored with an aqueous solution of 2N NaOH and washed until neutral pH with H$_2$O) to intermediate (57c) (58 mg, 0.13 mmol, 42%) as a white powder after lyophilization.

MS m/z ([M+H]$^+$) 331.
MS m/z ([M−H]$^−$) 329.

$^1$H-NMR (400 MHz, D$_2$O): δ(ppm) 1.39 (s, 9H), 3.48 (d, J=11.4 Hz, 1H), 3.70 (dd, J=11.4, 2.8 Hz, 1H), 4.32 (s, 2H), 4.40 (dd, J=17.7, 1.2 Hz, 1H), 4.48 (dd, J=17.7, 1.9 Hz, 1H), 4.62 (dd, J=5.6, 2.6 Hz, 1H), 6.86 (d, J=5.6 Hz, 1H), 8.13 (s, 1H).

Step 4: Preparation of sodium and 2,2,2-trifluoroacetate [3-[4-(ammoniummethyl)triazol-1-yl]-7-oxo-1,6-diazabicyclo[3.2.1]oct-3-en-6-yl]sulfate (example 57)

To a suspension of intermediate (57c) (46 mg, 0.11 mmol) in anhydrous DCM (2 mL) cooled to 0° C. was added slowly a solution of TFA (160 µL, 2.10 mmol) in anhydrous DCM (1 mL). After stirring for 1 h at 0° C. and 1 h at rt, the mixture was diluted in Et$_2$O (5 mL). The precipitate formed was isolated and washed with ACN and DCM then dried. The residue was purified by flash chromatography on C-18 reverse phase (H$_2$O/ACN: 99/1). Fractions containing the desired compound were combined, freezed and lyophilized to provide example (57) (4.9 mg, 0.01 mmol, 7%) as a white solid.

MS m/z ([M−H]$^−$) 315.

$^1$H-NMR (400 MHz, D$_2$O): δ(ppm) 3.49 (d, J=11.4 Hz, 1H), 3.71 (dd, J=11.4, 2.8 Hz, 1H), 4.33-4.55 (m, 4H), 4.63 (dd, J=5.6, 2.6 Hz, 1H), 6.88-6.95 (m, 1H), 8.37 (s, 1H). $^{19}$F NMR (367 MHz, D$_2$O) δ-75.54 (s, 3F).

Example 59: Synthesis of sodium [3-[4-(dimethylamino)methyltriazol-1-yl]-7-oxo-1,6-diazabicyclo[3.2.1]oct-3-en-6-yl]sulfate

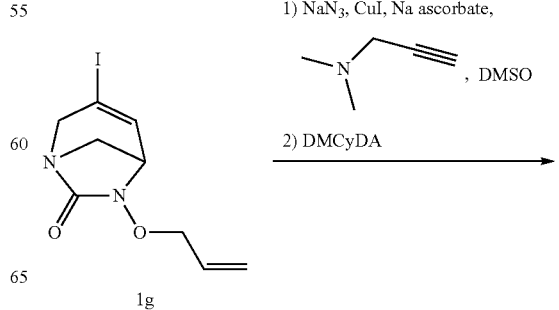

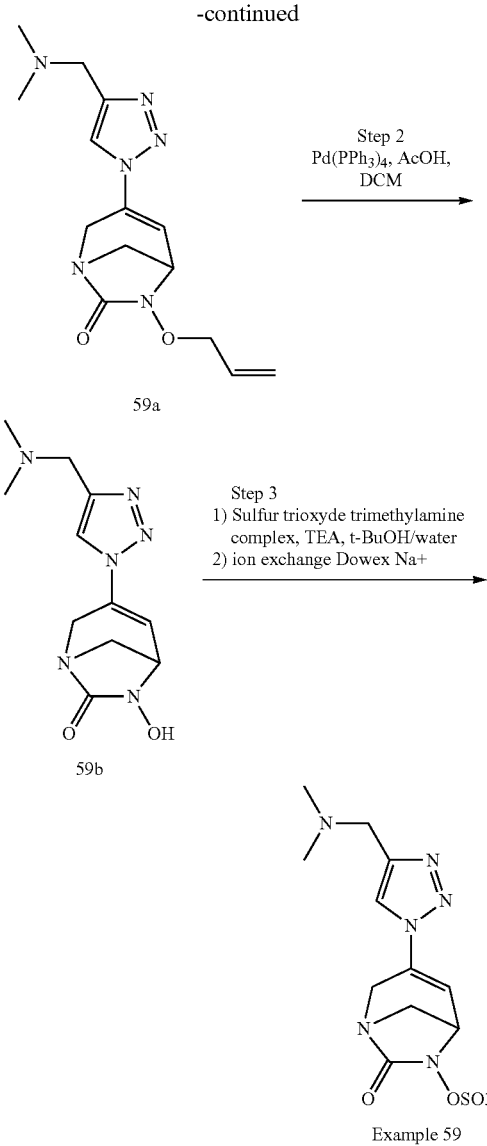

Step 1: Preparation of Intermediate 6-allyloxy-3-[4-(dimethylamino)methyltriazol-1-yl]-1,6-diazabicyclo[3.2.1]oct-3-en-7-one (59a)

In a 5 mL sealed flask under inert atmosphere, intermediate (1g) (250 mg, 0.82 mmol) was diluted with anhydrous DMSO (3 mL). CuI (16 mg, 0.08 mmol), sodium azide (80 mg, 1.22 mmol), sodium ascorbate (16 mg, 0.08 mmol), 3-dimethylamino-1-propyne (105 µL, 0.98 mmol) and DMCyDA (19 µL, 0.12 mmol) were successively added. The green solution turned rapidly to brown. The mixture was stirred at rt until reaction completion. After 1 h, the reaction mixture was concentrated under nitrogen flux. The crude was purified by flash chromatography on C18-reversed phase silica gel (H₂O/ACN: gradient 98/2 to 0/100). Fractions containing the desired compound were combined to give intermediate (59a) (196 mg, 0.64 mmol, 79%) as a brown oil.

MS m/z ([M+H]⁺) 305.
MS m/z ([M−H]⁻) 303.
¹H-NMR (400 MHz, CDCl₃): δ (ppm) 2.24 (s, 3H), 2.28 (s, 3H), 3.18 (dd, J=11.0, 2.2 Hz, 1H), 3.51-3.64 (m, 3H), 4.14 (dt, J=5.4, 2.0 Hz, 1H), 4.25-4.34 (m, 1H), 4.36-4.56 (m, 3H), 5.27-5.42 (m, 2H), 5.92-6.08 (m, 1H), 6.61 (d, J=5.4 Hz, 1H), 7.71 (s, 1H).

Step 2: Preparation of Intermediate 3-[4-(dimethylamino)methyltriazol-1-yl]-6-hydroxy-1,6-diazabicyclo[3.2.1]oct-3-en-7-one (59b)

Using the procedure described in example (4) (step 2), intermediate (59a) (196 mg, 0.64 mmol) was converted into intermediate (59b) (150 mg, 0.57 mmol, 88%) as a brown oil.

MS m/z ([M+H]⁺) 265.

Step 3: Preparation of sodium [3-[4-(dimethylamino)methyltriazol-1-yl]-7-oxo-1,6-diazabicyclo[3.2.1]oct-3-en-6-yl]sulfate (example 59)

Intermediate (59b) (150 mg, 0.57 mmol) was dissolved in a mixture of tBuOH (1 mL) and H₂O (1 mL). TEA (20 µL, 0.14 mmol) and sulfur trioxide trimethylamine complex (95 mg, 0.68 mmol) was added. The mixture was stirred overnight at rt and concentrated in vacuo. The residue was purified flash chromatography on C18-reversed phase silica gel (H₂O/ACN: 98/2 to 0/100). Fractions containing the expected intermediate were combined and concentrated in vacuo. The residue was dissolved in H₂O and converted after ion exchange with Dowex sodium form column (Dowex® 50WX8 hydrogen form stored with an aqueous solution of 2N NaOH and washed until neutral pH with H₂O) to example (59) (3.8 mg, 0.01 mmol, 1.8%) as a white powder after lyophilization.

MS m/z ([M+H]⁺) 345.
MS m/z ([M−H]⁻) 343.
¹H-NMR (300 MHz, D₂O): δ(ppm) 2.83 (s, 6H), 3.48 (d, J=11.4 Hz, 1H), 3.70 (dd, J=11.4, 2.8 Hz, 1H), 4.35-4.57 (m, 4H), 4.63 (dd, J=5.6, 2.6 Hz, 1H), 6.93 (d, J=5.6 Hz, 1H), 8.49 (s, 1H).

Example 60: Synthesis of [3-[4-(methylaminomethyl)triazol-1-yl]-7-oxo-1,6-diazabicyclo[3.2.1]oct-3-en-6-yl]hydrogen sulfate

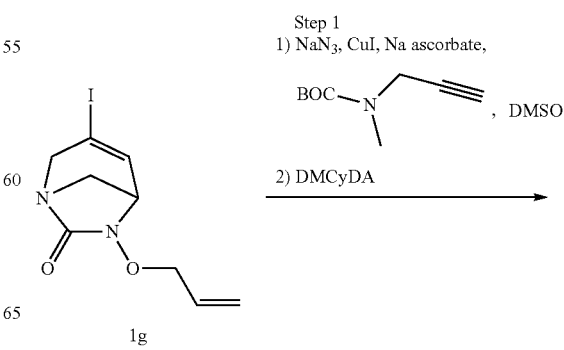

-continued

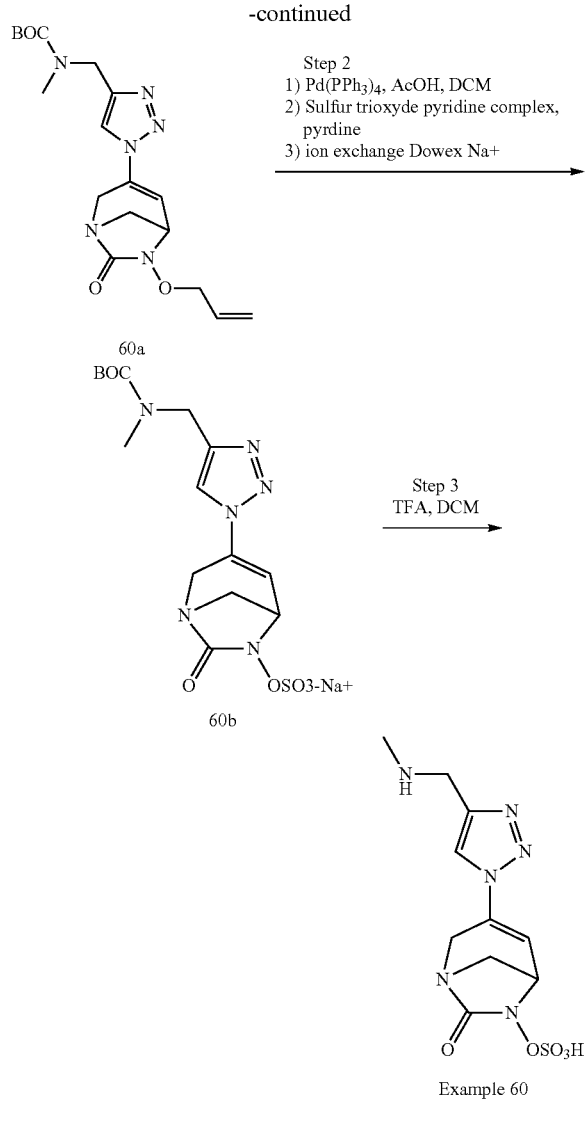

Step 2
1) Pd(PPh₃)₄, AcOH, DCM
2) Sulfur trioxyde pyridine complex, pyridine
3) ion exchange Dowex Na+

Step 3
TFA, DCM

Example 60

Step 1: Preparation of Intermediate tert-butyl N-[[1-(6-allyloxy-7-oxo-1,6-diazabicyclo[3.2.1]oct-3-en-3-yl)triazol-4-yl]aminomethyl]-N-methyl-carbamate (60a)

In a 5 mL sealed flask under inert atmosphere, intermediate (1g) (250 mg, 0.82 mmol) was diluted with anhydrous DMSO (3 mL). CuI (16 mg, 0.08 mmol), sodium azide (80 mg, 1.22 mmol), sodium ascorbate (16 mg, 0.08 mmol), Boc-N-methylpropargylamine (147 mg, 0.86 mmol) and DMCyDA (19 μL, 0.12 mmol) were successively added. The green solution turned rapidly to brown. The mixture was stirred at rt until reaction completion. After 1 h the reaction mixture was diluted in H₂O (5 mL) and extracted with EtOAc (3×5 mL). The organic phases were dried (Na₂SO₄) and concentrated. The crude was purified by flash chromatography on silica gel (cyclohexane/EtOAc: 100/0 to 0/100) to give intermediate (60a) (293 mg, 0.75 mmol, 92%) as a brown oil.

MS m/z ([M+H]⁺) 391.
¹H-NMR (300 MHz, CDCl₃): δ(ppm) 1.44 (s, 9H), 2.88 (s, 3H), 3.17 (d, J=11.0 Hz, 1H), 3.55 (dd, J=11.0, 2.7 Hz, 1H), 4.05-4.19 (m, 1H), 4.29 (dd, J=17.9, 2.0 Hz, 1H), 4.34-4.56 (m, 5H), 5.28-5.42 (m, 2H), 5.89-6.09 (m, 1H), 6.54-6.64 (m, 1H), 7.64 (br s, 1H).

Step 2: Preparation of Intermediate sodium [3-[4-[[tert-butoxycarbonyl(methyl)amino]methyl]triazol-1-yl]-7-oxo-1,6-diazabicyclo[3.2.1]oct-3-en-6-yl]sulfate (60b)

Using the procedure described in example (2) (step 2), intermediate (60a) (250 mg, 0.64 mmol) was converted into intermediate (60b) (72 mg, 0.16 mmol, 25%) as a beige solid.

MS m/z ([M+H]⁺) 431.
MS m/z ([M−H]⁻) 429.
¹H-NMR (300 MHz, D₂O): δ(ppm) 1.36 (s, 9H), 2.89 (s, 3H), 3.47 (d, J=11.4 Hz, 1H), 3.64-3.76 (m, 1H), 4.33-4.54 (m, 4H), 4.62 (dd, J=5.6, 2.5 Hz, 1H), 6.85 (d, J=5.6 Hz, 1H), 8.15 (s, 1H).

Step 3: Preparation of [3-[4-(methylaminomethyl)triazol-1-yl]-7-oxo-1,6-diazabicyclo[3.2.1]oct-3-en-6-yl]hydrogen sulfate (example 60)

Using the procedure described in example (15) (step 3), intermediate (60b) (88 mg, 0.19 mmol) was converted into example (60) (15 mg, 0.05 mmol, 24%).

MS m/z ([M−H]⁻) 330.
¹H-NMR (300 MHz, DMSO-d₆): δ(ppm) 2.61 (s, 3H), 3.35 (m, 1H), 3.45 (d, J=11.1 Hz, 1H), 4.23 (d, J=17.8 Hz, 1H), 4.29 (s, 2H), 4.41 (dd, J=17.5, 2.0 Hz, 1H), 4.47 (dd, J=5.6, 2.4 Hz, 1H), 7.00 (d, J=5.6 Hz, 1H), 8.67 (s, 1H), 8.89 (br s, 1H).

Example 61: Synthesis of disodium [[3-[4-(carboxymethyl)triazol-1-yl]-7-oxo-1,6-diazabicyclo[3.2.1]oct-3-en-6-yl]sulfate

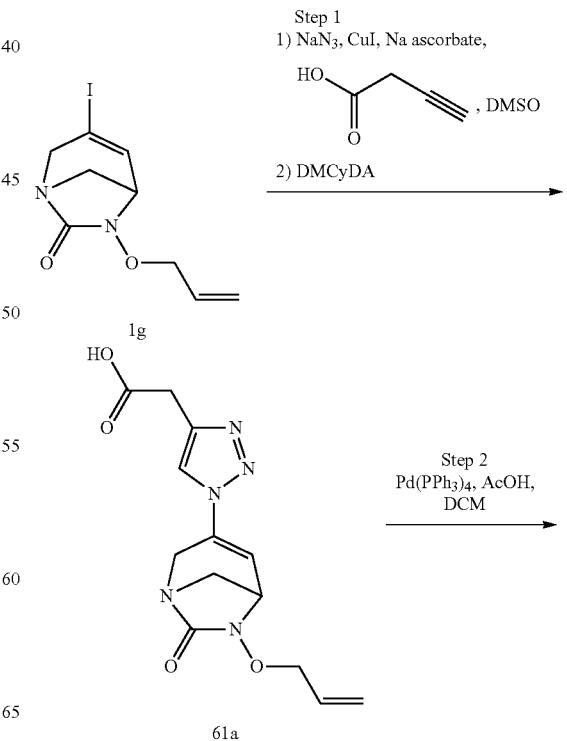

Step 1
1) NaN₃, CuI, Na ascorbate, DMSO
2) DMCyDA

Step 2
Pd(PPh₃)₄, AcOH, DCM

61a

155

-continued

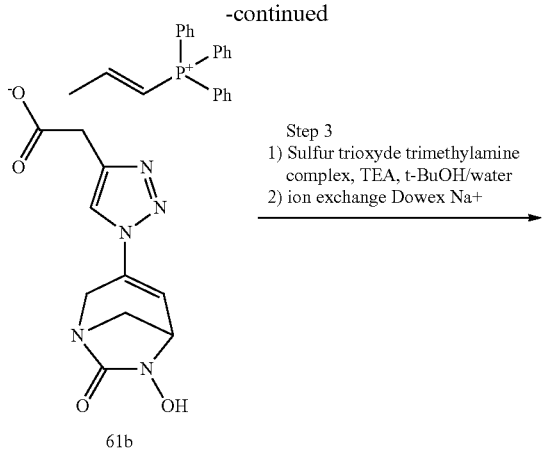

Step 3
1) Sulfur trioxyde trimethylamine complex, TEA, t-BuOH/water
2) ion exchange Dowex Na+

Example 61

Step 1: Preparation of Intermediate 2-[1-(6-allyloxy-7-oxo-1,6-diazabicyclo[3.2.1]oct-3-en-3-yl)triazol-4-yl]acetic acid (61a)

In a 10 mL sealed flask under inert atmosphere, intermediate (1g) (500 mg, 1.63 mmol) was diluted with anhydrous DMSO (6 mL). CuI (50 mg, 0.27 mmol), sodium azide (160 mg, 2.45 mmol), sodium ascorbate (53 mg, 0.27 mmol), but-3-ynoic acid (164 mg, 1.95 mmol) and DMCyDA (38 μL, 0.24 mmol) were successively added. The green solution turned rapidly to brown. The mixture was stirred ar rt until reaction completion. After 5 h, the reaction was treated with HCl 1N (10 mL) and extracted with EtOAc (5×5 mL). The combined organic phases were dried (Na$_2$SO$_4$), concentrated and purified by flash chromatography on C18-reversed phase silica gel (H$_2$O/ACN: gradient 95/5 to 0/100). Fractions containing the desired compound were combined and lyophilized to provide intermediate (61a) (189 mg, 0.62 mmol, 38%) as a green solid.

MS m/z ([M+H]$^+$) 306.
MS m/z ([M−H]$^−$) 304.
$^1$H-NMR (400 MHz, MeOD): δ(ppm) 3.32-3.39 (m, 1H), 3.44-3.55 (m, 1H), 3.64 (s, 2H), 4.28-4.48 (m, 5H), 5.24-5.46 (m, 2H), 5.93-6.13 (m, 1H), 6.83 (d, J=5.5 Hz, 1H), 8.16 (br s, 1H).

Step 2: Preparation of Intermediate propenyltriphenylphophonium 2-[1-(6-hydroxy-7-oxo-1,6-diazabicyclo[3.2.1]oct-3-en-3-yl)triazol-4-yl]acetate (61b)

Using the procedure described in example (4) (step 2), intermediate (61a) (185 mg, 0.61 mmol) was converted into intermediate (61b) (321 mg, 0.57 mmol, 93%) as a brown oil.

MS m/z ([M+H]$^+$) 266.
MS m/z ([M−H]$^−$) 264, ([2M−H]$^−$) 529.

156

Step 3: Preparation of disodium [[3-[4-(carboxymethyl)triazol-1-yl]-7-oxo-1,6-diazabicyclo[3.2.1]oct-3-en-6-yl](example 61)

Using the procedure described in example (5) (step 3), intermediate (61b) (300 mg, 0.53 mmol) was converted into example (61) (26 mg, 0.07 mmol, 13%) as a beige powder.

MS m/z ([M+H]$^+$) 346.
MS m/z ([M−H]$^−$) 344.
$^1$H-NMR (400 MHz, D$_2$O): δ(ppm) 3.51 (d, J=11.4 Hz, 1H), 3.60 (m, 2H), 3.72 (dd, J=11.4, 2.8 Hz, 1H), 4.39-4.60 (m, 2H), 4.63 (dd, J=5.6, 2.6 Hz, 1H), 6.90 (d, J=5.6 Hz, 1H), 8.17 (br s, 1H).

Example 63: Synthesis of [3-[4-(2-aminoethoxycarbamoyl)triazol-1-yl]-7-oxo-1,6-diazabicyclo[3.2.1]oct-3-en-6-yl]hydrogen sulfate

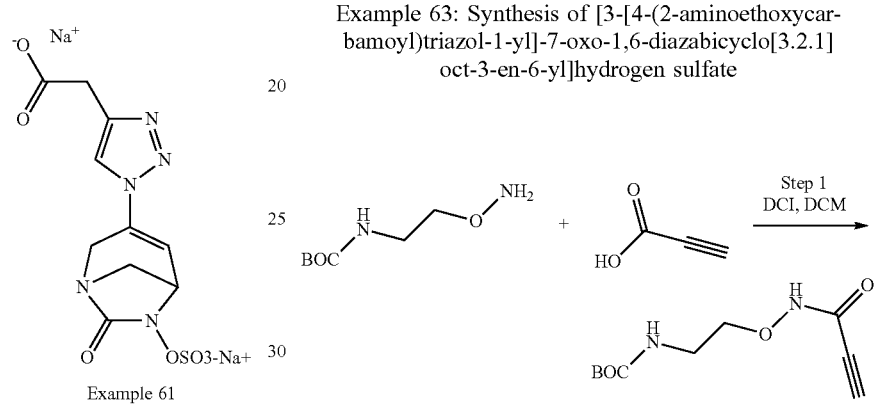

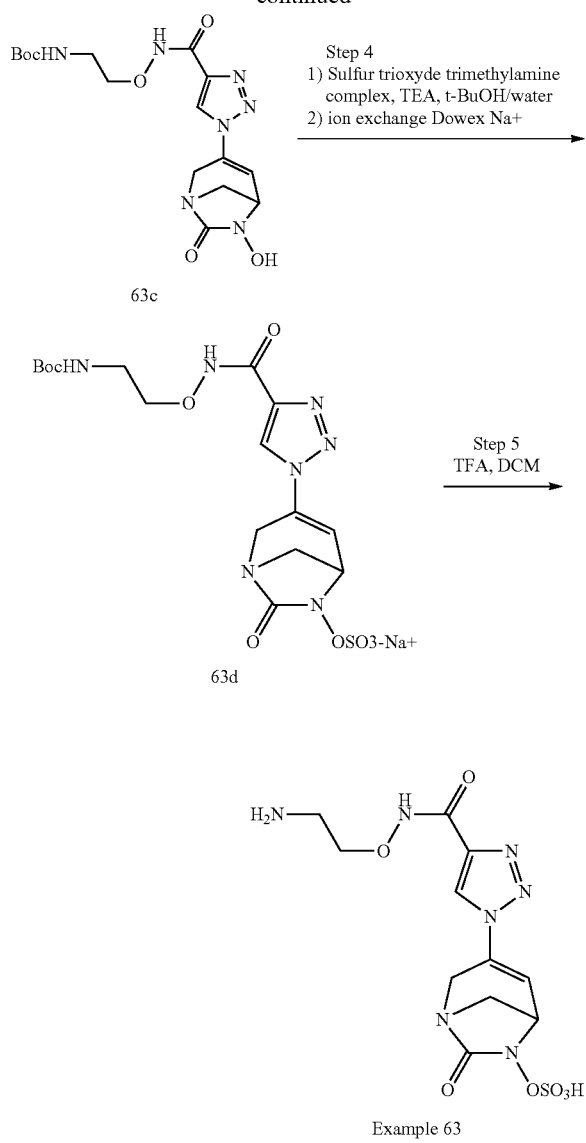

Step 1: Preparation of Intermediate tert-butyl N-[2-(prop-2-ynoylamino)oxyethyl]carbamate (63a)

To a solution of prop-2-ynoic acid (62 µL, 1.00 mmol) and EDC.HCl (206 mg, 1.00 mmol) in DCM (5 mL) was added to 0° C. a solution of tert-butyl N-(2-aminooxyethyl)carbamate (176 mg, 1.00 mmol) in DCM (3 mL). The reaction was stirred overnight at rt. The reaction mixture was then filtered to remove the solids. The filtrate was diluted in Et$_2$O (5 mL), filtrated and concentrated under reduced pressure to provide intermediate (63a) (229 mg, 1.00 mmol, quantitative yield) as a brown oil used in the next step without further purification.

MS m/z ([M+Na]$^+$) 251.

MS m/z ([M–H]$^-$) 227.

$^1$H-NMR (400 MHz, CDCl$_3$): δ(ppm) 1.45 (s, 9H), 2.88 (d, J=6.4 Hz, 1H), 3.35-3.44 (m, 2H), 3.91 (t, J=4.8 Hz, 2H), 5.09 (s, 1H), 9.51 (s, 1H).

Step 2: Preparation of tert-butyl N-[2-[[1-(6-allyloxy-7-oxo-1,6-diazabicyclo[3.2.1]oct-3-en-3-yl)triazole-4-carbonyl]amino]oxyethyl]carbamate (63b)

In a 5 mL sealed flask under inert atmosphere, intermediate (1g) (250 mg, 0.82 mmol) was diluted with anhydrous DMSO (3 mL). CuI (32 mg, 0.16 mmol), sodium azide (80 mg, 1.22 mmol), sodium ascorbate (32 mg, 0.16 mmol), intermediate (63a) (229 mg, 0.98 mmol) and DMCyDA (19 µL, 0.12 mmol) were successively added. The green solution turned rapidly to brown. The mixture was stirred at rt for 1 h and then concentrated under nitrogen flux. The crude was purified by flash chromatography on silica gel (DCM/Acetone: 100/0 to 0/100) to give intermediate (63b) (251 mg, 0.56 mmol, 68%) as a brown solid.

MS m/z ([M+H]$^+$) 450, ([2M+H]$^+$) 899.

MS m/z ([M–H]$^-$) 448, ([2M–H]$^-$) 897.

$^1$H-NMR (300 MHz, DMSO-d$_6$): δ(ppm) 1.39 (s, 9H), 3.16-3.26 (m, 2H), 3.28-3.43 (m, 2H), 3.86 (t, J=5.7 Hz, 2H), 4.25 (d, J=17.6 Hz, 1H), 4.33-4.46 (m, 4H), 5.33-5.46 (m, 2H), 5.88-6.07 (m, 1H), 6.84 (t, J=5.8 Hz, 1H), 7.06 (d, J=5.5 Hz, 1H), 9.13 (s, 1H), 11.94 (s, 1H).

Step 3: Preparation of Intermediate tert-butyl N-[2-[[1-(6-hydroxy-7-oxo-1,6-diazabicyclo[3.2.1]oct-3-en-3-yl)triazole-4-carbonyl]amino]oxyethyl]carbamate (63c)

Using the procedure described in example (4) (step 2), intermediate (63b) (251 mg, 0.56 mmol) was converted into intermediate (63c) (68 mg, 0.17 mmol, 30%) as a yellow solid contaminated with triphenylphosphine oxide.

MS m/z ([M+H]$^+$) 410.

MS m/z ([M–H]$^-$) 408.

Step 4: Preparation of Intermediate sodium [3-[4-[2-(tert-butoxycarbonylamino)ethoxycarbamoyl]triazol-1-yl]-7-oxo-1,6-diazabicyclo[3.2.1]oct-3-en-6-yl]sulfate (63d)

Using the procedure described in example (5) (step 3), intermediate (63c) (76 mg, 0.19 mmol) was converted into intermediate (63d) (11 mg, 0.02 mmol, 11%) as a beige solid.

MS m/z ([M–H]$^-$) 488.

Step 5: Preparation of [3-[4-(2-aminoethoxycarbamoyl)triazol-1-yl]-7-oxo-1,6-diazabicyclo[3.2.1]oct-3-en-6-yl]hydrogen sulfate (example 63)

Using the procedure described in example (15) (step 3), intermediate (63d) (11 mg, 0.02 mmol) was converted into example (63) (1.9 mg, 0.005 mmol, 23%) as white solid.

MS m/z ([M+H]$^+$) 390.

MS m/z ([M–H]$^-$) 388.

$^1$H-NMR (300 MHz, D$_2$O): δ(ppm) 3.27-3.37 (m, 2H), 3.49 (d, J=11.4 Hz, 1H), 3.72 (dd, J=11.4, 2.8 Hz, 1H), 4.17-4.27 (m, 2H), 4.37-4.58 (m, 2H), 4.64 (dd, J=5.6, 2.6 Hz, 1H), 6.97 (d, J=5.6 Hz, 1H), 8.57 (s, 1H).

Example 64: Synthesis of sodium [3-[4-(hydroxymethyl)triazol-1-yl]-7-oxo-1,6-diazabicyclo[3.2.1]oct-3-en-6-yl]sulfate

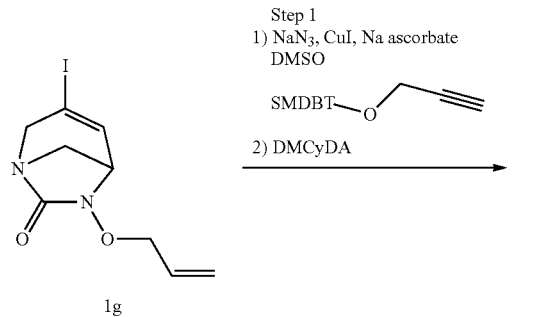

1g

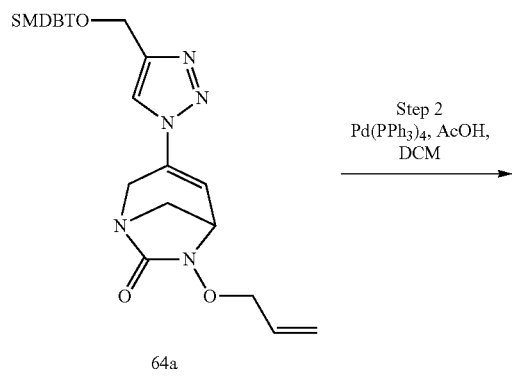

64a

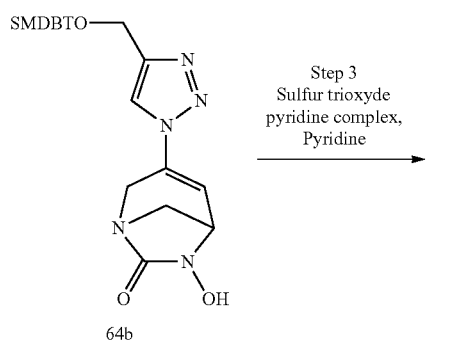

64b

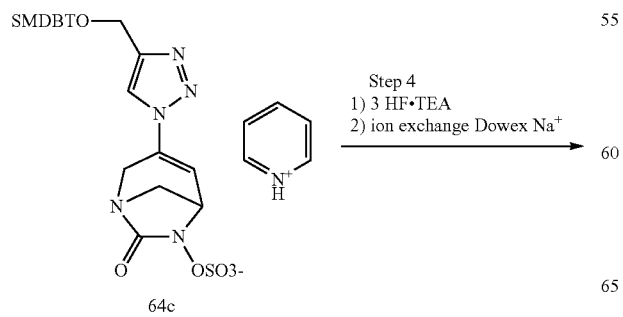

64c

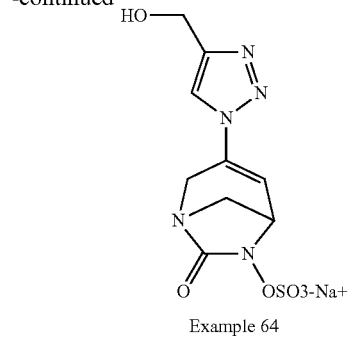

Example 64

Step 1: Preparation of Intermediate 6-allyloxy-3-[4-[[tert-butyl(dimethyl)silyl]oxymethyl]triazol-1-yl]-1,6-diazabicyclo[3.2.1]oct-3-en-7-one (64a)

In a 5 mL sealed flask under inert atmosphere, intermediate (1g) (250 mg, 0.82 mmol) was diluted with anhydrous DMSO (3 mL). CuI (16 mg, 0.08 mmol), sodium azide (80 mg, 1.22 mmol), sodium ascorbate (16 mg, 0.08 mmol), tert-butyl-dimethyl(2-propynyloxy)silane (192 µL, 0.95 mmol) and DMCyDA (19 µL, 0.12 mmol) were successively added. The green solution turned rapidly to orange. The mixture was stirred at rt until reaction completion. After 1 h30, the reaction mixture was diluted with $H_2O$ (5 mL) and extracted with EtOAc (5×5 mL). The organic phases were dried ($Na_2SO_4$) and concentrated. The crude was purified by flash chromatography on silica gel (cyclohexane/EtOAc: 100/0 to 0/100) to give intermediate (64a) (252 mg, 0.64 mmol, 79%) as a yellow oil.

MS m/z ([M+H]$^+$) 392, ([2M+H]$^+$) 783.

$^1$H-NMR (400 MHz, CDCl$_3$): δ (ppm) 0.09 (s, 3H), 0.13 (s, 3H), 0.92 (s, 9H), 3.19 (d, J=10.9 Hz, 1H), 3.52-3.63 (m, 1H), 4.15 (dd, J=5.6, 2.6 Hz, 1H), 4.32 (dd, J=17.9, 2.0 Hz, 1H), 4.36-4.58 (m, 3H), 4.84 (d, J=0.9 Hz, 2H), 5.26-5.45 (m, 2H), 5.92-6.12 (m, 1H), 6.57-6.66 (m, 1H), 7.65 (m, 1H).

Step 2: Preparation of Intermediate 3-[4-[[tert-butyl(dimethyl)silyl]oxymethyl]triazol-1-yl]-6-hydroxy-1,6-diazabicyclo[3.2.1]oct-3-en-7-one (64b)

Using the procedure described in example (4) (step 2), intermediate (64a) (252 mg, 0.64 mmol) was converted into intermediate (64b) (0.64 mmol, quantitative yield estimated) as an orange oil contaminated with triphenylphosphine oxide after purification on silica gel (DCM/Acetone: 100/0 to 0/100). The mixture will be used for the next step without further purification.

MS m/z ([M+H]$^+$) 352.

Step 3: Preparation of pyridinium [3-[4-[[tert-butyl(dimethyl)silyl]oxymethyl]triazol-1-yl]-7-oxo-1,6-diazabicyclo[3.2.1]oct-3-en-6-yl]sulfate (64c)

To a solution of intermediate (64b) (0.64 mmol) in anhydrous pyridine (6 mL) under inert atmosphere was added sulfur trioxide pyridine complex (512 mg, 3.22 mmol). After stirring for 1 h30, the heterogeneous mixture was concentrated in vacuo. DCM was added to the residue and the solids were filtered. The filtrate was purified by flash chromatography on silica gel (DCM/Acetone: 100/0 to 0/100) to give intermediate (64c) (110 mg, 0.22 mmol, 33% over 2 steps) as a white solid.
MS m/z ([M+H]⁺) 432.
MS m/z ([M−H]⁻) 430.
¹H-NMR (400 MHz, CDCl₃): δ (ppm) 0.09 (s, 3H), 0.11 (s, 3H), 0.91 (s, 9H), 3.15-3.25 (m, 1H), 3.78 (d, J=11.4 Hz, 1H), 4.32 (d, J=18.0 Hz, 1H), 4.51 (d, J=18.0 Hz, 1H), 4.65 (d, J=5.6 Hz, 1H), 4.81 (s, 2H), 6.64 (d, J=5.4 Hz, 1H), 7.75 (s, 1H), 7.92-8.01 (m, 2H), 8.45 (ddd, J=7.8, 7.8, 1.6 Hz, 1H), 8.99-9.06 (m, 2H).

Step 4: Preparation of sodium [3-[4-(hydroxymethyl)triazol-1-yl]-7-oxo-1,6-diazabicyclo[3.2.1]oct-3-en-6-yl]sulfate (example 64)

To a suspension of intermediate (64c) (110 mg, 0.22 mmol) in anhydrous THF (4.5 mL) was added slowly 3HF TEA (70 µL, 0.43 mmol). After stirring for 2 h at 20° C. and 3 h at 50° C., the mixture was concentrated to dryness. The oil was applied on a Dowex sodium form column (Dowex® 50WX8 hydrogen form stored with an aqueous solution of 2N NaOH and washed until neutral pH with H₂O). Fractions containing the desired compound were combined, freezed and lyophilized to provide example (64) (72 mg, 0.21 mmol, 99%) as a white solid.
MS m/z ([M+H]⁺) 318.
MS m/z ([M−H]⁻) 316.
¹H-NMR (400 MHz, D₂O): δ(ppm) 3.50 (d, J=11.4 Hz, 1H), 3.72 (ddd, J=11.4, 2.8, 1.0 Hz, 1H), 4.44 (dd, J=17.7, 1.3 Hz, 1H), 4.51 (dd, J=17.7, 1.9 Hz, 1H), 4.64 (dd, J=5.6, 2.7 Hz, 1H), 4.73 (s, 2H), 6.90 (d, J=5.6 Hz, 1H), 8.24 (s, 1H).

Example 65: Synthesis of disodium [3-[4-(propanoate)triazol-1-yl]-7-oxo-1,6-diazabicyclo[3.2.1]oct-3-en-6-yl]sulfate P

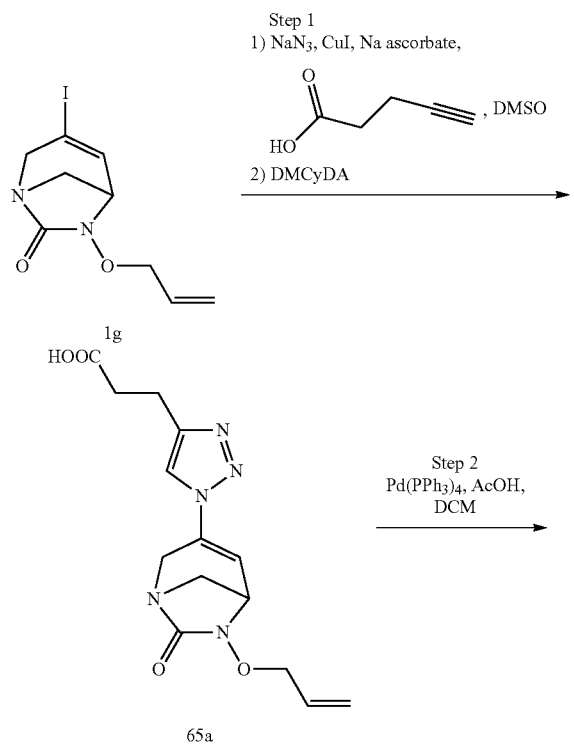

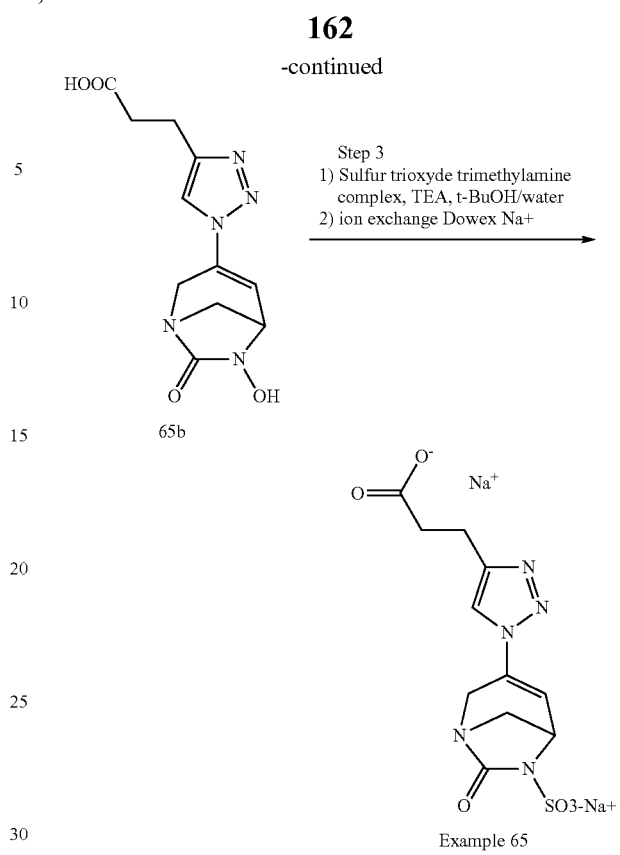

Example 65

Step 1: Preparation of Intermediate 3-[1-(6-allyloxy-7-oxo-1,6-diazabicyclo[3.2.1]oct-3-en-3-yl)triazol-4-yl]propanoic acid (65a)

In a 5 mL sealed flask under inert atmosphere, intermediate (1g) (250 mg, 0.82 mmol) was diluted with anhydrous DMSO (3 mL). CuI (50 mg, 0.26 mmol), sodium azide (80 mg, 1.22 mmol), sodium ascorbate (50 mg, 0.25 mmol), 4-pentynoic acid (92 mg, 0.94 mmol) and DMCyDA (20 µL, 0.12 mmol) were successively added. The green solution turned rapidly to brown. The mixture was stirred at rt for 2 h. The reaction mixture was then treated with HCl 1N (10 mL) and extracted with EtOAc (5×5 mL). The organic phases were dried (Na₂SO₄) and concentrated. The crude was purified by flash chromatography on C18-reversed phase silica gel (H₂O/ACN: 100/0 to 0/100) to give intermediate (65a) (137 mg, 0.43 mmol, 52%) as a brown oil.
MS m/z ([M+H]⁺) 320, ([2M+H]⁺) 639.
MS m/z ([2M−H]⁻) 637.
¹H NMR (400 MHz, CDCl₃): δ(ppm) 2.69 (dd, J=7.1, 7.1 Hz, 2H), 2.96 (dd, J=7.1, 7.1 Hz, 2H), 3.16 (d, J=11.0 Hz, 1H), 3.45-3.53 (m, 1H), 4.15 (dd, J=5.6, 2.6 Hz, 1H), 4.22 (dd, J=17.8, 1.9 Hz, 1H), 4.31-4.45 (m, 3H), 5.26 (dd, J=10.2, 1.4 Hz, 1H), 5.29-5.37 (m, 1H), 5.94 (ddt, J=16.9, 10.3, 6.4 Hz, 1H), 6.60 (d, J=5.6 Hz, 1H), 7.66 (s, 1H), 8.95 (br s, 1H).

Step 2: Preparation of Intermediate 3-[1-(6-hydroxy-7-oxo-1,6-diazabicyclo[3.2.1]oct-3-en-3-yl)triazol-4-yl]propanoic acid (65b)

A solution of intermediate (65a) (137 mg, 0.43 mmol) in anhydrous DCM (4 mL) was degazed 10 min under argon atmosphere. AcOH (49 L, 0.86 mmol) and Pd(PPh₃)₄ (248 mg, 0.22 mmol) were successively added. After stirring for 1 h at rt, the precipitate was filtered and washed with DCM to afford intermediate (65b) (120 mg, 0.43 mmol, quantitative yield).

MS m/z ([M+H]$^+$) 280.
MS m/z ([M−H]$^−$) 278, ([2M−H]$^−$) 557.

Step 3: Preparation of disodium [3-[4-(propanoate) triazol-1-yl]-7-oxo-1,6-diazabicyclo[3.2.1]oct-3-en-6-yl]sulfate (example 65)

Intermediate (65b) (0.43 mmol) was dissolved in a mixture of tBuOH (2 mL) and H$_2$O (2 mL). TEA (15 µL, 0.10 mmol) and sulfur trioxide trimethylamine complex (72 mg, 0.52 mmol) were added. The mixture was stirred at rt for 19 h then concentrated in vacuo. The residue was purified by flash chromatography on C18-reversed phase silica gel (H$_2$O/ACN: 98/2 to 0/100). Fractions containing the expected intermediate were combined and concentrated in vacuo. The residue was dissolved in H$_2$O and converted after ion exchange with Dowex sodium form column (Dowex® 50WX8 hydrogen form stored with an aqueous solution of 2N NaOH and washed until neutral pH with H$_2$O) to example (65) (10 mg, 0.03 mmol, 6% over 2 steps).

MS m/z ([M+H]$^+$) 360.
MS m/z ([M−H]$^−$) 358.
$^1$H NMR (300 MHz, D$_2$O): δ(ppm) 2.64-2.79 (m, 2H), 2.91-3.09 (m, 2H), 3.46 (d, J=11.4 Hz, 1H), 3.62-3.82 (m, 1H), 4.21-4.48 (m, 2H), 4.48-4.64 (m, 1H), 6.77-6.86 (m, 1H), 7.99-8.16 (m, 1H).

Example 66: Synthesis of [3-(4-(2-(methylamino)acetamide)triazol-1-yl)-7-oxo-1,6-diazabicyclo[3.2.1]oct-3-en-6]-yl hydrogen sulfate

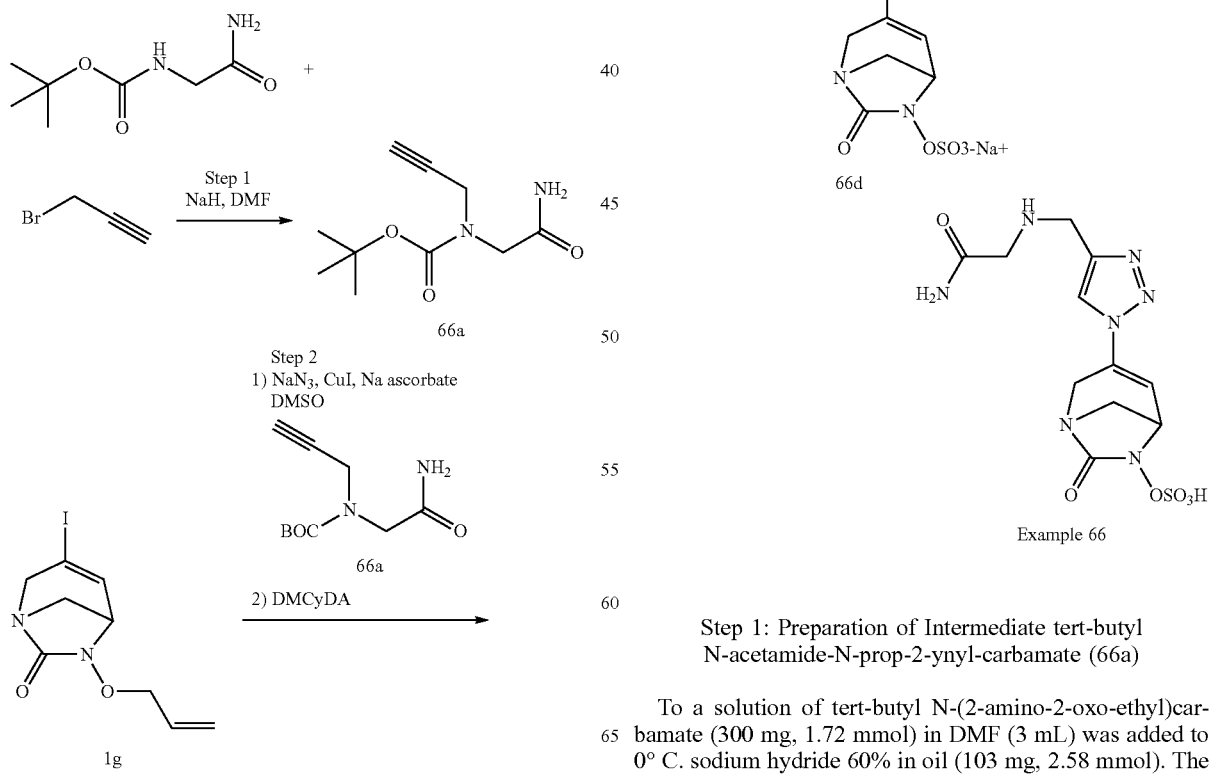

Step 1: Preparation of Intermediate tert-butyl N-acetamide-N-prop-2-ynyl-carbamate (66a)

To a solution of tert-butyl N-(2-amino-2-oxo-ethyl)carbamate (300 mg, 1.72 mmol) in DMF (3 mL) was added to 0° C. sodium hydride 60% in oil (103 mg, 2.58 mmol). The mixture was stirred 30 min then propargyl bromide (323 µL, 4.30 mmol) was added. At the end of introduction, reaction was stirred overnight at rt. MeOH (1 mL) then H$_2$O (10 mL) were added to the mixture. The solution was extracted with Et$_2$O (3×10 mL). The combined organic phases were dried (Na$_2$SO$_4$) and concentrated under reduced pressure. The crude was purified by flash chromatography on silica gel (cyclohexane/EtOAc: 100/0 to 0/100) to give to provide intermediate (66a) (146 mg, 0.69 mmol, 40%) as a yellow oil.

MS m/z ([M+H]$^+$) 213.

$^1$H-NMR (400 MHz, CDCl$_3$): δ(ppm) 1.47 (s, 9H), 2.28 (s, 1H), 3.96 (s, 2H), 4.15 (s, 2H), 5.62 (s, 1H), 6.06 (s, 1H).

Step 2: Preparation of tert-butyl N-[[1-(6-allyloxy-7-oxo-1,6-diazabicyclo[3.2.1]oct-3-en-3-yl)triazol-4-yl]methyl]-N-acetamidocarbamate (66b)

In a 5 mL sealed flask under inert atmosphere, intermediate (1g) (188 mg, 0.61 mmol) was diluted with anhydrous DMSO (2.5 mL). CuI (58 mg, 0.31 mmol), sodium azide (60 mg, 0.92 mmol), sodium ascorbate (58 mg, 0.31 mmol), intermediate (66a) (150 mg, 0.71 mmol) and DMCyDA (14 μL, 0.09 mmol) were successively added. The green solution turned rapidly to brown. The mixture was stirred at rt until reaction completion. After 1 h, the reaction mixture was treated with HCl 1N (10 mL) and extracted with EtOAc (5×5 mL). The organic phases were dried (Na$_2$SO$_4$), concentrated and the crude was purified by flash chromatography on silica gel (DCM/Acetone: 100/0 to 0/100) to give intermediate (66b) (136 mg, 0.31 mmol, 51%) as a brown oil.

MS m/z ([M+H]$^+$) 434.

Step 3: Preparation of Intermediate tert-butyl N-acetamide-N-[[1-(6-hydroxy-7-oxo-1,6-diazabicyclo[3.2.1]oct-3-en-3-yl)triazol-4-yl]methyl]carbamate (66c)

A solution of intermediate (66b) (136 mg, 0.31 mmol) in anhydrous DCM (4 mL) was degassed 10 min under argon atmosphere. AcOH (36 μL, 0.63 mmol) and Pd(PPh$_3$)$_4$ (181 mg, 0.16 mmol) were successively added. After 1 h, the reaction was concentrated under reduced pressure. The crude was purified by flash chromatography on C18-reversed phase silica gel (H$_2$O/ACN: 95/5 to 0/100) to give intermediate (66c) (38 mg, 0.10 mmol, 30%) as a white solid.

MS m/z ([M+H]$^+$) 394.
MS m/z ([2M−H]$^−$) 785.

$^1$H-NMR (400 MHz, D$_2$O): δ(ppm) 1.38 (s, 9H), 3.37 (d, J=11.1 Hz, 1H), 3.59 (dd, J=11.1, 2.9 Hz, 1H), 3.99 (dd, J=5.4, 2.6 Hz, 2H), 4.22-4.43 (m, 3H), 4.58 (s, 2H), 6.92 (d, J=5.4 Hz, 1H), 8.18 (s, 1H).

Step 4: Preparation of Intermediate sodium [3-[4-[[(2-amino-2-oxo-ethyl)-tert-butoxycarbonyl-amino]methyl]triazol-1-yl]-7-oxo-1,6-diazabicyclo[3.2.1]oct-3-en-6-yl]sulfate (66d)

Intermediate (66c) (38 mg, 0.10 mmol) was dissolved in a mixture of tBuOH (1 mL) and H$_2$O (1 mL). TEA (3 μL, 0.02 mmol) and sulfur trioxide trimethylamine complex (16 mg, 0.12 mmol) were added. The mixture was stirred at rt for 1 h then concentrated in vacuo. The residue was dissolved in H$_2$O and eluted on ion exchange Dowex sodium form column (Dowex® 50WX8 hydrogen form stored with an aqueous solution of 2N NaOH and washed until neutral pH with H$_2$O). Fractions with the desired compound were combined and concentrated. The residue was purified by flash chromatography on C18-reversed phase silica gel (H$_2$O/ACN: 100/0 to 0/100) to provide after lyophilization intermediate (66d) (27 mg, 0.06 mmol, 56%) as a white solid.

MS m/z ([M+H]$^+$) 474.
MS m/z ([M−H]$^−$) 472.

$^1$H-NMR (300 MHz, D$_2$O): δ(ppm) 1.41 (s, 9H), 3.49 (d, J=11.4 Hz, 1H), 3.71 (d, J=11.4 Hz, 1H), 4.00 (d, J=15.1 Hz, 2H), 4.37-4.54 (m, 2H), 4.57-4.67 (m, 3H), 6.87 (d, J=5.6 Hz, 1H), 8.20 (s, 1H).

Step 5: Preparation of [3-(4-(2-(methylamino)acetamide)triazol-1-yl)-7-oxo-1,6-diazabicyclo[3.2.1]oct-3-en-6-yl]hydrogen sulfate (example 66)

Using the procedure described in example (15) (step 3), intermediate (66d) (27 mg, 0.06 mmol) was converted into example (66) (4.6 mg, 0.01 mmol, 22%) as white solid.

MS m/z ([M+H]$^+$) 374.
MS m/z ([M−H]$^−$) 372.

$^1$H-NMR (300 MHz, D$_2$O): δ(ppm) 3.48 (d, J=11.4 Hz, 1H), 3.70 (dd, J=11.4, 2.8 Hz, 1H), 3.89 (s, 2H), 4.34-4.45 (m, 3H), 4.50 (dd, J=17.8, 1.9 Hz, 1H), 4.62 (dd, J=5.6, 2.6 Hz, 1H), 6.92 (d, J=5.6 Hz, 1H), 8.41 (s, 1H).

Example 67: Synthesis of [3-(4-(2-(methylamino)ethanol)triazol-1-yl)-7-oxo-1,6-diazabicyclo[3.2.1]oct-3-en-6-yl]hydrogen sulfate

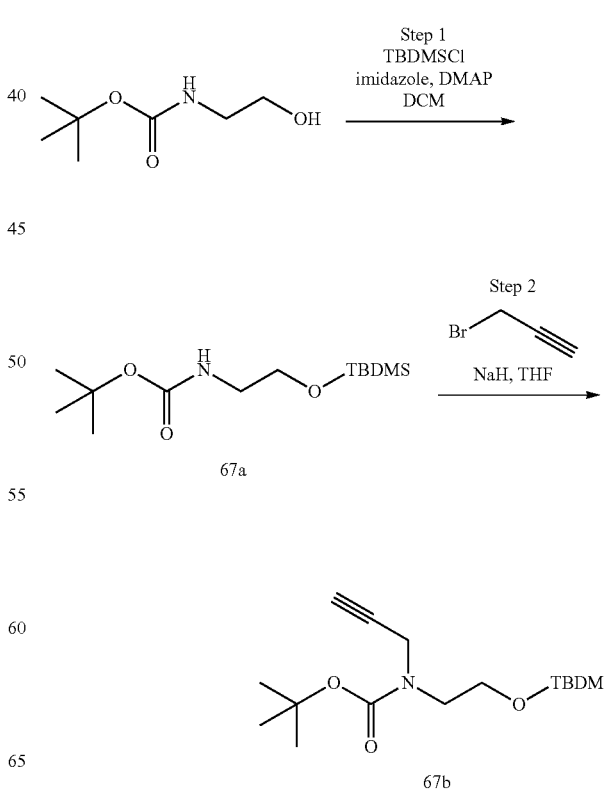

Step 2
1) NaN₃, CuI, Na ascorbate
DMSO

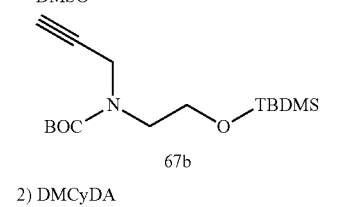
67b

2) DMCyDA

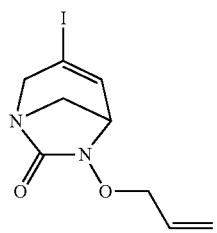
1g

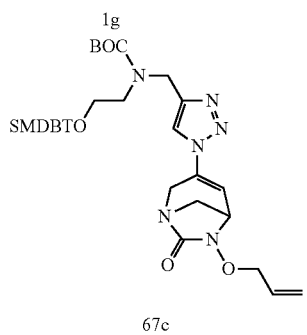
67c

Step 4
1) Pd(PPh₃)₄, AcOH, DCM
2) Sulfur trioxyde pyridinium complex, pyridine

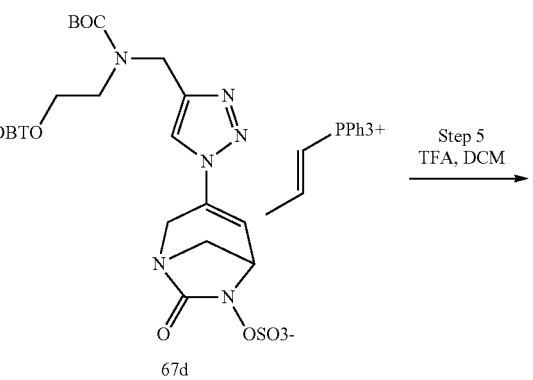
67d

Step 5
TFA, DCM

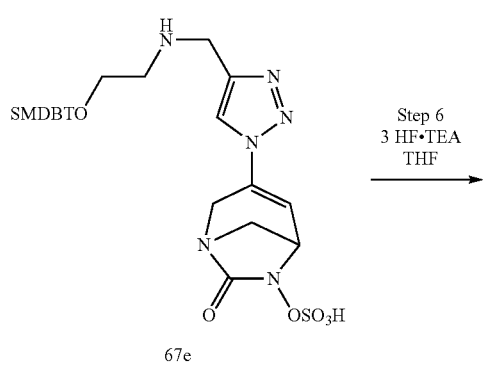
67e

Step 6
3 HF·TEA
THF

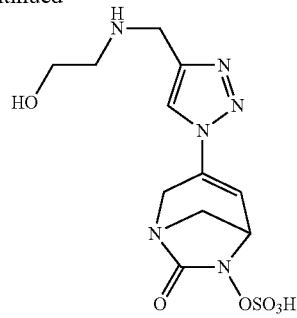
Example 67

Step 1: Preparation of Intermediate tert-butyl N-[2-[tert-butyl(dimethyl)silyl]oxyethyl]carbamate (67a)

To a solution of Boc-Glycinol (520 mg, 3.22 mmol) in DCM (7 mL) was added TBDMSCl (533 mg, 3.54 mmol), imidazole (329 mg, 4.83 mmol) and DMAP (59 mg, 0.48 mmol). The mixture was stirred overnight at rt. Saturated aqueous NH₄Cl solution (20 mL) was added to the mixture and the solution was extracted with DCM (3×20 mL). The combined organic phases were dried (Na₂SO₄) and concentrated under reduced pressure. The crude was purified by flash chromatography on silica gel (cyclohexane/EtOAc: 70/30 to 0/100) to give intermediate (67a) (336 mg, 1.22 mmol, 38%) as a yellow oil.

MS m/z ([M+H-Boc]⁺) 176.

¹H-NMR (300 MHz, CDCl₃): δ (ppm) 0.06 (s, 6H), 0.89 (s, 9H), 1.45 (s, 9H), 3.23 (dd, J=5.6, 5.2 Hz, 2H), 3.66 (dd, J=5.6, 5.2 Hz, 2H), 4.83 (s, 1H).

Step 2: Preparation of Intermediate tert-butyl N-[2-[tert-butyl(dimethyl)silyl]oxyethyl]-N-prop-2-ynyl-carbamate (67b)

To a solution of intermediate (67a) (336 mg, 1.22 mmol) in THF (3 mL) was added to 0° C. sodium hydride 60% in oil (73 mg, 1.83 mmol). The mixture was stirred 1 h30 then propargyl bromide (229 μL, 3.05 mmol) was added. At the end of introduction, the reaction was stirred overnight at rt. MeOH (1 mL) and then H₂O (10 mL) were added to the mixture. The solution was extracted with Et₂O (3×10 mL). The combined organic phases were dried (Na₂SO₄) and concentrated under reduced pressure. The crude was purified by flash chromatography on silica gel (cyclohexane/EtOAc: 90/10 to 0/100) to provide intermediate (67b) (130 mg, 0.41 mmol, 34%) as a yellow oil.

MS m/z ([M+H-Boc]⁺) 214, ([M+Na]⁺) 336.

¹H-NMR (300 MHz, CDCl₃): δ(ppm) 0.04 (s, 3H), 0.06 (s, 3H), 0.89 (s, 9H), 1.47 (s, 9H), 2.18 (s, 1H), 3.42 (dd, J=5.9, 5.4 Hz, 2H), 3.74 (s, 2H), 4.13 (m, 2H).

Step 3: Preparation of tert-butyl N-[[1-(6-allyloxy-7-oxo-1,6-diazabicyclo[3.2.1]oct-3-en-3-yl)triazol-4-yl]methyl]-N-[2-[tert-butyl(dimethyl)silyl]oxyethyl]carbamate (67c)

In a 5 mL sealed flask under inert atmosphere, intermediate (1g) (194 mg, 0.64 mmol) was diluted with anhydrous DMSO (2.5 mL). CuI (18 mg, 0.10 mmol), sodium azide (62 mg, 0.95 mmol), sodium ascorbate (18 mg, 0.10 mmol), intermediate (67b) (229 mg, 0.73 mmol) and DMCyDA (15

µL, 0.10 mmol) were successively added. The green solution turned rapidly to brown. The mixture was stirred at rt until reaction completion. After 1 h30, the reaction mixture was treated with H$_2$O (5 mL) and extracted with EtOAc (3×5 mL). The organic phases were dried (Na$_2$SO$_4$), concentrated and the crude was purified by flash chromatography on silica gel (cyclohexane/EtOAc: 100/0 to 0/100) to give intermediate (67c) (186 mg, 0.35 mmol, 55%) as a colorless oil.

MS m/z ([M+H]$^+$) 535.

$^1$H-NMR (400 MHz, CDCl$_3$): δ(ppm) 0.05 (s, 6H), 0.89 (s, 9H), 1.45 (s, 9H), 3.17 (d, J=11.4 Hz, 1H), 3.33-3.41 (m, 2H), 3.57 (d, J=11.0 Hz, 1H), 3.66-3.79 (m, 2H), 4.12-4.17 (m, 1H), 4.31 (d, J=17.8 Hz, 1H), 4.37-4.62 (m, 5H), 5.28-5.43 (m, 3H), 5.94-6.09 (m, 1H), 6.59 (d, J=5.4 Hz, 1H).

Step 4: Preparation of Intermediate propenyltriphenylphoshsphonium [3-[4-[[tert-butoxycarbonyl-[2-[tert-butyl(dimethyl)silyl]oxyethyl]amino]methyl]triazol-1-yl]-7-oxo-1,6-diazabicyclo[3.2.1]oct-3-en-6-yl]sulfate (67d)

To a solution of intermediate (67c) (186 mg, 0.35 mmol) in anhydrous DCM (4 mL) were added glacial AcOH (40 µL, 0.70 mmol) and Pd(PPh$_3$)$_4$ (201 mg, 0.17 mmol). After 1 h of stirring at rt, the reaction was concentrated under reduced pressure. Pyridine (4 mL) and sulfur trioxide pyridine complex (277 mg, 1.74 mmol) were added. The resulting suspension was protected from light and stirred until the reaction was completed. After 1 h30, the reaction mixture was concentrated, then diluted with DCM and filtered. The filtrate was concentrated under vacuum and then purified by flash chromatography on silica gel (DCM/acetone: 100/0 to 0/100) to afford intermediate (67d) (117 mg, 0.13 mmol, 38%) as a yellow oil.

MS m/z ([M+H]$^+$) 575.
MS m/z ([M–H]$^-$) 573.

Step 5: Preparation of Intermediate [3-[4-[[2-[tert-butyl(dimethyl)silyl]oxyethylamino]methyl]triazol-1-yl]-7-oxo-1,6-diazabicyclo[3.2.1]oct-3-en-6-yl] hydrogen sulfate (67e)

To a solution of intermediate (67d) (117 mg, 0.13 mmol) in anhydrous DCM (3 mL) cooled to 0° C. was added slowly a solution of TFA (225 µL, 2.94 mmol) in anhydrous DCM (2 mL). After stirring for 1 h at 0° C., the mixture was diluted in Et$_2$O (10 mL). The solution was concentrated under nitrogen flux. The residue was purified by flash chromatography on silica gel (gradient DCM/Acetone/MeOH: 100/0/0 to 0/100/0 to 0/0/100). Fractions containing the desired compound were combined and concentrated under reduced pressure to provide intermediate (67e) (26 mg, 0.06 mmol, 41%) as a beige solid.

MS m/z ([M+H]$^+$) 475.
MS m/z ([M–H]$^-$) 473.

Step 6: Preparation of [3-(4-(2-(methylamino)ethanol)triazol-1-yl)-7-oxo-1,6-diazabicyclo[3.2.1]oct-3-en-6-yl]hydrogen sulfate (example 67)

To a suspension of intermediate (67e) (26 mg, 0.06 mmol) in anhydrous THF (2 mL) was added slowly 3HF TEA (9 µL, 0.06 mmol) and the reaction was stirred overnight at rt. The mixture was concentrated to give a brown oil. This oil was applied on a Dowex sodium form column (Dowex® 50WX8 hydrogen form stored with an aqueous solution of 2N NaOH and washed until neutral pH with H$_2$O). Fractions containing the desired compound were combined and concentrated. The residue was purified by flash chromatography on C18-reversed phase silica gel (H$_2$O/ACN: 98/2 to 95/5). Fractions containing the desired compound were combined, freezed and lyophilized to provide example (67) (1.4 mg, 0.004 mmol, 7%) as a white solid.

MS m/z ([M+H]$^+$) 361.
MS m/z ([M–H]$^-$) 359.

$^1$H-NMR (400 MHz, D$_2$O): δ(ppm) 3.16-3.26 (m, 2H), 3.48 (d, J=11.4 Hz, 1H), 3.70 (dd, J=11.4, 2.8 Hz, 1H), 3.78-3.88 (m, 2H), 4.35-4.57 (m, 4H), 4.63 (dd, J=5.6, 2.5 Hz, 1H), 6.92 (d, J=5.5 Hz, 1H), 8.42 (s, 1H).

Example 68: Synthesis of sodium [3-[5-(2-hydroxyethyl)pyrazol-1-yl]-7-oxo-1,6-diazabicyclo[3.2.1]oct-3-en-6-yl]sulfate

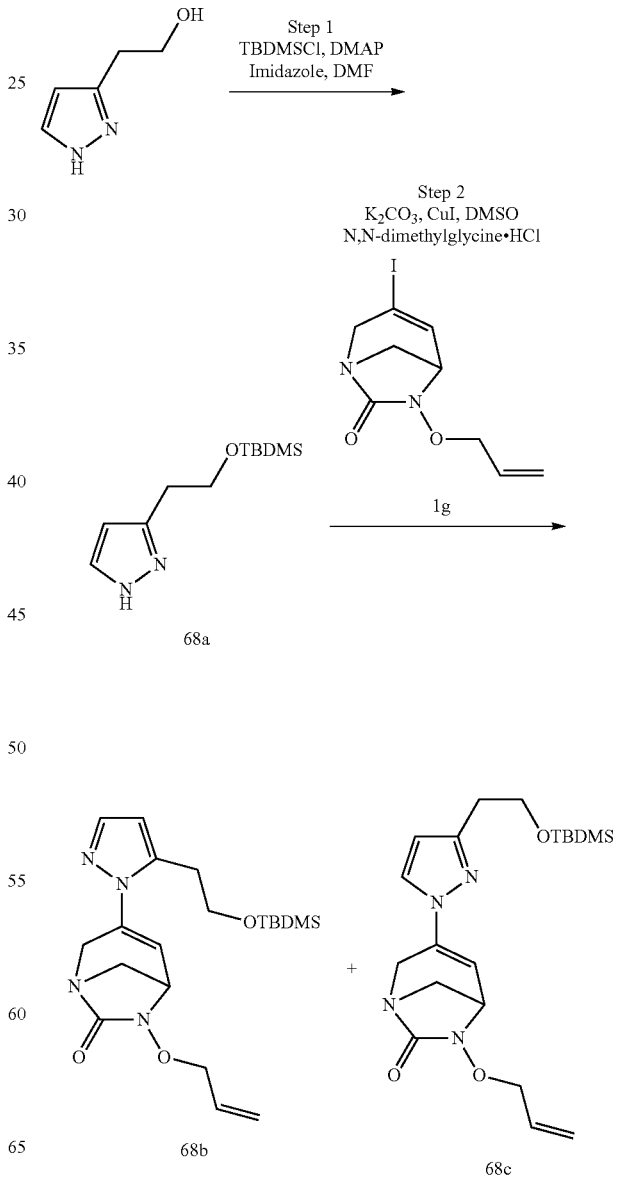

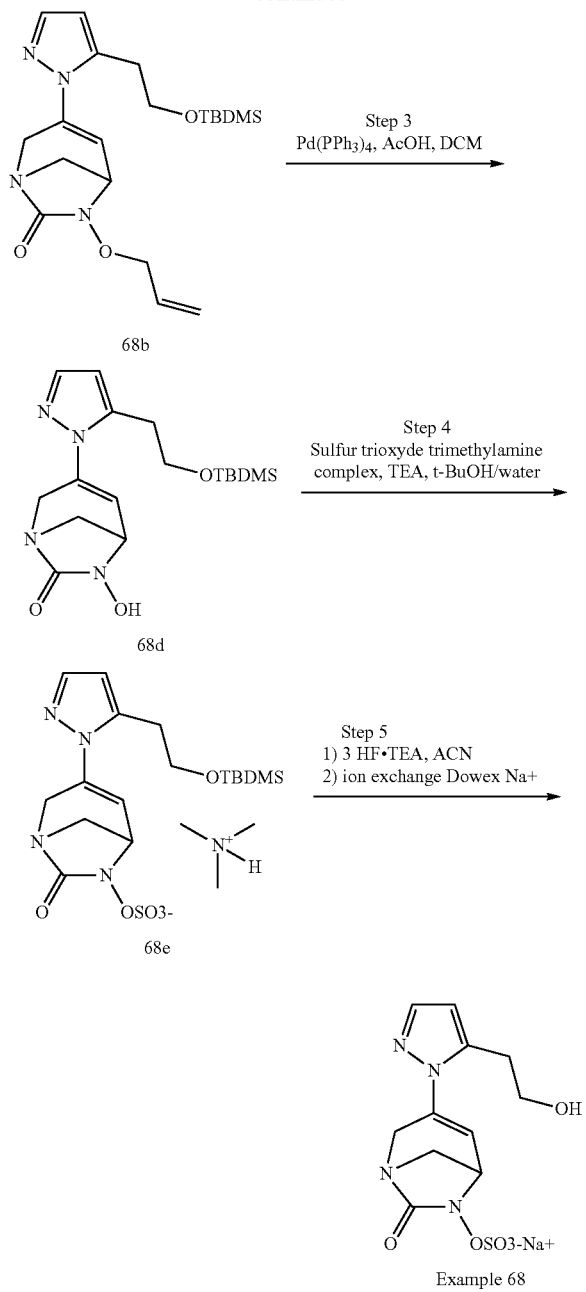

Step 2: Preparation of Intermediate 6-allyloxy-3-[5-[2-[tert-butyl(dimethyl)silyl]oxyethyl]pyrazol-1-yl]-1,6-diazabicyclo[33.2.1]oct-3-en-7-one (68b) and 6-allyloxy-3-[3-[2-[tert-butyl(dimethyl)silyl]oxyethyl]pyrazol-1-yl]-1,6-diazabicyclo[3.2.1]oct-3-en-7-one (68c)

Using the procedure described in example 1 (step 7), intermediate (1g) (400 mg, 1.31 mmol) was converted by reaction with intermediate (68a) (355 mg, 1.57 mmol) into intermediates (68b) (42 mg, 0.105 mmol, 8%) as an orange oil and (68c) (130 mg, 0.32 mmol, 25%) as yellow powder, after purification by flash chromatography on silica gel (cyclohexane/EtOAc then DCM/Acetone).

Intermediate 68b

MS m/z ([M+H]$^+$) 405.
$^1$H NMR (300 MHz, CDCl$_3$): δ (ppm) 0.00 (d, J=3.1 Hz, 6H), 0.84 (s, 9H), 2.88 (t, J=6.4 Hz, 2H), 3.20 (d, J=10.6 Hz, 1H), 3.44-3.51 (m, 1H), 3.75-3.90 (m, 2H), 4.05 (dd, J=5.5, 2.5 Hz, 1H), 4.11 (dd, J=17.8, 1.1 Hz, 1H), 4.21 (dd, J=17.8, 1.9 Hz, 1H), 4.34-4.50 (m, 2H), 5.23-5.38 (m, 2H), 6.00 (dddd, J=17.1, 10.3, 6.6, 6.0 Hz, 1H), 6.16 (d, J=1.6 Hz, 1H), 6.26-6.33 (m, 1H), 7.45 (d, J=1.8 Hz, 1H).
Intermediate 68c MS m/z ([M+H]$^+$) 405.
$^1$H NMR (300 MHz, CDCl$_3$): δ (ppm) 0.00 (s, 6H), 0.85 (s, 9H), 2.80 (t, J=6.9 Hz, 2H), 3.11 (d, J=10.7 Hz, 1H), 3.46-3.52 (m, 1H), 3.80 (t, J=6.9 Hz, 2H), 4.05 (dd, J=5.6, 2.5 Hz, 1H), 4.13 (dd, J=17.5, 1.9 Hz, 1H), 4.32-4.49 (m, 3H), 5.23-5.39 (m, 2H), 6.00 (dddd, J=17.0, 10.3, 6.7, 6.0 Hz, 1H), 6.18 (d, J=2.5 Hz, 1H), 6.35-6.40 (m, 1H), 7.44 (d, J=2.5 Hz, 1H).

Step 3: Preparation of Intermediate 3-[5-[2-[tert-butyl(dimethyl)silyl]oxyethyl]pyrazol-1-yl]-6-hydroxy-1,6-diazabicyclo[3.2.1]oct-3-en-7-one (68d)

A solution of intermediate (68b) (42 mg, 0.093 mmol) in anhydrous DCM (4.1 mL) was degazed for 10 min under argon atmosphere. AcOH (12 μL, 0.208 mmol) and Pd(PPh$_3$)$_4$ (60 mg, 0.052 mmol) were successively added. After stirring for 2 h at rt, AcOH (6 μL, 0.10 mmol) was added. After stirring for 3 h30 at rt, the mixture was concentrated in vacuo. The residue was purified by flash chromatography on silica gel (DCM/acetone: 100/0 to 0/100) to provide intermediate (68d) (30 mg) as a yellow oil contaminated with triphenylphosphine oxide.
MS m/z ([M+H]$^+$) 365.

Step 4: Preparation of trimethylammonium [3-[5-[2-[tert-butyl(dimethyl)silyl]oxyethyl]pyrazol-1-yl]-7-oxo-1,6-diazabicyclo[3.2.1]oct-3-en-6-yl]sulfate (68e)

To a solution of intermediate (68d) (30 mg) in tBuOH (0.412 mL) and H$_2$O (0.412 mL) under inert atmosphere was added sulfur trioxide trimethylamine complex (14 mg, 0.099 mmol) and TEA (2.9 μL, 0.021 mmol). After stirring for 1 h at rt, sulfur trioxide trimethylamine complex (7 mg, 0.045 mmol) was added. After stirring for 16 h at rt, the mixture was concentrated in vacuo. The residue was purified by flash chromatography on silica gel (DCM/acetone: 100/0 to 0/100) to provide intermediate (68e) (15 mg, 0.026 mmol, 28% over 2 steps) as white powder.
MS m/z ([M+H]$^+$) 445.
MS m/z ([M−H]$^−$) 443.

Step 1: Preparation of Intermediate tert-butyl-dimethyl-[2-(1H-pyrazol-3-yl)ethoxy]silane (68a)

A mixture of 2-(1H-pyrazol-3-yl)ethanol (400 mg, 3.57 mmol), TBDMSCl (928 μL, 5.35 mmol), imidazole (389 mg, 5.71 mmol) and DMAP (480 mg, 3.93 mmol) in DMF (17.8 mL) under argon was heated at 50° C. for 1 h. The mixture was concentrated in vacuo and the residue was purified by flash chromatography on silica gel (cyclohexane/EtOAc: 100/0 to 100/0) to provide intermediate (68a) (744 mg, 3.29 mmol, 92%) as a colorless oil.

MS m/z ([M+H]$^+$) 227.

$^1$H NMR (300 MHz, CDCl$_3$): δ (ppm) 0.00 (s, 6H), 0.85 (s, 9H), 2.82 (t, J=6.0 Hz, 2H), 3.82 (t, J=6.0 Hz, 2H), 6.03 (d, J=1.9 Hz, 1H), 7.42 (d, J=1.9 Hz, 1H).

Step 5: Preparation of sodium [3-[5-(2-hydroxy-ethyl)pyrazol-1-yl]-7-oxo-1,6-diazabicyclo[3.2.1]oct-3-en-6-yl]sulfate (example 68)

To a suspension of intermediate (68e) (15 mg, 0.030 mmol) in anhydrous ACN (0.3 mL) was added slowly 3HF.TEA (4.9 µL, 0.030 mmol). After stirring for 7 h at 40° C., the mixture was concentrated to give a yellow powder. This powder was applied on a Dowex sodium form column (Dowex® 50WX8 hydrogen form stored with an aqueous solution of 2N NaOH and washed until neutral pH with H$_2$O). The fractions containing the desired compound were combined, freezed and lyophilized to provide example (68) (7.5 mg, 0.021 mmol, 75%) as a white solid.

MS m/z ([M−H]$^-$) 329.

$^1$H NMR (400 MHz, D$_2$O): δ(ppm) 2.94 (t, J=6.3 Hz, 2H), 3.52 (d, J=11.3 Hz, 1H), 3.66-3.73 (m, 1H), 3.83 (td, J=6.3, 1.7 Hz, 2H), 4.04 (d, J=17.9 Hz, 1H), 4.23 (dd, J=17.9, 2.1 Hz, 1H), 4.60 (dd, J=5.5, 2.6 Hz, 1H), 6.35 (d, J=2.0 Hz, 1H), 6.49-6.59 (m, 1H), 7.61 (d, J=2.0 Hz, 1H).

Example 69: Synthesis of sodium [3-[3-[2-[tert-butyl(dimethyl)silyl]oxyethyl]pyrazol-1-yl]-7-oxo-1,6-diazabicyclo[3.2.1]oct-3-en-6-yl]sulfate

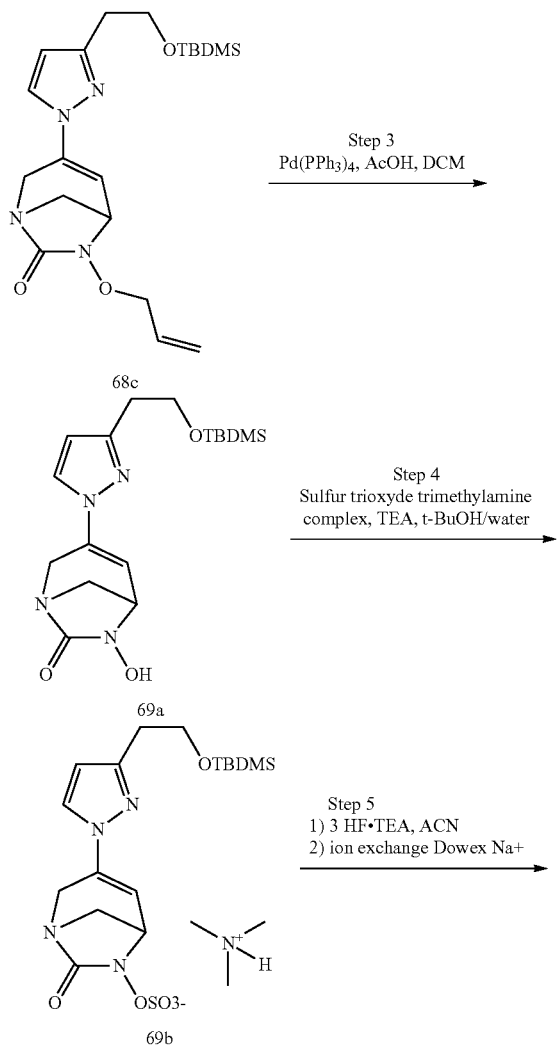

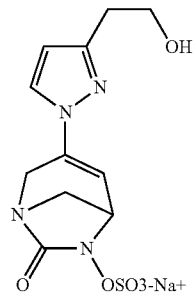

Example 69

Step 1: Preparation of Intermediate 3-[3-[2-[tert-butyl(dimethyl)silyl]oxyethyl]pyrazol-1-yl]-6-hydroxy-1,6-diazabicyclo[3.2.1]oct-3-en-7-one (69a)

A solution of intermediate (68c) (125 mg, 0.309 mmol) in anhydrous DCM (3.1 mL) was degazed for 10 min under argon atmosphere. AcOH (0.036 mL, 0.618 mmol) and Pd(PPh$_3$)$_4$ (179 mg, 0.154 mmol) were successively added. After stirring for 1 h at rt, the mixture was concentrated in vacuo. The residue was purified by flash chromatography on silica gel (DCM/acetone: 100/0 to 0/100) to provide intermediate (69a) (51 mg) as a colorless oil contaminated with triphenylphosphine oxide.

MS m/z ([M]$^+$) 365.

Step 2: Preparation of trimethylammonium [3-[3-[2-[tert-butyl(dimethyl)silyl]oxyethyl]pyrazol-1-yl]-7-oxo-1,6-diazabicyclo[3.2.1]oct-3-en-6-yl]sulfate (69b)

To a solution of intermediate (69a) (76 mg) in tBuOH (1.05 mL) and H$_2$O (1.05 mL) under inert atmosphere was added sulfur trioxide trimethylamine complex (35 mg, 0.251 mmol) and triethylamine (7.3 µL, 0.052 mmol). After stirring for 1 h at rt, sulfur trioxide trimethylamine complex (16 mg, 0.0115 mmol) was added. After stirring for 16 h at rt, the mixture was concentrated in vacuo and the residue was purified by chromatography on silica gel (DCM/acetone: 100/0 to 0/100) to provide trimethylammonium [3-[3-[2-[tert-butyl(dimethyl)silyl]oxyethyl]pyrazol-1-yl]-7-oxo-1,6-diazabicyclo[3.2.1]oct-3-en-6-yl]sulfate (69b) (39 mg, 0.077 mmol, 25% over 2 steps) as a white powder.

MS m/z ([M−H]$^-$) 443.

Step 3: Preparation of sodium [3-[3-[2-[tert-butyl(dimethyl)silyl]oxyethyl]pyrazol-1-yl]-7-oxo-1,6-diazabicyclo[3.2.1]oct-3-en-6-yl]sulfate (example 69)

To a suspension of intermediate (69b) (39 mg, 0.077 mmol) in anhydrous ACN (0.775 mL) was added slowly 3HF.TEA (12.6 µL, 0.078 mmol). After stirring for 2 h30 at 40° C., 3HF.TEA (12.6 µL, 0.078 mmol) was added. After stirring for 4 h30 at 40° C., 3HF.TEA (12.6 µL, 0.078 mmol) was added. After stirring for 8 h at 40° C. and 16 h at rt, the mixture was concentrated to give a yellow powder. This powder was applied on a Dowex sodium form column (Dowex® 50WX8 hydrogen form stored with an aqueous solution of 2N NaOH and washed until neutral pH with H$_2$O). The fractions containing the desired compound were combined, freezed and lyophilized to provide a white solid which was purified twice by flash chromatography on C18-reversed phase silica gel (H₂O/ACN: 98/2 to 95/5). The fractions containing the desired compound were combined, freezed and lyophilized to provide example (69) (3 mg, 0.0085 mmol, 11%) as a beige powder.

MS m/z ([M−H]⁻) 329.

$^1$H NMR (300 MHz, D₂O): δ(ppm) 2.85 (t, J=6.5 Hz, 2H), 3.43 (d, J=11.3 Hz, 1H), 3.67 (dd, J=11.3, 2.4 Hz, 1H), 3.83 (t, J=6.5 Hz, 2H), 4.33 (s, 2H), 4.55 (dd, J=5.7, 2.6 Hz, 1H), 6.37 (d, J=2.6 Hz, 1H), 6.54 (d, J=5.6 Hz, 1H), 7.80 (d, J=2.6 Hz, 1H).

Example 70: Synthesis of sodium [3-[2-(hydroxymethyl)imidazol-1-yl]-7-oxo-1,6-diazabicyclo[3.2.1]oct-3-en-6-yl]sulfate

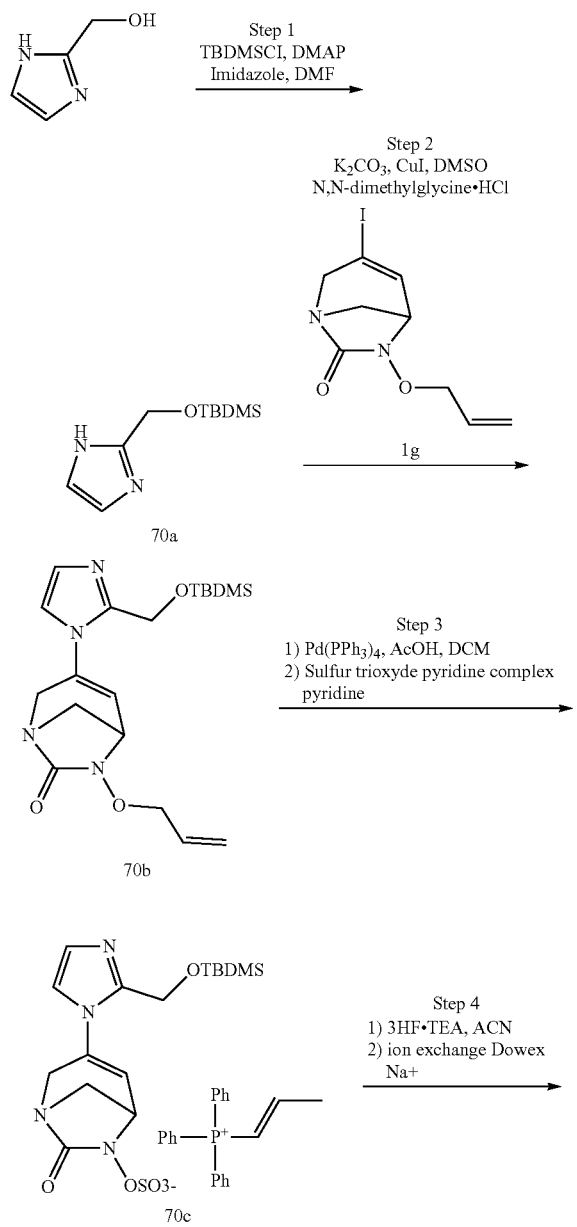

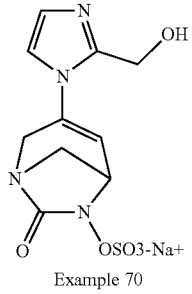

Example 70

Step 1: Preparation of Intermediate tert-butyl-(1H-imidazol-2-ylmethoxy)-dimethyl-silane (70a)

A mixture of 1H-imidazol-2-ylmethanol (30 mg, 3.06 mmol), TBDMSCI (795 μL, 4.59 mmol), imidazole (0,333 g, 4.89 mmol) and DMAP (411 mg, 3.366 mmol) in DMF (15.3 mL) under argon was stirring for 4 h30 at rt and was heated at 40° C. for 1 h to have total conversion of starting material. The mixture was concentrated in vacuo and the residue was purified by flash chromatography on silica gel (DCM/acetone: 100/0 to 50/50) to provide intermediate (70a) (592 mg, 2.45 mmol, 80%) as colorless oil.

MS m/z ([M+H]⁺) 213.

$^1$H NMR (300 MHz, CDCl₃): δ (ppm) 0.11 (s, 6H), 0.93 (s, 9H), 4.82 (s, 2H), 7.01 (s, 2H).

Step 2: Preparation of Intermediate 6-allyloxy-3-[2-[[tert-butyl(dimethyl)silyl]oxymethyl]imidazol-1-yl]-1,6-diazabicyclo[3.2.1]oct-3-en-7-one (70b)

Using the procedure described in example 2 (step 1a), intermediate (1g) (300 mg, 0.98 mmol) was converted by reaction with intermediate (70a) (0.32 g, 0.78 mmol) into intermediate (70b) (239 mg, 0.50 mmol, 51%) as yellow oil after purification by flash chromatography on silica gel (cyclohexane/EtOAc: 100/0 to 50/50).

MS m/z ([M+H]⁺) 391.

$^1$H NMR (300 MHz, CDCl₃): δ(ppm) 0.00 (d, J=2.3 Hz, 6H), 0.80 (s, 9H), 3.10 (d, J=10.8 Hz, 1H), 3.46 (ddd, J=10.9, 2.8, 1.2 Hz, 1H), 3.92-4.09 (m, 3H), 4.27-4.45 (m, 2H), 4.50-4.68 (m, 2H), 5.20-5.36 (m, 2H), 5.94 (dddd, J=17.1, 10.3, 6.7, 6.0 Hz, 1H), 6.55 (dd, J=5.7, 1.4 Hz, 1H), 6.81 (d, J=1.4 Hz, 1H), 6.91 (d, J=1.4 Hz, 1H).

Step 3: Preparation of Intermediate allyl(triphenyl)phosphonium [3-[2-[[tert-butyl(dimethyl)silyl]oxymethyl]imidazol-1-yl]-7-oxo-1,6-diazabicyclo[3.2.1]oct-3-en-6-yl]sulfate (70c)

A solution of intermediate (70b) (120 mg, 0.252 mmol) in anhydrous DCM (2.52 mL) was degazed for 10 min under argon atmosphere. AcOH (29 μL, 0.504 mmol) and Pd(PPh₃)₄ (146 mg, 0.126 mmol) were successively added. After 1 h30 of stirring at rt, pyridine (2.52 mL) and sulfur trioxide pyridine complex (200 mg, 1.26 mmol) were added to the reaction mixture. The resulting suspension was protected from light and stirred overnight until the reaction was completed. The reaction mixture was concentrated, then diluted with DCM and filtered. The filtrate was concentrated under vacuum and then purified by flash chromatography on silica gel (DCM/acetone: 100/0 to 0/100) to provide intermediate (70c) (78 mg, 0.106 mmol, 42%) as a yellow powder.

MS m/z ([M+H]⁺) 431.

Step 4: Preparation of sodium [3-[2-(hydroxymethyl)imidazol-1-yl]-7-oxo-1,6-diazabicyclo[3.2.1]oct-3-en-6-yl]sulfate (example 70)

To a suspension of intermediate (70c) (78 mg, 0.107 mmol) in anhydrous ACN (1.06 mL) was added slowly 3HF.TEA (17.4 µL, 0.107 mmol). After stirring for 7 h at 40° C. and 17 h at rt, the mixture was concentrated to give a yellow oil. The crude was purified by flash chromatography on C18-reversed phase silica gel (H$_2$O/ACN: 98/2 to 0/100). The fractions containing the desired compound were combined to provide 27 mg of a solid which was applied on a Dowex sodium form column (Dowex® 50WX8 hydrogen form stored with an aqueous solution of 2N NaOH and washed until neutral pH with H$_2$O). The fractions containing the desired compound were combined, freezed and lyophilized to provide example (70) (5.8 mg, 0.017 mmol, 16%) as a white solid.

MS m/z ([M−H]$^−$) 315.

$^1$H NMR (400 MHz, D$_2$O): δ(ppm) 3.50 (d, J=11.6 Hz, 1H), 3.70 (dd, J=11.6, 2.8 Hz, 1H), 4.02 (dd, J=18.0, 1.1 Hz, 1H), 4.27 (dd, J=17.9, 2.2 Hz, 1H), 4.61 (dd, J=5.4, 2.6 Hz, 1H), 4.81 (s, 2H), 6.80 (d, J=5.4 Hz, 1H), 7.37 (d, J=2.0 Hz, 1H), 7.43 (d, J=2.0 Hz, 1H).

Example 71: Synthesis of sodium [3-[4-(hydroxymethyl)pyrazol-1-yl]-7-oxo-1,6-diazabicyclo[3.2.1]oct-3-en-6-yl]sulfate

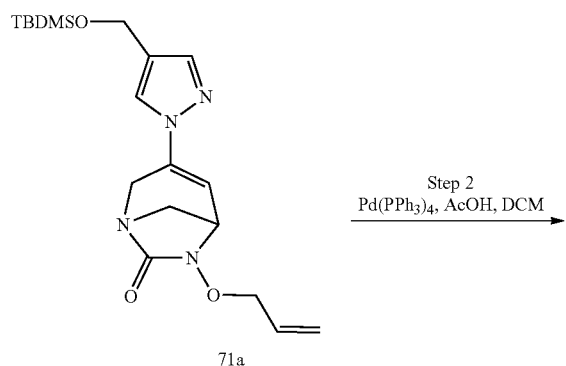

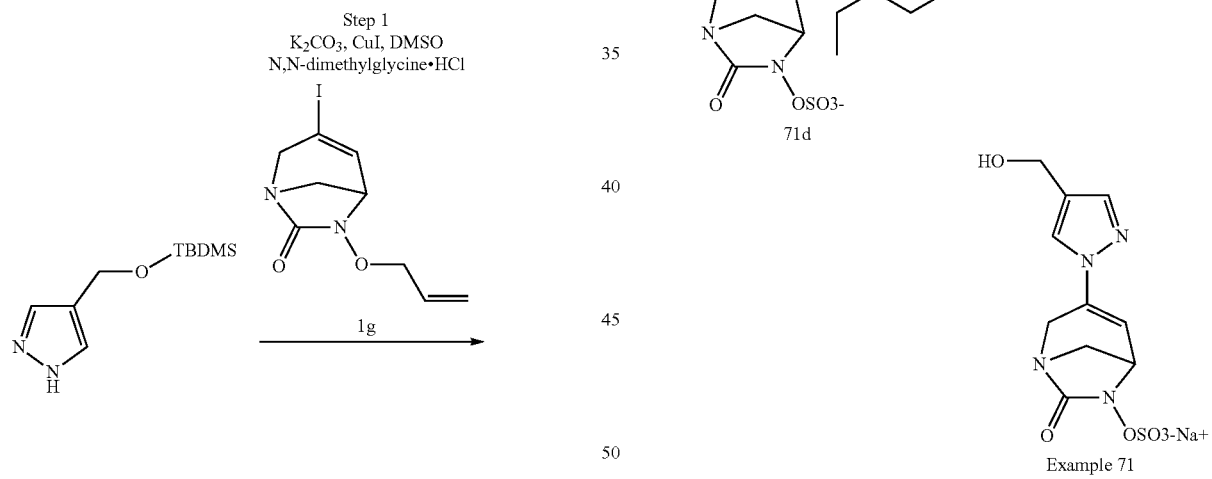

Step 1: Preparation of Intermediate 6-allyloxy-3-[4-[[tert-butyl(dimethyl) silyl]oxymethyl]pyrazol-1-yl]-1,6-diazabicyclo[3.2.1]oct-3-en-7-one (71a)

Using the procedure described in example 1 (step 7), intermediate (1g) (230 mg, 0.751 mmol) was converted by reaction with tert-butyl-dimethyl-(1H-pyrazol-4-ylmethoxy) silane (obtained according to the protocol described in WO 2010/108902) (239 mg, 1.113 mmol) into intermediate (71a) (209 mg, 0.535 mmol, 71%) after purification by flash chromatography on silica gel (DCM/acetone: 100/0 to 95/5).

MS m/z ([M+H]$^+$) 391.

$^1$H RMN (300 MHz, CDCl$_3$): δ (ppm) 0.07 (s, 6H), 0.90 (s, 9H), 3.13 (d, J=10.7 Hz, 1H), 3.52 (dd, J=10.4, 2.3 Hz, 1H), 4.08 (dd, J=2.4, 5.5 Hz, 1H), 4.18 (dd, J=1.8, 17.6 Hz, 1H), 4.40-4.48 (m, 3H), 4.60 (s, 2H), 5.30-5.40 (m, 2H), 5.96-6.08 (m, 1H), 6.40 (d, J=5.4 Hz, 1H), 7.48 (s, 1H), 7.52 (s, 1H).

Step 2: Preparation of Intermediate 3-[4-[[tert-butyl (dimethyl)silyl]oxymethyl]pyrazol-1-yl]-6-hydroxy-1,6-diazabicyclo[3.2.1]oct-3-en-7-one (71b)

Intermediate (71a) (140 mg, 0.358 mmol) is dissolved in anhydrous DCM (2.6 mL). The solution was degazed 10 min under argon atmosphere and AcOH (41 μL, 0.717 mmol) and Pd(PPh$_3$)$_4$ (207 mg, 0.179 mmol) were successively added. After stirring for 1 h at rt, the mixture was evaporated. The residue was purified by flash chromatography on silica gel (DCM/acetone: 100/0 to 0/100) to afford intermediate (71b) (55 mg, 0.158 mmol, 44%).
MS m/z ([M+H]$^+$) 351.

Step 3: Preparation of Intermediate pyridin-1-ium [3-[4-[[tert-butyl(dimethyl)silyl]oxymethyl]pyrazol-1-yl]-7-oxo-1,6-diazabicyclo[3.2.1]oct-3-en-6-yl] sulfate (71c)

To a solution of intermediate (71b) (55 mg, 0.157 mmol) in anhydrous pyridine (0.920 mL) under inert atmosphere was added sulfur trioxide pyridine complex (125 mg, 0.783 mmol). After stirring for 18 h at rt, the heterogeneous mixture was concentrated in vacuo. DCM was added to the residue and the solids were filtered off. The filtrate was purified by flash chromatography on silica gel (DCM/acetone: 100/0 to 0/100) to afford intermediate (71c) (62 mg, 0.122 mmol, 77%).
MS m/z ([M+H]$^+$) 431.
MS m/z ([M−H]$^-$) 429.

Step 4: Preparation of Intermediate triethylammonium [3-[4-(hydroxymethyl)pyrazol-1-yl]-7-oxo-1,6-diazabicyclo[3.2.1]oct-3-en-6-yl]sulfate (71d)

To a solution of intermediate (71c) (60 mg, 0.118 mmol) in ACN (1.2 mL) under inert atmosphere was added triethylamine trihydrofluoride (19 μL, 0.118 mmol). After stirring for 2.5 h at 40° C., the mixture was concentrated in vacuo and was purified by flash chromatography on C18-reversed phase silica gel (H$_2$O/ACN: 98/2 to 0/100) to afford intermediate (71d) (49 mg, 0.117 mmol, quantitative yield) as a white solid.
MS m/z ([M+H]$^+$) 317.
MS m/z ([M−H]$^-$) 315.

Step 5: Preparation of sodium [3-[4-(hydroxymethyl)pyrazol-1-yl]-7-oxo-1,6-diazabicyclo[3.2.1]oct-3-en-6-yl]sulfate (Example 71)

Intermediate (71d) (49 mg, 0.117 mmol) was dissolved in a minimum of H$_2$O and a few drops of ACN and applied on Dowex sodium form column (Dowex® 50WX8 hydrogen form stored with an aqueous solution of 2N NaOH and washed until neutral pH with H$_2$O). The fractions containing the desired compound were combined, freezed and lyophilized. MeOH was added to the residue and the solids were filtered off. The filtrate was concentrated in vacuo to afford example (71) (22 mg, 0.066 mmol, 56%).
MS m/z ([M+H]$^+$) 317.
MS m/z ([M−H]$^-$) 315.

$^1$H RMN (300 MHz, D$_2$O): δ(ppm) 3.44 (d, J=11.1 Hz, 1H), 3.65-3.70 (m, 1H), 4.35-4.36 (m, 2H), 4.54-4.57 (m, 3H), 6.56-6.63 (m, 1H), 7.69 (s, 1H), 7.95-7.85 (m, 1H).

Example 72: Synthesis of [3-[3-(2-morpholinoethylcarbamoyl)pyrazol-1-yl]-7-oxo-1,6-diazabicyclo [3.2.1]oct-3-en-6-yl]hydrogen sulfate

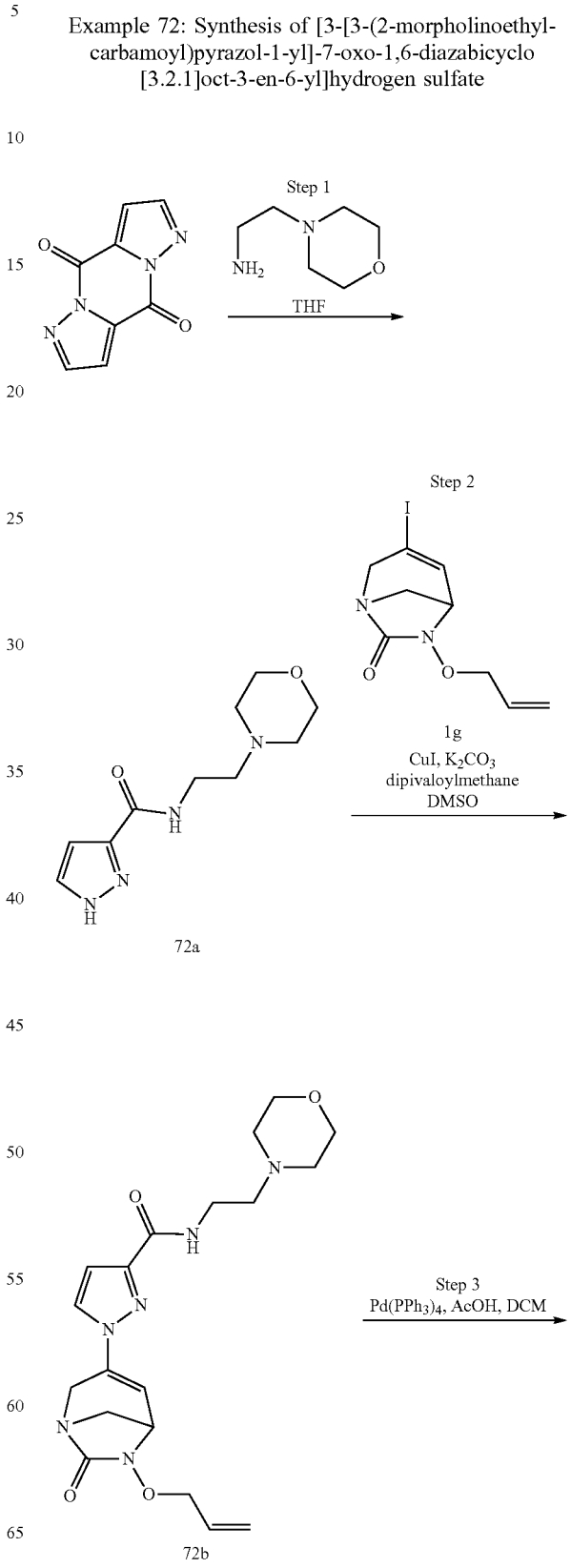

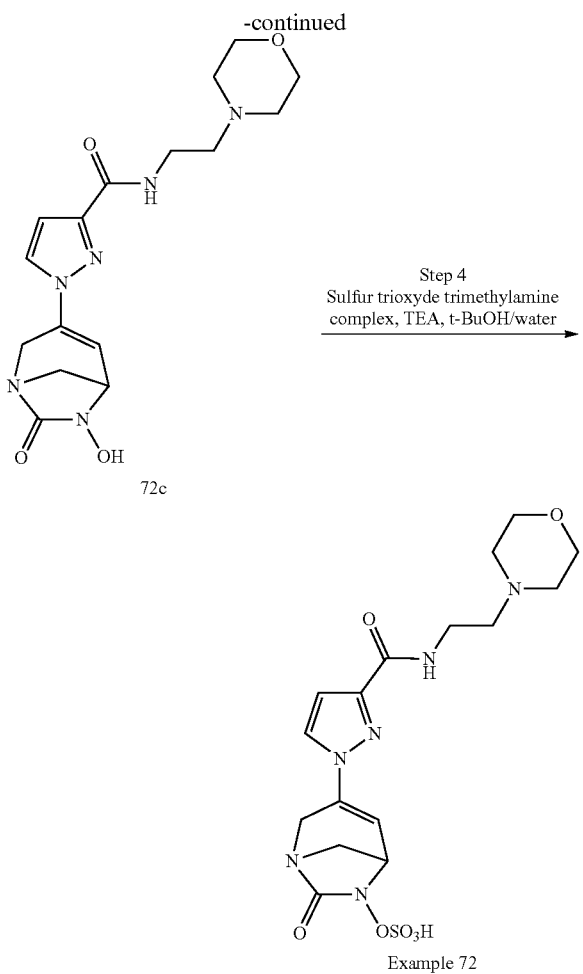

Example 72

Step 1: Preparation of Intermediate N-(2-morpholinoethyl)-1H-pyrazole-3-carboxamide (72a)

A mixture of dipyrazolo[3,1-a: 3',1'-d]pyrazine-4,9-dione (prepared according to *Bioorganic & Medicinal Chemistry Letters*, 2015, 25 (15), 3024-3029)) (30 mg, 0.159 mmol), 2-morpholinoethanamine (42 mg, 0.319 mmol) in THF (0.32 mL) was heated at 80° C. for 18 h. The mixture was concentrated in vacuo to provide intermediate (72a) (70 mg, 0.313 mmol, 98%) as a brown oil.

MS m/z ([M+H]$^+$) 225.

$^1$H NMR (400 MHz, CDCl$_3$): δ (ppm) 2.48 (s, 4H), 2.58 (t, J=6.1 Hz, 2H), 3.52 (q, J=5.9 Hz, 2H), 3.60-3.77 (m, 4H), 6.74 (d, J=2.4 Hz, 1H), 7.51 (d, J=2.4 Hz, 1H), 7.69 (br s, 1H).

Step 2: Preparation of Intermediate 1-(6-allyloxy-7-oxo-1,6-diazabicyclo[3.2.1]oct-3-en-3-yl)-N-(2-morpholinoethyl)pyrazole-3-carboxamide (72b)

Using the procedure described in example 2 (step 1a), intermediate (1g) (168 mg, 0.55 mmol) was converted by reaction with intermediate (72a) (185 mg, 0.824 mmol) into intermediate (72b) (217 mg, 0.54 mmol, 99%) as a yellow oil, after purification by flash chromatography on silica gel (DCM/acetone: 100/0 to 100/0).

MS m/z ([M+H]$^+$) 403.

$^1$H NMR (400 MHz, CDCl$_3$): δ(ppm) 2.50-2.63 (m, 4H), 2.60-2.69 (m, 2H), 3.18 (d, J=10.9 Hz, 1H), 3.50-3.63 (m, 3H), 3.78 (q, J=4.5 Hz, 4H), 4.13-4.26 (m, 2H), 4.36-4.59 (m, 3H), 5.31-5.48 (m, 2H), 6.04 (ddt, J=17.0, 10.3, 6.5 Hz, 1H), 6.55 (d, J=5.5 Hz, 1H), 6.90 (d, J=2.6 Hz, 1H), 7.67 (d, J=2.6 Hz, 1H).

Step 3: Preparation of Intermediate 1-(6-hydroxy-7-oxo-1,6-diazabicyclo[3.2.1]oct-3-en-3-yl)-N-(2-morpholinoethyl)pyrazole-3-carboxamide (72c)

A solution of intermediate (72b) (149 mg, 0.296 mmol) in anhydrous DCM (2.9 mL) was degazed for 10 min under argon atmosphere. AcOH (34 µL, 0.59 mmol) and Pd(PPh$_3$)$_4$ (172 mg, 0.148 mmol) were successively added. After stirring for 1 h30 at rt, the mixture was concentrated in vacuo. The residue was purified by flash chromatography on C18-reversed phase silica gel (H$_2$O/ACN: 98/2 to 0/100) to provide intermediate (72c) (46 mg, 0.127 mmol, 43%) as a yellow powder.

MS m/z ([M+H]$^+$) 363.

Step 4: Preparation of [3-[3-(2-morpholinoethylcarbamoyl)pyrazol-1-yl]-7-oxo-1,6-diazabicyclo[3.2.1]oct-3-en-6-yl]hydrogen sulfate (example 72)

To a solution of intermediate (72c) (28 mg, 0.077 mmol) in tBuOH (0.39 mL) and H$_2$O (0.39 mL) under inert atmosphere was added sulfur trioxide trimethylamine complex (12.9 mg, 0.093 mmol) and TEA (2.7 µL, 0.019 mmol). After stirring for 23 h, the heterogeneous mixture was concentrated in vacuo. The crude was purified by flash chromatography on C18-reversed phase silica gel (H$_2$O/ACN: 98/2 to 0/100). The fractions containing the desired compound were combined to provide example (72) (14 mg, 0.031 mmol, 41%) as a white powder.

MS m/z ([M+H]$^+$) 443.
MS m/z ([M−H]$^-$) 441.

$^1$H NMR (300 MHz, D$_2$O): δ(ppm) 3.11-3.29 (m, 6H), 3.44 (d, J=11.3 Hz, 1H), 3.63-3.77 (m, 2H), 3.84-3.96 (m, 5H), 4.39 (br s, 2H), 4.58 (dd, J=5.7, 2.6 Hz, 1H), 6.73 (d, J=6.0 Hz, 1H), 6.83 (d, J=2.7 Hz, 1H), 7.97 (d, J=2.7 Hz, 1H).

Example 73: Synthesis of trimethylammonium [3-[2-(3-amino-3-oxo-propyl)imidazol-1-yl]-7-oxo-1,6-diazabicyclo[3.2.1]oct-3-en-6-yl]sulfate

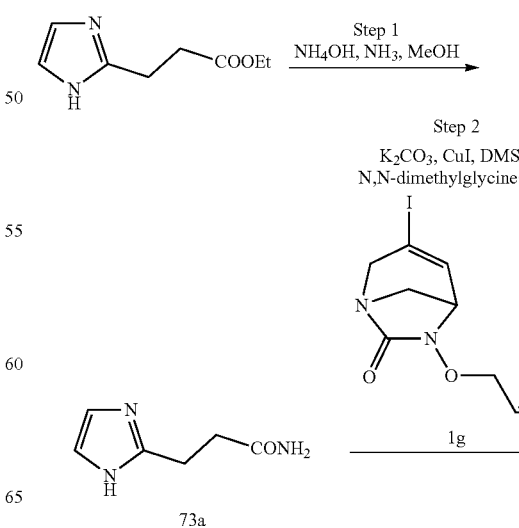

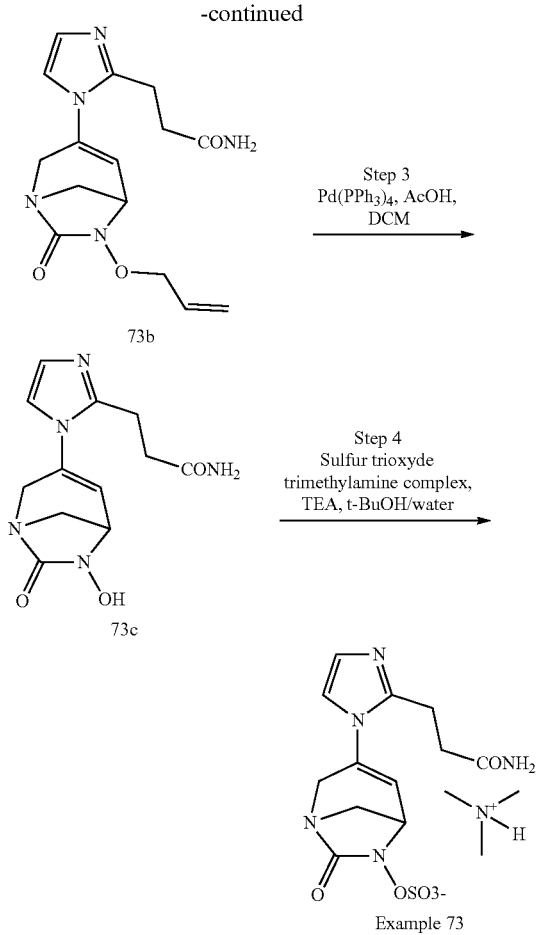

Step 1: Preparation of Intermediate 3-(1H-imidazol-2-yl)propenamide (73a)

Ethyl 3-(1H-imidazol-2-yl)propanoate (0.50 g, 2.826 mmol), aqueous ammonia 30% (2 mL) and methanolic ammonia solution 7M (2 mL) were successively added. After 42 h of stirring at rt, the reaction mixture was filtered. The filtrate was concentrated in vacuo to give intermediate (73a) (0.318 g, 2.28 mmol, 81%) as a white powder.

MS m/z ([M+H]$^+$) 140.

$^1$H NMR (300 MHz, DMSO-d$_6$): δ(ppm) 2.41-2.49 (m, 2H), 2.75-2.83 (m, 2H), 6.70-6.95 (m, 3H), 7.37 (br s, 1H), 11.65 (br s, 1H).

Step 2: Preparation of Intermediate 3-[1-(6-allyloxy-7-oxo-1,6-diazabicyclo[3.2.1]oct-3-en-3-yl)imidazol-2-yl]propenamide (73b)

Using the procedure described in example 1 (step 7), intermediate (1g) (400 mg, 1.31 mmol) was converted by reaction with intermediate (73a) (218 mg, 1.57 mmol) into intermediate (73b) (261 mg, 0.823 mmol, 63%) as a green oil, after purification by flash chromatography on C18-reversed phase silica gel (H$_2$O/ACN: 98/2 to 0/100).

MS m/z ([M+H]$^+$) 318.

$^1$H NMR (300 MHz, DMSO-d$_6$): δ(ppm) 2.42-2.61 (m, 2H), 2.70-2.90 (m, 2H), 3.27-3.43 (m, 3H), 3.81 (d, J=17.5 Hz, 1H), 4.03 (d, J=18.3 Hz, 1H), 4.31 (d, J=5.6 Hz, 1H), 4.40 (dt, J=6.0, 1.3 Hz, 1H), 5.23-5.44 (m, 2H), 5.89-6.06 (m, 1H), 6.44 (d, J=5.4 Hz, 1H), 6.79 (br s, 2H), 7.15 (br s, 1H), 7.32 (br s, 1H).

Step 3: Preparation of Intermediate 3-[1-(6-hydroxy-7-oxo-1,6-diazabicyclo[3.2.1]oct-3-en-3-yl)imidazol-2-yl]propenamide (73c)

A solution of intermediate (73b) (60 mg, 0.189 mmol) in anhydrous DCM (1.89 mL) was degazed for 10 min under argon atmosphere. AcOH (22 µL, 0.378 mmol) and Pd(PPh$_3$)$_4$ (109 mg, 0.095 mmol) were successively added. After 2 h30 of stirring at rt, the mixture was concentrated. The crude was purified by flash chromatography on C18-reversed phase on silica gel (H$_2$O/ACN: 98/2 to 0/100). The fractions containing the desired compound were combined, freezed and lyophilized to provide intermediate (73c) (70 mg) as a yellow powder with triphenylphosphine oxide.

MS m/z ([M+H]$^+$) 278.

Step 4: Preparation of trimethylammonium [3-[2-(3-amino-3-oxo-propyl)imidazol-1-yl]-7-oxo-1,6-diazabicyclo[3.2.1]oct-3-en-6-yl]sulfate (example 73)

To a solution of intermediate (73c) (70 mg, 0.25 mmol) in tBuOH (1.26 mL) and H$_2$O (1.26 mL) under inert atmosphere was added sulfur trioxide trimethylamine complex (42.2 mg, 0.303 mmol) and TEA (8.9 µL, 0.063 mmol). After stirring for 2 h20, the heterogeneous mixture was concentrated in vacuo. The crude was purified by flash chromatography on C18-reversed phase silica gel (H$_2$O/ACN: 98/2 to 0/100). The fractions containing the desired compound were combined and purified again by flash chromatography on C18 reversed phase silica gel (H$_2$O/ACN: 99/1 to 95/5) to provide example (73) (4 mg, 0.0055 mmol, 2%) as a white powder contaminated with sulfur trioxide trimethylamine complex.

MS m/z ([M+H]$^+$) 358.
MS m/z ([M−H]$^-$) 356.

$^1$H NMR (300 MHz, D$_2$O): δ(ppm) 2.69-2.82 (m, 2H), 3.15 (td, J=7.1, 3.1 Hz, 2H), 3.23 (s, 9H), 3.55 (d, J=11.6 Hz, 1H), 3.72 (dd, J=11.5, 2.6 Hz, 1H), 3.99 (d, J=18.6 Hz, 1H), 4.28 (dd, J=18.1, 2.2 Hz, 1H), 4.64 (dd, J=5.4, 2.6 Hz, 1H), 6.83 (d, J=5.2 Hz, 1H), 7.30-7.32 (m, 1H), 7.35 (d, J=2.0 Hz, 1H).

Example 74: Synthesis of sodium [3-[4-(2-hydroxyethylsulfamoyl)pyrazol-1-yl]-7-oxo-1,6-diazabicyclo[3.2.1]oct-3-en-6-yl]sulfate

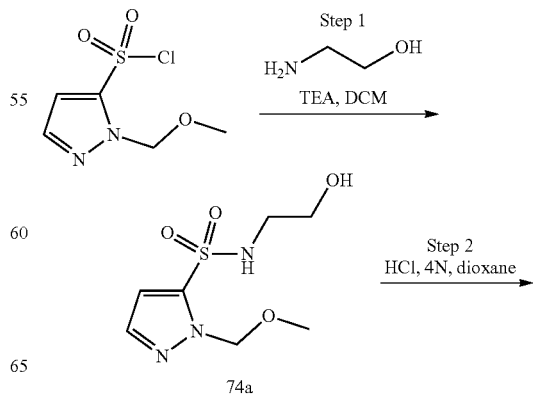

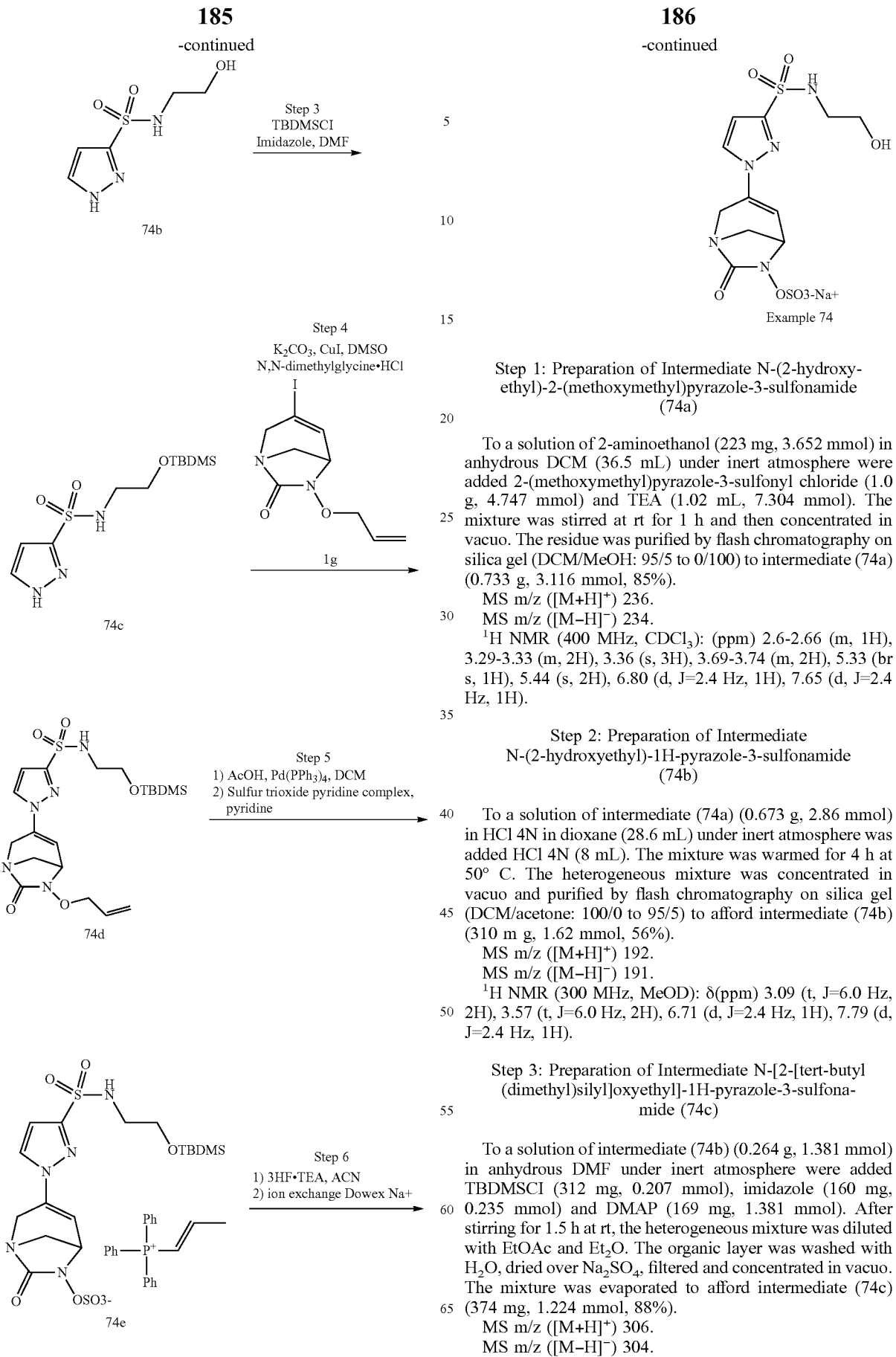

Step 1: Preparation of Intermediate N-(2-hydroxy-ethyl)-2-(methoxymethyl)pyrazole-3-sulfonamide (74a)

To a solution of 2-aminoethanol (223 mg, 3.652 mmol) in anhydrous DCM (36.5 mL) under inert atmosphere were added 2-(methoxymethyl)pyrazole-3-sulfonyl chloride (1.0 g, 4.747 mmol) and TEA (1.02 mL, 7.304 mmol). The mixture was stirred at rt for 1 h and then concentrated in vacuo. The residue was purified by flash chromatography on silica gel (DCM/MeOH: 95/5 to 0/100) to intermediate (74a) (0.733 g, 3.116 mmol, 85%).

MS m/z ([M+H]$^+$) 236.
MS m/z ([M−H]$^−$) 234.
$^1$H NMR (400 MHz, CDCl$_3$): (ppm) 2.6-2.66 (m, 1H), 3.29-3.33 (m, 2H), 3.36 (s, 3H), 3.69-3.74 (m, 2H), 5.33 (br s, 1H), 5.44 (s, 2H), 6.80 (d, J=2.4 Hz, 1H), 7.65 (d, J=2.4 Hz, 1H).

Step 2: Preparation of Intermediate N-(2-hydroxyethyl)-1H-pyrazole-3-sulfonamide (74b)

To a solution of intermediate (74a) (0.673 g, 2.86 mmol) in HCl 4N in dioxane (28.6 mL) under inert atmosphere was added HCl 4N (8 mL). The mixture was warmed for 4 h at 50° C. The heterogeneous mixture was concentrated in vacuo and purified by flash chromatography on silica gel (DCM/acetone: 100/0 to 95/5) to afford intermediate (74b) (310 m g, 1.62 mmol, 56%).

MS m/z ([M+H]$^+$) 192.
MS m/z ([M−H]$^−$) 191.
$^1$H NMR (300 MHz, MeOD): δ(ppm) 3.09 (t, J=6.0 Hz, 2H), 3.57 (t, J=6.0 Hz, 2H), 6.71 (d, J=2.4 Hz, 1H), 7.79 (d, J=2.4 Hz, 1H).

Step 3: Preparation of Intermediate N-[2-[tert-butyl(dimethyl)silyl]oxyethyl]-1H-pyrazole-3-sulfonamide (74c)

To a solution of intermediate (74b) (0.264 g, 1.381 mmol) in anhydrous DMF under inert atmosphere were added TBDMSCl (312 mg, 0.207 mmol), imidazole (160 mg, 0.235 mmol) and DMAP (169 mg, 1.381 mmol). After stirring for 1.5 h at rt, the heterogeneous mixture was diluted with EtOAc and Et$_2$O. The organic layer was washed with H$_2$O, dried over Na$_2$SO$_4$, filtered and concentrated in vacuo. The mixture was evaporated to afford intermediate (74c) (374 mg, 1.224 mmol, 88%).

MS m/z ([M+H]$^+$) 306.
MS m/z ([M−H]$^−$) 304.

Step 4: Preparation of Intermediate 1-(6-allyloxy-7-oxo-1,6-diazabicyclo[3.2.1]oct-3-en-3-yl)-N-[2-[tert-butyl(dimethyl)silyl]oxyethyl]pyrazole-4-sulfonamide (74d)

Using the procedure described in example 1 (step 7), intermediate (1g) (266 mg, 0.868 mmol) was converted by reaction with intermediate (74c) (371 mg, 1.273 mmol) into intermediate (74d) (96 mg, 0.198 mmol, 23%) after purification by flash chromatography on C18-reversed phase silica gel (DCM/acetone: 100/0 to 70/30).

MS m/z ([M+H]$^+$) 484.

MS m/z ([M−H]$^−$) 482.

$^1$H NMR (400 MHz, CDCl$_3$): δ(ppm) 0.05 (s, 6H), 0.08 (s, 9H), 3.13 (d, J=10.9 Hz, 1H), 3.20 (q, J=5.6 Hz, 2H), 3.55 (dd, J=10.6, 2.4 Hz, 1H), 3.69-3.74 (m, 2H), 4.13 (dd, J=5.5, 2.5 Hz, 1H), 4.16-4.25 (m, 1H), 4.38-4.50 (m, 3H), 4.99 (t, J=5.9 Hz, 1H), 5.31-5.41 (m, 2H), 5.97-6.07 (m, 1H), 6.61 (d, J=5.3 Hz, 1H), 6.78 (d, J=2.6 Hz, 1H), 7.61 (d, J=2.6 Hz, 1H).

Step 5: Preparation of Intermediate triphenyl-[(E)-prop-1-enyl]phosphonium [3-[4-[2-[tert-butyl(dimethyl)silyl]oxyethylsulfamoyl]pyrazol-1-yl]-7-oxo-1,6-diazabicyclo[3.2.1]oct-3-en-6-yl]sulfate (74e)

Intermediate (74d) (100 mg, 0.207 mmol) was dissolved in anhydrous DCM (1.5 mL). AcOH (2 μL, 0.414 mmol) and Pd(PPh$_3$)$_4$ (120 mg, 0.103 mmol) were added successively and stirred for 45 min at rt. Pyridine (1.2 mL) and sulfur trioxide pyridine complex (165 mg, 1.036 mmol) were added and stirred for 18 h. The heterogeneous mixture was concentrated in vacuo, DCM was added to the residue and the salts were filtered. The filtrate was purified by flash chromatography on silica gel (DCM/acetone: 100/0 to 0/100) to afford intermediate (74e) (49 mg, 0.059 mmol, 28% over 2 steps).

MS m/z ([M+H]$^+$) 524.

MS m/z ([M−H]$^−$) 522.

Step 6: Preparation of sodium [3-[4-(2-hydroxyethylsulfamoyl)pyrazol-1-yl]-7-oxo-1,6-diazabicyclo[3.2.1]oct-3-en-6-yl]sulfate (Example 74)

To a solution of intermediate (74e) (49 mg, 0.059 mmol) in ACN (590 μL) under inert atmosphere was added 3HF.TEA (10 μL, 0.059 mmol). After stirring for 18 h at rt, the mixture was concentrated in vacuo. The crude was dissolved in a mixture 8/2 H$_2$O/ACN and applied on Dowex sodium form column (Dowex® 50WX8 hydrogen form stored with an aqueous solution of 2N NaOH and washed until neutral pH with H$_2$O). The fractions containing the desired compound were combined, freezed and lyophilized. MeOH was added to the residue and the solids were filtered off. The filtrate was concentrated in vacuo to afford example (74) (22 mg, 0.050 mmol, 85%).

MS m/z ([M+H]$^+$) 410.

MS m/z ([M−H]$^−$) 408.

$^1$H NMR (400 MHz, D$_2$O): δ(ppm) 3.12 (t, J=5.4 Hz, 2H), 3.42 (d, J=11.3 Hz, 1H), 3.59 (t, J=5.4 Hz, 2H), 3.67 (dd, J=11.4, 2.2 Hz, 1H), 4.36 (d, J=3.5 Hz, 2H), 4.58 (dd, J=5.6, 2.6 Hz, 1H), 6.77 (d, J=5.0 Hz, 1H), 6.85 (d, J=2.7 Hz, 1H), 8.06 (d, J=2.7 Hz, 1H).

Example 76: Synthesis of sodium [3-[3-[(1S)-1,2-dihydroxyethyl]pyrazol-1-yl]-7-oxo-1,6-diazabicyclo[3.2.1]oct-3-en-6-yl]sulfate

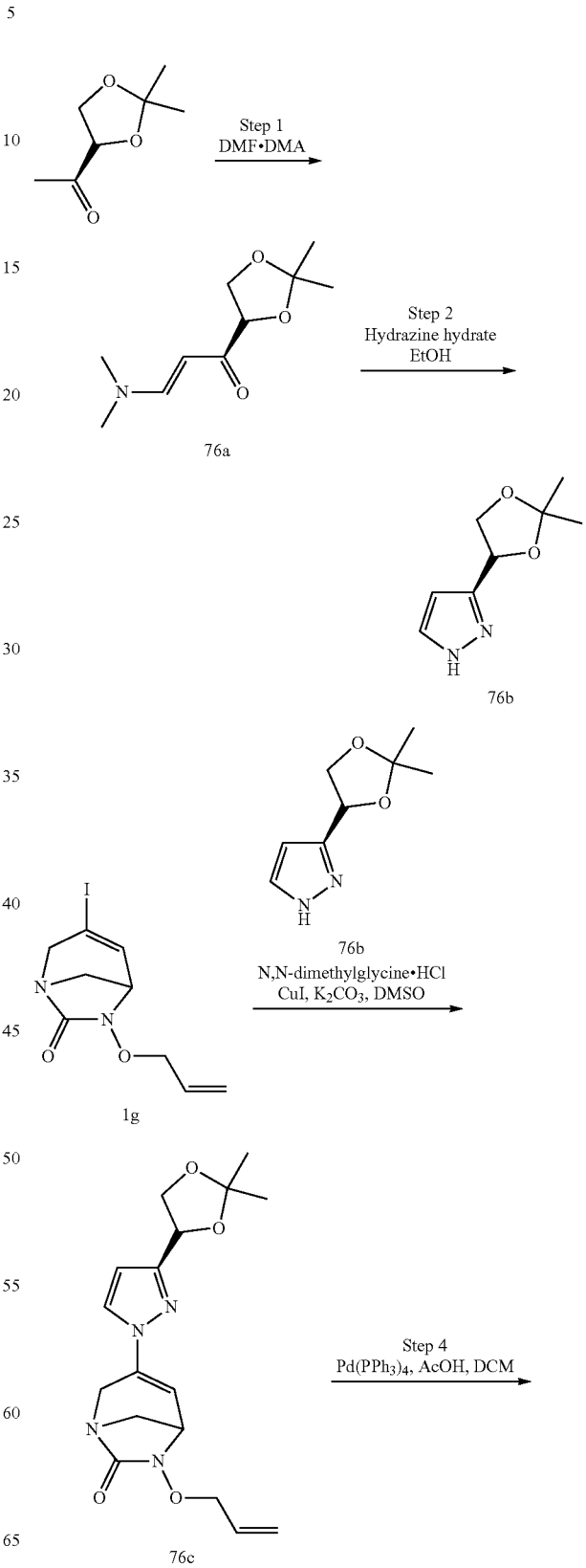

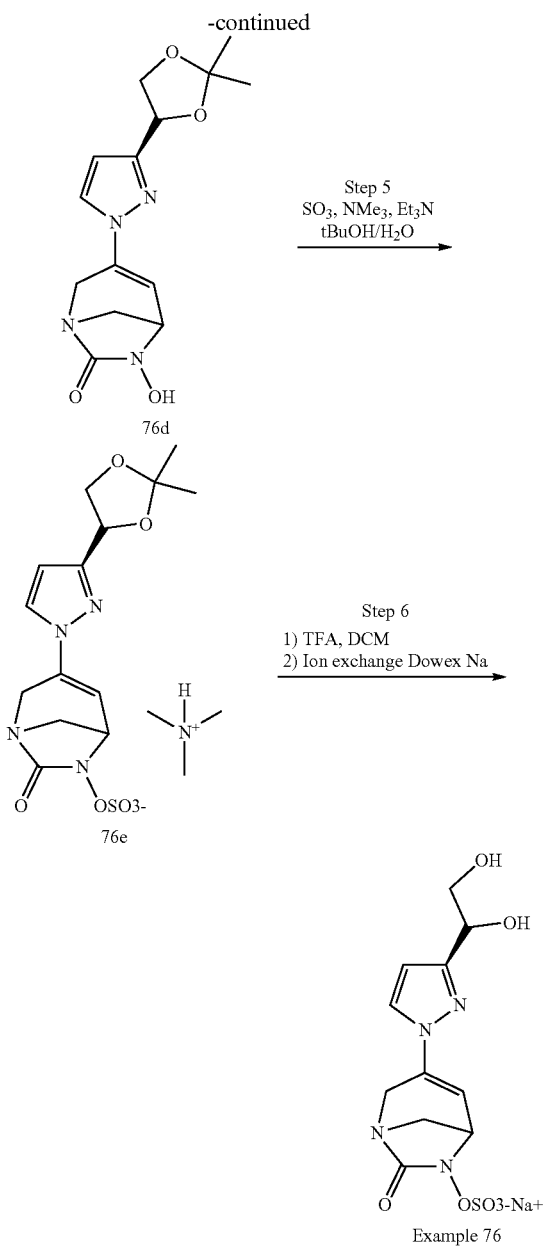

Step 5
SO₃, NMe₃, Et₃N
tBuOH/H₂O

Step 6
1) TFA, DCM
2) Ion exchange Dowex Na

Example 76

Step 1: Preparation of Intermediate (E)-3-(dimethylamino)-1-[(4R)-2,2-dimethyl-1,3-dioxolan-4-yl]prop-2-en-1-one (76a)

1-[(4R)-2,2-Dimethyl-1,3-dioxolan-4-yl]ethanone (obtained according to the protocol described in *Organic Letters*, 1999, 1 (7), 1067) (1.27 g, 8.64 mmol) in N,N-dimethylformamide dimethyl acetal (9.6 mL) was heated at 100° C. for 23 h. The reaction was poured into water (50 mL) and mixture was extracted with DCM (4×20 mL). The combined organic layers were dried with Na₂SO₄, and the solvent removed at reduced pressure. The residue was purified by chromatography on silica gel (DCM/acetone: 100/0 to 50/50) to provide intermediate (76a) (3.31 g, 6.32 mmol, 73%) as an orange oil contaminated with DMF.
¹H NMR (400 MHz, CDCl₃): δ (ppm) 1.43 (s, 3H), 1.50 (s, 3H), 2.89 (s, 3H), 2.97 (s, 3H), 3.99 (dd, J=8.4, 6.4 Hz, 1H), 4.27 (dd, J=8.4, 7.5 Hz, 1H), 4.48 (dd, J=7.5, 6.4 Hz, 1H), 5.49 (d, J=12.7 Hz, 1H), 7.70 (d, J=12.7 Hz, 1H).

Step 2: Preparation of Intermediate 3-[(4S)-2,2-dimethyl-1,3-dioxolan-4-yl]-1H-pyrazole (76b)

A mixture of intermediate (76a) (3.31 g, 6.32 mmol) and 50% aqueous solution of hydrazine hydrate (1.23 mL, 12.6 mmol) was dissolved in EtOH (63 mL). After stirring for 1 h at 90° C., the mixture was concentrated in vacuo. The residue was purified by flash chromatography on silica gel (cyclohexane/EtOAc: 100/0 to 0/100) to provide intermediate (76b) (832 mg, 4.45 mmol, 70%) as a yellow oil.
¹H NMR (400 MHz, CDCl₃): δ (ppm) 1.40 (br s, 3H), 1.43 (br s, 3H), 3.92 (dd, J=8.2, 7.2 Hz, 1H), 4.25 (dd, J=8.2, 6.3 Hz, 1H), 5.16 (dd, J=7.2, 6.3 Hz, 1H), 6.27 (d, J=2.3 Hz, 1H), 7.48 (d, J=2.3 Hz, 1H).

Step 3: Preparation of Intermediate 6-allyloxy-3-[3-[(4S)-2,2-dimethyl-1,3-dioxolan-4-yl]pyrazol-1-yl]-1,6-diazabicyclo[3.2.1]oct-3-en-7-one (76c)

Using the procedure described in example 1 (step 7), intermediate (1g) (250 mg, 0.82 mmol) was converted by reaction with intermediate (76b) (165 mg, 0.98 mmol) into intermediate (76c) (163 mg, 0.36 mmol, 44%) as a brown oil after purification by chromatography on silica gel (cyclohexane/EtOAc: 100/0 to 0/100).
MS m/z ([M+H]⁺) 347.
¹H NMR (400 MHz, CDCl₃): δ (ppm) 1.46 (s, 3H), 1.50 (s, 3H), 3.15 (d, J=10.8 Hz, 1H), 3.54 (ddd, J=10.8, 3.1, 1.0 Hz, 1H), 3.99 (dd, J=8.4, 7.2 Hz, 1H), 4.10 (dd, J=5.6, 2.7 Hz, 1H), 4.14-4.22 (m, 1H), 4.27-4.36 (m, 1H), 4.38-4.52 (m, 3H), 5.14 (t, J=6.8 Hz, 1H), 5.30-5.42 (m, 2H), 5.97-6.11 (m, 1H), 6.40-6.43 (m, 1H), 6.43-6.48 (m, 1H), 7.54-7.59 (m, 1H).

Step 4: Preparation of Intermediate 6-hydroxy-3-[3-[(4S)-2,2-dimethyl-1,3-dioxolan-4-yl]pyrazol-1-yl]-1,6-diazabicyclo[3.2.1]oct-3-en-7-one (76d)

A solution of intermediate (76c) (163 mg, 0.36 mmol) in anhydrous DCM (3.6 mL) was degazed for 10 min under argon atmosphere. AcOH (41 µL, 0.72 mmol) and Pd(PPh₃)₄ (210 mg, 0.18 mmol) were successively added. After stirring for 1 h30 at rt, AcOH (10 µL, 0.17 mmol) and Pd(PPh₃)₄ (50 mg, 0.04 mmol) were successively added. After stirring an additional 2 h at rt, the mixture was concentrated in vacuo. The residue was purified by flash chromatography on silica gel (DCM/acetone: 100/0 to 0/100) to provide intermediate (76d) (95 mg) as a yellow oil contaminated with triphenylphosphine oxide.
MS m/z ([M+H]⁺) 307.

Step 5: Preparation of Intermediate trimethylammonium [3-[3-[(4S)-2,2-dimethyl-1,3-dioxolan-4-yl]pyrazol-1-yl]-7-oxo-1,6-diazabicyclo[3.2.1]oct-3-en-6-yl]sulfate (76e)

To a solution of intermediate (76d) (95 mg) in tBuOH (1.1 mL) and water (1.1 mL) under inert atmosphere was added sulfur trioxide trimethylamine complex (36 mg, 0.26 mmol) and triethylamine (8 µL, 0.05 mmol). After stirring for 16 h, the heterogeneous mixture was concentrated in vacuo. The crude was purified by flash chromatography on C18-reversed phase silica gel (water/ACN: 98/2 to 0/100) to provide intermediate (76e) (46 mg, 0.10 mmol, 28% over 2 steps) as a brown powder.

MS m/z ([M+H]⁺) 387/307.
MS m/z ([M−H]⁻) 385.

Step 6: Preparation of sodium [3-[3-[(1 S)-1,2-dihydroxyethyl]pyrazol-1-yl]-7-oxo-1,6-diazabicyclo[3.2.1]oct-3-en-6-yl]sulfate (example 76)

Intermediate (76e) (46 mg, 0.10 mmol) was dissolved in a mixture DCM/TFA (3:1) (260 µL) at 0° C. under inert atmosphere. After stirring for 1 h15, cold Et₂O (3 mL) was added at 0° C. After stirring for 10 min at 0° C., the precipitate was filtered and washed with cold Et₂O and cold ACN. The filtrate was concentrated in vacuo. This solid was applied on a Dowex sodium form column (Dowex® 50WX8 hydrogen form stored with an aqueous solution of 2N NaOH and washed until neutral pH with H₂O). The fractions containing the desired compound were combined, freezed and lyophilized to provide a white solid which was purified by flash chromatography on C18-reversed phase silica gel (water/ACN: 99/1 to 95/5) to provide example (76) (0.5 mg, 0.0001 mmol, 1%) as a white powder contaminated with (1 S)-1-(1H-pyrazol-3-yl)ethane-1,2-diol.

MS m/z ([M+H]⁺) 347.
MS m/z ([M−H]⁻) 345.
¹H NMR (400 MHz, D₂O): δ(ppm) 3.39 (d, J=11.4 Hz, 1H), 3.63 (dd, J=11.4, 2.7 Hz, 1H), 3.70-3.82 (m, 2H), 4.29-4.33 (m, 2H), 4.51 (dd, J=5.7, 2.7 Hz, 1H), 4.74-4.86 (m, 1H), 6.44 (d, J=2.7 Hz, 1H), 6.55 (d, J=5.6 Hz, 1H), 7.82 (d, J=2.7 Hz, 1H).

Example 77: Synthesis of [3-[3-[thiazole-5-carbonyl]amino]pyrazol-1-yl]-7-oxo-1,6-diazabicyclo[3.2.1]oct-3-en-6-yl]hydrogen sulfate

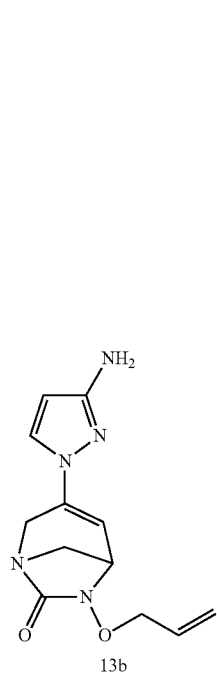

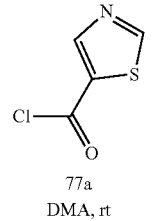

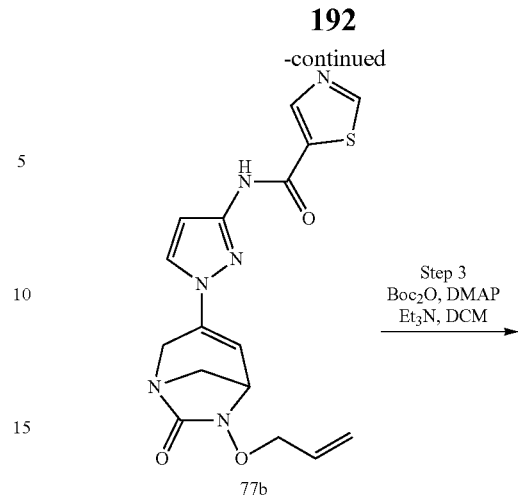

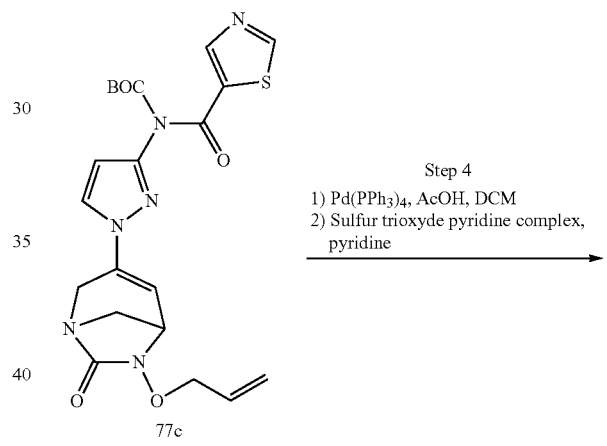

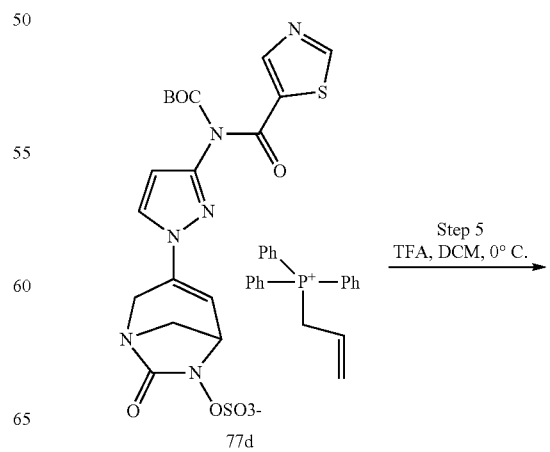

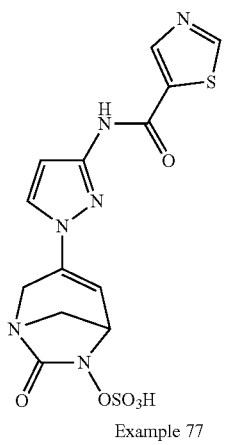

Example 77

Step 1: Preparation of Intermediate 5-thiazolecarbonyl chloride (77a)

In a sealed tube a solution of 5-thiazolecarboxylic acid (400 mg, 3.10 mmol) in thionyl chloride (2.3 mL) was heated at 80° C. for 5 h. The mixture was then concentrated under reduced pressure (twice co-evaporated with toluene) to provide intermediate (77a) (422 mg, 2.87 mmol, 92%) as a yellow solid which was used without further purification.

Step 2: Preparation of Intermediate 5-[[N-[6-allyloxy-7-oxo-1,6-diazabicyclo[3.2.1]oct-3-en-3-yl]]pyrazol-3-yl]carbamoyl]thiazol-2-yl (77b)

To a solution of intermediate (13b) (100 mg, 0.38 mmol) in DMA (1 mL) under inert atmosphere at 0° C. was dropwisely added a solution of intermediate (77a) (84 mg, 0.57 mmol) in DMA (0.9 mL). After stirring for 45 min at rt, the mixture was quenched with water (20 mL) and stirred at 0° C. for 10 min. The formed precipitate was filtered, washed twice with water and then pentane, dried under reduced pressure to provide intermediate (77b) (87 mg, 0.23 mmol, 61%) as an off-white solid.

MS m/z ([M+H]$^+$) 373.

$^1$H NMR (400 MHz, DMSO-d$_6$) δ(ppm): 3.28 (d, J=10.8 Hz, 1H), 3.33 (dd, J=10.8, 2.1 Hz, 1H), 4.21-4.25 (m, 2H), 4.29 (dd, J=5.6, 2.4 Hz, 1H), 4.37-4.41 (m, 2H), 5.27 (dd, J=10.4, 1.6 Hz, 1H), 5.37 (dd, J=17.3, 1.6 Hz, 1H), 5.91-6.01 (m, 1H), 6.55 (d, J=5.6 Hz, 1H), 6.79 (d, J=2.6 Hz, 1H), 8.11 (d, J=2.6 Hz, 1H), 8.79 (s, 1H), 9.29 (s, 1H), 11.43 (br s, 1H).

Step 3: Preparation of Intermediate tert-butyl N-[5-[[N-[6-allyloxy-7-oxo-1,6-diazabicyclo[3.2.1]oct-3-en-3-yl]pyrazol-3-yl]carbamoyl]thiazol-2-yl]carbamate (77c)

To a solution of intermediate (77b) (72 mg, 0.19 mmol) in DCM (1.9 mL) under inert atmosphere at rt were successively added Boc$_2$O (63 mg, 0.29 mmol), Et$_3$N (41 μL, 0.29 mmol) and DMAP (24 mg, 0.19 mmol). After stirring at rt for 4 h, the mixture was concentrated to dryness. The residue was purified by flash chromatography on silica gel (DCM/EtOAc: 100/0 to 0/100) to provide intermediate (77c) (63 mg, 0.13 mmol, 64%) as an orange solid.

MS m/z ([M+H]$^+$) 473.

$^1$H NMR (300 MHz, CDCl$_3$) δ(ppm): 1.45 (s, 9H), 3.10 (d, J=10.8 Hz, 1H), 3.51 (dd, J=10.8, 1.8 Hz, 1H), 4.08 (dd, J=5.6, 2.5 Hz, 1H), 4.11 (dd, J=17.8, 1.8 Hz, 1H), 4.32 (dd, J=17.8, 1.1 Hz, 1H), 4.36-4.48 (m, 2H), 5.31 (dd, J=10.3, 1.5 Hz, 1H), 5.36 (dd, J=17.2, 1.5 Hz, 1H), 5.96-6.06 (m, 1H), 6.37 (d, J=2.6 Hz, 1H), 6.44 (d, J=5.6 Hz, 1H), 7.60 (d, J=2.6 Hz, 1H), 8.23 (d, J=0.7 Hz, 1H), 8.91 (d, J=0.7 Hz, 1H).

Step 4: Preparation of Intermediate triphenyl(allyl)phosphonium [3-[3-[tert-butoxycarbonyl-[thiazole-5-carbonyl]amino]pyrazol-1-yl]-7-oxo-1,6-diazabicyclo[3.2.1]oct-3-en-6-yl]sulfate (77d)

Using the procedure described in example (2) (step 2), intermediate (77c) (63 mg, 0.13 mmol) was converted into intermediate (77d) (9 mg, 0.011 mmol, 98%) as a white solid after purification on silica gel (DCM/Acetone 100/0 to 0/100).

MS m/z ([M+H]$^+$) 513/433.
MS m/z ([M−H]$^-$) 511.

Step 5: Preparation of [3-[3-[thiazole-5-carbonyl]amino]pyrazol-1-yl]-7-oxo-1,6-diazabicyclo[3.2.1]oct-3-en-6-yl]hydrogen sulfate (Example 77)

A solution of intermediate (77d) (9 mg, 0.011 mmol) in a mixture DCM/TFA (3:1) (0.6 mL) under inert atmosphere at 0° C. was stirred for 1 h then Et$_2$O (1 mL) was added and the stirring at 0° C. continued for 5 min. Then solvents were taken off from the mixture and Et$_2$O (1 mL) was added to the residue and the stirring at rt continued for 5 min. This sequence was done twice with Et$_2$O (1 mL) and then twice with ACN (1 mL) to provide example (77) (0.5 mg, 0.001 mmol, 1%) as a white solid after purification by flash chromatography on C18-reversed phase silica gel (ACN/water: 2/98 to 30/70).

MS m/z ([M+H]$^+$) 413.

$^1$H NMR (300 MHz, D$_2$O) δ(ppm): 2.94 (d, J=12.8 Hz, 1H), 3.25 (d, J=12.8, 1.8 Hz, 1H), 3.47 (d, J=11.2 Hz, 1H), 3.72 (dd, J=11.2, 1.8 Hz, 1H), 4.60 (dd, J=5.7, 2.6 Hz, 1H), 6.64 (d, J=5.7 Hz, 1H), 6.73 (d, J=2.7 Hz, 1H), 7.90 (d, J=2.7 Hz, 1H), 8.55 (s, 1H), 9.22 (s, 1H).

Example 78: Synthesis of sodium [3-(2-oxazolyl)pyrazol-1-yl]-7-oxo-1,6-diazabicyclo[3.2.1]oct-3-en-6-yl]sulfate

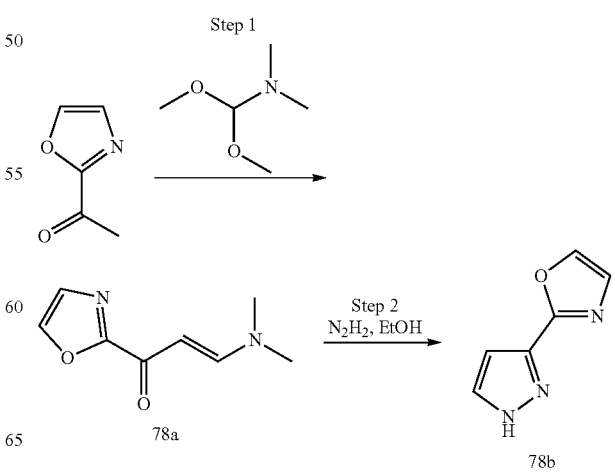

Step 2: Preparation of Intermediate 3-(2-oxazolyl)-1H-pyrazole (78b)

In a flask equipped with a condenser, intermediate (78a) (656 mg, 3.95 mmol) was solubilized in EtOH (39 mL). Hydrazine (0.76 mL, 7.77 mmol) was added and the mixture was heated at 90° C. After 1 h reaction, the mixture was concentrated. The residue was purified by flash chromatography on silica gel (DCM/acetone: 100/0 to 20/80) to give intermediate (78b) (374 mg, 2.77 mmol, 70%) as a yellow solid.

MS m/z ([M+H]$^+$) 136.
MS m/z ([M−H]$^−$) 134.
$^1$H NMR (400 MHz, CDCl$_3$) δ 6.92 (d, J=2.3 Hz, 1H), 7.31 (d, J=0.8 Hz, 1H), 7.75 (d, J=0.8 Hz, 1H), 7.85 (d, J=2.3 Hz, 1H), 8.22 (bs, 1H).

Step 3: Preparation of Intermediate 6-allyloxy-3-[3-(2-oxazolyl)pyrazol-1-yl]-1,6-diazabicyclo[3.2.1]oct-3-en-7-one (78c)

Under inert atmosphere, intermediate (1g) (200 mg, 0.653 mmol) was diluted with anhydrous DMSO (6.5 mL). Intermediate (78b) (106 mg, 0.784 mmol), dry K$_2$CO$_3$ (271 mg, 1.96 mmol), CuI (12 mg, 0.065 mmol) and N,N-dimethylglycine hydrochloride salt (14 mg, 0.098 mmol) were successively added. The blue suspension was heated at 100° C. After 18 h, the mixture was diluted in H$_2$O (20 mL) and EtOAc (20 mL) was added. The aqueous layer was extracted with EtOAc (5×20 mL) and the combined organic layers were washed with H$_2$O and then dried over Na$_2$SO$_4$, filtered and concentrated. The crude compound was purified by flash chromatography on silica gel (DCM/acetone: 100/0 to 50/50) to give intermediate (78c) (55 mg, 0.176 mmol, 25%) as a yellow oil.

MS m/z ([M+H]$^+$) 314.
MS m/z ([M−H]$^−$) 312.
$^1$H NMR (400 MHz, CDCl$_3$) δ3.16 (d, J=10.8 Hz, 1H), 3.56 (d, J=10.8 Hz, 1H), 4.13 (dd, J=5.5/2.5 Hz, 1H), 4.30 (dd, J=17.8/2.5 Hz, 1H), 4.38-4.50 (m, 2H), 4.51 (d, J=17.8 Hz, 1H), 5.31 (ddd, J=10.3/1.7/1.0 Hz, 1H), 5.38 (ddd, J=17.2/1.7/1.4 Hz, 1H), 5.97-6.07 (m, 1H), 6.62 (d, J=5.5 Hz, 1H), 6.94 (d, J=2.6 Hz, 1H), 7.24 (s, 1H), 7.68 (d, J=2.6 Hz, 1H), 7.73 (s, 1H).

Step 4: Preparation of sodium [3-(2-oxazolyl)pyrazol-1-yl-7-oxo-1,6-diazabicyclo[3.2.1]oct-3-en-6-yl] sulfate (Example 78)

Under inert atmosphere, intermediate (78c) (49 mg, 0.156 mmol) was diluted in anhydrous DCM (1.6 mL). AcOH (18 μL, 0.316 mmol) and Pd(PPh$_3$)$_4$ (91 mg, 0.078 mmol) were successively added. The reaction mixture was stirred at rt for 2 h. Then, anhydrous pyridine (1.6 mL) and sulfur trioxide pyridine complex (125 mg, 0.782 mmol) were added to the reaction mixture. The resulting suspension was protected from light and stirred overnight until the reaction was completed. The reaction mixture was concentrated and triturated with DCM then filtered. The filtrate was concentrated then purified by flash chromatography on silica gel (DCM/acetone: 100/0 to 0/100). Fractions containing the product were combined and concentrated. The residue was dissolved in a minimum of H$_2$O/ACN (2:1) and converted after ion exchange with Dowex sodium form column (Dowex® 50WX8 hydrogen form stored with an aqueous solution of

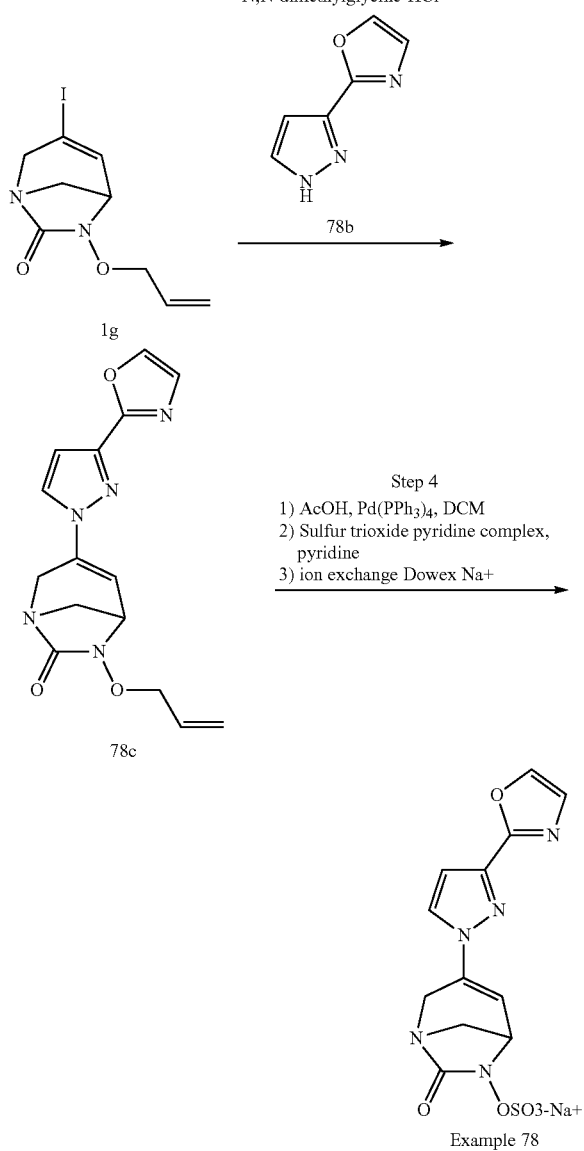

Step 1: Preparation of Intermediate (E)-3-(dimethylamino)-1-(2-oxazolyl)-prop-2-en-1-one (78a)

Under inert atmosphere, 1-(oxazol-2-yl)ethanone (500 mg, 4.50 mmol) was diluted in N,N-dimethylformamide dimethyl acetal (0.74 mL, 5.60 mmol). The mixture reaction was heated at 100° C. for 16 h. The mixture was then diluted with H$_2$O (5 mL) and DCM (5 mL) was added. The aqueous layer was extracted with DCM (5×5 mL) and the combined organic layers were dried over Na$_2$SO$_4$, filtered and concentrated to give intermediate (78a) (656 mg, 3.95 mmol, 88%) as an orange solid.

MS m/z ([M+H]$^+$) 167.
$^1$H NMR (400 MHz, CDCl$_3$) δ 2.96 (s, 3H), 3.18 (s, 3H), 6.01 (d, J=10.3 Hz, 1H), 7.23 (d, J=0.7 Hz, 1H), 7.74 (d, J=0.7 Hz, 1H), 7.93 (d, J=10.3 Hz, 1H).

2N NaOH and washed until neutral pH with H₂O) to provide example (78) (18 mg, 0.043 mmol, 36%) as an off-white solid.

MS m/z ([M+H]⁺) 354/274.

MS m/z ([M−H]⁻) 352.

¹H NMR (400 MHz, D₂O) δ 3.50 (d, J=11.3 Hz, 1H), 3.74 (dd, J=11.3/2.6 Hz, 1H), 4.42-4.48 (m, 2H), 4.64 (dd, J=5.6/2.6 Hz, 1H), 6.78 (d, J=5.6 Hz, 1H), 6.97 (d, J=2.7 Hz, 1H), 7.33 (t, J=0.9 Hz, 1H), 7.97 (d, J=0.9 Hz, 1H), 8.04 (d, J=2.7 Hz, 1H).

Example 79: Synthesis of [7-oxo-3-[3-(1,2,4-thiadiazol-5-ylcarbamoyl)pyrazol-1-yl]-1,6-diazabicyclo[3.2.1]oct-3-en-6-yl]hydrogen sulfate

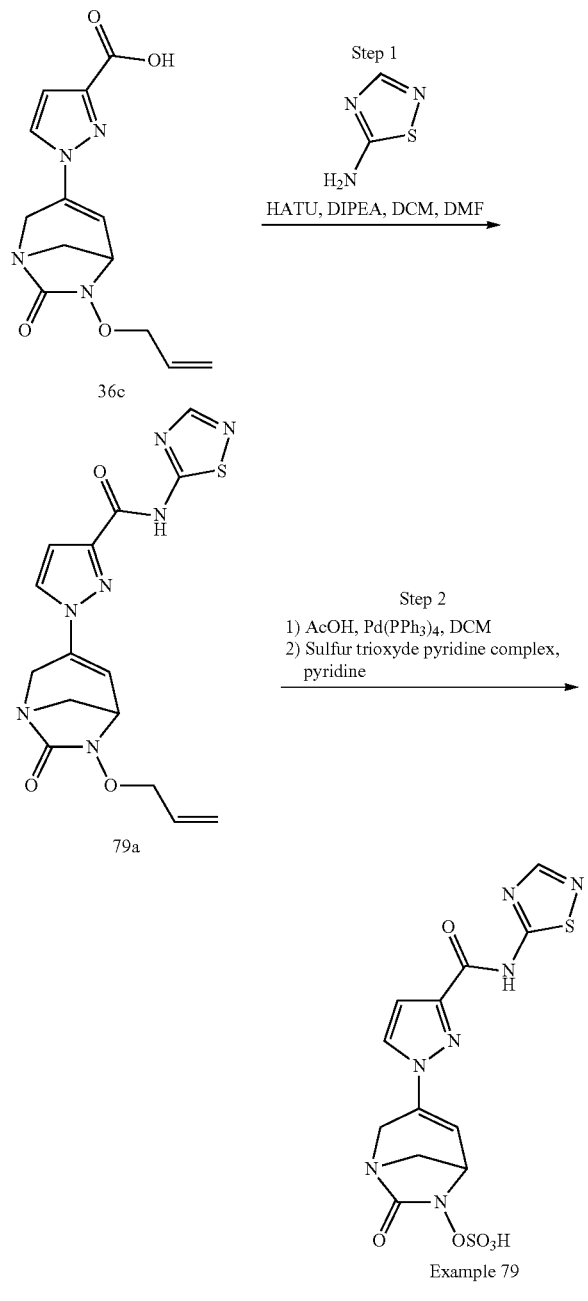

Step 1: Preparation of Intermediate 1-(6-allyloxy-7-oxo-1,6-diazabicyclo[3.2.1]oct-3-en-3-yl)-N-(1,2,4-thiadiazol-5-yl)pyrazole-3-carboxamide (79a)

Under inert atmosphere, intermediate (36c) (150 mg, 0.52 mmol) was diluted in a mixture of anhydrous DMF (3 mL). HATU (198 mg, 0.52 mmol), DIPEA (91 μL, 0.52 mmol) and 1,2,4-thiadiazol-5-amine (53 mg, 0.52 mmol) were successively added. The reaction mixture was stirred overnight at rt. Then the mixture was diluted with H₂O. The aqueous layer was extracted with EtOAc. The organic layers were combined, washed with a satured NaHCO₃, dried over Na₂SO₄, filtered and concentrated. The crude compound was purified by flash chromatography on silica gel (DCM/acetone: 100/0 to 60/40) to provide intermediate (79a) (194 mg, 0.71 mmol, quantitative yield) as a colorless oil.

MS m/z ([M+H]⁺) 374.

MS m/z ([M−H]⁻) 372.

¹H-NMR (400 MHz, CDCl₃): δ (ppm) 3.18 (d, J=11.0 Hz, 1H), 3.59 (dd, J=2.1, 11.0 Hz, 1H), 4.18 (dd, J=2.6, 5.5 Hz, 1H), 4.23 (dd, J=1.9, 17.6 Hz, 1H), 4.40-4.50 (m, 3H), 5.30-5.42 (m, 2H), 5.98-6.08 (m, 1H), 6.67 (d, J=5.6 Hz, 1H), 6.68 (br s, 1H), 7.07 (d, J=2.6 Hz, 1H), 7.76 (d, J=2.6 Hz, 1H), 8.37 (s, 1H).

Step 2: Preparation of [7-oxo-3-[3-(1,2,4-thiadiazol-5-ylcarbamoyl)pyrazol-1-yl]-1,6-diazabicyclo[3.2.1]oct-3-en-6-yl]hydrogen sulfate (Example 79)

To a solution of intermediate (79a) (130 mg, 0.35 mmol) in anhydrous DCM (3 mL) were added glacial AcOH (40 μL, 0.70 mmol) and Pd(PPh₃)₄ (203 mg, 0.18 mmol). The mixture was stirred at rt for 2 h then pyridine (3 mL) and sulfur trioxyde pyridine complex (280 mg, 1.75 mmol) were added. The resulting suspension was protected from light and stirred overnight. The reaction mixture was concentrated, then diluted with DCM and filtered. The filtrate was concentrated in vacuo then purified by flash chromatography on silica gel (DCM/acetone: 100/0 to 0/100). The solid was triturated with ACN to afford example (79) (14 mg, 0.03 mmol, 10% over two steps) as a beige solid.

MS m/z ([M+H]⁺) 414.

MS m/z ([M−H]⁻) 412.

¹H-NMR (300 MHz, D₂O): δ (ppm) 3.50 (d, J=11.4 Hz, 1H), 3.75 (d, J=11.4 Hz, 1H), 4.46 (m, 2H), 4.66 (dd, J=2.4, 5.6 Hz, 1H), 6.81 (d, J=5.6 Hz, 1H), 7.07 (d, J=2.6 Hz, 1H), 8.05 (d, J=2.6 Hz, 1H), 8.41 (s, 1H).

Example 80: Synthesis of sodium [7-oxo-3-[3-(2-pyridylcarbamoyl)pyrazol-1-yl]-1,6-diazabicyclo[3.2.1]oct-3-en-6-yl]sulfate

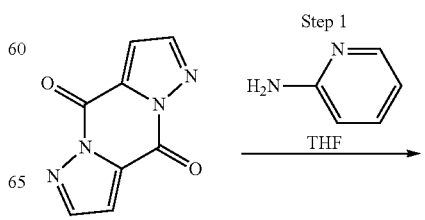

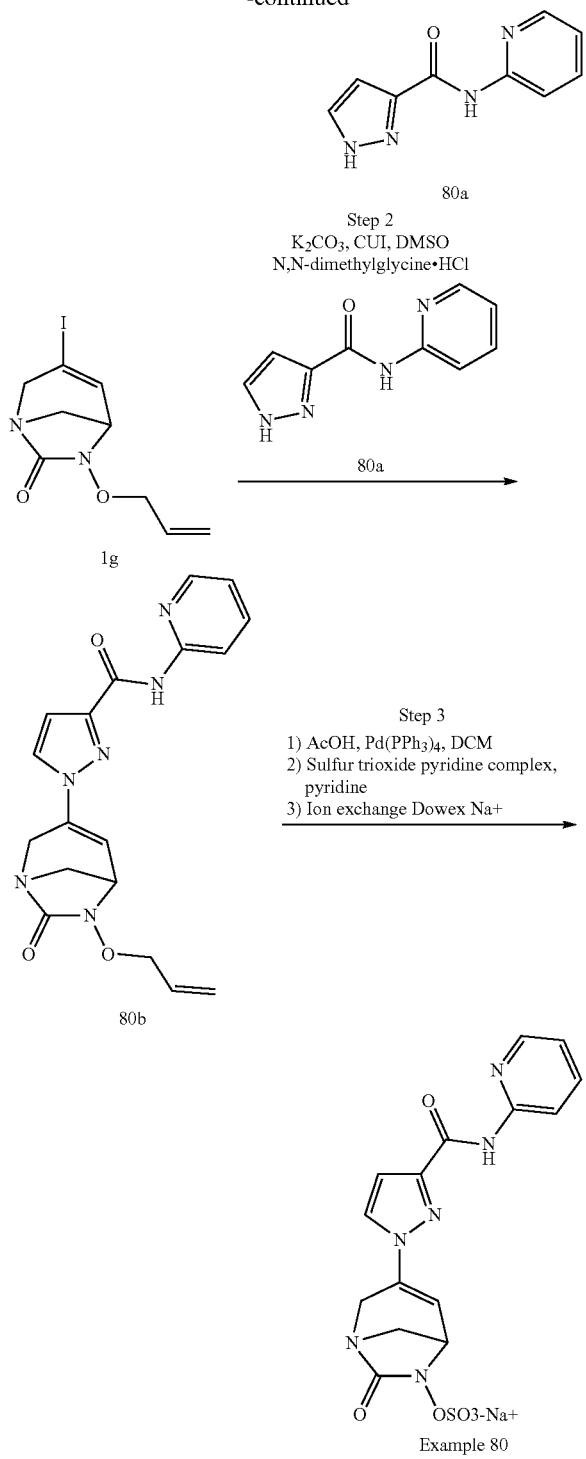

Step 1: Preparation of Intermediate
N-(2-pyridyl)-1H-pyrazole-3-carboxamide (80a)

Diketopiperazine (200 mg, 1.06 mmol) and 2-aminopyridine (300 mg, 3.19 mmol) were diluted in THF (2 mL). The mixture reaction was heated at 70° C. for 4 h. After cooling down to rt, the mixture was filtered, washed with ACN and Et$_2$O to give intermediate (80a) (129 mg, 0.62 mmol, 29%) as a white solid.

MS m/z ([M+H]$^+$) 189.
MS m/z ([M−H]) 187.

$^1$H NMR (400 MHz, CDCl$_3$) δ 7.03 (d, J=2.4 Hz, 1H), 7.16 (ddd, J=7.4/4.4/1.0 Hz, 1H), 7.70 (d, J=2.4 Hz, 1H), 7.86 (ddd, J=8.5/7.4/1.9 Hz, 1H), 8.37 (d, J=4.4 Hz, 1H), 8.53 (d, J=8.5 Hz, H), 10.10 (bs, 1H).

Step 2: Preparation of Intermediate 1-(6-allyloxy-7-oxo-1,6-diazabicyclo[3.2.1]oct-3-en-3-yl)-N-(2-pyridyl)pyrazole-3-carboxamide (80b)

Under inert atmosphere, intermediate (1g) (150 mg, 0.49 mmol) was diluted with anhydrous DMSO (4.9 mL). Intermediate (80a) (111 mg, 0.59 mmol), dry K$_2$CO$_3$ (203 mg, 1.47 mmol), CuI (9 mg, 0.05 mmol) and N,N-dimethylglycine hydrochloride salt (10 mg, 0.07 mmol) were successively added. The blue suspension was heated at 100° C. After 18 h, the mixture was diluted in H$_2$O (20 mL) and EtOAc (20 mL) was added. The aqueous layer was extracted with EtOAc (4×20 mL) and the combined organic layers were dried over Na$_2$SO$_4$, filtered and concentrated. The crude compound was purified by flash chromatography on silica gel (DCM/acetone: 100/0 to 50/50) to give intermediate (80b) (79 mg, 0.19 mmol, 40%) as a yellow oil.

MS m/z ([M+H]$^+$) 367.
MS m/z ([M−H]$^−$) 365.

$^1$H NMR (400 MHz, CDCl$_3$) δ 3.17 (d, J=10.9 Hz, 1H), 3.57 (dd, J=10.9/1.7 Hz, 1H), 4.14 (dd, J=5.6/2.6 Hz, 1H), 4.24 (dd, J=17.6/1.9 Hz, 1H), 4.39-4.51 (m, 2H), 4.50 (d, J=17.6 Hz, 1H), 5.32 (ddd, J=10.3/1.7/1.0 Hz, 1H), 5.38 (ddd, J=17.2/1.7/1.4 Hz, 1H), 5.98-6.08 (m, 1H), 6.63 (d, J=5.6 Hz, 1H), 6.99 (d, J=2.6 Hz, 1H), 7.06 (ddd, J=7.4/4.8/1.1 Hz, 1H), 7.67 (d, J=2.6 Hz, 1H), 7.74 (ddd, J=8.9/7.4/1.7 Hz, 1H), 8.32-8.34 (m, 2H), 9.21 (bs, 1H).

Step 3: Preparation of sodium [7-oxo-3-[3-(2-pyridylcarbamoyl)pyrazol-1-yl]-1,6-diazabicyclo[3.2.1]oct-3-en-6-yl]sulfate (Example 80)

Under inert atmosphere, intermediate (80b) (79 mg, 0.19 mmol) was diluted in anhydrous DCM (2.2 mL). AcOH (25 μL, 0.43 mmol) and Pd(PPh$_3$)$_4$ (125 mg, 0.11 mmol) were successively added. The reaction mixture was stirred at rt for 2 h. Then anhydrous pyridine (2.2 mL) and sulfur trioxide pyridine complex (2 mg, 1.08 mmol) were added to the reacting mixture. The resulting suspension was protected from light and stirred overnight until the reaction was completed. The reaction mixture was concentrated and triturated with DCM then filtered. The filtrate was concentrated then purified by flash chromatography on silica gel (DCM/acetone: 100/0 to 0/100). Fractions containing the product were combined and concentrated. The residue was dissolved in a minimum of H$_2$O/ACN (1:1) and converted after ion exchange with Dowex sodium form column (Dowex® 50WX8 hydrogen form stored with an aqueous solution of 2N NaOH and washed until neutral pH with H$_2$O) to give example (80) (8 mg, 0.02 mmol, 8%) as a yellow solid.

MS m/z ([M+H]$^+$) 407/327.
MS m/z ([M−H]$^−$) 405.

$^1$H NMR (400 MHz, D$_2$O) δ 3.49 (d, J=11.3 Hz, 1H), 3.74 (dd, J=11.3/2.6 Hz, 1H), 4.44 (dd, J=18.1/1.4 Hz, 1H), 4.49 (d, J=18.1 Hz, 1H), 4.64 (dd, J=5.7/2.6 Hz, 1H), 6.77 (d, J=5.7 Hz, 1H), 6.97 (d, J=2.7 Hz, 1H), 7.24-7.30 (m, 1H), 7.88-7.91 (m, 2H), 8.00 (d, J=2.7 Hz, 1H), 8.34 (d, J=5.1 Hz, 1H).

Example 82: Synthesis of [7-oxo-3-[3-[[(3S)-pyrrolidin-3-yl]carbamoyl]pyrazol-1-yl]-1,6-diazabicyclo[3.2.1]oct-3-en-6-yl]hydrogen sulfate

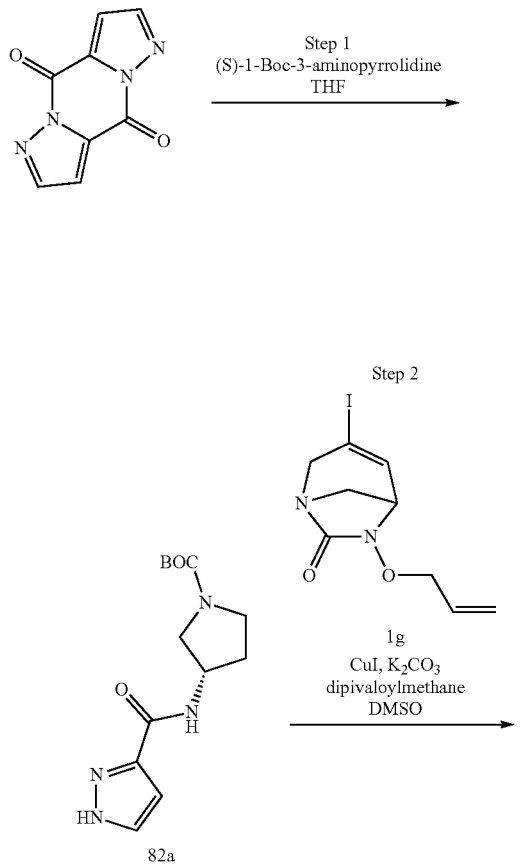

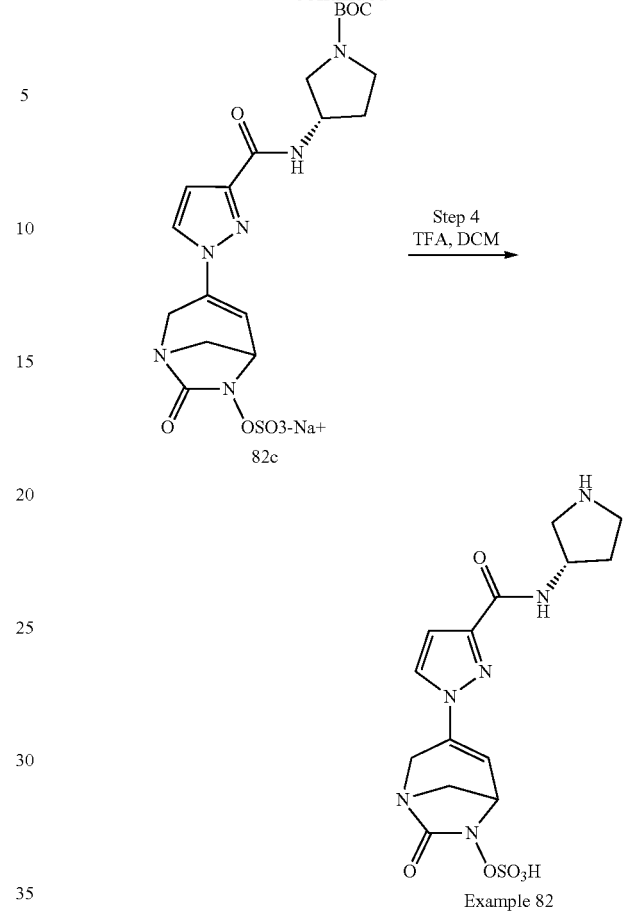

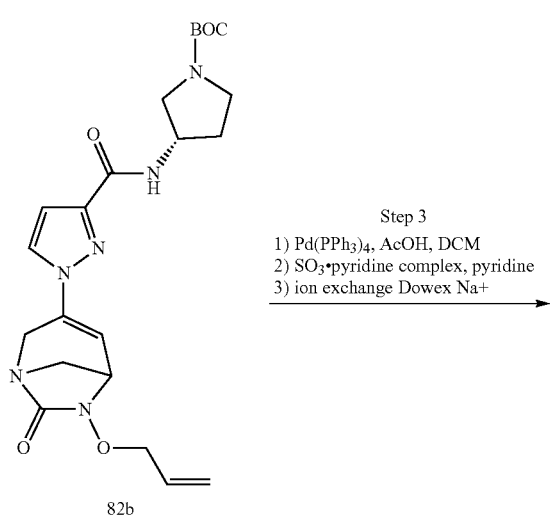

Step 1: Preparation of Intermediate tert-butyl (3S)-3-(1H-pyrazole-3-carbonylamino)pyrrolidine-1-carboxylate (82a)

A mixture of dipyrazolo[3,1-a: 3',1'-d]pyrazine-4,9-dione (200 mg, 1.06 mmol) and (S)-1-Boc-3-aminopyrrolidine (396 mg, 2.12 mmol) in THF (10 mL) was heated at 80° C. for 1 h. The mixture was concentrated in vacuo to provide intermediate (82a) which was used without further purification.

MS m/z ([M−H]⁻) 279.

Step 2: Preparation of Intermediate tert-butyl (3S)-3-[[1-(6-allyloxy-7-oxo-1,6-diazabicyclo[3.2.1]oct-3-en-3-yl)pyrazole-3-carbonyl]amino]pyrrolidine-1-carboxylate (82b)

Using the procedure described in example (2) (step 1a), intermediate (1g) (200 mg, 0.65 mmol) was converted by reaction with intermediate (82a) (192 mg, 0.69 mmol) into intermediate (82b) (190 mg, 0.41 mmol, 63%) after a purification by flash chromatography on silica gel (DCM/acetone 100/0 to 60/40).

MS m/z ([M+H−tBu]⁺) 403, ([M+H−Boc]⁺) 359.

$^1$H NMR (400 MHz, CDCl$_3$) δ 1.47 (s, 9H), 1.87-2.05 (m, 1H), 2.19-2.31 (m, 1H), 3.15 (d, J=10.9 Hz, 1H), 3.19-3.37 (m, 1H), 3.39-3.61 (m, 3H), 3.66-3.79 (m, 1H), 4.04-4.22 (m, 2H), 4.33-4.55 (m, 3H), 4.56-4.68 (m, 1H), 5.23-5.46

(m, 2H), 5.93-6.11 (m, 1H), 6.56 (m, 1H), 6.83 (d, J=2.6 Hz, 1H), 6.88 (d, J=2.6 Hz, 1H), 7.62 (br s, 1H).

Step 3: Preparation of Intermediate sodium [3-[3-[[(3S)-1-tert-butoxycarbonylpyrrolidin-3-yl]carbamoyl]pyrazol-1-yl]-7-oxo-1,6-diazabicyclo[3.2.1]oct-3-en-6-yl]sulfate (82c)

Using the procedure described in example (2) (step 2), intermediate (82b) (190 mg, 0.41 mmol) was converted into intermediate (82c) (103 mg, 0.20 mmol, 48% over 3 steps) as a white solid.
MS m/z ([M]⁻) 497.

Step 4: Preparation of [7-oxo-3-[3-[[(3S)-pyrrolidin-3-yl]carbamoyl]pyrazol-1-yl]-1,6-diazabicyclo[3.2.1]oct-3-en-6-yl]hydrogen sulfate (Example 82)

To a solution of intermediate (82c) (50 mg, 0.10 mmol) in DCM (1 mL) at 0° C. was added TFA (0.5 mL). The mixture was maintained at 0° C. for 1 h. Et₂O was added and the precipitate was filtered. The solid was triturated in ACN then filtered. The solid was then purified by flash chromatography on C18-reversed phase silica gel (water/ACN: 98/2 to 0/100) to provide example (82) (8 mg, 0.02 mmol, 21%) as a mixture of diastereoisomers.
MS m/z ([M+H]⁺) 399.
MS m/z ([M−H]⁻) 397.
¹H NMR (400 MHz, D₂O) δ (ppm) 2.14-2.28 (m, 1H), 2.39-2.53 (m, 1H), 3.38-3.53 (m, 3H), 3.55-3.76 (m, 3H), 4.40 (s, 2H), 4.61 (dd, J=5.7, 2.6 Hz, 1H), 4.64-4.73 (m, 1H), 6.74 (d, J=5.6 Hz, 1H), 6.84 (d, J=2.7 Hz, 1H), 7.94 and 7.95 (d, J=2.7 Hz, 1H).

Example 83: Synthesis of [7-oxo-3-[3-[[(3R)-pyrrolidin-3-yl]carbamoyl]pyrazol-1-yl]-1,6-diazabicyclo[3.2.1]oct-3-en-6-yl]hydrogen sulfate

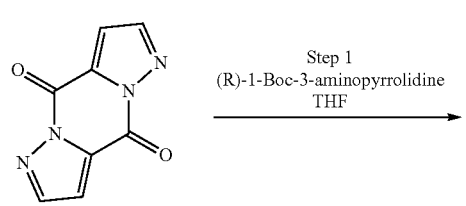

Step 1
(R)-1-Boc-3-aminopyrrolidine
THF

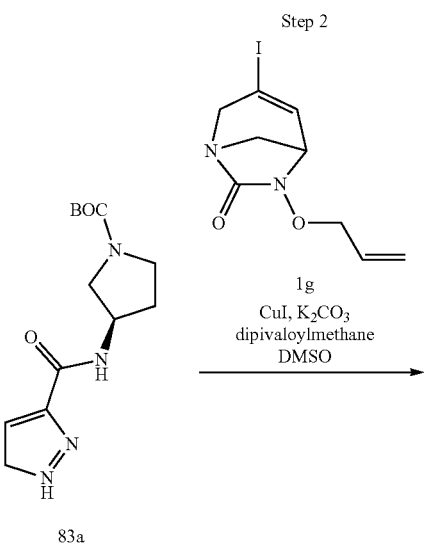

83a

Step 2

1g
CuI, K₂CO₃
dipivaloylmethane
DMSO

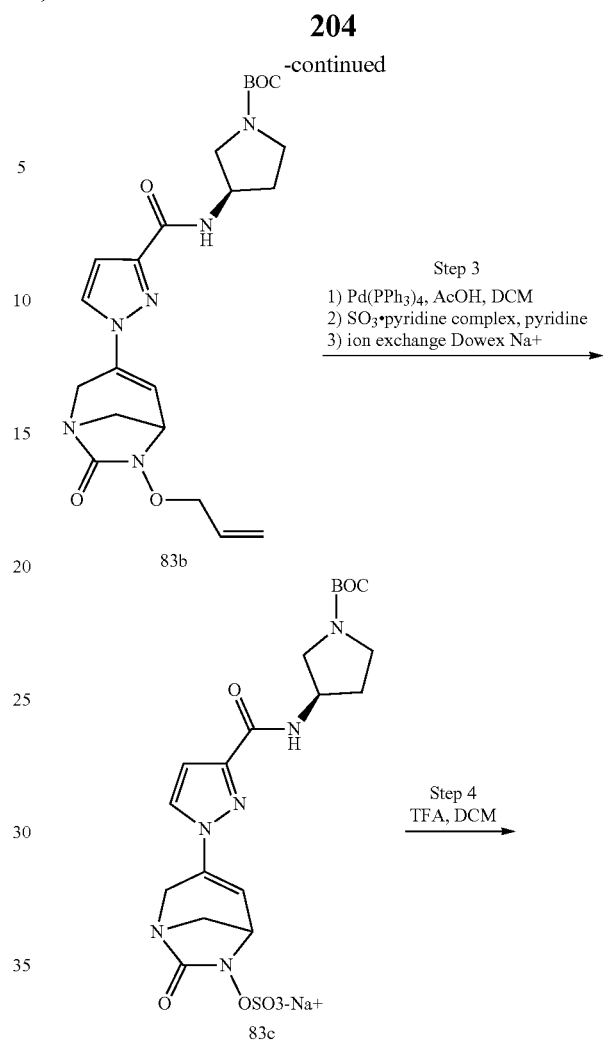

83b

Step 3
1) Pd(PPh₃)₄, AcOH, DCM
2) SO₃·pyridine complex, pyridine
3) ion exchange Dowex Na+

83c

Step 4
TFA, DCM

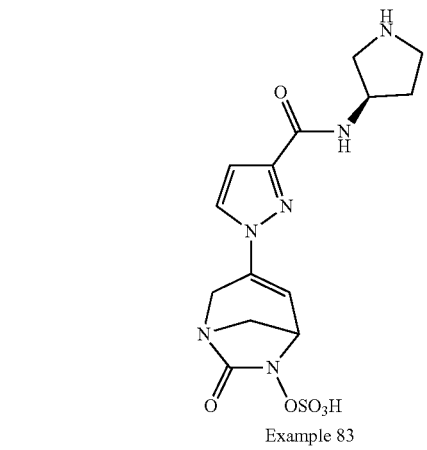

Example 83

Step 1: Preparation of Intermediate tert-butyl (3R)-3-(1H-pyrazole-3-carbonylamino)pyrrolidine-1-carboxylate (83a)

A mixture of dipyrazolo[3,1-a: 3',1'-d]pyrazine-4,9-dione (200 mg, 1.06 mmol) and (R)-1-Boc-3-aminopyrrolidine (396 mg, 2.12 mmol) in THF (10 mL) was heated at 80° C. for 1 h. The mixture was concentrated in vacuo to provide intermediate (83a) which was used without further purification.
MS m/z ([M−H]⁻) 279.

Step 2: Preparation of Intermediate tert-butyl (3R)-3-[[1-(6-allyloxy-7-oxo-1,6-diazabicyclo[3.2.1]oct-3-en-3-yl)pyrazole-3-carbonyl]amino]pyrrolidine-1-carboxylate (83b)

Using the procedure described in example (2) (step 1a), intermediate (1g) (200 mg, 0.65 mmol) was converted by reaction with intermediate (83a) (192 mg, 0.69 mmol) into intermediate (83b) (198 mg, 0.43 mmol, 66%) after a purification by flash chromatography on silica gel (DCM/acetone 100/0 to 60/40).

MS m/z ([M+H-tBu]$^+$) 403, ([M+H-Boc]$^+$) 359.

$^1$H NMR (400 MHz, CDCl$_3$) δ 1.47 (s, 9H), 1.87-2.05 (m, 1H), 2.19-2.31 (m, 1H), 3.15 (d, J=10.9 Hz, 1H), 3.19-3.37 (m, 1H), 3.39-3.61 (m, 3H), 3.66-3.79 (m, 1H), 4.04-4.22 (m, 2H), 4.33-4.55 (m, 3H), 4.56-4.68 (m, 1H), 5.23-5.46 (m, 2H), 5.93-6.11 (m, 1H), 6.56 (m, 1H), 6.83 (d, J=2.6 Hz, 1H), 6.88 (d, J=2.6 Hz, 1H), 7.62 (br s, 1H).

Step 3: Preparation of Intermediate sodium [3-[3-[[(3R)-1-tert-butoxycarbonylpyrrolidin-3-yl]carbamoyl]pyrazol-1-yl]-7-oxo-1,6-diazabicyclo[3.2.1]oct-3-en-6-yl]sulfate (83c)

Using the procedure described in example (2) (step 2), intermediate (83b) (198 mg, 0.43 mmol) was converted into intermediate (83c) (98 mg, 0.19 mmol, 43% over 3 steps) as a white solid.

MS m/z ([M]$^-$) 497.

Step 4: Preparation of [7-oxo-3-[3-[[(3R)-pyrrolidin-3-yl]carbamoyl]pyrazol-1-yl]-1,6-diazabicyclo[3.2.1]oct-3-en-6-yl]hydrogen sulfate (Example 83)

Using procedure described in example (82) (step 4), intermediate (83c) (80 mg, 0.15 mmol) was converted into example (83) (26 mg, 0.07 mmol, 42%) as a mixture of diastereoisomers.

MS m/z ([M+H]$^+$) 399.
MS m/z ([M-H]$^-$) 397.

$^1$H NMR (400 MHz, D$_2$O) δ (ppm) 2.10-2.29 (m, 1H), 2.35-2.57 (m, 1H), 3.34-3.54 (m, 3H), 3.56-3.76 (m, 3H), 4.37 (s, 2H), 4.59 (dd, J=5.7, 2.6 Hz, 1H), 4.62-4.71 (m, 1H), 6.70 (d, J=5.6 Hz, 1H), 6.79 and 6.80 (d, J=2.6 Hz, 1H), 7.89 and 7.90 (d, J=2.6, 1H).

Example 84: Synthesis of sodium [7-oxo-3-[3-(1,3,4-thiadiazol-2-ylcarbamoyl)pyrazol-1-yl]-1,6-diazabicyclo[3.2.1]oct-3-en-6-yl]sulfate

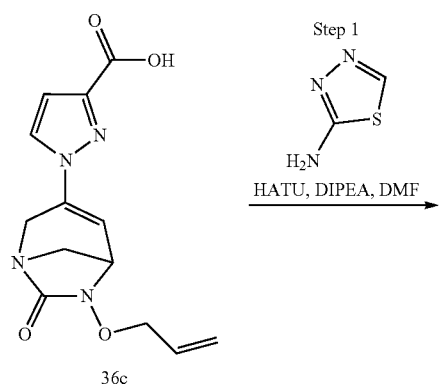

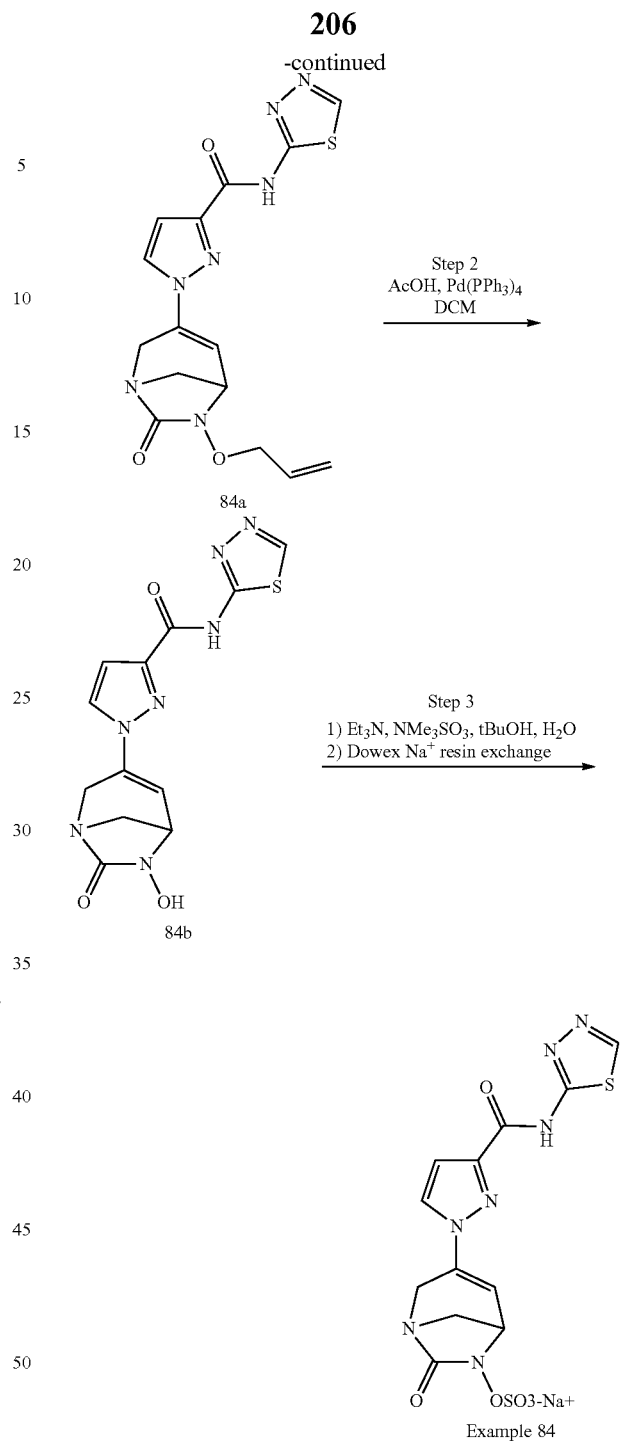

Step 1: Preparation of 1-(6-allyloxy-7-oxo-1,6-diazabicyclo[3.2.1]oct-3-en-3-yl)-N-(1,3,4-thiadiazol-2-yl)pyrazole-3-carboxamide (84a)

Using procedure described in example (79) (step 1), intermediate (36c) (80 mg, 0.28 mmol) was converted by reaction with 1,3,4-thiadiazol-2-amine (28 mg, 0.28 mmol) into intermediate (84a) (8 mg, 0.02 mmol, 8%) after purification by flash chromatography on silica gel (DCM/acetone: 100/0 to 0/100) and trituration in DCM.

MS m/z ([M+H]$^+$) 374.
MS m/z ([M-H]$^-$) 372.

$^1$H NMR (400 MHz, MeOD): δ (ppm) 3.33-3.35 (m, 1H), 3.52-3.54 (m, 1H), 4.32 (dd, J=5.6, 2.6 Hz, 1H), 4.36 (dd, J=2.1, 17.6 Hz, 1H), 4.42-4.46 (m, 2H), 4.49 (d, J=17.6 Hz, 1H), 5.28-5.42 (m, 2H), 6.01-6.08 (m, 1H), 6.83 (d, J=5.6 Hz, 1H), 7.05 (d, J=2.6 Hz, 1H), 8.15 (d, J=2.6 Hz, 1H), 9.09 (s, 1H).

Step 2: Preparation of 1-(6-hydroxy-7-oxo-1,6-diazabicyclo[3.2.1]oct-3-en-3-yl)-N-(1,3,4-thiadiazol-2-yl)pyrazole-3-carboxamide (84b)

Under inert atmosphere, to a suspension of intermediate (84a) (8.1 mg, 0.02 mmol) in anhydrous DCM (155 μL) were successively added AcOH (3 μL, 0.04 mmol) and Pd(PPh$_3$)$_4$ (13 mg, 0.01 mmol). The mixture was stirred at rt for 1 h. Et$_2$O was added to the resulting suspension and the precipitate was filtered to afford intermediate (84b) (5 mg, 0.016 mmol, 71%) as a white solid.

MS m/z ([M+H]$^+$) 334.

MS m/z ([M−H]$^−$) 332.

$^1$H NMR (400 MHz, DMSO-d$_6$): δ (ppm) 3.25 (d, J=10.9 Hz, 1H), 3.35-3.40 (m, 1H), 4.09 (dd, J=5.5, 2.5 Hz, 1H), 4.23 (dd, J=17.6, 1.9 Hz, 1H), 4.38 (d, J=17.6 Hz, 1H), 6.93 (br s, 1H), 7.11 (br s, 1H), 8.39 (s, 1H), 9.19 (br s, 1H), 11.93 (br s, 1H), 12.87 (br s, 1H).

Step 3: Preparation of sodium [7-oxo-3-[3-(1,3,4-thiadiazol-2-ylcarbamoyl)pyrazol-1-yl]-1,6-diazabicyclo[3.2.1]oct-3-en-6-yl]sulfate (Example 84)

To a solution of intermediate (84b) (5 mg, 0.016 mmol) in a mixture tBuOH/H$_2$O (1:1) (160 μL) were added NMe$_3$SO$_3$ (3 mg, 0.018 mmol) and Et$_3$N (0.5 μL, 0.004 mmol). The resulting suspension was protected from light and stirred for 45 min at rt. The mixture was concentrated in vacuo then purified by flash chromatography on C18-reversed phase silica gel (water/ACN: 95/5 to 0/100). Fractions containing the product were combined, freezed and lyophilized. The residue was dissolved in a mixture water/ACN (9:1) and converted after ion exchange with Dowex sodium form column (Dowex® 50WX8 hydrogen form stored with an aqueous solution of 2N NaOH and washed until neutral pH with H$_2$O). The fractions containing the desired compound were combined, freezed and lyophilized to afford example (84) (4 mg, 0.009 mmol, 69% over 2 steps) as an off-white solid.

MS m/z ([M+H]$^+$) 414.

MS m/z ([M−H]$^−$) 412.

$^1$H NMR (400 MHz, D$_2$O): δ(ppm) 3.50 (d, J=11.4 Hz, 1H), 3.75 (dd, J=11.4, 2.4 Hz, 1H), 4.46 (m, 2H), 4.65 (dd, J=5.6, 2.6 Hz, 1H), 6.78 (d, J=5.6 Hz, 1H), 7.04 (d, J=2.7 Hz, 1H), 8.01 (d, J=2.7 Hz, 1H), 9.12 (s, 1H).

Example 85: Synthesis of sodium [7-oxo-3-[3-(pyrazol-3-ylcarbamoyl)pyrazol-1-yl]-1,6-diazabicyclo[3.2.1]oct-3-en-6-yl]sulfate

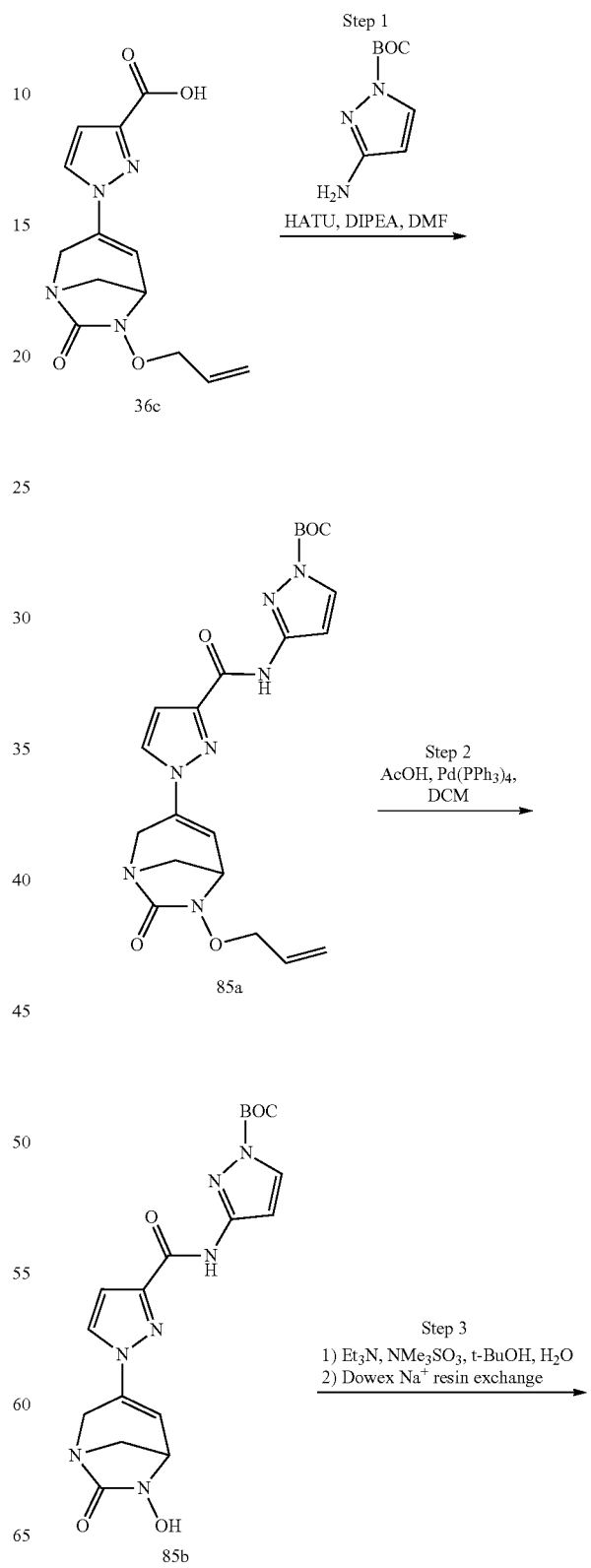

-continued

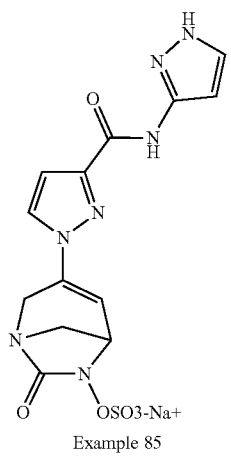

Example 85

Step 1: Preparation of tert-butyl 3-[[1-(6-allyloxy-7-oxo-1,6-diazabicyclo[3.2.1]oct-3-en-3-yl)pyrazol-3-carbonyl]aminol]pyrazole-1-carboxylate (85a)

Using procedure described in example (79) (step 1), intermediate (36c) (130 mg, 0.45 mmol) was converted by reaction with tert-butyl 3-aminopyrazole-1-carboxylate (82 mg, 0.45 mmol) into intermediate (85a) (117 mg, 0.26 mmol, 57%) after purification by flash chromatography on silica gel (DCM/acetone: 100/0 to 0/100).

MS m/z ([M+H]$^+$) 456.
MS m/z ([M–H]$^-$) 454.
$^1$H NMR (400 MHz, CDCl$_3$): δ (ppm) 1.66 (s, 9H), 3.18 (d, J=10.9 Hz, 1H), 3.57 (dd, J=10.9, 2.1 Hz, 1H), 4.15 (dd, J=5.5, 2.5 Hz, 1H), 4.22 (dd, J=17.6, 1.9 Hz, 1H), 4.39-4.52 (m, 3H), 5.30-5.43 (m, 2H), 5.98-6.09 (m, 1H), 6.60 (d, J=5.5 Hz, 1H), 6.97 (d, J=2.6 Hz, 1H), 7.07 (d, J=2.9 Hz, 1H), 7.67 (d, J=2.6 Hz, 1H), 8.01 (d, J=2.9 Hz, 1H), 9.31 (s, 1H).

Step 2: Preparation of tert-butyl 3-[[1-(6-hydroxy-7-oxo-1,6-diazabicyclo[3.2.1]oct-3-en-3-yl)pyrazol-3-carbonyl]amino]pyrazole-1-carboxylate (85b)

Under inert atmosphere, to a solution of intermediate (85a) (115 mg, 0.25 mmol) in anhydrous DCM (1.8 mL), were successively added AcOH (29 µL, 0.51 mmol) and Pd(PPh$_3$)$_4$ (146 mg, 0.13 mmol). After stirring for 1 h, the crude was concentrated in vacuo and the residue purified by chromatography on silica gel (DCM/acetone: 100/0 to 0/100) to afford intermediate (85b) (105 mg, 0.25 mmol, quantitative yield) as a pale yellow solid.

MS m/z ([M+H]$^+$) 416.
MS m/z ([M–H]$^-$) 414.
$^1$H NMR (400 MHz, MeOD): δ (ppm) 1.65 (s, 9H), 3.30 (d, J=10.9 Hz, 1H), 3.53 (dd, J=10.9, 2.4 Hz, 1H), 4.13 (dd, J=5.5, 2.6 Hz, 1H), 4.33 (dd, J=17.7, 2.0 Hz, 1H), 4.45 (dd, J=17.7, 1.1 Hz, 1H), 6.85 (d, J=5.5 Hz, 1H), 6.96 (d, J=2.6 Hz, 1H), 7.00 (d, J=2.9 Hz, 1H), 8.12 (d, J=2.6 Hz, 1H), 8.15 (d, J=2.9 Hz, 1H).

Step 3: Preparation of sodium [7-oxo-3-[3-(pyrazol-3-ylcarbamoyl)pyrazol-1-yl]-1,6-diazabicyclo[3.2.1]oct-3-en-6-yl]sulfate (Example 85)

To a solution of intermediate (85b) (102 mg, 0.25 mmol) in a mixture t-BuOH/H$_2$O (1:1) (1.2 mL) were added NMe$_3$SO$_3$ (41 mg, 0.30 mmol) and TEA (9 µL, 0.06 mmol). The resulting suspension was protected from light and stirred for 1 h at rt. The mixture was concentrated in vacuo then purified by flash chromatography on C18-reversed phase silica gel (water/ACN: 95/5 to 0/100). Fractions containing the product were combined, freezed and lyophilized. The residue was dissolved in a mixture H$_2$O/ACN (9:1) and converted after ion exchange with Dowex sodium form column (Dowex® 50WX8 hydrogen form stored with an aqueous solution of 2N NaOH and washed until neutral pH with H$_2$O). The fractions containing the desired compound were combined, freezed and lyophilized. The residue was purified by flash chromatography on C18-reversed phase silica gel (H$_2$O/ACN: 98/2 to 0/100). Fractions containing the expected intermediate were concentrated in vacuo to afford example (85) (10 mg, 0.02 mmol, 6% over 2 steps) as a white solid.

MS m/z ([M+H]$^+$) 396.
MS m/z ([M–H]$^-$) 394.
$^1$H RMN (400 MHz, D$_2$O) δ (ppm) 3.51 (d, J=11.4 Hz, 1H), 3.74 (dd, J=11.4, 2.4 Hz, 1H), 4.48-4.51 (m, 2H), 4.65 (dd, J=5.6, 2.6 Hz, 1H), 6.55-6.60 (m, 1H), 6.83 (d, J=5.6 Hz, 1H), 7.02 (d, J=2.7 Hz, 0.6H), 7.06 (d, J=2.7 Hz, 0.4H), 7.73-7.78 (m, 1H), 8.09 (d, J=2.7 Hz, 0.6H), 8.19 (d, J=2.7 Hz, 0.4H).

Example 86: Biological Activity

Method 1: β-Lactamase Inhibitory Activity, Determination of IC$_{50}$ (Tables 1 and 2)

Enzyme activity was monitored by spectrophotometric measurement of nitrocefin (NCF-TOKU-E, N005) hydrolysis at 485 nm, at room temperature and in assay buffer A: 100 mM Phosphate pH 7, 2% glycerol and 0.1 mg/mL Bovine serum albumin (Sigma, B4287). Enzymes were cloned in E. coli expression vector, expressed and purified in house using classical procedures. To a transparent polystyrene plate (Corning, 3628) were added in each well 5 µL DMSO or inhibitor dilutions in DMSO and 80 µL enzyme in buffer A. Plates were immediately read at 485 nm in a microplate spectrophotometer (BioTek, PowerWave HT) to enable background subtraction. After 30-min pre-incubation at room temperature, 15 µL of NCF (200 µM final) were finally added in each well. Final enzyme concentrations were 0.1 nM (TEM-1), 0.075 nM (SHV-1), 0.4 nM (CTX-M-15), 1 nM (KPC-2), 0.2 nM (P99 AmpC), 0.2 nM (CMY-37), 0.4 nM (AmpC P. aeruginosa), 0.2 nM (OXA-1), 1.2 nM (OXA-11), 0.4 nM (OXA-15) and 0.3 nM (OXA-48). After 20-min incubation at room temperature, plates were once again read at 485 nm. Enzyme activity was obtained by subtracting the final signal by the background, and was converted to enzyme inhibition using non inhibited wells. IC$_{50}$ curves were fitted to a classical Langmuir equilibrium model with Hill slope using XLFIT (IDBS).

TABLE 1

| | IC$_{50}$ (μM) for β-lactamase inhibitory activity | | | | |
|---|---|---|---|---|---|
| | IC$_{50}$ β-lactamase (μM) | | | | |
| | (A) | | | | (C) |
| | TEM-1 | SHV-1 | CTX-M-15 | KPC-2 | AmpC (P99) |
| Example 1 | 0.00025 | 0.0015 | 0.00055 | 0.013 | 0.030 |
| Example 2 | 0.00056 | 0.0040 | 0.00067 | 0.0047 | 0.010 |
| Example 3 | 0.00073 | 0.0097 | 0.0021 | 0.012 | 0.016 |
| Example 4 | 0.00081 | 0.0060 | 0.00066 | 0.077 | 0.27 |
| Example 5 | 0.00080 | 0.0044 | 0.00066 | 0.0030 | 0.016 |
| Example 6 | 0.00036 | 0.0019 | 0.00058 | 0.0021 | 0.0087 |
| Example 7 | 0.00072 | 0.0047 | 0.0027 | 0.012 | 0.021 |
| Example 8 | 0.00035 | 0.0025 | 0.00078 | 0.0033 | 0.0076 |
| Example 9 | 0.00041 | 0.0019 | 0.00050 | 0.022 | 0.015 |
| Example 10 | 0.00030 | 0.0032 | 0.0011 | 0.050 | 0.022 |
| Example 11 | 0.0012 | 0.0076 | 0.0014 | 0.012 | 0.027 |
| Example 12 | 0.00041 | 0.0021 | 0.00053 | 0.026 | 0.015 |
| Example 13 | 0.00065 | 0.0032 | 0.00062 | 0.0025 | 0.0026 |
| Example 14 | 0.00087 | 0.0040 | 0.0018 | 0.017 | 0.017 |
| Example 15 | 0.00079 | 0.0065 | 0.0015 | 0.12 | 0.080 |
| Example 16 | 0.00056 | 0.0034 | 0.0014 | 0.0046 | 0.013 |
| Example 17 | 0.00023 | 0.0010 | 0.00076 | 0.0037 | 0.030 |
| Example 18 | 0.00043 | 0.0028 | 0.00065 | 0.013 | 0.024 |
| Example 19 | 0.00038 | 0.0018 | 0.00090 | 0.0062 | 0.019 |
| Example 20 | 0.0013 | 0.0051 | 0.0030 | 0.12 | 0.23 |
| Example 21 | 0.0061 | 0.024 | 0.0037 | 0.27 | 0.23 |
| Example 22 | 0.00021 | 0.0011 | 0.00055 | 0.0030 | 0.017 |
| Example 23 | 0.00019 | 0.00036 | 0.0010 | 0.0057 | 0.038 |
| Example 24 | 0.00037 | 0.0024 | 0.00075 | 0.0052 | 0.012 |
| Example 25 | 0.00029 | 0.0012 | 0.00043 | 0.0025 | 0.0094 |
| Example 26 | 0.00023 | 0.0012 | 0.00072 | 0.0032 | 0.014 |
| Example 27 | 0.0011 | 0.0048 | 0.0012 | 0.010 | 0.033 |
| Example 28 | 0.00037 | 0.0022 | 0.00050 | 0.0048 | 0.010 |
| Example 29 | 0.00021 | 0.0011 | 0.00055 | 0.0087 | 0.025 |
| Example 30 | 0.00033 | 0.0027 | 0.0010 | 0.0053 | 0.028 |
| Example 31 | 0.0013 | 0.0044 | 0.00062 | 0.011 | 0.015 |
| Example 32 | 0.0011 | 0.0082 | 0.0010 | 0.0069 | 0.029 |
| Example 33 | 0.00067 | 0.0017 | 0.00072 | 0.011 | 0.0071 |
| Example 34 | 0.0010 | 0.0031 | 0.00092 | 0.0085 | 0.010 |
| Example 35 | 0.00073 | 0.0032 | 0.00050 | 0.013 | 0.012 |
| Example 37 | 0.00050 | 0.0032 | 0.00046 | 0.0029 | 0.0097 |
| Example 38 | 0.00043 | 0.0025 | 0.00070 | 0.0075 | 0.034 |
| Example 39 | 0.00021 | 0.0013 | 0.00056 | 0.0041 | 0.0095 |
| Example 40 | 0.00035 | 0.0018 | 0.00091 | 0.0034 | 0.0075 |
| Example 41 | 0.00058 | 0.0045 | 0.00091 | 0.057 | 0.036 |
| Example 42 | 0.00031 | 0.0015 | 0.00047 | 0.076 | 0.086 |
| Example 43 | 0.00085 | 0.0036 | 0.00087 | 0.029 | 0.012 |
| Example 44 | 0.00048 | 0.0033 | 0.00086 | 0.0073 | 0.013 |
| Example 45 | 0.0014 | 0.0045 | 0.0013 | 0.047 | 0.032 |
| Example 46 | 0.00089 | 0.0040 | 0.00070 | 0.011 | 0.025 |
| Example 47 | 0.0015 | 0.0091 | 0.0011 | 0.012 | 0.032 |
| Example 48 | 0.0014 | 0.0053 | 0.0024 | 0.13 | 0.11 |
| Example 49 | 0.0012 | 0.0085 | 0.0026 | 0.18 | 0.16 |
| Example 50 | 0.0012 | 0.0056 | 0.00059 | 0.012 | 0.012 |
| Example 51 | 0.00030 | 0.0019 | 0.00028 | 0.018 | 0.017 |
| Example 52 | 0.0019 | 0.0091 | 0.00067 | 0.011 | 0.016 |
| Example 55 | 0.00014 | 0.00061 | 0.00041 | 0.00082 | 0.0063 |
| Example 56 | 0.00017 | 0.0010 | 0.00044 | 0.0024 | 0.012 |
| Example 57 | 0.00037 | 0.0026 | 0.00075 | 0.011 | 0.021 |
| Example 59 | 0.00069 | 0.0025 | 0.00055 | 0.012 | 0.034 |
| Example 60 | 0.00035 | 0.0020 | 0.00073 | 0.014 | 0.027 |
| Example 61 | 0.0017 | 0.0061 | 0.0018 | 0.017 | 0.020 |
| Example 63 | 0.00086 | 0.0069 | 0.00053 | 0.0047 | 0.019 |
| Example 64 | 0.00052 | 0.0029 | 0.0010 | 0.0070 | 0.013 |
| Example 65 | 0.00027 | 0.0028 | 0.00096 | 0.0060 | 0.011 |
| Example 66 | 0.00036 | 0.0031 | 0.00054 | 0.0061 | 0.014 |
| Example 67 | 0.0012 | 0.0084 | 0.0013 | 0.020 | 0.038 |
| Example 68 | 0.00073 | 0.0028 | 0.0071 | 0.30 | 0.17 |
| Example 69 | 0.00061 | 0.0023 | 0.00095 | 0.032 | 0.018 |
| Example 70 | 0.00063 | 0.0023 | 0.0035 | 0.051 | 0.094 |
| Example 71 | 0.0014 | 0.0096 | 0.00078 | 0.042 | 0.019 |
| Example 72 | 0.00091 | 0.0067 | 0.00057 | 0.0070 | 0.043 |
| Example 73 | 0.0019 | 0.0098 | 0.0044 | 0.078 | 0.092 |
| Example 74 | 0.00034 | 0.0022 | 0.0011 | 0.0030 | 0.0095 |
| Example 76 | 0.0018 | 0.0073 | 0.0021 | 0.073 | 0.029 |
| Example 77 | 0.0011 | 0.0052 | 0.0015 | 0.011 | 0.011 |
| Example 78 | 0.00037 | 0.0015 | 0.00046 | 0.0027 | 0.014 |

TABLE 1-continued

IC$_{50}$ (μM) for β-lactamase inhibitory activity

| | IC$_{50}$ β-lactamase (μM) | | | | |
|---|---|---|---|---|---|
| | (A) | | | | (C) |
| | TEM-1 | SHV-1 | CTX-M-15 | KPC-2 | AmpC (P99) |
| Example 79 | 0.00036 | 0.00098 | 0.00046 | 0.0044 | 0.014 |
| Example 80 | 0.00027 | 0.0014 | 0.00029 | 0.0026 | 0.0079 |
| Example 82 | 0.00058 | 0.0049 | 0.00089 | 0.010 | 0.032 |
| Example 83 | 0.00027 | 0.0038 | 0.00064 | 0.0079 | 0.024 |
| Example 84 | 0.00078 | 0.0027 | 0.0010 | 0.0085 | 0.025 |
| Example 85 | 0.00035 | 0.0016 | 0.00059 | 0.0034 | 0.011 |

TABLE 2

IC$_{50}$ (μM) for β-lactamase inhibitory activity (continued)

| | IC$_{50}$ β-lactamase (μM) | | | | | |
|---|---|---|---|---|---|---|
| | (C) | | (D) | | | |
| | CMY-37 | AmpC (PAE) | OXA-1 | OXA-11 | OXA-15 | OXA-48 |
| Example 1 | 0.033 | 0.12 | 0.12 | 0.092 | 0.092 | 0.0019 |
| Example 2 | 0.031 | 0.15 | 0.058 | 0.040 | 0.040 | 0.00059 |
| Example 3 | 0.024 | 0.059 | 0.20 | 0.085 | 0.19 | 0.0016 |
| Example 4 | 0.15 | 0.098 | 1.1 | 0.040 | 0.12 | 0.0051 |
| Example 5 | 0.036 | 0.14 | 0.049 | 0.014 | 0.027 | 0.00045 |
| Example 6 | 0.020 | 0.11 | 0.031 | 0.021 | 0.021 | 0.00038 |
| Example 7 | 0.022 | 0.40 | 0.25 | 0.093 | 0.055 | 0.0078 |
| Example 8 | 0.016 | 0.14 | 0.10 | 0.020 | 0.0053 | 0.0035 |
| Example 9 | 0.0093 | 0.029 | 0.41 | 0.31 | 0.055 | 0.0070 |
| Example 10 | 0.018 | 0.16 | 0.27 | 0.067 | 0.18 | 0.014 |
| Example 11 | 0.053 | 0.43 | 0.095 | 0.021 | 0.078 | 0.0077 |
| Example 12 | 0.014 | 0.052 | 0.20 | 0.070 | 0.19 | 0.012 |
| Example 13 | 0.0011 | 0.0087 | 0.027 | 0.0040 | 0.011 | 0.0019 |
| Example 14 | 0.010 | 0.021 | 0.082 | 0.034 | 0.052 | 0.0086 |
| Example 15 | 0.076 | 0.36 | 0.70 | 0.27 | 0.049 | 0.018 |
| Example 16 | 0.021 | 0.18 | 0.10 | 0.65 | 0.042 | 0.012 |
| Example 17 | 0.087 | 0.28 | 0.10 | 0.063 | 0.030 | 0.0058 |
| Example 18 | 0.018 | 0.043 | 0.096 | 0.046 | 0.078 | 0.0082 |
| Example 19 | 0.041 | 0.17 | 0.11 | 0.027 | 0.061 | 0.0052 |
| Example 20 | 0.14 | 0.91 | 6.2 | 7.1 | 0.14 | 0.068 |
| Example 21 | 0.099 | 0.32 | 2.1 | 1.4 | 0.29 | 0.045 |
| Example 22 | 0.012 | 0.078 | 0.18 | 0.22 | 0.0091 | 0.0046 |
| Example 23 | 0.054 | 0.22 | 1.5 | 1.1 | 0.76 | 0.11 |
| Example 24 | 0.016 | 0.16 | 0.076 | 0.095 | 0.048 | 0.0046 |
| Example 25 | 0.0092 | 0.13 | 0.037 | 0.0042 | 0.012 | 0.0017 |
| Example 26 | 0.036 | 0.13 | 0.033 | 0.0098 | 0.013 | 0.0078 |
| Example 27 | 0.028 | 0.35 | 0.13 | 0.069 | 0.11 | 0.0061 |
| Example 28 | 0.037 | 0.20 | 0.064 | 0.029 | 0.030 | 0.0038 |
| Example 29 | 0.035 | 0.19 | 0.15 | 0.031 | 0.051 | 0.0030 |
| Example 30 | 0.099 | 0.37 | 0.35 | 0.029 | 0.17 | 0.036 |
| Example 31 | 0.028 | 0.21 | 0.064 | 0.033 | 0.088 | 0.0030 |
| Example 32 | 0.059 | 0.21 | 0.079 | 0.027 | 0.039 | 0.0015 |
| Example 33 | 0.0032 | 0.032 | 0.068 | 0.0084 | 0.044 | 0.0031 |
| Example 34 | 0.0062 | 0.056 | 0.13 | 0.013 | 0.034 | 0.0094 |
| Example 35 | 0.0081 | 0.052 | 0.13 | 0.054 | 0.079 | 0.0060 |
| Example 37 | 0.015 | 0.20 | 0.073 | 0.021 | 0.032 | 0.0025 |
| Example 38 | 0.038 | 0.21 | 0.18 | 0.050 | 0.017 | 0.0032 |
| Example 39 | 0.0081 | 0.082 | 0.15 | 0.073 | 0.0085 | 0.0018 |
| Example 40 | 0.0083 | 0.26 | 0.15 | 0.095 | 0.0086 | 0.0063 |
| Example 41 | 0.021 | 0.088 | 0.75 | 0.18 | 0.040 | 0.0089 |
| Example 42 | 0.059 | 0.18 | 1.6 | 0.85 | 0.034 | 0.0091 |
| Example 43 | 0.0064 | 0.0094 | 0.098 | 0.039 | 0.14 | 0.0060 |
| Example 44 | 0.026 | 0.15 | 0.036 | 0.020 | 0.032 | 0.00029 |
| Example 45 | 0.019 | 0.066 | 0.30 | 0.092 | 0.31 | 0.018 |
| Example 46 | 0.016 | 0.16 | 0.14 | 0.049 | 0.17 | 0.0039 |
| Example 47 | 0.032 | 0.48 | 0.20 | 0.10 | 0.16 | 0.0067 |
| Example 48 | 0.080 | 0.31 | 0.94 | 0.20 | 0.51 | 0.036 |
| Example 49 | 0.15 | 1.3 | 0.67 | 0.38 | 0.51 | 0.046 |
| Example 50 | 0.0059 | 0.067 | 0.079 | 0.011 | 0.060 | 0.0057 |
| Example 51 | 0.0063 | 0.078 | 0.097 | 0.012 | 0.076 | 0.0038 |
| Example 52 | 0.0088 | 0.11 | 0.31 | 0.13 | 0.26 | 0.0075 |
| Example 55 | 0.035 | 0.23 | 0.026 | 0.025 | 0.0034 | 0.00027 |

TABLE 2-continued

IC$_{50}$ (μM) for β-lactamase inhibitory activity (continued)

| | IC$_{50}$ β-lactamase (μM) | | | | | |
|---|---|---|---|---|---|---|
| | (C) | | (D) | | | |
| | CMY-37 | AmpC (PAE) | OXA-1 | OXA-11 | OXA-15 | OXA-48 |
| Example 56 | 0.038 | 0.29 | 0.030 | 0.037 | 0.0090 | 0.00048 |
| Example 57 | 0.031 | 0.55 | 0.066 | 0.17 | 0.0064 | 0.0011 |
| Example 59 | 0.072 | 0.59 | 0.21 | 0.17 | 0.0066 | 0.0012 |
| Example 60 | 0.068 | 0.33 | 0.13 | 0.13 | 0.0081 | 0.0012 |
| Example 61 | 0.041 | 1.1 | 0.11 | 0.36 | 0.019 | 0.00091 |
| Example 63 | 0.055 | 0.53 | 0.052 | 0.11 | 0.041 | 0.00097 |
| Example 64 | 0.043 | 0.37 | 0.086 | 0.096 | 0.0087 | 0.00070 |
| Example 65 | 0.013 | 0.49 | 0.053 | 0.27 | 0.0067 | 0.00080 |
| Example 66 | 0.026 | 0.25 | 0.087 | 0.14 | 0.0075 | 0.00064 |
| Example 67 | 0.10 | 0.72 | 0.27 | 0.25 | 0.018 | 0.0016 |
| Example 68 | 0.13 | 0.43 | 1.2 | 3.9 | 4.1 | 0.049 |
| Example 69 | 0.014 | 0.057 | 0.31 | 0.12 | 0.23 | 0.014 |
| Example 70 | 0.12 | 0.60 | 0.092 | 0.17 | 0.030 | 0.0062 |
| Example 71 | 0.010 | 0.047 | 0.45 | 0.26 | 0.055 | 0.012 |
| Example 72 | 0.086 | 0.54 | 0.10 | 0.036 | 0.043 | 0.0025 |
| Example 73 | 0.086 | 0.25 | 0.044 | 0.087 | 0.27 | 0.0037 |
| Example 74 | 0.025 | 0.11 | 0.022 | 0.020 | 0.048 | 0.0029 |
| Example 76 | 0.028 | 0.21 | 0.86 | 0.26 | 0.61 | 0.050 |
| Example 77 | 0.0071 | 0.058 | 0.14 | 0.016 | 0.046 | 0.0078 |
| Example 78 | 0.029 | 0.25 | 0.064 | 0.0065 | 0.024 | 0.0030 |
| Example 79 | 0.0086 | 0.095 | 0.065 | 0.019 | 0.046 | 0.0047 |
| Example 80 | 0.012 | 0.15 | 0.030 | 0.0055 | 0.011 | 0.00086 |
| Example 82 | 0.061 | 0.27 | 0.11 | 0.022 | 0.047 | 0.0032 |
| Example 83 | 0.063 | 0.23 | 0.037 | 0.024 | 0.032 | 0.0032 |
| Example 84 | 0.020 | 0.16 | 0.15 | 0.022 | 0.098 | 0.0072 |
| Example 85 | 0.014 | 0.13 | 0.022 | 0.0075 | 0.016 | 0.0017 |

Method 2: MIC of Compounds and Synergy with Ceftazidime Against Bacterial Isolates (Tables 3, 4, 5 and 6)

Compounds of the present invention were assessed against genotyped bacterial strains alone or in combination with the β-lactam ceftazidime (CAZ). In the assays, MICs of said compounds, or of ceftazidime at fixed concentrations of said compounds were determined by the broth microdilution method according to the Clinical Laboratory Standards Institute (CLSI-M7-A7). Briefly, compounds alone according to the invention were prepared in DMSO and spotted (2 μL each) on sterile polystyrene plates (Corning, 3788). Compounds and ceftazidime dilutions were prepared in DMSO and spotted (1 μL each) on sterile polystyrene plates (Corning, 3788). Log phase bacterial suspensions were adjusted to a final density of 5×10$^5$ cfu/mL in cation-adjusted Mueller-Hinton broth (Becton-Dickinson) and added to each well (98 μL). Microplates were incubated for 16-20 h at 35° C. in ambient air. The MIC of of the compounds was defined as the lowest concentration of said compounds that prevented bacterial growth as read by visual inspection. The MIC of ceftazidime at each compound concentration was defined as the lowest concentration of ceftazidime that prevented bacterial growth as read by visual inspection.

TABLE 3

Bacterial species used in MIC determination

| Strains | | Resistance mechanism |
|---|---|---|
| E. cloacae | 260508 | TEM-1, CTX-M-15 |
| E. coli | UFR61O | TEM-1, KPC-2 |
| K. pneumoniae | BAA-1898 | TEM-1, SHV-11, SHV-12, KPC-2 |
| K. pneumoniae | 160143 | TEM-1, SHV-1, CTX-M-15, KPC-2, OXA-1 |
| K. pneumoniae | UFR68 | TEM-1, SHV-11, CTX-M-15, KPC-3 |

TABLE 3-continued

Bacterial species used in MIC determination

| Strains | | Resistance mechanism |
|---|---|---|
| E. cloacae | P99 | AmpC |
| E. cloacae | UFR85 | TEM-1, CTX-M-15, AmpC |
| E. cloacae | UFR70 | TEM-1, CTX-M-15, CMY-2, OXA-1, Porin loss |
| K. pneumoniae | UFR77 | CMY-2 |
| E. coli | UFR74 | SHV-1, DHA-1 |
| E. coli | UFR18 | CTX-M-15, OXA-204 |
| E. coli | 131119 | TEM-1, OXA-48 |
| K. oxytoca | UFR21 | TEM-1, CTX-M-15, OXA-48 |
| K. pneumoniae | UFR24 | TEM-1, SHV-2, SHV-11, OXA-1, OXA-48, OXA-47 |
| K. pneumoniae | 6299 | TEM-1, SHV-11, OXA-163 |
| E. coli | RGN238 | OXA-1 |
| K. pneumoniae | 200047 | TEM-1, SHV-32, CTX-M-15, OXA-1 |
| E. coli | 190317 | TEM-1, SHV-12, CTX-M-15, OXA-1 |
| E. coli | UFR32 | TEM-1, VEB-1, OXA-10 |
| E. coli | UFR39 | CTX-M-15, NDM-1 |
| E. coli | UFR41 | TEM-1, CTX-M-15, CMY-2, OXA-1, NDM-4 |
| E. cloacae | UFR51 | SHV-12, IMP-8 |
| P. aeruginosa | CIP107051 | TEM-24 |

TABLE 4

MIC of compounds

MIC compounds of the invention alone (μg/mL)

| Strains | Example 1 | Example 2 | Example 3 | Example 4 | Example 5 | Example 6 |
|---|---|---|---|---|---|---|
| 260508 | 4 | 2 | 4 | 8 | 4 | 1 |
| UFR61O | 16 | 4 | 8 | 16 | 8 | 2 |
| BAA-1898 | 8 | 2 | 8 | 16 | 4 | 2 |

TABLE 4-continued

MIC of compounds

MIC compounds of the invention alone (μg/mL)

| Strains | Example 1 | Example 2 | Example 3 | Example 4 | Example 5 | Example 6 |
|---|---|---|---|---|---|---|
| 160143 | 4 | 2 | 4 | 4 | 2 | 1 |
| UFR68 | 8 | 4 | 8 | 16 | 4 | 1 |
| P99 | 4 | 1 | 8 | 16 | 4 | 1 |
| UFR85 | 4 | 1 | 4 | 16 | 4 | 1 |
| UFR70 | 4 | 1 | 4 | 8 | 2 | 0.5 |
| UFR77 | 8 | 2 | 4 | 8 | 4 | 1 |
| UFR74 | 16 | 2 | 8 | 8 | 4 | 1 |
| UFR18 | 2 | 1 | 2 | 8 | 2 | 0.5 |
| 131119 | 2 | 1 | 1 | 4 | 2 | 0.5 |
| UFR21 | 8 | 2 | 8 | >32 | 4 | 1 |
| UFR24 | 16 | 4 | 8 | 32 | 2 | 1 |
| 6299 | 32 | 4 | 16 | 16 | 4 | 2 |
| RGN238 | 8 | 2 | 2 | 8 | 2 | 1 |
| 200047 | 8 | 2 | 4 | 4 | 2 | 1 |
| 190317 | 2 | 1 | 2 | 4 | 1 | 0.5 |
| UFR32 | 4 | 1 | 2 | 8 | 2 | 0.5 |
| UFR39 | 2 | 1 | 8 | 8 | 2 | 1 |
| UFR41 | 4 | 2 | 16 | 8 | 4 | 2 |
| UFR51 | 4 | 2 | 2 | 8 | 4 | 1 |
| CIP107051 | >32 | >32 | >32 | >32 | >32 | 32 |

TABLE 5

MIC of Ceftazidime/compound combinations

| Strains | MIC CAZ alone (mg/L) | MIC combination of CAZ and compounds of the invention at 4 μg/mL | | | | | |
|---|---|---|---|---|---|---|---|
| | | Example 1 | Example 2 | Example 3 | Example 4 | Example 5* | Example 6 |
| 260508 | 128 | <0.25 | <0.25 | <0.25 | ≤0.25 | <0.25 | <0.25 |
| UFR61O | 128 | ≤0.25 | <0.25 | ≤0.25 | <0.25 | <0.25 | <0.25 |
| BAA-1898 | 256 | ≤0.25 | <0.25 | 0.5 | 0.5 | <0.25 | <0.25 |
| 160143 | 128 | ≤0.25 | <0.25 | <0.25 | <0.25 | <0.25 | <0.25 |
| UFR68 | >128 | <0.25 | <0.25 | 0.5 | 4 | <0.25 | <0.25 |
| P99 | 128 | <0.25 | <0.25 | ≤0.25 | ≤0.25 | <0.25 | <0.25 |
| UFR85 | 128 | <0.25 | <0.25 | <0.25 | 1 | <0.25 | <0.25 |
| UFR70 | >128 | ≤0.25 | <0.25 | <0.25 | <0.25 | <0.25 | <0.25 |
| UFR77 | 64 | ≤0.25 | <0.25 | <0.25 | <0.25 | <0.25 | <0.25 |
| UFR74 | 64 | ≤0.25 | <0.25 | <0.25 | <0.25 | <0.25 | <0.25 |
| UFR18 | >128 | <0.25 | <0.25 | <0.25 | <0.25 | <0.25 | <0.25 |
| 131119 | 0.5 | <0.25 | <0.25 | <0.25 | <0.25 | <0.25 | <0.25 |
| UFR21 | 128 | 0.5 | <0.25 | 0.5 | 4 | <0.25 | <0.25 |
| UFR24 | >128 | 0.5 | ≤0.25 | ≤0.25 | 0.5 | <0.25 | <0.25 |
| 6299 | 256 | ≤0.25 | <0.25 | <0.25 | ≤0.25 | <0.25 | <0.25 |
| RGN238 | 0.5 | <0.25 | <0.25 | <0.25 | <0.25 | <0.25 | <0.25 |
| 200047 | 128 | ≤0.25 | <0.25 | <0.25 | <0.25 | <0.25 | <0.25 |
| 190317 | 128 | <0.25 | <0.25 | <0.25 | <0.25 | <0.25 | <0.25 |
| UFR32 | >128 | <0.25 | <0.25 | <0.25 | <0.25 | <0.25 | <0.25 |
| UFR39 | >1024 | <0.25 | <0.25 | >128 | <0.25 | <0.25 | <0.25 |
| UFR41 | >128 | 0.5 | <0.25 | >128 | <0.25 | <0.25 | <0.25 |
| UFR51 | >128 | <0.25 | <0.25 | <0.25 | <0.25 | <0.25 | <0.25 |
| CIP107051 | 256 | 8 | 4 | 4 | 4 | 4 | 4 |

*MIC combination of CAZ and compound at 8 μg/mL

TABLE 6

MIC of compounds and Ceftazidime/compound combinations

| Strains | MIC compounds of the invention alone (μg/mL) | | | | | MIC combination of CAZ and compounds of the invention at 4 μg/mL | | | | |
|---|---|---|---|---|---|---|---|---|---|---|
| | 190317 | 6299 | BAA-1898 | P99 | CIP107051 | 190317 | 6299 | BAA-1898 | P99 | CIP107051 |
| None | | | | | | 128 | 256 | 256 | 128 | 256 |
| Example 7 | 16 | >32 | >32 | >32 | >32 | 0.25 | 0.5 | 32 | 2 | 4 |
| Example 8 | 8 | >32 | >32 | >32 | >32 | 0.25 | 0.5 | 0.5 | 2 | 8 |
| Example 9 | >32 | >32 | >32 | >32 | >32 | 0.5 | 4 | 16 | 4 | 8 |
| Example 10 | 1 | >32 | 16 | 8 | 32 | <0.25 | ≤0.25 | ≤0.25 | ≤0.25 | 2 |
| Example 11 | 16 | >32 | >32 | 32 | >32 | ≤0.25 | 1 | 32 | 4 | 16 |
| Example 12 | 1 | 16 | 8 | 4 | >32 | <0.25 | ≤0.25 | ≤0.25 | ≤0.25 | 4 |
| Example 13 | 32 | >32 | >32 | >32 | >32 | 0.5 | 4 | 16 | 4 | 4 |
| Example 14 | 4 | 16 | 8 | 16 | >32 | <0.25 | ≤0.25 | 1 | 0.5 | 4 |
| Example 15 | 2 | >32 | >32 | 8 | 16 | <0.25 | 0.25 | ≤0.25 | ≤0.25 | 2 |
| Example 16 | 8 | >32 | 32 | 32 | >32 | ≤0.25 | 0.5 | 8 | 1 | 4 |
| Example 17 | 4 | >32 | 16 | 16 | >32 | <0.25 | 0.25 | 0.25 | 1 | 8 |

TABLE 6-continued

MIC of compounds and Ceftazidime/compound combinations

| | MIC compounds of the invention alone (μg/mL) | | | | | MIC combination of CAZ and compounds of the invention at 4 μg/mL | | | | |
|---|---|---|---|---|---|---|---|---|---|---|
| Strains | 190317 | 6299 | BAA-1898 | P99 | CIP107051 | 190317 | 6299 | BAA-1898 | P99 | CIP107051 |
| Example 18 | 1 | 4 | 8 | 8 | >32 | <0.25 | ≤0.25 | ≤0.25 | <0.25 | 4 |
| Example 19 | 4 | 16 | 16 | 8 | >32 | <0.25 | ≤0.25 | ≤0.25 | ≤0.25 | 4 |
| Example 20 | >32 | >32 | >32 | >32 | >32 | 128 | >128 | >128 | >128 | >128 |
| Example 21 | 16 | >32 | >32 | >32 | >32 | 0.25 | 4 | 64 | 16 | 4 |
| Example 22 | >32 | >32 | >32 | >32 | >32 | 1 | 16 | 8 | 32 | 8 |
| Example 23 | >32 | >32 | >32 | >32 | >32 | 0.5 | 4 | 4 | 8 | 16 |
| Example 24 | 2 | >32 | 16 | 16 | >32 | <0.25 | 0.25 | 1 | 0.25 | 4 |
| Example 25 | >32 | >32 | >32 | >32 | >32 | 1 | 32 | 16 | 64 | 16 |
| Example 26 | 4 | 16 | 16 | 16 | >32 | <0.25 | ≤0.25 | 0.5 | 1 | 4 |
| Example 27 | 8 | 32 | 32 | 16 | >32 | 0.25 | 0.5 | 16 | 2 | 16 |
| Example 28 | 16 | >32 | >32 | >32 | >32 | ≤0.25 | 1 | 1 | 2 | 8 |
| Example 29 | 8 | >32 | 32 | 32 | >32 | <0.25 | 0.5 | 1 | 1 | 4 |
| Example 30 | 32 | >32 | >32 | >32 | >32 | 0.25 | 1 | 2 | 8 | 16 |
| Example 31 | >32 | >32 | >32 | >32 | >32 | 0.5 | 4 | 64 | 16 | 32 |
| Example 32 | 8 | 32 | 16 | 16 | >32 | ≤0.25 | 0.5 | 0.5 | 0.5 | 4 |
| Example 33 | 8 | 32 | 32 | 16 | >32 | ≤0.25 | 0.25 | 16 | 1 | 8 |
| Example 34 | >32 | >32 | >32 | >32 | >32 | 1 | 64 | 128 | 64 | 32 |
| Example 35 | 16 | >32 | >32 | >32 | >32 | 0.5 | 32 | 32 | 32 | 16 |
| Example 37 | 8 | >32 | >32 | >32 | >32 | ≤0.25 | 2 | 2 | 8 | 8 |
| Example 38 | 4 | >32 | >32 | 16 | 32 | <0.25 | ≤0.25 | ≤0.25 | 0.25 | 8 |
| Example 39 | >32 | >32 | >32 | >32 | >32 | 1 | 16 | 128 | 16 | 8 |
| Example 40 | 32 | >32 | >32 | >32 | >32 | 0.25 | 2 | 8 | 4 | 8 |
| Example 41 | 2 | >32 | >32 | 4 | 32 | <0.25 | ≤0.25 | ≤0.25 | <0.25 | 2 |
| Example 42 | 4 | >32 | >32 | 16 | >32 | ≤0.25 | 1 | 8 | 0.5 | 4 |
| Example 43 | 1 | 8 | 8 | 4 | >32 | <0.25 | ≤0.25 | ≤0.25 | <0.25 | 4 |
| Example 44 | 1 | 4 | 4 | 4 | >32 | <0.25 | <0.25 | <0.25 | <0.25 | 8 |
| Example 45 | 4 | >32 | 32 | 16 | >32 | <0.25 | ≤0.25 | 8 | 0.25 | 4 |
| Example 46 | 2 | >32 | 16 | 16 | >32 | <0.25 | ≤0.25 | 0.25 | ≤0.25 | 4 |
| Example 47 | 8 | 32 | 32 | 32 | >32 | ≤0.25 | 0.5 | 8 | 2 | 16 |
| Example 48 | 4 | >32 | >32 | 32 | >32 | <0.25 | 0.25 | 4 | 0.5 | 4 |
| Example 49 | 2 | >32 | >32 | 16 | >32 | <0.25 | ≤0.25 | ≤0.25 | ≤0.25 | 4 |
| Example 50 | 8 | 16 | 32 | 16 | >32 | <0.25 | ≤0.25 | 8 | 0.5 | 4 |
| Example 51 | 8 | 16 | 32 | 16 | >32 | ≤0.25 | 0.5 | 32 | 1 | 8 |
| Example 52 | 8 | 16 | 32 | 16 | >32 | ≤0.25 | 0.5 | 16 | 2 | 16 |
| Example 55 | >32 | >32 | >32 | >32 | >32 | 0.25 | 4 | 1 | 8 | 8 |
| Example 56 | 4 | 32 | 32 | 8 | >32 | <0.25 | ≤0.25 | ≤0.25 | ≤0.25 | 8 |
| Example 57 | 0.5 | >32 | 16 | 1 | 16 | <0.25 | ≤0.25 | ≤0.25 | <0.25 | 4 |
| Example 59 | 1 | >32 | >32 | 2 | >32 | <0.25 | ≤0.25 | ≤0.25 | <0.25 | 8 |
| Example 60 | 0.5 | >32 | >32 | 1 | 32 | <0.25 | ≤0.25 | ≤0.25 | <0.25 | 8 |
| Example 61 | 32 | 32 | >32 | 32 | >32 | 0.5 | 4 | 64 | 8 | 4 |
| Example 63 | 8 | >32 | 32 | 16 | >32 | ≤0.25 | 0.25 | ≤0.25 | 1 | 8 |
| Example 64 | 2 | 32 | 8 | 4 | >32 | <0.25 | ≤0.25 | ≤0.25 | <0.25 | 8 |
| Example 65 | 32 | 32 | 32 | 32 | >32 | 0.5 | 2 | 64 | 8 | 8 |
| Example 66 | 4 | 32 | 16 | 8 | >32 | ≤0.25 | ≤0.25 | ≤0.25 | ≤0.25 | 8 |
| Example 67 | 2 | >32 | >32 | 4 | >32 | <0.25 | 0.25 | ≤0.25 | ≤0.25 | 8 |
| Example 68 | >32 | >32 | >32 | >32 | >32 | 1 | >128 | 32 | 16 | 16 |
| Example 69 | 4 | 32 | 32 | 32 | >32 | ≤0.25 | 1 | 64 | 1 | 8 |
| Example 70 | 32 | >32 | 32 | >32 | >32 | 0.5 | 1 | 2 | 4 | 8 |
| Example 71 | 4 | 32 | 16 | 16 | >32 | <0.25 | ≤0.25 | 0.5 | 0.25 | 2 |
| Example 72 | >32 | >32 | >32 | >32 | >32 | 0.5 | 8 | 32 | 16 | 32 |
| Example 73 | >32 | >32 | >32 | >32 | >32 | 0.5 | 4 | 1 | 4 | 8 |
| Example 74 | 8 | 16 | 16 | 16 | >32 | ≤0.25 | ≤0.25 | 0.25 | 0.5 | 8 |
| Example 76 | 8 | >32 | >32 | 32 | >32 | 0.25 | 0.5 | 128 | 2 | 16 |
| Example 77 | >32 | >32 | >32 | >32 | >32 | 2 | 128 | 128 | 64 | 64 |
| Example 78 | >32 | >32 | >32 | >32 | >32 | 0.5 | 2 | 16 | 8 | 8 |
| Example 79 | >32 | >32 | >32 | >32 | >32 | 1 | 64 | 64 | 128 | 16 |
| Example 80 | >32 | >32 | >32 | >32 | >32 | 0.5 | 16 | 32 | 64 | 16 |
| Example 82 | 2 | 32 | 32 | 4 | >32 | <0.25 | ≤0.25 | ≤0.25 | ≤0.25 | 4 |
| Example 83 | 2 | 32 | 8 | 8 | >32 | <0.25 | ≤0.25 | ≤0.25 | ≤0.25 | 4 |
| Example 84 | >32 | >32 | >32 | >32 | >32 | 1 | 32 | 128 | 128 | 32 |
| Example 85 | 32 | >32 | >32 | >32 | >32 | 0.5 | 4 | 16 | 16 | 16 |

The invention claimed is:
1. A compound of formula (I)

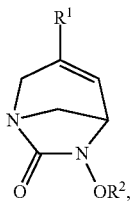

wherein:
R¹ represents a 5-membered heterocycle, optionally substituted by one or more T¹, that is saturated, partially unsaturated, or aromatic and that comprises a nitrogen atom, wherein said 5-membered heterocycle is linked to the structure by said nitrogen atom, and wherein said nitrogen atom may be quaternized;
R² represents —SO₃H, —CFHCOOH, or —CF₂COOH;
☐T¹, identical or different, independently represents a fluorine atom; =O; —C(O)Q¹; —(CH₂)ₘ—S(O)₂—NQ¹Q²; —(CH₂)ₘ—C(=NOQ¹)Q³; —(X)—(CH₂)ₚ—S(O)₂NQ¹Q²; —C(O)—(CH₂)ₙ—S(O)₂NQ¹Q²; —(CH₂)ₘ—O—(CH₂)ₚ—O—(CH₂)ₚ—NQ¹Q²; —(CH₂)ₘOQ¹; —(CH₂)ₘ—CN; —(CH₂)ₘ—OC(O)Q¹; —(CH₂)ₘ—C(O)OQ¹; —(CH₂)ₘ—OC(O)OQ¹; —(CH₂)ₘ—OC(O)NQ¹Q²; —(CH₂)ₘ—C(O)NQ¹Q²; —(CH₂)ₘ—C(O)ONQ¹Q²; —(CH₂)ₘ—C(O)NQ¹OQ²; —(CH₂)ₘ—C(O)NQ¹-NQ¹Q²; —(CH₂)ₘ—NQ¹C(O)Q²; —(CH₂)ₘ—NQ¹S(O)₂NQ¹Q²; —(CH₂)ₘ—NQ¹S(O)₂Q²; —(CH₂)ₘ—NQ¹C(O)OQ²; —(CH₂)ₘ—NQ¹C(O)NQ¹Q²; —(CH₂)ₘ—NQ¹Q²; —(CH₂)ₘ—NH—C(NHQ³)=NQ⁴; —(CH₂)ₘ—NH—CH=NQ³; —(CH₂)ₘ—C(NHQ³)=NQ⁴; —(X)—(CH₂)ₚOQ¹; —(X)—(CH₂)ₙ—CN; —(X)—(CH₂)ₚOC(O)Q¹; —(X)—(CH₂)ₙ—C(O)OQ¹; —(X)—(CH₂)ₚ—OC(O)OQ¹; —(X)—(CH₂)ₚ—OC(O)NQ¹Q²; —(X)—(CH₂)ₙ—C(O)NQ¹Q²; —(X)—(CH₂)ₙ—C(O)ONQ¹Q²; —(X)—(CH₂)ₙ—C(O)NQ¹OQ²; —(X)—(CH₂)ₙ—C(O)NQ¹-NQ¹Q²; —(X)—(CH₂)ₚ—NQ¹C(O)Q²; —(X)—(CH₂)ₚ—NQ¹S(O)₂NQ¹Q²; —(X)—(CH₂)ₚ—NQ¹S(O)₂Q²; —(X)—(CH₂)ₚ—NQ¹C(O)OQ²; —(X)—(CH₂)ₚ—NQ¹C(O)NQ¹Q²; —(X)—(CH₂)ₚ—NQ¹Q²; —(X)—(CH₂)ₚ—NH—C(NHQ³)=NQ⁴; —(X)—(CH₂)ₚ—NH—CH=NQ³; —(X)—(CH₂)ₙ—C(NHQ³)=NQ⁴; —C(O)—(CH₂)ₙOQ¹; —C(O)—(CH₂)ₙ—CN; —C(O)—(CH₂)ₙ—OC(O)Q¹; —C(O)—(CH₂)ₙ—C(O)OQ¹; —C(O)—(CH₂)ₙ—OC(O)OQ¹; —C(O)—(CH₂)ₙ—OC(O)NQ¹Q²; —C(O)—(CH₂)ₙ—C(O)NQ¹Q²; —C(O)—(CH₂)ₙ—C(O)ONQ¹Q²; —C(O)—(CH₂)ₙ—C(O)NQ¹OQ²; —C(O)—(CH₂)ₙ—C(O)NQ¹-NQ¹Q²; —C(O)—(CH₂)ₙ—NQ¹C(O)Q²; —C(O)—(CH₂)ₙ-NQ¹S(O)₂NQ¹Q²; —C(O)—(CH₂)ₙ-NQ¹S(O)₂Q²; —C(O)—(CH₂)ₙ—NQ¹C(O)OQ²; —C(O)—(CH₂)ₙ-NQ¹C(O)NQ¹Q²; —C(O)—(CH₂)ₙ-NQ¹Q²; —C(O)—(CH₂)ₙ—NH—C(NHQ³)=NQ⁴; —C(O)—(CH₂)ₙ—NH—CH=NQ³; or —C(O)—(CH₂)ₙ—C(NHQ³)=NQ⁴; or
☐T¹, identical or different, independently represents an unsubstituted or substituted by one or more T², —(CH₂)ₘ-(4-, 5- or 6-membered saturated, partially or totally unsaturated, or aromatic heterocycle; —(X)—(CH₂)ₘ-(4-, 5- or 6-membered saturated, partially or totally unsaturated, or aromatic heterocycle); (C₁-C₃)-alkyl; (C₁-C₃)-fluoroalkyl; —(X)—(C₁-C₃)-alkyl; —(X)—(C₁-C₃)-fluoroalkyl; —(CH₂)ₘ—(C₃-C₆)-cycloalkyl; —(X)—(CH₂)ₘ—(C₃-C₆)-cycloalkyl; —(CH₂)ₘ—(C₃-C₆)-cyclofluoroalkyl; —(X)—(CH₂)ₘ—(C₃-C₆)-cyclofluoroalkyl; —C(O)—(CH₂)ₘ-(4-, 5- or 6-membered saturated, partially or totally unsaturated, or aromatic heterocycle); —C(O)—(C₁-C₃)-alkyl; —C(O)—(C₁-C₃)-fluoroalkyl; —C(O)O—(C₁-C₃)-fluoroalkyl; —C(O)—(CH₂)ₘ—(C₃-C₆)-cycloalkyl; —C(O)—(CH₂)ₘ—(C₃-C₆)-cycloalkyl; —C(O)—(CH₂)ₘ—(C₃-C₆)-cyclofluoroalkyl; or —C(O)—(CH₂)ₘ—(C₃-C₆)-cyclofluoroalkyl;
T², identical or different, independently represents —OH; —NH₂; or —CONH₂;
☐Q¹ and Q², identical or different, independently represent a hydrogen atom; —(CH₂)ᵣ—NHQ³; —(CH₂)ᵣ—NH—C(NHQ³)=NQ⁴; —(CH₂)ᵣ—NH—CH=NQ³; (CH₂)ₙ—C(NHQ³)=NQ⁴; —(CH₂)ᵣ—OQ³; —(CH₂)ₙ—CONHQ³; an unsubstituted or substituted by one or more T², (C₁-C₃)-alkyl; (C₁-C₃)-fluoroalkyl; or a saturated, partially or totally unsaturated, or aromatic-(CH₂)ₘ-(4-, 5- or 6-membered heterocycle comprising at least one nitrogen atom); or
☐Q¹, Q², and the nitrogen atom to which they are bonded, form together an unsubstituted or substituted by one or more T², saturated or partially unsaturated 4-, 5- or 6-membered heterocycle comprising 1, 2, or 3 heteroatoms;
Q³ and Q⁴, identical or different, independently represent a hydrogen atom or (C₁-C₃)-alkyl;
m, identical or different, independently represents 0, 1, 2 or 3;
n, identical or different, independently represents 1, 2 or 3;
p, identical or different, independently represents 2 or 3;
r is 1, 2 or 3 when the (CH₂), is directly linked to a carbon atom or 2 or 3 otherwise; and
X, identical or different, independently represents O; S; S(O); S(O)₂ or N(Q³); and
wherein:
any carbon atom present within a group selected from alkyl, cycloalkyl, fluoroalkyl, cyclofluoroalkyl and heterocycle can be oxidized to form a C=O group;
any sulphur atom present within a heterocycle can be oxidized to form a S=O group or a S(O)₂ group; and
any nitrogen atom present within a heterocycle or present within group wherein it is trisubstituted thus forming a tertiary amino group, can be further quaternized by a methyl group;
or a racemate, an enantiomer, a diastereoisomer, a geometric isomer or a pharmaceutically acceptable salt of the formula (I) compound, but excluding the following compounds:

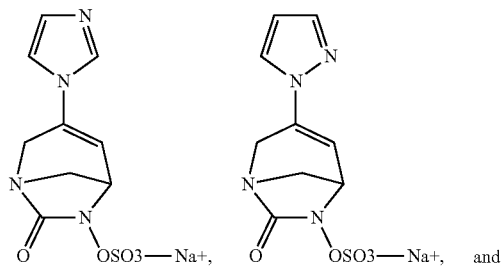

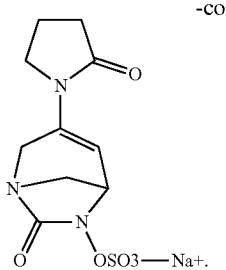

2. The compound of claim 1, wherein the compound of formula (I) is a compound of formula (I)

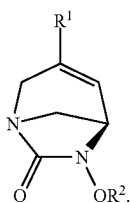

(I*)

3. The compound of claim 1, wherein the 5-membered heterocycle of $R^1$ further comprises one, two, or three additional heteroatoms selected from the group consisting of N, O, and S, wherein one or more of said additional N heteroatoms may be quaternized.

4. The compound of claim 1, wherein:

- $T^1$ identical or different, independently represents a fluorine atom; =O; —C(O)Q'; —$(CH_2)_m$—$S(O)_2$—$NQ^1Q^2$; —$(CH_2)_m$—C(=$NOQ^1$)$Q^3$; —$(CH_2)_n OQ^1$; —$(CH_2)_m$—CN; —$(CH_2)_m$—C(O)O$Q^1$; —$(CH_2)_m$—C(O)N$Q^1Q^2$; —$(CH_2)_m$—C(O)N$Q^1OQ^2$; —$(CH_2)_m$—N$Q^1$C(O)Q$^2$; or —$(CH_2)_m$-N$Q^1Q^2$; or
- $T^1$, identical or different, independently represents an unsubstituted or substituted by one or more $T^2$, —$(CH_2)_m$-(4-, 5- or 6-membered saturated, partially or totally unsaturated, or aromatic heterocycle); ($C_1$-$C_3$)-alkyl; or ($C_1$-$C_3$)-fluoroalkyl.

5. The compound of claim 1, wherein $R^1$ is selected from the group consisting of:

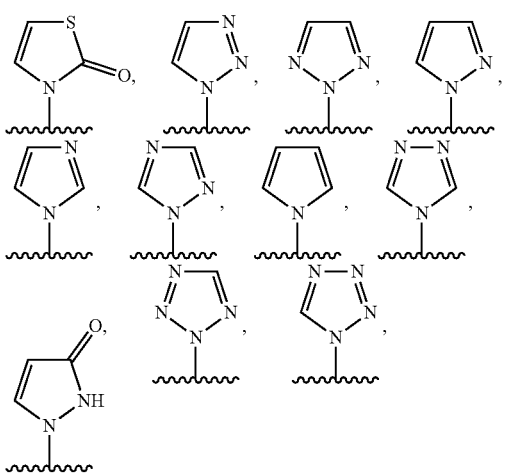

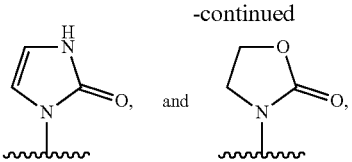

wherein each of the foregoing $R^1$ cycles may be substituted by one or more $T^1$.

6. The compound of claim 1, wherein $R^1$ is selected from the group consisting of:

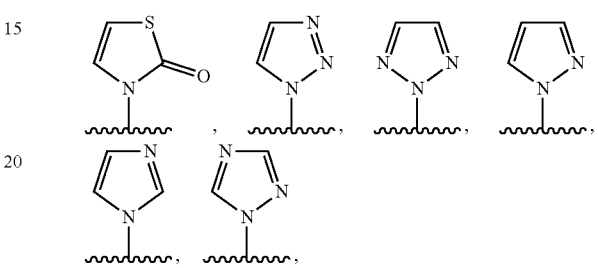

wherein each of the foregoing $R^1$ cycles may be substituted by one or more $T^1$.

7. The compound of claim 1, wherein $R^2$ represents —$SO_3H$ or —$CF_2COOH$.

8. A pharmaceutical composition comprising the compound of claim 1 and a pharmaceutically acceptable excipient.

9. The pharmaceutical composition of claim 8 further comprising at least one antibacterial compound, at least one β-lactam compound, or a combination thereof.

10. The pharmaceutical composition of claim 9, wherein: the at least one antibacterial compound is selected from the group consisting of aminoglycosides, β-lactams, glycylcyclines, tetracyclines, quinolones, fluoroquinolones, glycopeptides, lipopeptides, macrolides, ketolides, lincosamides, streptogramins, oxazolidinones, polymyxins, and combinations thereof; and the at least one β-lactam compound is selected from the group consisting of penicillin, cephalosporins, penems, carbapenems, monobactam, and combinations thereof.

11. A pharmaceutical composition comprising the compound of claim 1 and ceftazidime.

12. A kit comprising at least two different pharmaceutical compositions of claim 8.

13. A kit comprising a first pharmaceutical composition that comprises the compound of claim 1 and a second pharmaceutical composition that comprises ceftazidime.

14. A method for treating a bacterial infection comprising administering to a person in need thereof a pharmaceutically effective amount of the compound of claim 1.

15. The method of claim 14, wherein the bacterial infection is caused by bacteria producing one or more β-lactamase, or by a gram-positive bacteria, or by gram-negative bacteria.

16. A method for treating a bacterial infection comprising administering to a person in need thereof a pharmaceutically effective amount of the pharmaceutical composition of claim 8.

17. A method for treating a bacterial infection comprising administering to a person in need thereof pharmaceutically effective amounts of the first and second pharmaceutical compositions of the kit of claim 13 simultaneously or separately or sequentially.

18. A compound of formula

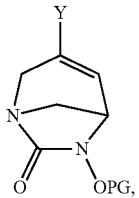

wherein:
Y is selected from the group consisting of a halogen, —B(OR)$_2$, and SnR$_3$, wherein R is an alkyl or the OR are linked together with the B to form a 5-membered cycle; and
PG, is a protective group selected from the group consisting allyl, benzyl, tertbutyldimethylsilyl (TBDMS), and tert-butoxycarbonyl (Boc).

19. A compound of formula

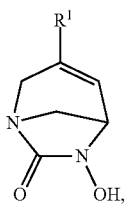

wherein:
R$^1$ represents a 5-membered heterocycle, optionally substituted by one or more T$^1$, that is saturated, partially unsaturated, or aromatic and that comprises a nitrogen atom, wherein said 5-membered heterocycle is linked to the structure by said nitrogen atom, and wherein said nitrogen atom may be quaternized;

☐T$^1$, identical or different, independently represents a fluorine atom; =O; —C(O)Q$^1$; —(CH$_2$)$_m$—S(O)$_2$-NQ$^1$Q$^2$; —(CH$_2$)$_m$—C(=NOQ$^1$)Q$^3$; —(X)—(CH$_2$)$_p$—S(O)$_2$NQ$^1$Q$^2$; —C(O)—(CH$_2$)$_n$—S(O)$_2$NQ$^1$Q$^2$; —(CH$_2$)$_m$—O—(CH$_2$)$_p$—O—(CH$_2$)$_p$—NQ$^1$Q$^2$; —(CH$_2$)$_m$OQ$^1$; —(CH$_2$)$_m$—CN; —(CH$_2$)$_m$—OC(O)Q$^1$; —(CH$_2$)$_m$—C(O)OQ$^1$; —(CH$_2$)$_m$—OC(O)OQ$^1$; —(CH$_2$)$_m$—OC(O)NQ$^1$Q$^2$; —(CH$_2$)$_m$—C(O)NQ$^1$Q$^2$; —(CH$_2$)$_m$—C(O)ONQ$^1$Q$^2$; —(CH$_2$)$_m$—C(O)NQ$^1$Q$^2$; —(CH$_2$)$_m$—C(O)NQ$^1$-NQ$^1$Q$^2$; —(CH$_2$)$_m$—NQ$^1$C(O)Q$^2$; —(CH$_2$)$_m$—NQ$^1$S(O)$_2$NQ$^1$Q$^2$; —(CH$_2$)$_m$—NQ$^1$S(O)$_2$Q$^2$; —(CH$_2$)$_m$-NQ$^1$C(O)OQ$^2$; —(CH$_2$)$_m$NQ$^1$C(O)NQ$^1$Q$^2$; —(CH$_2$)$_m$NQ$^1$Q$^2$; —(CH$_2$)$_m$—NH—C(NHQ$^3$)=NQ$^4$; —(CH$_2$)$_m$NH—CH=NQ$^3$; —(CH$_2$)$_m$—C(NHQ$^3$)=NQ$^4$; —(X)—(CH$_2$)$_p$OQ$^1$; —(X)—(CH$_2$)$_n$—CN; —(X)—(CH$_2$)$_p$—OC(O)Q$^1$; —(X)—(CH$_2$)$_n$—C(O)OQ$^1$; —(X)—(CH$_2$)$_p$—OC(O)OQ$^1$; —(X)—(CH$_2$)$_p$—OC(O)NQ$^1$Q$^2$; —(X)—(CH$_2$)$_n$—C(O)NQ$^1$Q$^2$; —(X)—(CH$_2$)$_n$—C(O)ONQ$^1$Q$^2$; —(X)—(CH$_2$)$_n$—C(O)NQ$^1$OQ$^2$; —(X)—(CH$_2$)$_n$—C(O)NQ$^1$NQ$^2$; —(X)—(CH$_2$)$_p$-NQ$^1$C(O)Q$^2$; —(X)—(CH$_2$)$_p$—NQ$^1$S(O)$_2$NQ$^1$Q$^2$; —(X)—(CH$_2$)$_p$—NQ$^1$S(O)$_2$Q$^2$; —(X)—(CH$_2$)$_p$—NQ$^1$C(O)OQ$^2$; —(X)—(CH$_2$)$_p$—NQ$^1$C(O)NQ$^1$Q$^2$; —(X)—(CH$_2$)$_p$—NQ$^1$Q$^2$; —(X)—(CH$_2$)$_p$—NH—C(NHQ$^3$)=NQ$^4$; —(X)—(CH$_2$)$_p$—NH—CH=NQ$^3$; —(X)—(CH$_2$)$_n$—C(NH-Q$^3$)=NQ$^4$; —C(O)—(CH$_2$)$_n$OQ$^1$; —C(O)—(CH$_2$)$_n$—CN; —C(O)—(CH$_2$)$_n$—OC(O)Q$^1$; —C(O)—(CH$_2$)$_n$—C(O)OQ$^1$; —C(O)—(CH$_2$)$_n$—OC(O)OQ$^1$; —C(O)—(CH$_2$)$_n$—OC(O)NQ$^1$Q$^2$; —C(O)—(CH$_2$)$_n$—C(O)NQ$^1$Q$^2$; —C(O)—(CH$_2$)$_n$—C(O)ONQ$^1$Q$^2$; —C(O)—(CH$_2$)$_n$—C(O)NQ$^1$OQ$^2$; —C(O)—(CH$_2$)$_n$—C(O)NQ$^1$-NQ$^1$Q$^2$; —C(O)—(CH$_2$)$_n$—NQ$^1$C(O)Q$^2$; —C(O)—(CH$_2$)$_n$—NQ$^1$S(O)$_2$NQ$^1$Q$^2$; —C(O)—(CH$_2$)$_n$—NQ$^1$S(O)$_2$Q$^2$; —C(O)—(CH$_2$)$_n$—NQ$^1$C(O)OQ$^2$; —C(O)—(CH$_2$)$_n$—NQ$^1$C(O)NQ$^1$Q$^2$; —C(O)—(CH$_2$)$_n$—NQ$^1$Q$^2$; —C(O)—(CH$_2$)$_n$—NH—C(NHQ$^3$)=NQ$^4$; —C(O)—(CH$_2$)$_n$—NH—CH=NQ$^3$; or —C(O)—(CH$_2$)$_n$—C(NHQ$^3$)=NQ$^4$; or ☐T$^1$, identical or different, independently represents an unsubstituted or substituted by one or more T$^2$, —(CH$_2$)$_m$-(4-, 5- or 6-membered saturated, partially or totally unsaturated, or aromatic heterocycle); —(X)—(CH$_2$)$_m$-(4-, 5- or 6-membered saturated, partially or totally unsaturated, or aromatic heterocycle); (C$_1$-C$_3$)-alkyl; (C$_1$-C$_3$)-fluoroalkyl; —(X)—(C$_1$-C$_3$)-alkyl; —(X)—(C$_1$-C$_3$)-fluoroalkyl; —(CH$_2$)$_m$—(C$_3$-C$_6$)-cycloalkyl; —(X)—(CH$_2$)$_m$(C$_3$-C$_6$)-cycloalkyl; —(CH$_2$)$_m$ (C$_3$-C$_6$)-cyclofluoroalkyl; —(X)—(CH$_2$)$_m$ (C$_3$-C$_6$)-cyclofluoroalkyl; —C(O)—(CH$_2$)$_m$-(4-, 5- or 6-membered saturated, partially or totally unsaturated, or aromatic heterocycle); —C(O)—(C$_1$-C$_3$)-alkyl; —C(O)—(C$_1$-C$_3$)-fluoroalkyl; —C(O)O—(C$_1$-C$_3$)-fluoroalkyl; —C(O)—(CH$_2$)$_m$(C$_3$-C$_6$)-cycloalkyl; —C(O)—(CH$_2$)$_m$(C$_3$-C$_6$)-cycloalkyl; —C(O)—(CH$_2$)$_m$ (C$_3$-C$_6$)-cyclofluoroalkyl; or —C(O)—(CH$_2$)$_m$ (C$_3$-C$_6$)-cyclofluoroalkyl;

T$^2$, identical or different, independently represents —OH; —NH$_2$; or —CONH$_2$;

☐Q$^1$ and Q$^2$, identical or different, independently represent a hydrogen atom; —(CH$_2$)$_r$—NHQ$^3$; —(CH$_2$)$_r$—NH—C(NHQ$^3$)=NQ$^4$; —(CH$_2$)$_r$—NH—CH=NQ$^3$; (CH$_2$)$_n$—C(NHQ$^3$)=NQ$^4$; —(CH$_2$)$_r$—OQ$^3$; —(CH$_2$)$_n$—CONHQ$^3$; an unsubstituted or substituted by one or more T$^2$, (C$_1$-C$_3$)-alkyl; (C$_1$-C$_3$)-fluoroalkyl; or a saturated, partially or totally unsaturated, or aromatic-(CH$_2$)$_m$(4-, 5- or 6-membered heterocycle comprising at least one nitrogen atom); or ☐Q$^1$, Q$^2$, and the nitrogen atom to which they are bonded, form together an unsubstituted or substituted by one or more T$^2$, saturated or partially unsaturated 4-, 5- or 6-membered heterocycle comprising 1, 2, or 3 heteroatoms;

Q$^3$ and Q$^4$, identical or different, independently represent a hydrogen atom or (C$_1$-C$_3$)-alkyl;

m, identical or different, independently represents 0, 1, 2 or 3;

n, identical or different, independently represents 1, 2 or 3;

p, identical or different, independently represents 2 or 3;

r is 1, 2 or 3 when the (CH$_2$), is directly linked to a carbon atom or 2 or 3 otherwise; and X, identical or different, independently represents O; S; S(O); S(O)$_2$ or N(Q$^3$); and wherein:
any carbon atom present within a group selected from alkyl, cycloalkyl, fluoroalkyl, cyclofluoroalkyl and heterocycle can be oxidized to form a C=O group;

any sulphur atom present within a heterocycle can be oxidized to form a S=O group or a S(O)$_2$ group; and any nitrogen atom present within a heterocycle or present within group wherein it is trisubstituted thus forming a tertiary amino group, can be further quaternized by a methyl group.

* * * * *